(12) United States Patent
Foster et al.

(10) Patent No.: US 11,999,943 B2
(45) Date of Patent: Jun. 4, 2024

(54) MATERIALS AND METHODS FOR MAXIMIZING BIOSYNTHESIS THROUGH ALTERATION OF PYRUVATE-ACETYL-CoA-TCA BALANCE IN SPECIES OF THE GENERA RALSTONIA AND CUPRIAVIDUS AND ORGANISMS RELATED THERETO

(71) Applicant: INV Nylon Chemicals Americas, LLC, Wilmington, DE (US)

(72) Inventors: Alexander Brett Foster, Redcar (GB); Emilie Sophie Fritsch, Redcar (GB)

(73) Assignee: INV NYLON CHEMICALS AMERICAS, LLC, Wilmington, DE (US)

( * ) Notice: Subject to any disclaimer, the term of this patent is extended or adjusted under 35 U.S.C. 154(b) by 0 days.

(21) Appl. No.: 16/398,401

(22) Filed: Apr. 30, 2019

(65) Prior Publication Data

US 2019/0338377 A1 Nov. 7, 2019

Related U.S. Application Data

(60) Provisional application No. 62/665,777, filed on May 2, 2018.

(51) Int. Cl.
| | | |
|---|---|---|
| *C12N 1/20* | (2006.01) | |
| *C12N 9/02* | (2006.01) | |
| *C12N 9/14* | (2006.01) | |
| *C12N 15/52* | (2006.01) | |
| *C12N 15/68* | (2006.01) | |
| *C12P 7/16* | (2006.01) | |
| *C12R 1/38* | (2006.01) | |

(52) U.S. Cl.
CPC ........... *C12N 1/205* (2021.05); *C12N 9/0073* (2013.01); *C12N 9/14* (2013.01); *C12N 15/52* (2013.01); *C12N 15/68* (2013.01); *C12P 7/16* (2013.01); *C12R 2001/38* (2021.05); *C12Y 401/01031* (2013.01); *C12Y 401/01032* (2013.01); *C12Y 604/01001* (2013.01)

(58) Field of Classification Search
None
See application file for complete search history.

(56) References Cited

U.S. PATENT DOCUMENTS

| | | | |
|---|---|---|---|
| 3,957,876 A | 5/1976 | Rapoport et al. | |
| 4,554,101 A | 11/1985 | Hopp | |
| 6,207,217 B1 | 3/2001 | Peoples et al. | |
| 6,888,034 B1 | 5/2005 | Landray et al. | |
| 7,384,783 B2 | 6/2008 | Kunas et al. | |
| 8,603,518 B2 | 12/2013 | Boon et al. | |
| 8,809,027 B1 | 8/2014 | Lynch et al. | C12P 7/40 |
| 8,986,960 B2 | 3/2015 | Sichwart | |
| 9,221,737 B2 | 12/2015 | Valdez | |
| 9,580,733 B2 | 2/2017 | Botes et al. | C12P 13/02 |
| 9,637,764 B2 | 5/2017 | Botes et al. | |
| 9,650,653 B2 | 5/2017 | Pearlman et al. | |
| 9,862,973 B2 | 1/2018 | Botes et al. | C12P 5/007 |
| 9,920,339 B2 | 3/2018 | Kadi et al. | C12P 7/62 |
| 10,072,150 B2 | 9/2018 | Botes et al. | |
| 10,196,657 B2 | 2/2019 | Pearlman et al. | |
| 10,577,634 B2 | 3/2020 | Pearlman et al. | |
| 2002/0192786 A1 | 12/2002 | Yamada et al. | |
| 2005/0181499 A1 | 8/2005 | Brahmbhatt | |
| 2007/0264688 A1 | 11/2007 | Venter et al. | |
| 2007/0269862 A1 | 11/2007 | Glass et al. | |
| 2010/0120104 A1 | 5/2010 | Reed | |
| 2010/0167371 A1 | 7/2010 | Chotani et al. | |
| 2011/0125118 A1 | 5/2011 | Lynch | |
| 2011/0171702 A1 | 7/2011 | Reinecke et al. | |
| 2012/0003706 A1 | 1/2012 | Hickey | |
| 2012/0064622 A1 | 3/2012 | Fischer et al. | |
| 2012/0295334 A1 | 11/2012 | Brahmbhatt | |
| 2013/0034884 A1* | 2/2013 | Burgard | C12P 7/42 435/126 |
| 2013/0065285 A1 | 3/2013 | Sefton | |
| 2013/0177957 A1 | 7/2013 | Du et al. | |
| 2013/0189763 A1 | 7/2013 | Dalla-Betta et al. | |
| 2013/0323714 A1 | 12/2013 | Cheng et al. | |
| 2014/0248687 A1 | 9/2014 | Kelly et al. | |
| 2014/0330398 A1 | 11/2014 | Fan et al. | |
| 2015/0132815 A1 | 5/2015 | Hickey | |
| 2015/0315599 A1 | 11/2015 | Shetty et al. | |

(Continued)

FOREIGN PATENT DOCUMENTS

| | | |
|---|---|---|
| CN | 1735691 A | 2/2006 |
| CN | 102459579 A | 5/2012 |

(Continued)

OTHER PUBLICATIONS

Sinqh RK et al. Protein Engineering Approaches in the Post-Genomic Era. 2017. Current Protein and Peptide Science. 18, 1-11. (Year: 2017).*
Zhang M etal. Propagated Perturbations from a Peripheral Mutation Show Interactions Supporting WW Domain Thermostablity. 2018. Structure. 26, 1474-1485. (Year: 2018).*
Kizer L et al. Application of Functional Genomics to Pathway Optimization for Increased Isoprenoid Production. Applied and Environmental Microbiology. 2008. vol. 74, No. 10. p. 3229-3241. (Year: 2008).*

(Continued)

*Primary Examiner* — Paul J Holland

(57) ABSTRACT

Methods of redirecting carbon flux and increasing C2/C3 or a C4/5/6 carbon chain length carbon-based chemical product yield in an organism, nonnaturally occurring organisms with redirected carbon flux and increased C2/C3 or C4/5/6 carbon chain length carbon-based chemical product yield and methods for using these organisms in production of C2/C3 or C4/5/6 carbon chain length carbon-based chemical products are provided.

6 Claims, 1 Drawing Sheet
Specification includes a Sequence Listing.

(56) References Cited

U.S. PATENT DOCUMENTS

| | | | |
|---|---|---|---|
| 2016/0176813 A1 | 6/2016 | Valdez | |
| 2016/0222420 A1* | 8/2016 | Botes | C12N 9/88 |
| 2017/0107474 A1 | 4/2017 | Farmer et al. | |
| 2017/0159082 A1 | 6/2017 | Conradie et al. | |
| 2017/0218406 A1 | 8/2017 | Conradie et al. | |
| 2018/0023088 A1 | 1/2018 | Van Eck Conradie et al. | |
| 2018/0023103 A1 | 1/2018 | Foster et al. | |
| 2018/0023104 A1 | 1/2018 | Cartman et al. | |
| 2018/0100160 A1 | 4/2018 | Bawdon et al. | C12N 15/74 |
| 2019/0124947 A1 | 5/2019 | Pearlman et al. | |
| 2019/0300838 A1 | 10/2019 | Smith et al. | |
| 2019/0300839 A1 | 10/2019 | Smith et al. | |
| 2019/0316072 A1 | 10/2019 | Smith et al. | |
| 2019/0338320 A1 | 11/2019 | Foster et al. | |

FOREIGN PATENT DOCUMENTS

| | | |
|---|---|---|
| CN | 106795537 A | 5/2017 |
| CN | 107849300 A | 3/2018 |
| EP | 0995490 A2 | 4/2000 |
| EP | 1728853 A1 | 12/2006 |
| EP | 1938892 A1 | 7/2008 |
| EP | 3399015 A1 | 11/2018 |
| JP | S49124358 A | 11/1974 |
| JP | H03127983 A | 5/1991 |
| JP | 2007185133 A | 7/2007 |
| JP | 2009225662 A | 10/2009 |
| JP | 2013179909 A | 9/2013 |
| RU | 2644344 C1 | 2/2018 |
| WO | 2008094282 A1 | 8/2008 |
| WO | 2010003007 A2 | 1/2010 |
| WO | 2010069313 A2 | 6/2010 |
| WO | 2013090769 A2 | 6/2013 |
| WO | 2013152051 A2 | 10/2013 |
| WO | 2013186340 A1 | 12/2013 |
| WO | 2014093505 A2 | 6/2014 |
| WO | 2014105793 A1 | 7/2014 |
| WO | 2014105797 A2 | 7/2014 |
| WO | 2017115855 A1 | 7/2014 |
| WO | 2015032375 A1 | 3/2015 |
| WO | 2015117019 | 8/2015 |
| WO | 2015149147 A1 | 10/2015 |
| WO | 2015195654 A1 | 12/2015 |
| WO | 2017165244 A1 | 9/2017 |
| WO | 2018005770 | 1/2018 |
| WO | 2018022595 A1 | 2/2018 |
| WO | 2018022633 A1 | 2/2018 |
| WO | 2018106549 A1 | 6/2018 |
| WO | 2019191761 A1 | 10/2019 |
| WO | 2019191763 A1 | 10/2019 |
| WO | 2019191767 A1 | 10/2019 |
| WO | 2019191770 A1 | 10/2019 |
| WO | 2019191772 A1 | 10/2019 |
| WO | 2019213108 A1 | 11/2019 |
| WO | 2019213118 A1 | 11/2019 |

OTHER PUBLICATIONS

Prather KLJ et al. De novo biosynthetic pathways: Rational design of microbial chemical factories. Current Opinion in Biotechnology. 2008. 19:468-474 (Year: 2008).*

Inui M et al. Metabolic Engineering of Corynebacterium glutamicum for Fuel Ethanol Production under Oxygen Deprivation Conditions. 2004. J. Mol. Microbiol. Biotechnol. 8:243-254. (Year: 2004).*

GenBank Q0K7M4. 2006. GenBank. p. 1 (Year: 2006).*

GenBank Q0K5F4. 2006. GenBank. p. 1 (Year: 2006).*

GenBank Q0KC80. 2006. GenBank. p. 1 (Year: 2006).*

GenBank Q2Z1A9. 2006. GenBank. p. 1 (Year: 2006).*

Ogawa T et al. Role of Phosphoenolpyruvate in the NADP-Isocitrate Dehydrogenase and Isocitrate Lyase Reaction in *Escherichia coli*. 2007. Journal of Bacteriology. vol. 189, No. 3. p. 1176-1178. (Year: 2007).*

GenBank A6VKV4, GenBank, 2012; p. 1-4.*

GenBank Q474V2, GenBank, 2006; p. 1-2.*

GenBank Q46WX6, GenBank, 2006; p. 1-2.*

GenBank Q0K4C1, GenBank, 2006; p. 1.*

GenBank Q0K790, GenBank, 2006; p. 1.*

GenBank CAQ69169.1. 2015. p. 1-2. (Year: 2015).*

GenBank Q8XWW2.1. 2015. p. 1-2 (Year: 2015).*

Non-final office action received for U.S. Appl. No. 16/399,145, dated Aug. 12, 2020, 16 pages.

Winnen, B., et al., "The tripartite tricarboxylate transporter (TTT) family" Res. Microbial., 2003, vol. 154, Issue 7, pp. 457-465.

Kazakov, A.E., et al., "Comparative genomics of regulation of fatty acid and branched-chain amino acid utilization in proteobacteria", Journal of Bacteriology, 2009, vol. 191, pp. 52-64.

Kluge, J., et al., "Inducible promoters and functional genomic approaches for the genetic engineering of filamentous fungi", Applied Microbiology and Iotechnology, vol. 102, Jun. 2, 2018 (Jun. 2, 2018), pp. 6357-6372.

Koller et al., "Potential and Prospects of Continuous Polyhydroxyalkanoate (PHA) Production", Bioengineering,May 29, 2015, pp. 94-121.

Koller, M., "A review on established and emerging fermentation schemes for microbial production of polyhydroxyalkanoate (PHA) biopolyesters", Fermentation, vol. 4, Apr. 23, 2018 (Apr. 23, 2018), pp. 1-30.

Koller, M., et al., "Continuous production mode as a viable process-engineering tool for efficient poly (hydroxyalkanoate) (PHA) bio-production", Chemical and Biochemical Product Engineering, vol. 28, Issue 1, 2014, pp. 65-77.

Krausse et al., "Essential role of the hprK gene inRalstonia eutropha HI6", J Mol Microbiol Biotechnol, 2009, vol. 17, pp. 146-152.

Kunasundari et al., "Revisiting the Single Cell Protein Application of Cupriavidus Necator H16 and Recovering Bioplastic Granules Simultaneously", Plos One, vol. 8, No. 10, Oct. 2013, 15 pages.

Lardi, M., et al., "o54-Dependent Response to Nitrogen Limitation and Virulence in Burkholderia cenocepacia Strain H111" Appl. Environ. Microbiol., 2015, vol. 81, Issue 12, pp. 4077-4089.

Lee, J.N., et al., "Metabolic Engineering of Pentose Phosphate Pathway in Ralsonia eutropha for Enhanced Biosynthesis of Poly--hydroxybutyrate", Biotechnology Progress, 2003, vol. 19, Issue 5, pp. 1444-1449.

Lee, et al., "Regulation of poly--hydroxybutyrate biosynthesis by nicotinamide nucleotide in Alcaligene eutrophus" FEMS Microbiological letters, 1995, vol. 131, pp. 35-39.

Lee, et al., "Microbial Production of Ethanol from Acetate by Engineered Ralstonia Eutropha", Biotechnology and Bioprocess Engineering, vol. 21, 2016, pp. 402-407.

Leyn et al., "Control of proteobacterial centralcarbon metabolism by the HexR transcriptionalregulator: a case study in Shewanella oneidensis", Journal of Biological Chemistry, 2011, vol. 286, Issue 41, pp. 35782-35794.

Leyn, S.A., et al. "Comparative genomics and evolution of transcriptional regulons in Proteobacteria", Microbial Genomics, 2016, pp. 1-15.

Li, Z.J., et al., "Overexpression of NAD kinase in recombinant *Escherichia coli* harboring the phbCAB operon improves poly(3-hydroxybutyrate) production", Appl Microbial Biotechnol., 2009, vol. 83, Issue 5, pp. 939-947.

Liu, X., et al., "Comparative analysis of genes frequently regulated by drugs based on connectivity map transcriptome data" PLoS One, 2017, vol. 12, Issue 6, e0179037.

Marc, J., et al., "Over expression of GroESL in Cupriavidus necator for heterotrophic and autotrophic isopropanol production", Metabolic Engineering, vol. 42, 2017, pp. 74-84.

Martin, Koller, et al., "Continuous production mode as a viable process-engineering tool for efficient poly (hydroxyalkanoate) (PHA) bio-production", Chemical And Biochemical Engineering Quarterly, vol. 28, XP002792820 ,2014, pp. 65-77.

McKinlay, J.B., et al., "Carbon dioxide fixation as a central redox cofactor recycling mechanism in bacteria" PNAS, 2010, vol. 107, Issue 26, pp. 11669-11675.

(56) References Cited

OTHER PUBLICATIONS

Montiel-Jarillo, G., et al., "Enrichment of a mixed microbial culture for polyhydroxyalkanoates production: Effect of pH and N and P concentrations", Science of the Total Environment, vol. 583, 2017, pp. 300-307.

Nguyen, C., et al., "Trapping the dynamic acyl carrier protein in fatty acid biosynthesis", Nature, vol. 505, No. 7483 ,Dec. 22, 2013, pp. 427-431.

Obruca, S., et al. "Application of random mutagenesis to enhance the production of polyhydroxyalkanoates by Cupriavidus necator H16 on waste frying oil", World J Microbiol Biotechnol, 2013, vol. 29, pp. 2417-2428.

Olaya-Abril et al., "Poly(3-hydroxybutyrate) hyperproduction by a global nitrogen regulator NtrB mutant strain of Paracoccus denitrificans PD1222", FEMS Microbiology Letters, 2008, vol. 365:fnx251, pp. 8.

Orita, L., et al., "Identification of mutation points in Cupriavidus necator NCIMB 11599 and genetic reconstitution of glucose-utilization ability in wild strain H16 for polyhydroxyalkanoate production" Journal of Bioscience and Bioengineering, 2012, vol. 113, Issue 1, pp. 63-69.

Persuhn, D.C., et al. "The transcriptional activator NtrC controls the expression and activity of glutamine synthetase in Herbaspirillum seropedicae" FEMS Microbiology Letters, 2000, vol. 192, pp. 217-221.

Pohlmann, A., et al., "Genome sequence of the bioplastic-producing "Knallgas" bacterium Ralsonia eutropha HI6" Nature Biotechnology, 2007, vol. 24, No. 10, pp. 1257-1262.

Pryzbylski, D., et al., "Synthesis of the building block 2-hydroxyisobutyrate from fructose and butyrate by Cupriavidus necator HI6", Appl. Microbial. Biotechnol., 2013, vol. 97, 20, pp. 8875-8885.

Qi et al., "Model-driven redox pathway manipulation for improved isobutanol production in Bacillus subtilis complemented with experimental validation and metabolic profiling analysis" PLoS One, 2014, vol. 9, Issue 4, :e93815, pp. 1-11.

Raberg, M., "Ralstoni a eutropha H16 in progress: applications beside PHAs and establishment as production platform by advanced genetic tools", Critical Reviews in Biotechnology, vol. 38, Dec. 12, 2017 (Dec. 12, 2017), pp. 494-510.

Rosa, L.T., et al., "Tripartite ATP-Independent Periplasmic (TRAP) Transporters and Tripartite Tricarboxylate Transporters (TTT): From Uptake to Pathogenicity", Frontiers in Microbiology, 2018, vol. 8, pp. 16.

Sacamboio, E.N.M., et al. "The transcriptional regulator NtrC controls glucose-6-phosphate dehydrogenase expression and polyhydroxybutyrate synthesis through NADPH availability in Herbaspirillum seropedicae" Scientific Reports, 2017, vol. 7, Article No. 13546, pp. 1-12.

Sanchez, A.M., et al., "Effect of overexpression of a soluble pyridine nucleotide transhydrogenase (UdhA) on the production of poly(3-hydroxybutyrate) in *Escherichia coli*" Biotechnol Prog., 2006, vol. 22, Issue 2, pp. 420-425.

Schramke, h., et al., "Revisiting Regulation of Potassium Homeostasis in *Escherichia coli*: The Connection to Phosphate Limitation", Wiley Microbiologyopen, vol. 6, No. 3, 2017, pp. 1-16.

Sekar, B.S., et al., "Co-production of hydrogen and ethanol from glucose in *Escherichia coli* by activation of pentose-phosphate pathway through deletion of phosphoglucose somerase (pgi) and overexpression of glucose-6-phosphate dehydrogenase (zwf) and 6-phosphogluconate dehydrogenase ( gnd)", Biotechnology for Biofuels, 2017, vol. 10, 85, pp. 12.

Shang et al., "Poly(3-hydroxybutyrate) Synthesis in Fed-batch Culture of Ralstonia Eutropha with Phosphate Limitation Under Different Glucose Concentrations", Biotechnology Letters, vol. 25, Issue 17, 2003, pp. 1415-1419.

Shively, J.M., et al., "Something From Almost Nothing: Carbon Dioxide Fixation In Chemoautotrophs", Annu. Rev. Microbiol., vol. 52, 1998, pp. 191-230.

Silva, F., et al., "Impact of nitrogen feeding regulation on polyhydroxyalkanoates production by mixed microbial cultures", New Biotechnology, vol. 37, 2017, pp. 90-98.

Steinbuchel, A., et al., "A multifunctional fermentative alcohol dehydrogenase from the strict aerobe Alcaligenes eutrophus: purification and properties" Eur J Biochem, 1984, vol. 141, Issue 3, pp. 555-564.

Stokke, R., et al., "Biochemical characterization of isocitrate dehydrogenase from Methylococcus capsulatus reveals a unique NAD+-dependent homotetrameric enzyme" Arch Microbiol., 2007, vol. 187, Issue 5, pp. 361-370.

Sun, J., et al., "Involvement of glnB, glnZ, and glnD genes in the regulation of poly-3-hydroxybutyrate biosynthesis by ammonia in Azospirillum brasilense Sp7", Appl. Environ. Microbiol, 2002, vol. 68, Issue 2, pp. 985-988.

Sun, J., et al., "The ntrB and ntrC genes are involved in the regulation of poly-3-hydroxybutyrate biosynthesis by ammonia in Azospirillum brasilense Sp7", Appl. Environ. Microbiol., 2000, vol. 66, Issue 1, pp. 113-117.

Tanaka, K, et al., Production Of Poly (D-3-Hydroxybutyrate) From CO2, H2, And O2 By High Cell Density Autotropic Cultivation Of Alcaligenes Eutrophus Biotechnology And Bioengineering, Wiley, vol. 45, No. 3, (Feb. 5, 1995), XP000489583 ,Feb. 5, 1995, 268-275.

Valderrama, J.A., et al., "AccR is a master regulator involved in carbon catabolite repression of the anaerobic catabolism of aromatic compounds in *Azoarcus* sp. CIB" Journal of Biological Chemistry, 2014, vol. 289, Issue 4, pp. 1892-1904.

Vollbrecht, D., et al., "Excretion of Metabolites by hydrogen Bacteria III. D(-)-3-hydroxybutanoate", European J. Appl. Microbiol. Biotechnol., 1979, vol. 7, pp. 259-266.

Volodina, E., et al., "Characterization of propionate CoA-transferase from Ralstonia eutropha HI6", Appl Microbial Biotechnol., 2014, vol. 98, Issue 8, pp. 3579-3589.

Wang, F., et al., "Poly(3-Hydroxybutyrate) Production with High Productivity and High Polymer Content by a Fed-Bath Culture of Alcaligene lat us under Nitrogen Limitation", Applied and Environmental Microbiology, 1997, vol. 63, No. 9, pp. 3703-3706.

Wang, R., et al., "Isocitrate dehydrogenase from *Streptococcus mutans*: biochemical properties and evaluation of a butative phosphorylation site at Ser102" PLoS One, 2013, vol. 8, Issue 3, e58918.

Weiden et al., "Cation Transport in *Escherichia coli* Vii. Potassium Requirement for Phosphate Uptake", The Journal of General Physiology, vol. 50, No. 6, 1967, pp. 1641-1661.

Weinberg, Z., et al. "Identification of 22 candidate structured RNAs in bacteria using the Cmfinder comparative genomics pipeline" Nucleic Acids Research, 2007, vol. 35, pp. 4809-4819.

Wu, M-C., et al., "A Novel Type II NAD+-Specific Isocitrate Dehydrogenase from the Marine Bacterium Congregibacter litoralis KT71" PLoS One., 2015, vol. 10, Issue 5, pp. 1-17.

Youngquist et al., "Functional Genomics Analysis of Free Fatty Acid Production under Continuous PhosphateLimiting Conditions", J. Ind. Microbial. Biotechnol., vol. 44, May 2017, pp. 759-772.

Zhu, J., et al., "Factors for promoting polyhydroxyalkanoate (PHA) synthesis in bio-nutrient-removal and recovery system", 4th International Conference on nvironmental Systems Research (ICESR 2017) Conference paper, 2018, pp. 1-4.

Ziesack, M., et al., "Chimeric Fatty Acyl-Acyl Carrier Protein Thioesterases Provide Mechanistic Insight into Enzyme Specificity and Expression", Applied And Environmental Microbiology, vol. 84, No. 10 ,Mar. 16, 2018, pp. 12.

Alagesan et al. "$^{13}$C-assisted metabolic flux analysis to investigate heterotrophic and mixotrophic metabolism in *Cupriavidus necator* H16" Metabolomics 2018 14:9.

Brämer & Steinbüchel "The malate dehydrogenase of Ralstonia eutropha and functionality of the C(3) /C(4) metabolism in a Tn5-induced mdh mutant" FEMS Microbiol Lett. 2002 2;212(2):159-64.

Bruland et al. "Unravelling the C3/C4 carbon metabolism in Ralstonia eutropha H16" Journal of Applied Microbiology 2010 109:79-90.

Byrd et al. "Bacterial Control of Agromyces ramosus in soil" Can J Microbiol 1985 31:1157-1163.

(56) References Cited

OTHER PUBLICATIONS

Kim et al. "Effect of overexpression of Actinobacillus succinogenes phosphoenolpyruvate carboxykinase on succinate production in *Escherichia coli*" Applied and Environmental Microbiology 2004 70(2):1238-1241.
Lu et al. "Studies on the production of branched-chain alcohols in engineered Ralstonia eutropha" Appl Microbiol Biotechnol 2012 96:283-297.
Makkar, N.S. & Casida, L.E. "*Cupriavidus necator* gen. nov., sp. nov.: a Nonobligate Bacterial Predator of Bacteria in Soil" Int. J. of Systematic Bacteriology 1987 37(4): 323-326.
March et al. "Expression of an anaplerotic enzyme, pyruvate carboxylase, improves recombinant protein production in *Escherichia coli*" Applied and Environmental Microbiology 2002 68(11): 5620-5624.
Meng et al. "High-yield anaerobic succinate production by strategically regulating multiple metabolic pathways based on stoichiometric maximum in *Escherichia coli*" Microbial Cell Factories 2016 15:141.
Papagianni, M. "Recent advances in engineering the central carbon metabolism of industrially important bacteria" Microbial Cell Factories 2012 11:50.
Park and Lee "Metabolic Characteristics of Isocitrate Dehydrogenase Leaky Mutant of Alcaligene eutrophus and Its Utilization for Poly-β-Hydroxybutyrate Production" Journal of Fermentation and Bioengineering 1996 81(3):197-205.
Park et al. "Oxaloacetate and malate production in engineered *Escherichia coli* by expression of codon-optimized phosphoenolpyruvate carboxylase2 gene from Dunaliella salina" Bioprocess Biosyst Eng. 2013 36(1):127-31.
Raberg et al. "A closer look on the polyhydroxybutyrate-(PHB-) negative phenotype of Ralstonia eutropha PHB-4" PLoS One 2014 9(5):e95907.
Russell, J.B. "The energy spilling reactions of bacteria and other organisms" J Mol Microbiol Biotechnol. 2007 13(1-3):1-11.
Sauer & Eikmanns "The PEP-pyruvate-oxaloacetate node as the switch point for carbon flux distribution in bacteria" FEMS Microbiology Reviews 2005 29(4):765-794.
Schlegel & Vollbrecht "Formation of the Dehyroganses for Lactate, Ethanol and Butanediol in the Strictly Aerobi Bacterium Alcaligene eutrophus" Microbiology 1980 117:475-481.
Schobert & Bowien "Unusual C3 and C4 metabolism in the chemoautotroph Alcaligenes eutrophus" J Bacteriol. 1984 159(1):167-172.
Schwartz et al. "A proteomic view of the facultatively chemolithoautotrophic lifestyle of Ralstonia eutropha H16" Proteomics 2009 9(22):5132-5142.
Segura & Espin "Inactivation of pycA, encoding pyruvate carboxylase activity, increases poly-beta-hydroxybutyrate accumulation in Azotobacter vinelandii on solid medium" Appl Microbiol Biotechnol. 2004 65(4):414-8.
Sillman, C. E. & Casida, L. E. "Isolation of nonobligate bacterial predators of bacteria from soil" Can J Microbiol 1986 32:760-762.
Tan et al. "Activating phosphoenolpyruvate carboxylase and phosphoenolpyruvate carboxykinase in combination for improvement of succinate production" Appl. Environ. Microbiol. 2013 79(16):4838-4844.
Vemuri et al. "Physiological response of central metabolism in *Escherichia coli* to deletion of pyruvate oxidase and introduction of heterologous pyruvate carboxylase" Biotechnology and Bioengineering 2005 90(1):64-76.
Vollbrecht and Schlegel "Excretion of Metabolites by Hydrogen Bacteria I. Autotrophic and Heterotrophic Fermentations" European Journal of Applied Microbiology and Biotechnology 1978 6(2):145-155.
Vollbrecht and Schlegel "Excretion of Metabolites by Hydrogen Bacteria II. Influence of Aeration, pH, Temperature, and Age of Cells" European Journal of Applied Microbiology and Biotechnology 1978 6(2):157-166.
Vollbrecht and Schlegel "Excretion of Metabolites by Hydrogen Bacteria IV. Respiration Rate-Dependent Formation of Primary Metabolites and of Poly-3-hydroxybutanoate" European Journal of Applied Microbiology and Biotechnology 1979 7(3):267-276.
Zeph, L.E. & Casida, L.E. "Gram-negative versus gram-positive (actinomycete) nonobligate bacterial predators of bacteria in soil" Applied and Environmental Microbiology 1986 52(4):819-823.
Invitation to Pay Additional Fees and, Where Applicable, Protest Fee in PCT/US2019/029827 dated Jul. 23, 2019.
Alagesan, S., et al., "Functional genetic elements for controlling gene expression in Cupriavidus necator H16", Applied and Environmental Microbiology, vol. 84, Oct. 2018 (Oct. 2018), pp. 1-17.
Anderson, A.J., et al., "Occurrence, metabolism, metabolic role, and industrial uses of bacterial polyhydroxyalkanoates", Microbiology Review, 1990, vol. 54, pp. 450-472.
Atlic et al., "Continuous Production of Poly([R]-3-Hydroxybutyrate) by Cupriavidus Necator in a Multistage Bioreactor Cascade", Appl Microbial Biotechnology, vol. 91, 2011, pp. 295-304.
Brandt, U., et al., "Elevated poly(3-hydroxybutyrate) synthesis in mutants of Ralstonia eutropha HI6 defective in lipopolysaccharide biosynthesis" Applied Microbiology and Biotechnology, 2012, vol. 95, pp. 471-483.
Brigham, C.J., et al., "Correction for Whole-genome microarray and gene deletion studies reveal regulation of the polyhydroxyalkanoate production cycle by the stringent response in Ralstonia eutropha H16", Appl Environ Microbiol., 2017, vol. 83, Issue 15, pp. 1-2.
Brigham, C.J., et al., "Whole-genome microarray and gene deletion studies reveal regulation of the polyhydroxyalkanoate production cycle by the stringent response in Ralstonia eutropha HI6", Appl Environ Microbial., 2012, vol. 78, Issue 22, pp. 8033-8044.
Brown, D.R., et al., "Nitrogen stress response and stringent response are coupled in *Escherichia coli*", Nature Communications, 2014, vol. 5, 4115, pp. 8.
Chae, T.U., et al., "Metabolic engineering of *Escherichia coli* for the production of four-, five- and six-carbon lactams Metabolic Engineering", Academic Press, Us, vol. 41 ,Apr. 5, 2017, pp. 82-91.
Chakravarty, J., et al., "Solvent production by engineered Ralstonia eutropha: channeling carbon to biofuel", Applied Microbiology and Biotechnology, vol. 102, Apr. 29, 2018 (Apr. 29, 2018), pp. 5021-5031.
Chen, R., et al., "A highly active decarboxylating dehydrogenase with rationally inverted coenzyme specificity", PNAS, 1996, vol. 92, Issue 25, pp. 11666-11670.
Chen, R., et al. "Redesigning secondary structure to invert coenzyme specificity in isopropylmalate dehyrogenase" PNAS, 1996, vol. 93, pp. 12171-12176.
Choi, J.C., et al. "Modulation of 3-hydroxyvalerate molar fraction in poly(3-hydroxybutyrate-3-hydroxyvalerate) using Ralstonia eutropha transformant co-amplifying phbC and NADPH generation-related zwf genes", Enzyme and Microbial Technology, 2003, vol. 32, Issue 1, pp. 178-185.
Cramm, R. J. "Genomic view of energy metabolism in Ralstonia eutropha HI6", Journal of Molecular Microbiology and Biotechnology, 2009, vol. 16, pp. 38-52.
Darani, K.K., et al., "Simulation of bioreactors for poly(3-hydroxybutyrate) production from natural gas", Iranian Journal of Chemistry and Chemical Engineering, vol. 39, 2018, pp. 1-24.
Ding, H., et al., "Glycerol utilization by Rhizobium leguminosarum requires an ABC transporter and affects competition for nodulation", Microbiology, 2012, vol. 158, pp. 1369-1378.
Doberstein, C., et al., "Polythioester synthesis in Ralstonia eutropha H16: novel insights into 3,3'-thiodipropionic acid and 3,3'-dithiodipropionic acid catabolism" Journal of Biotechnology, 2014, vol. 184, pp. 187-198.
Du et al., "Effects of Environmental Conditions on Cell Growth and Poly-B-Hydroxybutyrate Accumulation in Alcaligenes Eutrophus", World Journal of Microbiology & Biotechnology, vol. 16, 2000, pp. 9-13.
Eggers et al., "Impact of Ralstonia Eutropha's Poly(3-Hydroxybutyrate) (PHB) Depolymerases and Phasins on PHB Storage in Recombinant *Escherichia Coli*", Applied and Environmental Microbiology, vol. 80, No. 24,Dec. 2014, pp. 7702-7709.

(56) References Cited

OTHER PUBLICATIONS

Frng, Y., et al., "Tuning of acyl-ACP thioesterase activity directed for tailored fatty acid synthesis", Applied Microbiology And Biotechnology, Springer, De, vol. 102, No. 7 ,Feb. 22, 2018, pp. 3173-3182.
Gao, C., et al. "Lactate utilization is regulated by the FadR-type regulator LldR in Pseudomonas aeruginosa", Journal of Bacteriology, 2012, vol. 194, pp. 2687-2692.
Girdhar, A., et al., "Process Parameters for Influencing Polyhyroxyalkanoate Producing Bacterial Factories: An Overview", Petroleum & Environmental Biotechnology, 2013, vol. 4, Issue 5, pp. 9.
Grousseau, E., et al., "Isopropanol production with engineered Cupriavidus necator as bioproduction platform" Appl Microbiol Biotechnol, 2014, vol. 98, pp. 4277-4290.
Gyaneshwar et al., "Sulfur and Nitrogen Limitation in *Escherichia coli* K-12: Specific Homeostatic Responses", Journal of Bacteriology, vol. 187, No. 3, Feb. 2005, pp. 1074-1090.
Hanko, E.K.R., et al., "Characterisation of a 3-hydroxypropionic acid-inducible system from Pseudomonas putida for orthogonal gene expression control in *Escherichia coli* and Cupriavidus necator", Scientific Reports, vol. 7, 2017, pp. 1-12.
Hauryliuk, V., et al. "Recent functional insights into the role of (p)ppGpp in bacterial physiology", Nature Reviews Microbiology, 2015, vol. 13, pp. 298-309.
Haushalter, R.W., et al., "Production of Odd-Carbon Dicarboxylic Acids in *Escherichia coli* Using an Engineered Biotin-Fatty Acid Biosynthetic Pathway" Journal Of The American Chemical Society, vol. 139, No. 13 ,Mar. 21, 2017, pp. 4615-4618.
Horvat et al., "Mathematical Modelling and Process Optimization of a Continuous 5-Stage Bioreactor Cascade for11 Production of Poly[-(R)-3-Hydroxybutyrate] by Cupriavidus Necator", Bioprocess Biosyst Eng, vol. 36, 2013, pp. 1235-1250.
Hun-Suk Song et al: Enhanced isobutanolproduction from acetate by combinatorialoverexpression of acetyl-CoA synthetaseand anaplerotic enzymes in engineered*Escherichia coli*, Biotechnology and Bioengineering,vol. 115, May 2, 2018 (May 2, 2018), pp. 1971-1978.
Lenczak, J.L., et al., "High cell density strategy for poly(3-hydroxybutyrate) production by Cupriavidus necator", Brazilian Journal of Chemical Engineering, 2011, vol. 28, Issue 4, pp. 585-596.
Inoue, H., et al., "Biochemical and molecular characterization of the NAD(+)-dependent isocitrate dehydrogenase from the chemolithotrophAcidithiobacillus thiooxidans", FEMS Microbial Letters, 2002, vol. 214, Issue 1, pp. 127-132.
International Search Report and Written Opinion for International Application Serial No. PCT/US2019/025189, dated Jul. 2, 2019, pp. 12.
International Search Report and Written Opinion for International Application Serial No. PCT/US2019/025194, dated Aug. 22, 2019, pp. 24.
International Search Report and Written Opinion for International Application Serial No. PCT/US2019/025202, dated Jul. 30, 2019, pp. 15.
International Search Report and Written Opinion for International Application Serial No. PCT/US2019/025211, dated Jul. 29, 2019, pp. 16.
International Search Report and Written Opinion for International Application Serial No. PCT/US2019/025218, dated Sep. 5, 2019, pp. 17.
International Search Report and Written Opinion for International Application Serial No. PCT/US2019/029973 dated Jul. 23, 2019, dated Jul. 23, 2019, 5 pgs.
International Search Report and Written Opinion in PCT/US2019/029795 dated Jul. 11, 2019, pp. 10.
International Search Report and Written Opinion in PCT/US2019/029798 dated Sep. 12, 2019, pp. 19.
International Search Report and Written Opinion in PCT/US2019/029817 dated Sep. 23, 2019.
International Search Report and Written Opinion in PCT/US2019/029827 dated Sep. 23, 2019.
International Search Report and Written Opinion in PCT/US2019/029956 dated Aug. 13, 2019.
Invitation to Pay Additional Fees and, Where Applicable, Protest Fee in PCT/082019/029798 dated Jul. 22, 2019.
Invitation to Pay Additional Fees and, WhereApplicable, Protest Fee in PCT/US2019/029817 dated Aug. 1, 2019.
Jhonson, A., et al., "An engineered constitutive promoter set with broad activity range for Cupriavidus necator H16", ACS Synthetic Biology, vol. 7, Jun. 27, 2018 (Jun. 27, 2018), pp. 1918-1928.
Joris, Beld, et al., "Evolution of acyl-ACP thioesterases and [beta]-ketoacyl-ACP synthases revealed by protein-protein Interactions", Journal Of Applied Phycology, vol. 26, No. 4 ,Nov. 22, 2013, pp. 1619-1629.
Juengert, J.R, et al., "Absence of ppGpp Leads to Increased Mobilization of Intermediately Accumulated Poly(3- Hydroxybutyrate) in Ralstonia eutropha HI6" Applied and Environmental Microbiology, 2017, vol. 83, Issue 13, pp. e00755-17.
Justyna Mozejko-Ciesielska et al: "Bacterial polyhydroxyalkanoates: Still fabulous ?", Microbiological Research, vol. 192, 2016, pp. 271-282.
Kaddor, C., et al., "Effects of homologous phosphoenolpyruvate-carbohydrate phosphotransf erase system proteins on carbohydrate uptake and poly(3-ydroxybutyrate) accumulation in Ralstonia eutropha HI6", Appl. Environ. Microbiol., 2011, vol. 77, pp. 3582-3590.
Kaddor, C., et al., "Implications of various phosphoenolpyruvate-carbohydrate phosphotransf erase system mutations on glycerol utilization and poly(3-hydroxybutyrate) accumulation in Ralstonia eutropha H16", AMB Express, 2011, vol. 1, pp. 16.
Karstens, K., et al., "Phosphotransferase protein EIIANtr interacts with SpoT, a key enzyme of the stringent response, in Ralstonia eutropha HI6", Microbiology, 2014, vol. 160, pp. 711-722.
Devos et al., "Practical Limits of Function Prediction", Proteins: Structure, Function and Genetics, vol. 41, pp. 98-107 (2000).
International Preliminary Report on Patentability in PCT/US2019/029817 dated Nov. 3, 2020, 14 pages.
International Preliminary Report on Patentability in PCT/US2019/029795, dated Nov. 3, 2020, 7 pages.
International Preliminary Report on Patentability in PCT/US2019/029798 dated Nov. 3, 2020, 13 pages.
Kisselev, "Polypeptide Release Factors in Prokaryotes and Eukaryotes: Same Function, Different Structure", Structure, vol. 10, pp. 8-9 (2002).
Non-Final office action received for U.S. Appl. No. 16/398,384, dated Oct. 23, 2020, 13 pages.
Whisstock et al., "Prediction of protein function from protein sequence and structure", Quarterly Reviews of BioPhysics, vol. 36, Issue 3, pp. 307-340 (2003).
Witkowski et al., "Conversion of B-Ketoacyl Synthase to a Malonyl Decarboxylase by Replacement of the Active- Site Cysteine with Glutamine", Biochemistry, vol. 38, pp. 11643-11650 (1999).
International Preliminary Report on Patentability in PCT/US2019/029827 dated Nov. 3, 2020.
Non-final Office Action received for U.S. Appl. No. 16/398,365, dated Jan. 25, 2021, 10 Pages.
Uniprot database, entry A0A0U2WHGO, Mar. 2016.
Cavalheiro et al., "Poly(3-hydroxybutyrate) production by Cupriavidus necator using waste glycerol", Process Biochemistry, vol. 44, pp. 509-515 (2009).
Final Office Action received for U.S. Appl. No. 16/398,351, dated Jul. 2, 2021, 24 Pages.
Final office action received for U.S. Appl. No. 16/398,351, dated Feb. 28, 2022, 11 pages.
KEGG Enzyme 1.6.1.1. Retrieved Feb. 22, 2022 (Year: 2022) pp. 1-2.
KEGG Enzyme 1.6.1.2. Retrieved Feb. 22, 2022 (Year: 2022) pp. 1-2.
KEGG Enzyme 7.1.1.1. Retrieved Feb. 22, 2022 (Year: 2022) pp. 1-2.
Office Action received for U.S. Appl. No. 16/398,351, dated Jul. 5, 2022, 12 Pages.

(56) References Cited

OTHER PUBLICATIONS

Non-Final office action for U.S. Appl. No. 16/399,145 dated Jul. 27, 2023, 29 pages.
PTO STIC search in GenEmbl run on Jun. 27, 2022, pp. 1-6.
"aminotransferase class III-fold pyridoxal phosphate-dependent enzyme [Aquitalea denitrificans]", NCBI Reference Sequence: WP_159877958.1, Jan. 19, 2020, 1 page.
"aminotransferase class III-fold pyridoxal phosphate-dependent enzyme [*Aquitalea* sp. LB_tupeE]", NCBI Reference Sequence: WP_178973970.1, Jul. 11, 2020, 1 page.
"aminotransferase class III-fold pyridoxal phosphate-dependent enzyme [Chromobacterium haemolyticum]", NCBI Reference Sequence: WP_166453011.1, Apr. 6, 2020, 1 page.
"aminotransferase class III-fold pyridoxal phosphate-dependent enzyme [Chromobacterium vaccinii]", NCBI Reference Sequence: WP_166440807.1, Apr. 6, 2020, 1 page.
Aminotransferase class III-fold pyridoxal phosphate-dependent enzyme [Crenobacter sedimenti], NCBI Reference Sequence: WP_163315775.1, Apr. 6, 2020, 1 page.
"aminotransferase class III-fold pyridoxal phosphate-dependent enzyme [Neisseriaceae bacterium B2N2-7]", GenBank: MXR37125.1, Jan. 6, 2020, 2 pages.
"aminotransferase class III-fold pyridoxal phosphate-dependent enzyme [Paludibacterium paludis]", NCBI Reference Sequence: WP_189532963.1, Sep. 28, 2020, 1 page.
"aminotransferase class III-fold pyridoxal phosphate-dependent enzyme [*Paludibacterium* sp. dN 18-1]", GenBank: MTD33855.1, Nov. 24, 2019, 1 page.
"aminotransferase class III-fold pyridoxal phosphate-dependent enzyme [Vogesella alkaliphila]", NCBI Reference Sequence: WP_189374996.1, Sep. 28, 2020, 1 page.
"aminotransferase class III-fold pyridoxal phosphate-dependent enzyme [Vogesella fluminis]", NCBI Reference Sequence: WP_189352298.1, Sep. 28, 2020, 1 page.
"aminotransferase class III-fold pyridoxal phosphate-dependent enzyme [Vogesella oryzae]", NCBI Reference Sequence: WP_174874069.1, Jun. 22, 2020, 1 page.
"aspartate aminotransferase family protein [Aquitalea magnusonii]", NCBI Reference Sequence: WP_059287319.1, Dec. 31, 2020. 1 page.
"aspartate aminotransferase family protein [Aquitalea magnusonii]", NCBI Reference Sequence: WP_089085350.1, Jul. 15, 2017, 1 page.
"aspartate aminotransferase family protein [*Aquitalea* sp. FJL05]", NCBI Reference Sequence: WP_124643387.1, Apr. 12, 2019, 1 page.
"aspartate aminotransferase family protein [*Aquitalea* sp. THG-DN7.12]", NCBI Reference Sequence: WP_137009623.1, Oct. 16, 2019, 1 page.
"aspartate aminotransferase family protein [Chromobacterium amazonense]", NCBI Reference Sequence: WP_106076402.1, Mar. 16, 2018, 1 page.
"aspartate aminotransferase family protein [Chromobacterium haemolyticum]", GenBank: OQS32233.1, Apr. 6, 2017, 2 pages.
"aspartate aminotransferase family protein [Chromobacterium haemolyticum]", GenBank: OQS37730.1, Apr. 6, 2017, 2 pages.
"aspartate aminotransferase family protein [Chromobacterium haemolyticum]", NCBI Reference Sequence: WP_043593957.1, Apr. 15, 2016, 1 page.
"aspartate aminotransferase family protein [Chromobacterium haemolyticum]", NCBI Reference Sequence: WP_081556739.1, Apr. 8, 2017, 1 page.
"aspartate aminotransferase family protein [Chromobacterium haemolyticum]", NCBI Reference Sequence: WP_081576047.1, Apr. 8, 2017, 1 page.
"aspartate aminotransferase family protein [Chromobacterium haemolyticum]", NCBI Reference Sequence: WP_161523523.1, Oct. 5, 2020, 1 page.
"aspartate aminotransferase family protein [Chromobacterium paludis]", NCBI Reference Sequence: WP_149295777.1, Oct. 5, 2020, 1 page.
"aspartate aminotransferase family protein [Chromobacterium phragmitis]", NCBI Reference Sequence: WP_114062556.1, Dec. 20, 2020.
"aspartate aminotransferase family protein [*Chromobacterium* sp. ATCC 53434]", NCBI Reference Sequence: WP_101708025.1, Jan. 10, 2018.
"aspartate aminotransferase family protein [*Chromobacterium* sp. LK11]", NCBI Reference Sequence: WP_048412320.1, Apr. 15, 2016, 1 page.
"aspartate aminotransferase family protein [*Chromobacterium* sp. LK1]", NCBI Reference Sequence: WP_048411976.1, Apr. 15, 2016, 1 page.
"aspartate aminotransferase family protein [*Chromobacterium* sp. MWU13-2610]", NCBI Reference Sequence: WP_103321487.1, Jan. 31, 2018, 1 page.
"aspartate aminotransferase family protein [*Chromobacterium* sp. MWU14-2602]", NCBI Reference Sequence: WP_103903523.1, Feb. 10, 2018, 1 page.
"aspartate aminotransferase family protein [*Chromobacterium* sp. Panama]", NCBI Reference Sequence: WP_107799474.1, Apr. 25, 2018, 1 page.
"aspartate aminotransferase family protein [Chromobacterium sphagni]", NCBI Reference Sequence: WP_071116856.1, Aug. 23, 2017, 1 page.
"aspartate aminotransferase family protein [Chromobacterium subtsugae]", NCBI Reference Sequence: WP_047237256.1, Mar. 20, 2018, 1 page.
"aspartate aminotransferase family protein [Chromobacterium subtsugae]", NCBI Reference Sequence: WP_047243213.1, Apr. 15, 2016, 1 page.
"aspartate aminotransferase family protein [Chromobacterium subtsugae]", NCBI Reference Sequence: WP_047257673.1, Apr. 15, 2016, 1 page.
"aspartate aminotransferase family protein [Chromobacterium vaccinii]", NCBI Reference Sequence: WP_046156378.1, Oct. 25, 2019, 1 page.
"aspartate aminotransferase family protein [Chromobacterium vaccinii]", NCBI Reference Sequence: WP_104946997.1, Mar. 4, 2018, 1 page.
"aspartate aminotransferase family protein [Chromobacterium violaceum]", NCBI Reference Sequence: WP_011135573.1, Jul. 28, 2019, 1 page.
"aspartate aminotransferase family protein [Chromobacterium violaceum]", NCBI Reference Sequence: WP_048405256.1, Apr. 15, 2016, 1 page.
"aspartate aminotransferase family protein [Chromobacterium violaceum]", NCBI Reference Sequence: WP_081573061.1, Apr. 8, 2017, 1 page.
"aspartate aminotransferase family protein [Chromobacterium violaceum]", NCBI Reference Sequence: WP_152637556.1, Oct. 31, 2019, 1 page.
"aspartate aminotransferase family protein [*Crenobacter* sp. GY 70310]", NCBI Reference Sequence: WP_136552942.1, Oct. 16, 2019, 1 page.
"aspartate aminotransferase family protein [Gulbenkiania indica]", NCBI Reference Sequence: WP_055434103.1, May 14, 2017, 1 page.
"aspartate aminotransferase family protein [Gulbenkiania mobilis]", NCBI Reference Sequence: WP_054286466.1, May 14, 2017, 1 page.
"aspartate aminotransferase family protein [Paludibacterium purpuratum]", NCBI Reference Sequence: WP_133682408.1, May 12, 2019, 1 page.
"aspartate aminotransferase family protein [Paludibacterium yongneupense]", NCBI Reference Sequence: WP_028535161.1, Apr. 15, 2016, 2 pages.
"aspartate aminotransferase family protein [Pseudogulbenkiania ferrooxidans]", NCBI Reference Sequence: WP_008952788.1, Apr. 15, 2016, 2 pages.
"aspartate aminotransferase family protein [Pseudogulbenkiania ferrooxidans]", NCBI Reference Sequence: WP_021478068.1, Apr. 15, 2016, 1 page.

(56) References Cited

OTHER PUBLICATIONS

"aspartate aminotransferase family protein [*Pseudogulbenkiania* sp. MAI-1]", NCBI Reference Sequence: WP_024302818.1, Apr. 15, 2016, 2 pages.
"aspartate aminotransferase family protein [*Pseudogulbenkiania* sp. NH8B]", NCBI Reference Sequence: WP_014087389.1, Apr. 15, 2016, 2 pages.
"aspartate aminotransferase family protein [Pseudogulbenkiania subflava]", NCBI Reference Sequence: WP_085275708.1, Apr. 22, 2017, 1 page.
"aspartate aminotransferase family protein [Rhodobacteraceae bacterium CH30]", GenBank: RQW28969.1, Dec. 2, 2018, 2 pages.
"aspartate aminotransferase family protein [Vogesella indigofera]", NCBI Reference Sequence: WP_120809711.1, Nov. 4, 2018, 1 page.
"aspartate aminotransferase family protein [Vogesella mureinivorans]", NCBI Reference Sequence: WP_147694092.1, Oct. 5, 2020, 1 page.
"aspartate aminotransferase family protein [Vogesella perlucida]", NCBI Reference Sequence: WP_147687830.1, Oct. 5, 2020, 1 page.
"aspartate aminotransferase family protein [*Vogesella* sp. EB]", NCBI Reference Sequence: WP_047966302.1, Apr. 15, 2016, 1 page.
"aspartate aminotransferase family protein [*Vogesella* sp. LIG4]", NCBI Reference Sequence: WP_088967522.1, Jul. 11, 2017, 1 page.
"aspartate aminotransferase family protein [Vogesella urethralis]", NCBI Reference Sequence: WP_144371715.1, Oct. 5, 2020, 1 page.
"aspartate aminotransferase family protein [*Xenophilus* sp. AP218F]", NCBI Reference Sequence: WP_088737038.1, Jul. 3, 2017, 1 page.
"Crystal structure of the omega transaminase from Chromobacterium violaceum in complex with PMP", PDB:5S4G_A, Dec. 1, 2020, 03 pages.
"Multispecies: aspartate aminotransferase family protein [Aquitalea]", NCBI Reference Sequence: WP_045848621.1, Apr. 15, 2016, 1 page.
"Multispecies: aspartate aminotransferase family protein [Aquitalea]", NCBI Reference Sequence: WP_103523625.1, Aug. 6, 2020, 1 page.
"Multispecies: aspartate aminotransferase family protein [Chromobacterium]", NCBI Reference Sequence: WP_019104435.1, Apr. 18, 2017, 1 page.
"Multispecies: aspartate aminotransferase family protein [Chromobacterium]", NCBI Reference Sequence: WP_043572477.1, Apr. 15, 2016, 1 page.
"Multispecies: aspartate aminotransferase family protein [Chromobacterium]", NCBI Reference Sequence: WP_043629242.1, Oct. 31, 2016, 1 page.
"Multispecies: aspartate aminotransferase family protein [Chromobacterium]", WP_043638691.1, Nov. 11, 2020, 1 page.
"Multispecies: aspartate aminotransferase family protein [Microvirgula]", NCBI Reference Sequence: WP_028498438.1, Jul. 14, 2018, 1 page.
Advisory Action received for U.S. Appl. No. 16/372,092, mailed on Oct. 7, 2021, 3 pages.
Advisory Action received for U.S. Appl. No. 16/372,099, mailed on Feb. 22, 2022, 3 pages.
Advisory Action received for U.S. Appl. No. 16/372,106, mailed on Mar. 9, 2022, 3 pages.
Advisory Action received for U.S. Appl. No. 16/399,145, mailed on Mar. 4, 2022, 4 pages.
U.S. Appl. No. 16/372,072, Corrected Notice of Allowability mailed Jan. 26, 2021, 2 pages.
U.S. Appl. No. 16/372,072, Notice of Allowance mailed Jul. 17, 2020, 11 pages.
U.S. Appl. No. 16/372,072, Notice of Allowance mailed Dec. 16, 2020, 9 pages.
U.S. Appl. No. 16/372,072, Preliminary Amendment filed Jul. 30, 2019, 5 pages.
U.S. Appl. No. 16/372,072, Preliminary Amendment filed Aug. 14, 2019, 5 pages.
U.S. Appl. No. 16/372,072, Response filed Feb. 11, 2020 to Restriction Requirement mailed Dec. 11, 2019, 7 pages.
U.S. Appl. No. 16/372,072, Response filed Jun. 8, 2020 to Non Final Office Action mailed Mar. 6, 2020, 11 pages.
U.S. Appl. No. 16/372,072, Restriction Requirement mailed Dec. 11, 2019, 9 pages.
U.S. Appl. No. 16/372,083, Notice of Allowability mailed Sep. 22, 2021, 5 pages.
U.S. Appl. No. 16/372,083, Notice of Allowance mailed Aug. 31, 2021, 9 pages.
U.S. Appl. No. 16/372,083, Preliminary Amendment filed Jul. 30, 2019, 4 pages.
U.S. Appl. No. 16/372,083, Response filed Apr. 12, 2021 to Restriction Requirement mailed Mar. 8, 2021, 8 pages.
U.S. Appl. No. 16/372,083, Response filed Jul. 27, 2021 to Non Final Office Action mailed Apr. 27, 2021, 11 pages.
U.S. Appl. No. 16/372,083, Response filed Dec. 18, 2020 to Restriction Requirement mailed Oct. 19, 2020, 7 pages.
U.S. Appl. No. 16/372,083, Restriction Requirement mailed Mar. 8, 2021, 6 pages.
U.S. Appl. No. 16/372,083, Restriction Requirement mailed Oct. 19, 2020, 8 pages.
U.S. Appl. No. 16/372,083, Supplemental Amendment filed for Non-Final Office Action mailed Apr. 27, 2021, 8 pages.
U.S. Appl. No. 16/372,092, Non Final Office Action mailed Mar. 4, 2021, 9 pages.
U.S. Appl. No. 16/372,092, Response filed Jun. 2, 2021 to Non Final Office Action mailed Mar. 4, 2021, 11 pgs.
U.S. Appl. No. 16/372,092, Response filed Sep. 21, 2021 to Final Office Action mailed Jul. 26, 2021, 11 pages.
U.S. Appl. No. 16/372,092, Response filed Dec. 17, 2020 to Restriction Requirement mailed Oct. 21, 2020, 6 pages.
U.S. Appl. No. 16/372,092, Restriction Requirement mailed Oct. 21, 2020, 7 pages.
U.S. Appl. No. 16/372,099, Non Final Office Action mailed on Jul. 9, 2021, 14 pages.
U.S. Appl. No. 16/372,099, Response filed May 18, 2021 to Restriction Requirement mailed Mar. 19, 2021, 6 pages.
U.S. Appl. No. 16/372,099, Restriction Requirement mailed Mar. 19, 2021, 6 pages.
U.S. Appl. No. 16/372,106, Non Final Office Action mailed Apr. 30, 2021, 26 pages.
U.S. Appl. No. 16/372,106, Response filed Jan. 19, 2021 to Restriction Requirement mailed Dec. 28, 2020, 8 pages.
U.S. Appl. No. 16/372,106, Response filed Jun. 15, 2021 to Non Final Office Action mailed Apr. 30, 2021, 12 pages.
U.S. Appl. No. 16/372,106, Restriction Requirement mailed Dec. 28, 2020, 7 pages.
U.S. Appl. No. 16/398,351, Non Final Office Action mailed Feb. 1, 2021, 24 pages.
U.S. Appl. No. 16/399,145, Advisory Action mailed Feb. 1, 2021, 4 pages.
U.S. Appl. No. 16/399,145, Final Office Action mailed Dec. 4, 20, 2017 pages.
U.S. Appl. No. 16/399,145, Non Final Office Action mailed Jun. 17, 2021, 20 pages.
U.S. Appl. No. 16/399,145, Response filed Jan. 25, 2021 to Final Office Action mailed Dec. 4, 2020, 12 pages.
U.S. Appl. No. 16/399,145, Response filed Jun. 3, 2020 to Restriction Requirement mailed Apr. 17, 2020, 7 pages.
U.S. Appl. No. 16/399,145, Response filed Sep. 15, 2021 to Non Final Office Action mailed Jun. 17, 2021, 11 Pages.
U.S. Appl. No. 16/399,145, Response filed Nov. 6, 2020 to Non Final Office Action mailed Aug. 12, 2020, 12 pages.
U.S. Appl. No. 16/399,145, Restriction Requirement mailed Apr. 17, 2020, 9 pages.
U.S. Appl. No. 16/399,155, Advisory Action mailed Jun. 1, 2020, 3 pages.
U.S. Appl. No. 16/399,155, Final Office Action mailed Mar. 5, 2020, 23 pages.
U.S. Appl. No. 16/399,155, Final Office Action mailed Jul. 28, 2021, 14 pages.

(56) References Cited

OTHER PUBLICATIONS

U.S. Appl. No. 16/399,155, Non Final Office Action mailed Feb. 16, 2021, 17 pages.
U.S. Appl. No. 16/399,155, Response filed May 5, 2020 to Final Office Action mailed Mar. 5, 2020, 12 pages.
U.S. Appl. No. 16/399,155, Response filed May 14, 2021 to Non Final Office Action mailed Feb. 16, 2021, 11 pages.
U.S. Appl. No. 16/399,155, Response filed Jun. 5, 2020 to Advisory Action mailed Jun. 1, 2020, 13 pages.
U.S. Appl. No. 16/399,155, Response filed Jun. 5, 2020 to Final Office Action mailed Mar. 5, 2020, 13 pages.
Baltz et al. "Manual of Industrial Microbiology and Biotechnology", ASM Press, 2010, 4 Pages (Abstract).
Berg et al. "Biochemistry 5th ed.", WH Freeman and Company, 2002, 1 Page (Abstract).
Brigham, C.J., et al., "Engineering Ralstonia eutropha for Production of Isobutanol from C02, H2 and 02", Advanced Biofuels and Bioproducts, (2013) Chapter 39, pp. 1065-1090.
Cupriavidus necator, Wikipedia, Retrieved from Internet URL: https://en.wikipedia.org/wiki/Cupriavidus_necator# :-: text=Cupriavidus%20necator/o20is%20a%20hydrogen,a%20source%20of/o20energy%20C., Feb. 25, 2021, 07 Pages.
Database UniProt [Online] Mar. 15, 2017 , "RecName: Full=Thiopurine S-methyltransferase ; EC=2.1.1.67 ; AltName: Full=Thiopurine methyltransferase ;", Database accession No. A0A1L8MA47.
Database UniProt [Online] Jul. 24, 2013 (Jul. 24, 2013), "SubName: Full=Acyl-ACP thioesterase ;", retrieved from EBI accession No. Uniprot: R7CHF5 Database accession No. R7CHF5.
Database UniProt [Online] Jun. 11, 2014, "RecName: Full= Thiopurine S-methyltransferase ; EC=2.1.1.67 ; AltName: Full= Thiopurine methyltransferase ;", retrieved from EBI accession No. Uniprot: AOA009ZVV4.
Devereaux, J., et al., "A comprehensive set of sequence analysis programs for the VAX", Nucleic Acids Research, vol. 12, Issue 1, Part 1, Jan. 11, 1984, pp. 387-395.
Final office action received for U.S. Appl. No. 16/372,092, mailed on Dec. 7, 2023, 14 pages.
Final Office Action received for U.S. Appl. No. 16/372,092, mailed on Jul. 26, 2021, 10 Pages.
Final Rejection received for U.S. Appl. No. 16/372,099, mailed on Dec. 21, 2021, 17 pages.
Final Rejection received for U.S. Appl. No. 16/372,106, mailed on Dec. 22, 2021, 32 pages.
Final Rejection received for U.S. Appl. No. 16/372,106, mailed on Oct. 4, 2021, 29 pages.
Final Rejection received for U.S. Appl. No. 16/399,145, mailed on Dec. 22, 2021, 20 pages.
Folsom, J.P. et al., "Physiological and Proteomic Analysis of *Escherichia coli* Iron-Limited Chemostat Growth," Journal of Bacteriology, vol. 196, No. 15, Aug. 2014, pp. 2748-2761.
Ghosalkar et al., Oxygen Uptake Rate Measurement by Modified Dynamic Method and Effect of Mass-Transfer Rates on Growth of Pichia Stipitis : Modeling and Experimental Data Comparison, Austin Journal of Biotechnology & Bioengineering, vol. 3, Issue 3, 2016, 6 pages.
Harder et al., "Physiological responses to nutrient limitation", Annual Review of Microbiology, vol. 37, 1983, pp. 1-23.
Hensirisak et al. "Scale-Up of Microbubble Dispersion Generator for Aerobic Fermentation", Applied Biochemistry and Biotechnology, vol. 101, 2002, p. 211-227.
https://www.clrblu.com/aeration/, "Aeration" (Year: 2021).
Huang et al., "Bacterial and Yeast Cultures—Process Characteristics, Products, and Applications", Bioprocessing for Value-Added Products from Renewable Resources, Dec. 2007, pp. 185-223.
International Application Serial No. PCT/US2019/025189, International Preliminary Report on Patentability mailed Oct. 15, 2020, 9 pages.
International Application Serial No. PCT/US2019/025194, International Preliminary Report on Patentability mailed Oct. 15, 2020, 15 pages.
International Application Serial No. PCT/US2019/025194, Invitation to Pay Additional Fees dated Jul. 1, 2019, 14 pages.
International Application Serial No. PCT/US2019/025202, International Preliminary Report on Patentability mailed Oct. 15, 2020, 12 pages.
International Application Serial No. PCT/US2019/025218, Invitation to Pay Additional Fees dated Jun. 25, 2019, 09 pages.
International Application Serial No. PCT/US2019/029956, International Preliminary Report on Patentability mailed Nov. 12, 2020, 12 pages.
International Application Serial No. PCT/US2019/029973, International Preliminary Report on Patentability mailed Nov. 12, 2020, 12 pages.
International Preliminary Report on Patentability for PCT application No. PCT/US2019/025211, dated Oct. 15, 2020, 13 pages.
Ishii et al., Uniprot database, accession No. G2J4X6, Nov. 2011, p. 2.
Ishizaki, A., et al., "Microbial production of poly-D-3-hydroxybutyrate from C02", Applied Microbiology and Biotechnology, vol. 57, Oct. 2001, pp. 6-12.
Ishizuka, H., et al., "Putrescine Oxidase of Micrococcus Rubens: Primary Structure and Escherichia Coli", Journal of General Microbiology, vol. 139, 1993, pp. 425-432.
Jones, G.W. and Kennedy, Re., "Prevention of Gas Explosions by Controlling Oxygen Concentration", Industrial and Engineering Chemistry, vol. 27, Issue 11, 1935, pp. 1344-1346.
Judger, B-E., et al., "An analysis of the changes in soluble hydrogenase and global gene expression in Cupriavidusnecator (Ralstonia eutropha) HI6 grown in heterotrophic diauxic batch culture", Microbial Cell Factories, vol. 14, 2015, pp. 1-11.
Kaster et al., "Increased Oxygen Transfer in a Yeast Fermentation Using a Microbubble Dispersion", Applied Biochemistry and Biotechnology vol. 24/25, 1990, p. 469-484.
Kihlberg, "The Microbe as a Source of Food" Annual Review of Microbiology, vol. 26, 1972, 427-466.
Kirk et al., "Quantification of the oxygen uptake rate in a dissolved oxygen-controlled oscillating jet-driven microbioreactor", Journal of Chemical Technology& Biotechnology, vol. 91, pp. 823-831, 2016.
Klasson, K.T., et al., "Bioreactor design for synthesis gas fermentations", Fuel, vol. 70, Issue 5, 1991, pp. 605-614.
Kovacs et al., "Metabolic engineering of Cupriavidus necator H16 for the sustainable production of C3 and C5 monomers and polymers", Clnet Conference 4, Jan. 20-23, 2019 Conference paper (Abstract), 2019, p. 26.
Kyte, J., et al., "A simple method for displaying the hydropathic character of a protein", Journal of Molecular Biology, vol. 157, No. 1, May 5, 1982, pp. 105-132.
Lin, S., et al., "Biotin Synthesis Beings by Hijacking the Fatty Acid Synthesis Pathway," Nature Chemical Biology, vol. 6, No. 9, Sep. 2010, pp. 682-688.
Lucas et al., GenBank accession No. ACU95033, Aug. 26, 2009, p. 1.
Maddipati, P., "Ethanol production from syngas by Clostridium strain P11 using com steep liquor as a nutrientreplacement to yeast extract", Bioresoure Technology, vol. 102, Issue 11, 2011, pp. 6494-6501.
Manandhar, M., et al., "Pimelic acid, the first precursor of the Bacillus subtilis biotin synthesis pathway. exists as the free acid and is assembled by fatty acid synthesis: Bacillus subtilis biotin synthesis", Molecular Microbiology, vol. 104, No. 4, Mar. 3, 2017, pp. 595-607.
Maqbool, A. et al., "MultiSpecies: CmpA/NrtA family ABC transporter substrate-binding protein [Cupriavidus]", Retrieved from internet https://www.ncbi.nlm.nih.gov/protein/WP_010814804.1/, Mar. 20, 2023, 2 pages.
Myers, et al., "Optimal alignments in linear space", Computer Applications in the Biosciences, vol. 4, 1988, pp. 11-17.

(56) References Cited

OTHER PUBLICATIONS

Needleman, S.B., et al., "A general method applicable to the search for similarities in the amino acid sequence of two proteins", Journal of Molecular Biology, vol. 48, Issue 3, Mar. 1970, pp. 443-453.
NETL brochure, "Syngas composition", accessed online on (www.netl.doe.gov/research/coal/energy systems/gasification/gasifipedia/syngas-composition), Jul. 3, 2021, total pp. 1-2.
Non Final Office Action received for U.S. Appl. No. 16/372,072, mailed on Mar. 6, 2020, 20 Pages.
Non Final Office Action received for U.S. Appl. No. 16/372,083, mailed on Apr. 27, 2021, 14 Pages.
Non Final Rejection received for U.S. Appl. No. 16/372,092, mailed on Sep. 15, 2022, 11 Pages.
Non-final office action received for U.S. Appl. No. 16/372,106, mailed on Apr. 5, 2022, 33 pages.
Non-Final Rejection received for U.S. Appl. No. 16/372,092, mailed on Nov. 26, 2021, 10 Pages.
Notice of Allowance received for U.S. Appl. No. 16/372,099, mailed on Apr. 15, 2022, 11 pages.
Pearson, W.R., et al., "Improved tools for biological sequence comparison", Proceedings of the National Academy of Science of the United States of America, vol. 85, Issue 8, Apr. 1988, pp. 2444-2448.
Phillips, J.R., et al., "Syngas Fermentation: A Microbial Conversion Process of Gaseous Substrates to Various Products", Fermentation, vol. 3, Issue 2, 2017, p. 26.
Response to Final Office Action for U.S. Appl. No. 16/372,099, filed Feb. 8, 2022, 9 pages.
Response to Final Office Action received for U.S. Appl. No. 16/399,145, filed Feb. 22, 2022, 10 pages.
Response to Final Rejection for U.S. Appl. No. 16/372,106, filed Dec. 9, 2021, 9 pages.
Response to Final Rejection for U.S. Appl. No. 16/372,106, filed Feb. 16, 2022, 9 pages.
Response to Non Final Office Action for U.S. Appl. No. 16/372,099, filed Oct. 7, 2021, 8 pages.
Response to Non-Final Rejection for U.S. Appl. No. 16/372,092, filed Feb. 28, 2022, 9 pages.
Sadowski et al. "The sequence-structure relationship and protein function prediction", Current Opinion in Structural Biology, 2009, 19, pp. 357-362.
Seffernick, J L., et al., "Melamine Deaminase and Atrazine Chlorohydrolase: 98 Percent Identical but Functionally Different", Journal of Bacteriology, 183, 2001, pp. 2405-2410.
Shulman, A.I., et al. "Structural determinants of allosteric ligand activation in RXR heterodimers," Cell, vol. 116, Issue 3, Feb. 6, 2004, pp. 417-429.
Slabu et al., "Discovery, Engineering and Synthetic Application of Transaminase Biocatalysts," ACS Catalysis 7, 2017, pp. 8263-8284.
Smith, T.F., et al., "Comparison of biosequences", Advances in Applied Mathematics, vol. 2, Issue 4, Dec. 1981, pp. 482-489.
Stanbury et al. "Principles of Fermentation Technology", 3rd Edition, Aug. 31, 2016, 4 Pages.(Abstract).
Tanaka, K. and Ishizaki, A., "Production of poly-d-3-hydroxybutyric acid from carbon dioxide by a two-stage culture method employing Alcaligenes eutrophus ATCC 17697T", Journal of Fermentation and Bioengineering, vol. 77, Issue 4, 1994, pp. 425-427.
Tang et al., "Identification of Dehalobacter reductive dehalogenases that catalyse dechlorination of chloroform, 1, 1,1- trichloroethane and 1, 1-dichloroethane", Phil Trans Royal Society Publishing, 2013, 368:20120318, pp. 1-10.
TPA: aspartate aminotransferase family protein [Betaproteobacteria bacterium], GenBank: HEL32111.1, Mar. 2, 2020, 1 page.
U.S. Appl. No. 16/399, 155, Non Final Office Action dated Jul. 15, 2019, 19 pages.
U.S. Appl. No. 16/399,155, Response filed Oct. 15, 2019 to Non-Final Office Action dated Jul. 15, 2019, 12 pages.
Yuzawa Satoshi et al., "Synthetic biology of polyketide synthases", Journal of Industrial Microbiology & Biotechnology, vol. 45, No. 7, Feb. 9, 2018, pp. 621-633.
Yonezuka, K. et al., "Phosphonate C-P lyase system protein PhnG [Cupriavidus necator]", Retrived from internet https://www.ncbi.nlm.nih.gov/protein/KUE89182.1, Dec. 23, 2015, 2 pages.

* cited by examiner

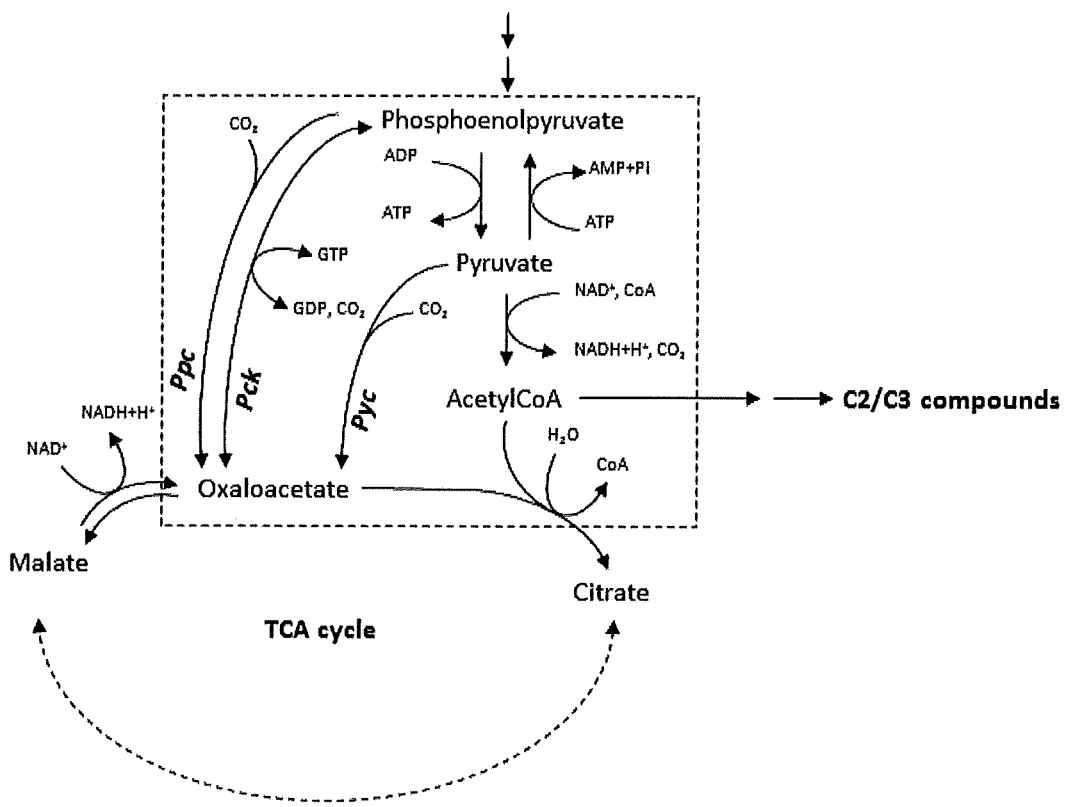

MATERIALS AND METHODS FOR MAXIMIZING BIOSYNTHESIS THROUGH ALTERATION OF PYRUVATE-ACETYL-CoA-TCA BALANCE IN SPECIES OF THE GENERA RALSTONIA AND CUPRIAVIDUS AND ORGANISMS RELATED THERETO

This patent application claims the benefit of priority from U.S. Provisional Patent Application Ser. No. 62/665,777 filed May 2, 2018, teachings of which are herein incorporated by reference in their entirety.

FIELD

The present invention relates to methods of redirecting carbon flux and increasing C2/C3 or C4/5/6 carbon chain length carbon-based chemical product yield in an organism, nonnaturally occurring organisms with redirected carbon flux and increased C2/C3 or C4/5/6 carbon chain length carbon-based chemical product yield and methods for using these organisms in production of C2/C3 or C4/5/6 carbon chain length carbon-based chemical products.

BACKGROUND

The PEP-pyruvate-oxaloacetate node, also described as the anaplerotic node, has been described as a switch point for carbon distribution within the central metabolism (Sauer & Eikmanns FEMS Microbiology Reviews 2005 29(4):765-794). It involves a set of interconnected reactions, which can mediate the conversion of C3 and C4 compounds, notably via differential levels of acetyl-CoA and oxaloacetate (FIG. 1).

In silico analysis of the *C. necator* H16 genome has revealed the presence of a gene encoding a GTP-dependent phosphoenolpyruvate carboxykinase Pck (EC 4.1.1.32), H16_A3711, a gene encoding a phosphoenolpyruvate carboxylase Ppc (EC 4.1.1.31), H16_A2921, and a gene encoding a pyruvate carboxylase Pyc (EC 6.4.1.1), H16_A1251 (Bruland et al. Journal of Applied Microbiology 2010 109:79-90). Some studies suggest that in *C. necator*, ppc and pyc are not expressed (Bruland et al. Journal of Applied Microbiology 2010 109:79-90; Schwartz et al. Proteomics 2009 9(22):5132-5142) while others have disclosed their expression (Alagesan et al. Metabolomics 2018 14:9).

Both Ppc and Pyc generate oxaloacetate from phosphoenolpyruvate or pyruvate, respectively. Pck catalyzes the reversible carboxylation of phosphoenolpyruvate to oxaloacetate (Schobert & Bowien J Bacteriol. 1984 159(1):167-172; Brámer & Steinbichel FEMS Microbiol Lett. 2002 2; 212(2):159-64). However, in *E. coli*, where there is a phosphoenolpyruvate carboxylase activity, it has been described that, due to Ppc and Pck's kinetic properties, Pck functions as the decarboxylating enzyme (Kim et al. Applied and Environmental Microbiology 2004 70(2):1238-1241).

Several studies have shown that deregulating enzymes involved in the anaplerotic node allowed redirection of the carbon flux into the TCA cycle for production of C4/C5/C6 compounds or towards the production of C2/C3 compounds (e.g. Segura & Espin Appl Microbiol Biotechnol. 2004 65(4):414-8; Kim et al. Applied and Environmental Microbiology 2004 70(2):1238-1241; Meng et al. Microbial Cell Factories 2016 15:141).

Inactivation of pyruvate carboxylase within *A. vinelandii* UW136 has been shown to increase the specific production of poly(3-hydroxybutyrate) (PHB) three-fold (Segura & Espin Appl Microbiol Biotechnol. 2004 65(4):414-8). This anaplerotic enzyme catalyzes the ATP dependent carboxylation of pyruvate to generate oxaloacetate that replenishes the TCA cycle. By diminishing flux of acetyl-CoA into the TCA cycle and slowing down the TCA cycle due to low concentrations of oxaloacetate, acetyl-CoA instead becomes more available and is diverted toward PHB synthesis.

It has also been shown that the overexpression of ppc encoding a phosphoenolpyruvate carboxylase diverts flux in the TCA cycle towards the production of C4 compounds such as oxaloacetate and malate (Park et al. Bioprocess Biosyst Eng. 2013 36(1):127-31) and reduces acetate production in *E. coli* (Papagianni, M. Microbial Cell Factories 2012 11:50). This reduction of acetate production was also observed for *E. coli* strains overexpressing pyc, encoding a pyruvate carboxylase, suggesting that the pool of acetyl-CoA is redirected towards the TCA cycle (March et al. Applied and Environmental Microbiology 2002 68(11):5620-5624; Vemuri et al. Biotechnology and Bioengineering 2005 90(1):64-76).

Additionally, in an *E. coli* strain deleted for ppc, heterologous expression of pck from *Actinobacillus succinogenes* was shown to replace the phosphoenolpyruvate carboxylase activity, and resulted in increased succinate production (Kim et al. Applied and Environmental Microbiology 2004 70(2):1238-1241; Papagianni, M. Microbial Cell Factories 2012 11:50).

Replacement of traditional chemical production processes relying on, for example fossil fuels and/or potentially toxic chemicals, with environmentally friendly and sustainable solutions is being considered, including work to identify suitable building blocks for use in the manufacturing of chemicals. Organisms and methods for their production and use are needed.

SUMMARY

Methods for increasing product yield of organisms and organisms capable of increased product yield are provided.

An aspect of the present invention related to methods of redirecting carbon flux in an organism. The methods comprises modulating one or more polypeptides, or functional fragments thereof, having an activity of a phosphoenolpyruvate carboxykinase and/or a phosphoenolpyruvate carboxylase and/or a pyruvate carboxylase and/or a citrate lyase or citrate lyase subunit in an organism.

In one nonlimiting embodiment, phosphoenolpyruvate carboxykinase classified under EC 4.1.1.32, EC 4.1.1.38, or EC 4.1.1.49 is modulated.

In one nonlimiting embodiment, the phosphoenolpyruvate carboxykinase modulated comprises SEQ ID NO: 2, 8, 10, 12, 14, 16 or 18 or a functional fragment thereof or is a polypeptide with similar enzymatic activities exhibiting at least 50% sequence identity to an amino acid sequence set forth in SEQ ID NO: 2, 8, 10, 12, 14, 16 or 18 or a functional fragment thereof or is encoded by a nucleic acid sequence comprising SEQ ID NO: 1, 7, 9, 11, 13, 15 or 17 or a functional fragment thereof or a nucleic acid sequence encoding a polypeptide with similar enzymatic activities exhibiting at least 50% sequence identity to the nucleic acid sequence set forth in SEQ ID NO: 1, 7, 9, 11, 13, 15 or 17 or a functional fragment thereof.

In one nonlimiting embodiment, phosphoenolpyruvate carboxylase classified under EC 4.1.1.31 is modulated.

In one nonlimiting embodiment, the phosphoenolpyruvate carboxylase modulated comprises SEQ ID NO: 4, 30, 32, 34, 36, 38 or 40 or a functional fragment thereof or is a polypeptide with similar enzymatic activities exhibiting at least 50% sequence identity to an amino acid sequence set forth in SEQ ID NO: 4, 30, 32, 34, 36, 38 or 40 or a functional fragment thereof or is encoded by a nucleic acid sequence comprising SEQ ID NO: 3, 29, 31, 33, 35, 37 or 39 or a functional fragment thereof or a nucleic acid sequence encoding a polypeptide with similar enzymatic activities exhibiting at least 50% sequence identity to the nucleic acid sequence set forth in SEQ ID NO: 3, 29, 31, 33, 35, 37 or 39 or a functional fragment thereof.

In one nonlimiting embodiment, pyruvate carboxylase classified under EC 6.4.1.1 is modulated.

In one nonlimiting embodiment, the pyruvate carboxylase modulated comprises SEQ ID NO: 6, 20, 22, 24, 26 or 28 or a functional fragment thereof or is a polypeptide with similar enzymatic activities exhibiting at least 50% sequence identity to an amino acid sequence set forth in SEQ ID NO: 6, 20, 22, 24, 26 or 28 or a functional fragment thereof or is encoded by a nucleic acid sequence comprising SEQ ID NO: 5, 19, 21, 23, 25 or 27 or a functional fragment thereof or a nucleic acid sequence encoding a polypeptide with similar enzymatic activities exhibiting at least 50% sequence identity to the nucleic acid sequence set forth in SEQ ID NO: 5, 19, 21, 23, 25 or 27 or a functional fragment thereof.

In one nonlimiting embodiment, a citrate lyase subunit classified under EC 4.1.3.34 and EC 2.8.3.10 is modulated.

In one nonlimiting embodiment the citrate lyase subunit modulated comprises SEQ ID NO: 42, 44, 46, 48, 50 and/or 52 or a functional fragment thereof or is a polypeptide with similar enzymatic activities exhibiting at least 50% sequence identity to an amino acid sequence set forth in SEQ ID NO: 42, 44, 46, 48, 50 and/or 52 or a functional fragment thereof or is encoded by a nucleic acid sequence comprising SEQ ID NO: 41, 43, 45, 47, 49 and/or 51 or a functional fragment thereof or a nucleic acid sequence encoding a polypeptide with similar enzymatic activities exhibiting at least 50% sequence identity to the nucleic acid sequence set forth in SEQ ID NO: 41, 43, 45, 47, 49 and/or 51 or a functional fragment thereof.

In one nonlimiting embodiment, modulating an activity level of one or more polypeptides comprises overexpressing an endogenous or exogenous nucleic acid sequence in the organism.

In one nonlimiting embodiment, modulating an activity level of one or more polypeptides comprises downregulating, deleting or mutating an endogenous or exogenous nucleic acid sequence in the organism.

In one nonlimiting embodiment, carbon flux is redirected toward products having a C2/C3 or a C4/C5/C6 chain length, derivatives thereof and/or compounds related thereto.

Another aspect of the present invention relates to methods for increasing carbon-based chemical product yield in an organism. The methods comprise modulating one or more polypeptides, or functional fragments thereof, having an activity of a phosphoenolpyruvate carboxykinase and/or a phosphoenolpyruvate carboxylase and/or a pyruvate carboxylase and/or a citrate lyase or citrate lyase subunit in an organism. In the methods yield of a C2/C3 or a C4/5/6 carbon chain length product is increase.

Another aspect of the present invention relates to nonnaturally occurring organisms capable of redirecting carbon flux toward products having a C2/C3 or a C4/C5/C6 chain length, derivatives thereof and/or compounds related thereto. In these nonnaturally occurring organisms an activity level of one or more polypeptides, or functional fragments thereof, having an activity of a phosphoenolpyruvate carboxykinase and/or a phosphoenolpyruvate carboxylase and/or a pyruvate carboxylase and/or a citrate lyase or citrate lyase subunit is modulated in the organism.

Another aspect of the present invention relates to a method for producing a carbon-based chemical product in an organism with a nonnaturally occurring organism of the present invention.

BRIEF DESCRIPTION OF THE DRAWINGS

FIG. 1 shows the pathways through which flux may be altered by modulating the activity of an enzyme involved in the PEP-pyruvate-oxaloacetate node in an organism.

DETAILED DESCRIPTION

Provided by this disclosure and teachings are methods and materials for maximizing the production of products having a C2/C3 or a C4/C5/C6 chain length, derivatives thereof and/or compounds related thereto through modulation of enzymes involved in the PEP-pyruvate-oxaloacetate node. The inventors have found that it is possible to differentiate flux going to C4/C5/C6 compounds via the TCA cycle from compounds derived from acetyl-CoA for C2/C3 products. More specifically, in the methods and organism of the present invention one or more polypeptides having an activity of a phosphoenolpyruvate carboxykinase (Pck) and/or a phosphoenolpyruvate carboxylase (Ppc) and/or a pyruvate carboxylase (Pyc) and/or a citrate lyase or citrate lyase subunit (Cit) is modulated to redirect carbon flux.

By "modulated" or "modulate" or "modulating' for purposes of the present invention, it is meant to include overexpressing, downregulating, deleting, mutating or replacing an endogenous or exogenous nucleic acid sequence or polypeptide in an organism.

In certain aspects, the organism is modulated by altering, engineering, or introducing one or more nucleic acid sequences within the organism. The altering of modifying of the nucleic acid sequences can be, for example and without limitation, via genetic engineering, by adaptive mutation, or by selective isolation of naturally occurring mutant strains.

In some nonlimiting embodiments, one or more enzymes or nucleic acids of the organism are modified via non-direct or rational enzyme design approaches with aims of improving activity, improving specificity, reducing feedback inhibition, reducing repression, improving enzyme solubility, changing stereo-specificity, or changing co-factor specificity. In some embodiments, the enzymes in the pathways outlined herein can be gene dosed (i.e., overexpressed by having a plurality of copies of the gene in the host organism), into the resulting genetically modified organism via episomal or chromosomal integration approaches. In some nonlimiting embodiments, genome-scale system biology techniques such as Flux Balance Analysis can be utilized to devise genome scale attenuation or knockout strategies for directing carbon flux. Attenuation strategies include, but are not limited to, the use of transposons, homologous recombination (double cross-over approach), mutagenesis, enzyme inhibitors, and RNA interference (RNAi). In some embodiments, fluxomic, metabolomic and transcriptomal data can be utilized to inform or support genome-scale system biology techniques, thereby devising genome-scale attenuation or knockout strategies in directing carbon flux. In some embodiments, the tolerance of the host microorganism to high concentrations of the extracellular product can be improved through continuous cultivation in a selective environment.

The modified nucleic acid sequences of the organism can include, for example, one or more enzymes, one or more promoters, one or more transcription factors, or combinations thereof. The modifications can be to nucleic acids encoding polypeptides functioning as a transhydrogenase, reductase, dehydrogenase, or hydrogenase enzyme or functional fragments thereof. The modifications can be to nucleic acids not directly involved in encoding polypeptides functioning as a transhydrogenase, reductase, dehydrogenase, or hydrogenase enzyme or functional fragments thereof, but indirectly affecting the polypeptides through the interconnected metabolic network and metabolic control strategy of the organism. The modification of the nucleic acid sequences can include one or more deletions, one or more substitutions, one or more insertions, or combinations thereof.

Enzymes with substitutions will generally have not more than 50 (e.g., not more than 1, not more than 2, not more than 3, not more than 4, not more than 5, not more than 6, not more than 7, not more than 8, not more than 9, not more than 10, not more than 12, not more than 15, not more than 20, not more than 25, not more than 30, not more than 35, not more than 40, or not more than 50) amino acid substitutions (e.g., conservative or non-conservative substitutions). This applies to any of the enzymes described herein and functional fragments thereof. A conservative substitution is a substitution of one amino acid for another with similar characteristics. Conservative substitutions include substitutions within the following groups: valine, alanine and glycine; leucine, valine, and isoleucine; aspartic acid and glutamic acid; asparagine and glutamine; serine, cysteine, and threonine; lysine and arginine; and phenylalanine and tyrosine. The nonpolar hydrophobic amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Any substitution of one member of the above-mentioned polar, basic, or acidic groups by another member of the same group can be deemed a conservative substitution. In contrast, a non-conservative substitution is a substitution of one amino acid for another with dissimilar characteristics. Deletion variants can, for example, lack 1, 2, 3, 4, 5, 6, 7, 8, 9, 10, 11, 12, 13, 14, 15, 16, 17, 18, 19, or 20 amino acid segments (of two or more amino acids) or non-contiguous single amino acids.

In one nonlimiting embodiment, modification of the organism is carried out by allele exchange. In this embodiment, genome edits are made in a *Cupriavidus* or *Ralstonia* organism with perturbed PHB synthesis or an organism with properties similar thereto by allele exchange (also referred to as allelic exchange). In one non-limiting embodiment, the organism is a ΔphaCAB H16 *C. necator* strain generated using allele exchange.

The term 'allele' is often used interchangeably with the term 'gene' more generally, and refers to a defined genomic locus. In allele exchange, a specific run of DNA sequence (i.e., the native allele) in a genome of an organism is literally exchanged for a recombinant, mutant, or synthetic run of DNA sequence (i.e., the recombinant allele). Depending on the nature of the recombinant allele, this allele exchange can result in a gene deletion, a gene substitution, or a gene insertion.

In one nonlimiting embodiment, recombinant/synthetic alleles can be constructed via gene synthesis and/or standard molecular biology techniques. These alleles are then cloned into a plasmid vector for transfer into the organism and execution of the allele exchange procedure.

In some nonlimiting embodiments, the organism is modified to include one or more exogenous nucleic acid sequences.

The term "exogenous" as used herein with reference to a nucleic acid (or a protein) and an organism refers to a nucleic acid that does not occur in (and cannot be obtained from) a cell of that particular type as it is found in nature or a protein encoded by such a nucleic acid. Thus, a non-naturally-occurring nucleic acid is considered to be exogenous to a host once in the host. It is important to note that non-naturally-occurring nucleic acids can contain nucleic acid subsequences or fragments of nucleic acid sequences that are found in nature provided the nucleic acid as a whole does not exist in nature. For example, a nucleic acid molecule containing a genomic DNA sequence within an expression vector is non-naturally-occurring nucleic acid, and thus is exogenous to a host cell once introduced into the host, since that nucleic acid molecule as a whole (genomic DNA plus vector DNA) does not exist in nature. Thus, any vector, autonomously replicating plasmid, or virus (e.g., retrovirus, adenovirus, or herpes virus) that as a whole does not exist in nature is considered to be non-naturally-occurring nucleic acid. It follows that genomic DNA fragments produced by PCR or restriction endonuclease treatment as well as cDNAs are considered to be non-naturally-occurring nucleic acid since they exist as separate molecules not found in nature. It also follows that any nucleic acid containing a promoter sequence and polypeptide-encoding sequence (e.g., cDNA or genomic DNA) in an arrangement not found in nature is non-naturally-occurring nucleic acid. A nucleic acid that is naturally-occurring can be exogenous to a particular host microorganism. For example, an entire chromosome isolated from a cell of yeast x is an exogenous nucleic acid with respect to a cell of yeast y once that chromosome is introduced into a cell of yeast y.

In contrast, the term "endogenous" as used herein with reference to a nucleic acid (e.g., a gene) (or a protein) and a host refers to a nucleic acid (or protein) that does occur in (and can be obtained from) that particular host as it is found in nature. Moreover, a cell "endogenously expressing" a nucleic acid (or protein) expresses that nucleic acid (or protein) as does a host of the same particular type as it is found in nature. Moreover, a host "endogenously producing" or that "endogenously produces" a nucleic acid, protein, or other compound produces that nucleic acid, protein, or compound as does a host of the same particular type as it is found in nature.

In certain aspects, the organism is modulated to include one or more functional fragments of enzymes, other polypeptides, or nucleic acids. The phrase "functional fragment" as used herein refers to a peptide fragment of a polypeptide or a nucleic acid sequence fragment encoding a peptide fragment of a polypeptide that has at least 25%, e.g., at least 30%, at least 40%, at least 50%, at least 60%, at least 70%, at least 75%, at least 80%, at least 85%, at least 90%, at least 95%, at least 98%, at least 99%, or at least 100% of the activity of the corresponding mature, full-length, polypeptide. The functional fragment can generally, but not always, be comprised of a continuous region of the polypeptide, wherein the region has functional activity.

For purposes of the present invention, by "redirecting carbon flux" it is meant that the modulated organisms and methods of the present invention are capable of producing increased levels of products having either a C2/C3 or a C4/C5/C6 chain length, derivatives thereof and/or compounds related thereto as compared to the same organism without modulation.

For purposes of the present invention, by "derivatives and compounds related thereto" it is meant to encompass compounds derived from the same substrates and/or enzymatic reactions as compounds having a C2/C3 or a C4/C5/C6 chain length, byproducts of these enzymatic reactions and compounds with similar chemical structure including, but not limited to, structural analogs wherein one or more substituents of compounds having a C2/C3 or a C4/C5/C6 chain length are replaced with alternative substituents. Nonlimiting examples of C2/C3 chain length compounds include lactic acid, ethanol, acetone, acetic acid, malonic acid, 3-hydroxypropanoic acid and 1,3-propanediol and derivatives and compounds related thereto. Nonlimiting examples of C4/C5/C6 chain length compounds comprise one or more of citric acid, maleic acid, succinic acid, glutaric acid, glutamic acid, pentamethylene diamine, 1,4-diaminobutane, fumaric acid, itaconic acid, lysine and adipic acid and derivatives and compounds related thereto. In some nonlimiting embodiments, the organism has been modified to exhibit an increased synthesis of the extracellular product relative to that of the corresponding wild type organism.

Additional descriptions of the synthesis of similar carbon-based chemical products with *Ralstonia, Cupriavidus*, or an organism similar thereto can be found in U.S. Pat. Nos. 10,196,657; 9,920,339; 9,862,973; and 9,580,733, the disclosures of which are incorporated by reference herein in their entirety for all purposes.

For compounds of the present invention containing carboxylic acid groups such as organic monoacids, hydroxyacids, aminoacids and dicarboxylic acids, these compounds may be formed or converted to their ionic salt form when an acidic proton present in the parent compound either is replaced by a metal ion, e.g., an alkali metal ion, an alkaline earth ion, or an aluminum ion; or coordinates with an organic base. Acceptable organic bases include ethanolamine, diethanolamine, triethanolamine, tromethamine, N-methylglucamine, and the like. Acceptable inorganic bases include aluminum hydroxide, calcium hydroxide, potassium hydroxide, sodium carbonate and/or bicarbonate, sodium hydroxide, ammonia and the like. The salt can be isolated as is from the system as the salt or converted to the free acid by reducing the pH to below the lowest pKa through addition of acid or treatment with an acidic ion exchange resin.

For compounds of the present invention containing amine groups such as but not limited to organic amines, aminoacids and diamine, these compounds may be formed or converted to their ionic salt form by addition of an acidic proton to the amine to form the ammonium salt, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid. The salt can be isolated as is from the system as a salt or converted to the free amine by raising the pH to above the lowest pKa through addition of base or treatment with a basic ion exchange resin. Acceptable inorganic bases are known in the art and include aluminum hydroxide, calcium hydroxide, potassium hydroxide, sodium carbonate and/or bicarbonate, ammonia, sodium hydroxide, and the like.

For compounds of the present invention containing both amine groups and carboxylic acid groups such as but not limited to aminoacids, these compounds may be formed or converted to their ionic salt form by either 1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid. Acceptable inorganic bases include aluminum hydroxide, calcium hydroxide, potassium hydroxide, sodium carbonate and/or bicarbonate, sodium hydroxide, ammonia and the like or 2) when an acidic proton present in the parent compound either is replaced by a metal ion, e.g., an alkali metal ion, an alkaline earth ion, or an aluminum ion; or coordinates with an organic base. Acceptable organic bases are known in the art and include ethanolamine, diethanolamine, triethanolamine, tromethamine, N-methylglucamine, and the like. Acceptable inorganic bases are known in the art and include aluminum hydroxide, calcium hydroxide, potassium hydroxide, sodium carbonate, sodium hydroxide, and the like. The salt can be isolated as is from the system or converted to the free acid by reducing the pH to below the lowest pKa through addition of acid or treatment with an acidic ion exchange resin.

For the generation of C4, C5 and C6 containing compounds in accordance with the methods and organism of the present invention, in one nonlimiting embodiment, this modulation can take the form of enhanced activity or expression of a Pck in an organism in which Ppc has been deleted. In another nonlimiting embodiment, the organism may be modulated by altering activity or expression or replacing the endogenous or exogenous Pyc and/or endogenous or exogenous Ppc. In one nonlimiting embodiment, the organism may be modulated by increasing activity or expression of Pyc and/or Ppc.

Nonlimiting examples of C4, C5 and C6 containing compounds include citric acid, maleic acid, succinic acid, glutaric acid, glutamic acid, pentamethylene diamine, 1,4-diaminobutane, fumaric acid, itaconic acid, lysine and adipic acid and derivatives and compounds related thereto.

For the generation of C2 and C3 containing compounds, fatty acids and PHBs, isoprenoid and branched chain amino acids in accordance with the methods and organisms of the present invention, this modulation can take the form of decreased activity or expression of Pyc and/or endogenous Ppc.

Nonlimiting examples of C2/C3 chain length compounds include lactic acid, ethanol, acetone, acetic acid, malonic acid, 3-hydroxypropanoic acid and 1,3-propanediol and derivatives and compounds related thereto. In another embodiment, modulation may comprise mutation of isocitrate dehydrogenase in the organism as described, for example, by Park and Lee (Journal of Fermentation and Bioengineering 1996 81(3):197-205).

Additional nonlimiting examples of modulations to the organism to generate C4, C5 and C6 containing compounds or C2 and C3 containing compounds are set forth in the Examples.

Nonnaturally occurring organisms produced and used in accordance with the present invention are selected from a species of *Cupriavidus* or *Ralstonia* with diminished polyhydroxybutyrate synthesis or an organism with properties similar thereto.

For purposes of the present invention, by "diminishing" or "diminished" polyhydroxybutyrate synthesis, it is meant that the organism is altered to synthesize less polyhydroxybutyrate as compared to an unaltered wild-type organism of the same species. Organisms used in this disclosure can exhibit at least 20%, 25%, 30%, 40%, 50% or even greater decreased polyhydroxybutyrate synthesis as compared to an unperturbed wild-type organism of the same species.

Nonlimiting examples of species of *Cupriavidus* or *Ralstonia* useful in accordance with this disclosure include *Cupriavidus necator*, *Cupriavidus metallidurans*, *Cupriavidus taiwanensis*, *Cupriavidus pinatubonensis*, *Cupriavidus basilensis* and *Ralstonia pickettii*.

*C. necator* (also referred to as *Hydrogenomonas eutrophus*, *Alcaligenes eutropha*, *Ralstonia eutropha*, and *Wautersia eutropha*) is a Gram-negative, flagellated soil bacterium of the Betaproteobacteria class. This hydrogen-oxidizing bacterium is capable of growing at the interface of anaerobic and aerobic environments and easily adapts between heterotrophic and autotrophic lifestyles. Sources of energy for the bacterium include both organic compounds and hydrogen. Additional properties of *C. necator* include microaerophilicity, copper resistance (Makar, N. S. & Casida, L. E. Int. J. of Systematic Bacteriology 1987 37(4):323-326), bacterial predation (Byrd et al. Can J Microbiol 1985 31:1157-1163; Sillman, C. E. & Casida, L. E. Can J Microbiol 1986 32:760-762; Zeph, L. E. & Casida, L. E. Applied and Environmental Microbiology 1986 52(4):819-823) and polyhydroxybutyrate (PHB) synthesis. In addition, the cells have been reported to be capable of either aerobic or nitrate dependent anaerobic growth. A nonlimiting example of a *C. necator* organism useful in the present invention is a *C. necator* of the H16 strain. In one nonlimiting embodiment, a *C. necator* host of the H16 strain with at least a portion of the phaC1AB1 gene locus knocked out (ΔphaCAB) is used. In one nonlimiting embodiment, the organism is further modified to eliminate phaCAB, involved in PHBs production and/or H16-A0006-9 encoding endonucleases thereby improving transformation efficiency as described in U.S. patent application Ser. No. 15/717,216, teachings of which are incorporated herein by reference. However, other means of eliminating PHB synthesis are included within the scope of the invention.

By "an organism with properties similar thereto" it is meant an organism having one or more of the above-mentioned properties of *C. necator*.

In one nonlimiting embodiment for the processes of the present invention, one or more polypeptides having an activity of a Pck and/or a Ppc and/or a Pyc and/or a Cit in the organism is modulated.

In one nonlimiting embodiment, the Pck is classified under EC 4.1.1.32, EC 4.1.1.38, or EC 4.1.1.49. In one nonlimiting embodiment, the Pck comprises SEQ ID NO: 2, 8, 10, 12, 14, 16 or 18 or a functional fragment thereof or is a polypeptide with similar enzymatic activities exhibiting at least 50%, 60%, 70%, 75%, 80%, 85%, 90%, 91%, 92%, 93%, 94%, 95%, 96%, 97%, 98%, 99% or 99.5% sequence identity to an amino acid sequence set forth in SEQ ID NO: 2, 8, 10, 12, 14, 16 or 18 or a functional fragment thereof. In one nonlimiting embodiment, the Pck is encoded by a nucleic acid sequence comprising SEQ ID NO: 1, 7, 9, 11, 13, 15 or 17 or a functional fragment thereof or a nucleic acid sequence encoding a polypeptide with similar enzymatic activities exhibiting at least 50%, 60%, 70%, 75%, 80%, 85%, 90%, 91%, 92%, 93%, 94%, 95%, 96%, 97%, 98%, 99% or 99.5% sequence identity to the nucleic acid sequence set forth in SEQ ID NO: 1, 7, 9, 11, 13, 15 or 17 or a functional fragment thereof.

In one nonlimiting embodiment, the Ppc is classified under EC 4.1.1.31. In one nonlimiting embodiment, the Ppc comprises SEQ ID NO: 4, 30, 32, 34, 36, 38 or 40 or a functional fragment thereof or is a polypeptide with similar enzymatic activities exhibiting at least 50%, 60%, 70%, 75%, 80%, 85%, 90%, 91%, 92%, 93%, 94%, 95%, 96%, 97%, 98%, 99% or 99.5% sequence identity to an amino acid sequence set forth in SEQ ID NO: 4, 30, 32, 34, 36, 38 or 40 or a functional fragment thereof. In one nonlimiting embodiment, the Ppc is encoded by a nucleic acid sequence comprising SEQ ID NO: 3, 29, 31, 33, 35, 37 or 39 or a functional fragment thereof or a nucleic acid sequence encoding a polypeptide with similar enzymatic activities exhibiting at least 50%, 60%, 70%, 75%, 80%, 85%, 90%, 91%, 92%, 93%, 94%, 95%, 96%, 97%, 98%, 99% or 99.5% sequence identity to the nucleic acid sequence set forth in SEQ ID NO: 3, 29, 31, 33, 35, 37 or 39 or a functional fragment thereof.

In one nonlimiting embodiment, the Pyc is classified under EC 6.4.1.1. In one nonlimiting embodiment, the Pyc comprises SEQ ID NO: 6, 20, 22, 24, 26 or 28 or a functional fragment thereof or is a polypeptide with similar enzymatic activities exhibiting at least 50%, 60%, 70%, 75%, 80%, 85%, 90%, 91%, 92%, 93%, 94%, 95%, 96%, 97%, 98%, 99% or 99.5% sequence identity to an amino acid sequence set forth in SEQ ID NO: 6, 20, 22, 24, 26 or 28 or a functional fragment thereof. In one nonlimiting embodiment, the Pyc is encoded by a nucleic acid sequence comprising SEQ ID NO: 5, 19, 21, 23, 25 or 27 or a functional fragment thereof or a nucleic acid sequence encoding a polypeptide with similar enzymatic activities exhibiting at least 50%, 60%, 70%, 75%, 80%, 85%, 90%, 91%, 92%, 93%, 94%, 95%, 96%, 97%, 98%, 99% or 99.5% sequence identity to the nucleic acid sequence set forth in SEQ ID NO: 5, 19, 21, 23, 25 or 27 or a functional fragment thereof.

Cit is composed of multiple subunits such as, but not limited to, CitF (citrate CoA-transferase) and CitE (citryl-CoA lyase) being classified under EC 2.8.3.10 or EC 4.1.3.34, respectively. In one nonlimiting embodiment, the CitE comprises SEQ ID NO: 42, 44, 46, 48 or 50 or a functional fragment thereof or is a polypeptide with similar enzymatic activities exhibiting at least 50%, 60%, 70%, 75%, 80%, 85%, 90%, 91%, 92%, 93%, 94%, 95%, 96%, 97%, 98%, 99% or 99.5% sequence identity to an amino acid sequence set forth in SEQ ID NO: 42, 44, 46, 48 or 50 or a functional fragment thereof.

In one nonlimiting embodiment, the CitE is encoded by a nucleic acid sequence comprising SEQ ID NO: 41, 43, 45, 47 or 49 or a functional fragment thereof or a nucleic acid sequence encoding a polypeptide with similar enzymatic activities exhibiting at least 50%, 60%, 70%, 75%, 80%, 85%, 90%, 91%, 92%, 93%, 94%, 95%, 96%, 97%, 98%, 99% or 99.5% sequence identity to the nucleic acid sequence set forth in SEQ ID NO: 41, 43, 45, 47 or 49 or a functional fragment thereof. In one nonlimiting embodiment, the CitF comprises SEQ ID NO: 52 or a functional fragment thereof or is a polypeptide with similar enzymatic activities exhibiting at least 50%, 60%, 70%, 75%, 80%, 85%, 90%, 91%, 92%, 93%, 94%, 95%, 96%, 97%, 98%, 99% or 99.5% sequence identity to an amino acid sequence set forth in SEQ ID NO: 52 or a functional fragment thereof. In one nonlimiting embodiment, the CitF is encoded by a nucleic acid sequence comprising SEQ ID NO: 51 or a functional fragment thereof or a nucleic acid sequence encoding a polypeptide with similar enzymatic activities exhibiting at least 50%, 60%, 70%, 75%, 80%, 85%, 90%, 91%, 92%, 93%, 94%, 95%, 96%, 97%, 98%, 99% or 99.5% sequence identity to the nucleic acid sequence set forth in SEQ ID NO: 51 or a functional fragment thereof.

In one nonlimiting embodiment for processes of the present invention, isocitrate dehydrogenase is modulated. In one nonlimiting embodiment, the isocitrate dehydrogenase comprises SEQ ID NO: 54, 56 or 58 or a functional fragment thereof or is a polypeptide with similar enzymatic activities exhibiting at least 50%, 60%, 70%, 75%, 80%, 85%, 90%, 91%, 92%, 93%, 94%, 95%, 96%, 97%, 98%, 99% or 99.5% sequence identity to an amino acid sequence set forth in SEQ ID NO: 54, 56 or 58 or a functional fragment thereof. In one nonlimiting embodiment, the isocitrate dehydrogenase is encoded by a nucleic acid sequence comprising SEQ ID NO: 53, 55 or 57 or a functional fragment thereof or a nucleic acid sequence encoding a polypeptide with similar enzymatic activities exhibiting at least 50%, 60%, 70%, 75%, 80%, 85%, 90%, 91%, 92%, 93%, 94%, 95%, 96%, 97%, 98%, 99% or 99.5% sequence identity to the nucleic acid sequence set forth in SEQ ID NO: 53, 55 or 57 or a functional fragment thereof.

The percent identity (and homology) between two amino acid sequences as disclosed herein can be determined as follows. First, the amino acid sequences are aligned using the BLAST 2 Sequences (Bl2seq) program from the stand-alone version of BLAST containing BLASTP version 2.0.14. This stand-alone version of BLAST can be obtained from the U.S. government's National Center for Biotechnology Information web site (www with the extension ncbi.nlm.nih.gov). Instructions explaining how to use the Bl2seq program can be found in the readme file accompanying BLASTZ. Bl2seq performs a comparison between two amino acid sequences using the BLASTP algorithm. To compare two amino acid sequences, the options of Bl2seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\Bl2seq -i c:\seq1.txt -j c:\seq2.txt -p blastp -o c:\output.txt. If the two compared sequences share homology (identity), then the designated output file will present those regions of homology as aligned sequences. If the two compared sequences do not share homology (identity), then the designated output file will not present aligned sequences. Similar procedures can be followed for nucleic acid sequences except that blastn is used.

Once aligned, the number of matches is determined by counting the number of positions where an identical amino acid residue is presented in both sequences. The percent identity (and homology) is determined by dividing the number of matches by the length of the full-length polypeptide amino acid sequence followed by multiplying the resulting value by 100. It is noted that the percent identity (homology) value is rounded to the nearest tenth. For example, 90.11, 90.12, 90.13, and 90.14 is rounded down to 90.1, while 90.15, 90.16, 90.17, 90.18, and 90.19 is rounded up to 90.2. It also is noted that the length value will always be an integer.

It will be appreciated that a number of nucleic acids can encode a polypeptide having a particular amino acid sequence. The degeneracy of the genetic code is well known to the art; i.e., for many amino acids, there is more than one nucleotide triplet that serves as the codon for the amino acid. For example, codons in the coding sequence for a given enzyme can be modified such that optimal expression in a particular species (e.g., bacteria or fungus) is obtained, using appropriate codon bias tables for that species.

In one nonlimiting embodiment, the organism is further modified to eliminate phaCAB, involved in PHBs production and/or A0006-9 encoding endonucleases thereby improving transformation efficiency as described in U.S. patent application Ser. No. 15/717,216, teachings of which are incorporated herein by reference.

In the process of the present invention, the modulated organism is then subjected to conditions wherein products having a C2/C3 or a C4/C5/C6 chain length, derivatives thereof and/or compounds related thereto are produced.

In the process described herein, a fermentation strategy can be used that entails anaerobic, micro-aerobic or aerobic cultivation. A fermentation strategy can entail nutrient limitation such as nitrogen, phosphate or oxygen limitation.

Under conditions of nutrient limitation a phenomenon known as overflow metabolism (also known as energy spilling, uncoupling or spillage) occurs in many bacteria (Russell, J. B. J Mol Microbiol Biotechnol. 2007 13(1-3): 1-11). In growth conditions in which there is a relative excess of carbon source and other nutrients (e.g. phosphorous, nitrogen and/or oxygen) are limiting cell growth, overflow metabolism results in the use of this excess energy (or carbon), not for biomass formation but for the excretion of metabolites, typically organic acids. In *R. eutropha* a modified form of overflow metabolism occurs in which excess carbon is sunk intracellularly into the storage carbohydrate polyhydroxybutyrate (PHB). In strains of *R. eutropha* which are deficient in PHB synthesis this overflow metabolism can result in the production of extracellular overflow metabolites. The range of metabolites that have been detected in PHB deficient *R. eutropha* strains include acetate, acetone, butanoate, cis-aconitate, citrate, ethanol, fumarate, 3-hydroxybutanoate, propan-2-ol, malate, methanol, 2-methyl-propanoate, 2-methyl-butanoate, 3-methyl-butanoate, 2-oxoglutarate, meso-2,3-butanediol, acetoin, DL-2,3-butanediol, 2-methylpropan-1-ol, propan-1-ol, lactate 2-oxo-3-methylbutanoate, 2-oxo-3-methylpentanoate, propanoate, succinate, formic acid and pyruvate. The range and quantity of overflow metabolites produced in a particular fermentation can depend upon the limitation applied (e.g. nitrogen, phosphate, oxygen), the extent of the limitation, the carbon source provided and fermentation conditions such as, but not limited to, pH, source of phosphates or ammonia. See for example, Schlegel and Vollbrecht Microbiology 1980 117:475-481; Vollbrecht et al. European Journal of Applied Microbiology and Biotechnology 1978 6(2): 145-155; Vollbrecht and Schlegel European Journal of Applied Microbiology and Biotechnology 1978 6(2):157-166; and Vollbrecht et al. European Journal of Applied Microbiology and Biotechnology 1979 7(3):267-276.

Applying a suitable nutrient limitation in defined fermentation conditions can thus result in an increase in the flux through a particular metabolic node. The application of this knowledge to *R. eutropha* strains genetically modified to produce desired chemical products via the same metabolic node can result in increased production of the desired product.

For example, in glycolysis conditions, TCA cycle is favored. This can be switched by modifying the carbon flux towards the increase of the acetyl-coA pool. Under gluconeogenic conditions, the formation of pyruvate and PEP is favored, and this can be switched by modifying the carbon flux towards TCA cycle. A higher flux through the TCA cycle has also been described in mixotrophic conditions of glycerol and $CO_2$ (Alagesan et al. Metabolomics 2018 14:9).

A cell retention strategy using a ceramic hollow fiber membrane can be employed to achieve and maintain a high cell density during fermentation.

Feedstocks for fermentation may be gases such as carbon dioxide or hydrogen; sugars such as glucose, xylose or fructose; sugar acids such as gluconate; fatty acids or fats/oils, carboxylic acids such as propionic acid, lactic acid, and formic acid; amino acids, aromatics such as phenol and benzoic acid and/or alcohols such as glycerol.

The feedstocks may be carbon sources derived from by-product or waste streams such as brewing, dairy, plant oil, ethanol, corn, soy, fish, or sugar industries or any other food or agricultural waste such as used cooking oil.

The biological feedstock can be, or can derive from, monosaccharides, disaccharides, lignocellulose, hemicellulose, cellulose, paper-pulp waste, black liquor, lignin, levulinic acid and formic acid, triglycerides, glycerol, fatty acids, agricultural waste, thin stillage, condensed distillers' solubles or waste streams from the food processing or dairy industries municipal waste such as fruit peel/pulp or whey. The non-biological feedstock can be, or can derive from, natural gas, syngas, $CO_2/H_2$, CO, $H_2$, $O_2$, methanol, ethanol, waste streams from processes to produce monomers for the Nylon-66 and Nylon-6 industries such as but not limited to non-volatile residues (NVRs) and caustic wash waste streams from the cyclohexane oxidation process used to manufacture adipic acid or caprolactam or waste stream from other chemical industry processes such as, but not limited to a carbon black industry or a hydrogen-refining industry, or petrochemical industry, a nonlimiting example being a PTA-waste stream.

In one nonlimiting embodiment, at least one of the enzymatic conversions of the production method comprises gas fermentation within the modulated *Ralstonia* or *Cupriavidus* organism or other organism with properties similar thereto. In this embodiment, the gas fermentation may comprise at least one of natural gas, syngas, CO, $H_2$, $O_2$, $CO_2/H_2$, methanol, ethanol, non-volatile residue, caustic wash from cyclohexane oxidation processes, or waste stream from a chemical industry such as, but not limited to a carbon black industry or a hydrogen-refining industry, or petrochemical industry. In one nonlimiting embodiment, the gas fermentation comprises $CO_2/H_2$.

The methods of the present invention may further comprise recovering produced products having a C2/C3 or a C4/C5/C6 chain length, derivatives thereof and/or compounds related thereto. Once produced, any method can be used to isolate these products or derivatives or compounds related thereto. The isolation of at least one product can involve any one or more downstream processes generally known to be suitable for the at least partial separation and/or isolation of material from a reaction or bioprocess. The collection can, for example, involve centrifugations, cell disruptions, concentrations, precipitations, extractions, filtrations, crystallizations, distillations, chemical conversions, or combinations thereof. One or more biosynthetic products can be collected from the liquid or solid phase of the culture, or from the gas phase present in the headspace of a bioreactor or the off-gas.

The present invention also provides nonnaturally occurring organisms capable of redirecting carbon flux toward and increasing yield of carbon-based chemical products having a C2/C3 or a C4/C5/C6 chain length, derivatives thereof and/or compounds related thereto. The nonnaturally occurring organisms are selected from a species of *Cupriavidus* or *Ralstonia* with diminished polyhydroxybutyrate synthesis or an organism with properties similar thereto. Nonlimiting examples of species of *Cupriavidus* or *Ralstonia* useful in accordance with this disclosure include *Cupriavidus necator*, *Cupriavidus metallidurans*, *Cupriavidus taiwanensis*, *Cupriavidus pinatubonensis*, *Cupriavidus basilensis* and *Ralstonia pickettii*.

In one nonlimiting embodiment, the present invention relates to a substantially pure culture of the nonnaturally occurring organism capable of redirecting carbon flux toward and increasing yield of carbon-based chemical products having a C2/C3 or a C4/C5/C6 chain length, derivatives thereof and/or compounds related thereto.

As used herein, a "substantially pure culture" of an altered organism is a culture of that microorganism in which less than about 40% (i.e., less than about 35%; 30%; 25%; 20%; 15%; 10%; 5%; 2%; 1%; 0.5%; 0.25%; 0.1%; 0.01%; 0.001%; 0.0001%; or even less) of the total number of viable cells in the culture are viable cells other than the altered microorganism, e.g., bacterial, fungal (including yeast), mycoplasmal, or protozoan cells. The term "about" in this context means that the relevant percentage can be 15% of the specified percentage above or below the specified percentage. Thus, for example, about 20% can be 17% to 23%. Such a culture of nonnaturally occurring microorganisms includes the cells and a growth, storage, or transport medium. Media can be liquid, semi-solid (e.g., gelatinous media), or frozen. The culture includes the cells growing in the liquid or in/on the semi-solid medium or being stored or transported in a storage or transport medium, including a frozen storage or transport medium. The cultures are in a culture vessel or storage vessel or substrate (e.g., a culture dish, flask, or tube or a storage vial or tube).

In one nonlimiting embodiment, one or more polypeptides having an activity of a Pck and/or a Ppc and/or a Pyc and/or a Cit in the organism is modulated.

In one nonlimiting embodiment for processes of the present invention, isocitrate dehydrogenase is modulated.

In one nonlimiting embodiment, the organism is further modified to eliminate phaCAB, involved in PHBs production and/or A0006-9 encoding endonucleases thereby improving transformation efficiency, as described in U.S. patent application Ser. No. 15/717,216, teachings of which are incorporated herein by reference. However, other means of eliminating PHB synthesis are included within the scope of the invention.

In addition, the present invention provides bio-derived, bio-based, or fermentation-derived products produced using the methods and/or altered organisms disclosed herein. In one nonlimiting embodiment, a bio-derived, bio-based or fermentation derived product is produced in accordance with the exemplary central metabolism depicted in FIG. 1. Examples of such products include, but are not limited to, compositions comprising at least one bio-derived, bio-based, or fermentation-derived compound or any combination thereof, as well as molded substances, formulations and semi-solid or non-semi-solid streams comprising one or more of the bio-derived, bio-based, or fermentation-derived compounds or compositions, combinations or products thereof.

While the invention has been described in detail, in some instances making reference to a specific aspect thereof, it is apparent to one of skill in the art that various changes and modifications can be made thereto without departing from its spirit and scope. The following section provides further illustration of the methods and materials of the present invention. These Examples are illustrative only and are not intended to limit the scope of the invention in any way.

EXAMPLES

Example 1

Two strains were used for the generation of RNAseq data: C. necator H16 ΔphaCAB and ΔphaCABΔpimACD. The strains were grown in triplicates at 30° C. on Cupriavidus defined medium with 1% fructose. Samples were collected for RNA extraction at OD600 between 0.2 and 0.5. The RNAs were extracted and processed to generate cDNA libraries, which were then sequenced on Illumina MiSeq with chemistry v2.

Table 1 summarizes the RNA sequencing results for the genes ppc, pyc and pck. The expression units correspond to the relative expression unit, which is the expression normalized to the total number of mapped reads for each sample with an average of 3 biological replicates. DF and DDF refer to the strains ΔphaCAB and ΔphaCABΔpimACD respectively grown with fructose as sole carbon source.

TABLE 1

RNA sequencing results of the genes ppc, pyc and pck

| | DF AVER- AGE | DDF AVER- AGE | Protein Name | Gene | Description |
|---|---|---|---|---|---|
| YP_727365 | 71.84 | 70.35 | Ppc | H16_A2921 | Phosphoenol-pyruvate carboxylase |
| YP_725759 | 11.66 | 5.52 | Pyc | H16_A1251 | Pyruvate carboxylase |
| YP_728135 | 155.24 | 152.24 | Pck | H16_A3711 | Phosphoenol-pyruvate carboxykinase |

As shown by the RNAseq experiment, three genes ppc, pyc and pck were expressed in C. necator when grown on fructose and can thus be modulated.

Example 2: Deletion/Downregulation of Pyc and/or Ppc

The deletions of one or both pyc and/or ppc genes block the replenishment of the oxaloacetate. This is expected to lead to a decrease of the pool of available oxaloacetate, thus a slowdown of the TCA cycle and a higher availability of the acetyl-coA pool for synthesis of PHB (C2/C3 route) as described by Segura and Espin (Appl Microbiol Biotechnol. 2004 65(4):414-8).

Example 3: Overexpression of Pyc and/or Ppc

The overexpression of one or both pyc and/or ppc genes, either endogenous or exogenous, increases the anaplerotic flux to oxaloacetate and thus replenishes the oxaloacetate pool. The pool of acetyl-CoA will preferentially be fed into the TCA cycle. The overexpression will thus direct the carbon flux towards the production of C4/C5/C6 compounds. In addition to the overexpression of the endogenous ppc gene, the gene encoding the PEP carboxylase A from Methanothermobacter thermoautotrophicus can also be overexpressed as the enzyme activity is not influenced by the levels of acetyl-CoA and the enzyme is less sensitive to levels of aspartate (Sauer & Eikmanns FEMS Microbiology Reviews 2005 29(4):765-794). This effect of overexpression(s) may be even further accentuated in conjunction with the deletion of pck as it has been described in E. coli that Pck's kinetic properties favor the oxolacetate decarboxylation rather than the phosphoenolpyruvate carboxylation (Kim et al. Applied and Environmental Microbiology 2004 70(2): 1238-41).

Example 4: Overexpression of Pck in Mutants in which Ppc is Deleted or Downregulated In R. eutropha, Pck catalyzes the reversible carboxylation of phosphoenolpyruvate to oxaloacetate (Schobert & Bowien J Bacteriol. 1984 159(1):167-172). Results in E. coli suggest however that Pck's kinetic properties favor the production of PEP from oxaloacetate rather than the reverse reaction. Nevertheless, it has also been described that this equilibrium can be shifted towards the production of oxaloacetate when pck is overexpressed in a ppc mutant (Kim et al. Applied and Environmental Microbiology. 2004 70(2): 1238-1241; Meng et al. Microbial Cell Factories 201615: 141; Papagianni, M. Microbial Cell Factories 2012 11:50). For instance, the heterologous expression of A. succinogenes Pck in E. coli has been shown to increase the flux to succinate production (Kim et al. Applied and Environmental Microbiology. 2004 70(2):1238-1241; Meng et al. Microbial Cell Factories 201615:141).

In R. eutropha, the endogenous or an exogenous pck gene can be expressed in a Δppc mutant. The exogenous Pck can replace the defective phosphoenolpyruvate carboxylase activity and thus diverts the flux in the TCA cycle towards the production of C4, C5 and C6 compounds.

Example 5: Overexpression of Pck and Combination with Ppc

Tan et al. have demonstrated in E. coli that modulating the expression of Pck and Ppc independently, had a positive impact on succinate production, indicating that the higher flux towards the production of C4 compounds was achieved (Appl. Environ. Microbiol. 2013 79(16): 4838-4844). In addition, they showed that combining activation of Pck and Ppc resulted in higher titers than the independent activations.

In R. eutropha, modulating the expression of Pck using different promoters, RBS or regulators or by protein engineering, independently or in combination with the modulation of Ppc's expression could result in higher flux for the production of C4/C5/C6 compounds.

Example 6: Overexpression of a Citrate Lyase

It has been shown in the *C. necator* PHB-4 mutant that an excess of pyruvate is produced, which can thus be used to generate acetyl-CoA. This acetyl-coA can enter the TCA cycle and can react with oxaloacetate to generate citrate. A citrate lyase activity can catalyze the conversion of citrate to acetate and oxaloacetate, which corresponds to an anaplerotic reaction to produce oxaloacetate that circumvents the full TCA cycle.

The citrate lyase is composed of several subunits, including CitF, the subunit alpha (EC 2.8.3.10), which converts acetyl-coA and citrate to acetate and citryl-CoA, and CitE, the subunit beta (EC 4.1.3.34), which catalyzes the conversion of citryl-CoA to acetyl-CoA and oxaloacetate.

In the PHB-4 mutant, it has been found that CitE4, the subunit Beta of a citrate lyase, is more highly expressed (Raberg et al. PLoS ONE 2014 9(5):e95907).

In *C. necator* H16, four genes have been annotated as encoding a citryl-CoA lyase activity: citE1 (H16_A2635, YP_727085), citE2 (H16_B0353, YP_728518), citE3 (H16_B0680, YP_728842) and citE4 (H16_B2113, YP_841625). No orthologs of CitF have been found in *C. necator* H16, however in *C. necator* N-1 strain, both CitE and CitF are present, encoded by citF (CNE_BB1p09780) and citE (CNE_BB1p01450).

Heterologous overexpression of one or more of the citE genes together with citF in *R. eutropha*, in which PHB production is down-regulated or blocked, is expected to lead to higher levels of oxaloacetate, which could then be converted to C4 compounds such as malate or succinate.

In a strain in which PHB production has been blocked or downregulated, this strategy can also be combined with the overexpression of pyc and/or ppc (as high levels of pyruvate are expected in the mutant) or the overexpression of pck in mutants in which the phosphoenolpyruvate carboxylase activity (Ppc) has also been blocked.

Example 7: Down-Regulation/Deletion of Isocitrate Dehydrogenase Activity

The partial blockage of the TCA cycle due to down-regulation/deletion of isocitrate dehydrogenase activity encoded by the genes icd1, icd2 and icd3 in *C. necator* increases the carbon flow to the PHB biosynthesis pathway rather than the TCA cycle. This has been observed in *C. necator* for an isocitrate dehydrogenase leaky mutant (Park & Lee Journal of Fermentation and Bioengineering 1996 81(3):197-205). This modification can be performed independently or in conjunction with the deletion/downregulation of pyc and/or ppc (see Example 2) to increase the flux towards the production of C2/C3 compounds.

What is claimed is:

1. A method of redirecting carbon flux in an organism toward carbon-based chemical products having a C4/C5/C6 chain length, said method comprising overexpressing one or more pck gene encoding a phosphoenolpyruvate carboxykinase and/or pyc gene encoding a phosphoenolpyruvate carboxylase and/or ppc gene encoding a pyruvate carboxylase and one or more CitE genes and a CitF gene encoding a citryl-CoA lyase to increase an activity of one or more phosphoenolpyruvate carboxykinase having phosphoenolpyruvate carboxykinase activity and/or a phosphoenolpyruvate carboxylase having phosphoenolpyruvate carboxylase activity and/or a pyruvate carboxylase having pyruvate carboxylase activity and a citrate lyase or citrate lyase subunit as compared to an organism which does not overexpress one or more pck gene and/or pyc gene and/or ppc gene and one or more CitE genes and a CitF gene and fermenting the organism under glycolysis or mixotrophic conditions to redirect carbon flux in the organism toward products having a C4/C5/C6 chain length, wherein the phosphoenolpyruvate carboxykinase comprises at least 90% amino acid sequence identity the to the amino acid sequence of SEQ ID NO: 8, 12, 14, 16, or 18;

the phosphoenolpyruvate carboxylase comprises at least 90% amino acid sequence identity to the amino acid sequence of SEQ ID NO: 32, 34, 36, 38, or 40;

the pyruvate carboxylase comprises at least 90% amino acid sequence identity to the amino acid sequence of SEQ ID NO: 26 or 28;

the citrate lyase or citrate lyase subunit comprises at least 90% amino acid sequence identity the amino acid sequence of SEQ ID NO: 44, 46, 48, 50, and/or 52; and wherein the organism is *Cupriavidus necator* and wherein said *Cupriavidus necator* comprises diminished polyhydroxybutyrate synthesis as a result of said overexpression as compared to an unperturbed wild-type *Cupravidus necator* organism.

2. The method of claim 1, wherein the phosphoenolpyruvate carboxykinase comprises the amino acid sequence of SEQ ID NO: 8, 12, 14, 16, or 18, or comprises at least 95% amino acid sequence identity to the amino acid sequence set forth in SEQ ID NO: 8, 12, 14, 16, or 18.

3. The method of claim 1, wherein the phosphoenolpyruvate carboxylase comprises the amino acid sequence of SEQ ID NO: 32, 34, 36, 38, or 40, or comprises at least 95% amino acid sequence identity to the amino acid sequence set forth in SEQ ID NO: 32, 34, 36, 38, or 40.

4. The method of claim 1, wherein the pyruvate carboxylase comprises the amino acid sequence of SEQ ID NO: 26 or 28, or comprises at least 95% amino acid sequence identity to the amino acid sequence set forth in SEQ ID NO: 26 or 28.

5. The method of claim 1, wherein the citrate lyase subunit comprises the amino acid sequence of SEQ ID NO: 44, 46, 48, 50, and/or 52, or comprises at least 95% amino acid sequence identity to the amino acid sequence set forth in SEQ ID NO: 44, 46, 48, 50, or 52.

6. The method of claim 1, wherein said products having a C4/C5/C6 chain length comprises one or more of citric acid, maleic acid, succinic acid, glutaric acid, glutamic acid, pentamethylene diamine, 1,4-diaminobutane, fumaric acid, itaconic acid, lysine or adipic acid.

* * * * *

SEQUENCE LISTING

```
<160> NUMBER OF SEQ ID NOS: 58

<210> SEQ ID NO 1
<211> LENGTH: 1857
<212> TYPE: DNA
<213> ORGANISM: C. necator

<400> SEQUENCE: 1
atgaaccacc ccacgatgca aggtacggcg cccgtcaatg cgccggcctg ggtcaagcac      60
cccaagctgg tggcctgggt cgcggaaatc gccgccctga ccaagcctga caatatctat     120
tggtgcgacg gctcccagga agaatacgac cgcctgtgcg agcagatggt cgccgccggc     180
accatgaagc ggctgaaccc ggccaagcgc aagaattcct tcctggcact gtcggacccc     240
tcggacgtgg cgcgggtgga agatcgcacc tttatctgct ctgaaaagca ggaagacgcc     300
ggccccacca caaactggac cgcacccgcc gagatgcgcg agacgctgaa cggcctgttc     360
gacggctgca tgcgcggccg cacgctgtat gtggtgccgt tctcgatggg cccgctgggt     420
tcgccgatcg cccatattgg cgtggaactg tccgattcgc cgtatgtggc ggtcaatatg     480
cgcatcatga cgcgcatggg ccgcgccgtg tacgacgtgc tgggcaccaa cggcgagttc     540
gtgccgtgcg tgcacaccgt gggcaagccg ctggccgccg cgagcagga cgtggcctgg     600 ccgtgcaatc cgaccaagta catcgtccat ttcccggaaa cgcgcgagat ctggtcgttc     660
ggctccggct acggcggcaa cgcgctgctg ggcaagaagt gctttgcact gcgcattgca     720
tcgaccatgg gccgcgatga aggctggctg gccgagcaca tgctgatcct tggcgtgacc     780
tcgcccgagg gcaagaaata ccacgtcgcc gccgcgttcc cgtcggcctg cggcaagacc     840
aacttcgcca tgctgatccc gcccaagggc ttcgagggct ggaaggtcac caccatcggc     900
gacgacatcg cctggatcaa gcgggccag gacgccgcc tgtacgcgat caacccggaa      960
gccggctact tcggcgtggc cccgggcacc agcgagaaga ccaactacaa cgcgatggcg    1020
```

-continued

```
acgctgaagg aaaacgtcat cttcaccaac gtggcgctga ccgacgacgg cgacgtgtgg    1080
tgggaaggca tgaccaagga agcgccggcg cacctgatcg actggcaggg caaggactgg    1140
accccggaaa tcgccaaggc caccggcgcc aaggctgcgc acccgaacgc ccgcttcacc    1200
gcgccggcat cgcagtgccc gtcgatcgac gacaactggg acaacccggc cggcgtaccc    1260
attgatgcgt ttatcttcgg cggccgccgc tcgaccaccg tgccgctggt gaccgaggcc    1320
cgcaactgga ccgaaggcgt ctacatggcc gccaccatgg gttcggaaac caccgccgcg    1380
gccgccggcc agcagggcgt ggtgcgccgc gacccgttcg ccatgctgcc gttctgcggc    1440
tacaacatga gtgattactt cggccactgg ctcgaactcg gcaagaagct ggaagccgcg    1500
ggcgcgaaac tgccgaggat ttactgcgtc aactggttcc gcaaggacgc cgacggcaac    1560
ttcgtgtggc caggcttcgg cgagaacatg cgcgtgctgt cgtggatgat cgaccgcgtg    1620
gaaggcaagg ggcaagccgc cgagcatatg ttcggcacta ccccgcgcta ccaggacttg    1680
aactggaatg cgttgacttc acaccggcg cagttcgcgc aggtgacttc aatcgaccgt    1740
gaagcgtggc agcaggagct ggtgctgcat gatgagttgt tcaccaagct gcggcatcgg    1800
ctgccgcagg cgctggcgga tgtgcgggcg cgctgggca gcggctgga aggctga        1857
```

<210> SEQ ID NO 2
<211> LENGTH: 618
<212> TYPE: PRT
<213> ORGANISM: C. necator

<400> SEQUENCE: 2

```
Met Asn His Pro Thr Met Gln Gly Thr Ala Pro Val Asn Ala Pro Ala
1               5                   10                  15

Trp Val Lys His Pro Lys Leu Val Ala Trp Val Ala Glu Ile Ala Ala
            20                  25                  30

Leu Thr Lys Pro Asp Asn Ile Tyr Trp Cys Asp Gly Ser Gln Glu Glu
        35                  40                  45

Tyr Asp Arg Leu Cys Glu Gln Met Val Ala Ala Gly Thr Met Lys Arg
    50                  55                  60

Leu Asn Pro Ala Lys Arg Lys Asn Ser Phe Leu Ala Leu Ser Asp Pro
65                  70                  75                  80

Ser Asp Val Ala Arg Val Glu Asp Arg Thr Phe Ile Cys Ser Glu Lys
                85                  90                  95

Gln Glu Asp Ala Gly Pro Thr Asn Asn Trp Thr Ala Pro Ala Glu Met
            100                 105                 110

Arg Gln Thr Leu Asn Gly Leu Phe Asp Gly Cys Met Arg Gly Arg Thr
        115                 120                 125

Leu Tyr Val Val Pro Phe Ser Met Gly Pro Leu Gly Ser Pro Ile Ala
    130                 135                 140

His Ile Gly Val Glu Leu Ser Asp Ser Pro Tyr Val Ala Val Asn Met
145                 150                 155                 160

Arg Ile Met Thr Arg Met Gly Arg Ala Val Tyr Asp Val Leu Gly Thr
                165                 170                 175

Asn Gly Glu Phe Val Pro Cys Val His Thr Val Gly Lys Pro Leu Ala
            180                 185                 190

Ala Gly Glu Gln Asp Val Ala Trp Pro Cys Asn Pro Thr Lys Tyr Ile
        195                 200                 205

Val His Phe Pro Glu Thr Arg Glu Ile Trp Ser Phe Gly Ser Gly Tyr
    210                 215                 220

Gly Gly Asn Ala Leu Leu Gly Lys Lys Cys Phe Ala Leu Arg Ile Ala
```

```
            225                 230                 235                 240

Ser Thr Met Gly Arg Asp Glu Gly Trp Leu Ala Glu His Met Leu Ile
                245                 250                 255

Leu Gly Val Thr Ser Pro Glu Gly Lys Lys Tyr His Val Ala Ala Ala
                260                 265                 270

Phe Pro Ser Ala Cys Gly Lys Thr Asn Phe Ala Met Leu Ile Pro Pro
                275                 280                 285

Lys Gly Phe Glu Gly Trp Lys Val Thr Thr Ile Gly Asp Asp Ile Ala
            290                 295                 300

Trp Ile Lys Pro Gly Gln Asp Gly Arg Leu Tyr Ala Ile Asn Pro Glu
305                 310                 315                 320

Ala Gly Tyr Phe Gly Val Ala Pro Gly Thr Ser Glu Lys Thr Asn Tyr
                325                 330                 335

Asn Ala Met Ala Thr Leu Lys Glu Asn Val Ile Phe Thr Asn Val Ala
                340                 345                 350

Leu Thr Asp Asp Gly Asp Val Trp Trp Glu Gly Met Thr Lys Glu Ala
                355                 360                 365

Pro Ala His Leu Ile Asp Trp Gln Gly Lys Asp Trp Thr Pro Glu Ile
            370                 375                 380

Ala Lys Ala Thr Gly Ala Lys Ala Ala His Pro Asn Ala Arg Phe Thr
385                 390                 395                 400

Ala Pro Ala Ser Gln Cys Pro Ser Ile Asp Asp Asn Trp Asp Asn Pro
                405                 410                 415

Ala Gly Val Pro Ile Asp Ala Phe Ile Phe Gly Gly Arg Arg Ser Thr
            420                 425                 430

Thr Val Pro Leu Val Thr Glu Ala Arg Asn Trp Thr Glu Gly Val Tyr
            435                 440                 445

Met Ala Ala Thr Met Gly Ser Glu Thr Thr Ala Ala Ala Gly Gln
            450                 455                 460

Gln Gly Val Val Arg Arg Asp Pro Phe Ala Met Leu Pro Phe Cys Gly
465                 470                 475                 480

Tyr Asn Met Ser Asp Tyr Phe Gly His Trp Leu Glu Leu Gly Lys Lys
                485                 490                 495

Leu Glu Ala Ala Gly Ala Lys Leu Pro Arg Ile Tyr Cys Val Asn Trp
            500                 505                 510

Phe Arg Lys Asp Ala Asp Gly Asn Phe Val Trp Pro Gly Phe Gly Glu
            515                 520                 525

Asn Met Arg Val Leu Ser Trp Met Ile Asp Arg Val Glu Gly Lys Gly
530                 535                 540

Gln Ala Ala Glu His Met Phe Gly Thr Thr Pro Arg Tyr Gln Asp Leu
545                 550                 555                 560

Asn Trp Asn Gly Val Asp Phe Thr Pro Ala Gln Phe Ala Gln Val Thr
                565                 570                 575

Ser Ile Asp Arg Glu Ala Trp Gln Gln Glu Leu Val Leu His Asp Glu
                580                 585                 590

Leu Phe Thr Lys Leu Arg His Arg Leu Pro Gln Ala Leu Ala Asp Val
            595                 600                 605

Arg Ala Ala Leu Gly Lys Arg Leu Glu Gly
610                 615

<210> SEQ ID NO 3
<211> LENGTH: 3039
<212> TYPE: DNA
<213> ORGANISM: C. necator
```

<400> SEQUENCE: 3

```
atgacgcagc atgctgcgcg ccccaacggc cggcggaccg ccccggctgc gaaagaccaa      60
agccctgccc tcggcgccgc ccagggtgac gcaaacggcg catccgccgc cgaaccgaaa     120
cgccccgcca gccgcagcgg gaccaaacgt tcccccaagc ccaagctttc catcgtgtcg     180
agcaacggaa ccaccatcgc ccccaccgcc cgccgcaccg ccgacaagga cgtgccgctg     240
cgcgaggaca tccgcttcct gggccgcctg ctgggcgaat gcctgcgtga acaggaaggc     300
gacgccgcct cgaggtggt cgagaccatc cgccagaccg cggtgcgctt ccgccgcgag     360
aacgaccgcg ccgccggcgc cgagctggac cgcctgctca gcgcctgtc gcgcgaccag     420
accaaccagg tcgtgcgcgc gttcagctat ttctcgcacc tggccaatat cgccgaggac     480
cagcaccaca accgccgccg ccgcgtgcac gcgctggccg gctcgccgcc gcaggcgggc     540
agcctggccc acgcgctgga ggcgatcgac gccgccggcg tgaccggcaa gcagctgcgc     600
aagttcctgg acgaggccct gatcgtgccg gtgctgaccg cgcacccgac cgaagtccag     660
cgcaagagta ttctcgacgc cgagcgcgag atcgcccgcc tgctggccga gcgcgacctg     720
ccgatgaccg cgcgcgagcg cgaccacaac ccgcgcagc tgcgcgccaa ggtcaccacg     780
ctgtggcaga cccgcatgct gcgcgattcg cgcctgacgg tggccgacga gatcgaaaac     840
gccctgtcct actaccgcac ctgtttcctg cgcggcatcc gcagttgat gagcgagctg     900
gaagaagaca tcgccgcggt gttcccgacc acgcgcaagc gcaagggcac tccgggcgcg     960
cagccggcgc cgctggcgcc gttcctgcag atgggttcct ggatcggcgg cgaccgcgac    1020
ggcaacccca acgtcaccgc cgagacgctg gagcatgccg ccagccagca ggggcagatg    1080
atcatcgact ggtacctgga tgaagtccat gcgctgggcg cggagctgtc gatgtcgacg    1140
ctgatggtcg acgccagccc ggaactgctg gcgctggccg agcgctcgcc cgaccactcc    1200
gagcatcgcg ccgacgaacc ctaccgccgc gcgctgatcg gcatctacgc gcgcctggcc    1260
gcaaccagca aggcgctgac cggccacgcc gtgccgcgcc gccggtggc gccggccgag    1320
ccctatgaca cgcgccgaggc cttttgccgcc gacgtgcagg tggtggtcga ctcgctgcgc    1380
gccaaccatg ccaggcgct ggccaatggc cgtatcgaag cgctggcgcg cgccatcggc    1440
gtgttcggtt ccacctggc atcggtcgac atgcgccagg tctcggacgt gcacgaggcg    1500
gtcatcgccg agctgttcgc cgccgccggc atcgcccccg actacgccgc cctgcccgag    1560
gcgcgcaagc tggaactgct gctggccgaa ctgcgccagc cgcgcctgct gacgctgccg    1620
tggcacgagt attccgagca gacccgcaag gaactggcga tcttcgccgc cgcgcgcgag    1680
ctgcgcgcgc gctatggcaa gcgcattgcg cgcaactaca tcatctcgca caccgagacg    1740
ctgtcggacc tggtcgaagt gatgctgctg cagaaggaat ccggcatgct gcagggcacg    1800
ctgggcagca agaccgaccc ggcgcgcatg gagctgatgg tgatcccgct gttcgagacc    1860
atcgaggact gcgcaacgc cgccggcatc atgcagtcgc tgctggacct gccgggcttc    1920
gactcggtga tcgcgcacca tggcgtcgag caggaagtga tgcttggcta ctcggactcg    1980
aacaaggacg gcggcttcct gacttccacc tgggagctgt acaaggccga gctggagctg    2040
gtgcagctgt tcgagcagcg ccaggtcaag ctgcgcctgt tccacggccg cggcggcacc    2100
gtcggccgcg gcggcggccc gacctaccag gccatcctgt cgcagccgcc gggcacggtg    2160
aacgccagga tccgtctgac cgagcagggc gagatcatca acagcaagtt cgccaacgcc    2220
gagatcggcc ggcgcaacct ggaaacggtg gtcgccgcca cgctggaagc ctcgctgttg    2280
```

```
ccgcagcaga acgcacccaa ggacctcgac atgttcgagg ccgtgatgca gcagctgtcg    2340
gaccgagcct tcaccgccta ccgcgacctg gtctacgaga ccccgggctt caaggactac    2400
ttcttcgcca ccacgccgat caccgagatc gccgacctga acctgggttc gcgcccggcc    2460
tcgcgcaagc tgatggacaa gaagaaccgc gcatcgaag acctgcgcgc aatcccgtgg     2520
ggcttctcgt ggggccagtg ccggctgctg ctgccgggct ggtacggctt cggcagcgcg    2580
gtcaagtcgc tgctggacac cgcgccggac gacaaggcgc gcaagctggc cgtgaccacg    2640
ctgcgccgca tggtcaagac ctggccgttc ttctcgacgc tgctgtccaa catggacatg    2700
gtgctggcca agaccgacct ggccgtggcc tcgcgctatg cccagctgtg cgatgacgcg    2760
gccctgcgcc gcaccgtgtt caaccgcatc agcaaggaat ggcacctgac ctgcgagatg    2820
ctgacactgg tcaccggcca ccaggaacgg ctggcggaca cccgctgct ggcgcgctcg     2880 atcaagaacc gctttgccta cctcgacccg ctcaaccact tgcaggttga gttgctgaaa    2940
cgctaccgct cgggcaagga tggcgacgac atcgggtgc ggcgcggcat ccacctgacc     3000
atcaacgggg tcgcggcggg cctgcgcaat acgggctga                           3039
```

<210> SEQ ID NO 4
<211> LENGTH: 1012
<212> TYPE: PRT
<213> ORGANISM: C. necator

<400> SEQUENCE: 4

```
Met Thr Gln His Ala Ala Arg Pro Asn Gly Arg Arg Thr Ala Pro Ala
1               5                   10                  15

Ala Lys Asp Gln Ser Pro Ala Leu Gly Ala Ala Gln Gly Asp Ala Asn
            20                  25                  30

Gly Ala Ser Ala Ala Glu Pro Lys Arg Pro Ala Ser Arg Ser Gly Thr
        35                  40                  45

Lys Arg Ser Pro Lys Pro Lys Leu Ser Ile Val Ser Ser Asn Gly Thr
    50                  55                  60

Thr Ile Ala Pro Thr Ala Arg Arg Thr Ala Asp Lys Asp Val Pro Leu
65                  70                  75                  80

Arg Glu Asp Ile Arg Phe Leu Gly Arg Leu Gly Glu Cys Leu Arg
                85                  90                  95

Glu Gln Glu Gly Asp Ala Ala Phe Glu Val Val Glu Thr Ile Arg Gln
            100                 105                 110

Thr Ala Val Arg Phe Arg Arg Glu Asn Asp Arg Ala Ala Gly Ala Glu
        115                 120                 125

Leu Asp Arg Leu Leu Lys Arg Leu Ser Arg Asp Gln Thr Asn Gln Val
    130                 135                 140

Val Arg Ala Phe Ser Tyr Phe Ser His Leu Ala Asn Ile Ala Glu Asp
145                 150                 155                 160

Gln His His Asn Arg Arg Arg Val His Ala Leu Ala Gly Ser Pro
                165                 170                 175

Pro Gln Ala Gly Ser Leu Ala His Ala Leu Glu Ala Ile Asp Ala Ala
            180                 185                 190

Gly Val Thr Gly Lys Gln Leu Arg Lys Phe Leu Asp Glu Ala Leu Ile
        195                 200                 205

Val Pro Val Leu Thr Ala His Pro Thr Glu Val Gln Arg Lys Ser Ile
    210                 215                 220

Leu Asp Ala Glu Arg Glu Ile Ala Arg Leu Leu Ala Glu Arg Asp Leu
225                 230                 235                 240
```

```
Pro Met Thr Ala Arg Glu Arg Asp His Asn Thr Ala Gln Leu Arg Ala
            245                 250                 255

Lys Val Thr Thr Leu Trp Gln Thr Arg Met Leu Arg Asp Ser Arg Leu
            260                 265                 270

Thr Val Ala Asp Glu Ile Glu Asn Ala Leu Ser Tyr Tyr Arg Thr Cys
            275                 280                 285

Phe Leu Arg Gly Ile Pro Gln Leu Met Ser Glu Leu Glu Glu Asp Ile
            290                 295                 300

Ala Ala Val Phe Pro Thr Arg Lys Arg Lys Gly Thr Pro Gly Ala
305                 310                 315                 320

Gln Pro Ala Pro Leu Ala Pro Phe Leu Gln Met Gly Ser Trp Ile Gly
            325                 330                 335

Gly Asp Arg Asp Gly Asn Pro Asn Val Thr Ala Glu Thr Leu Glu His
            340                 345                 350

Ala Ala Ser Gln Gln Gly Gln Met Ile Ile Asp Trp Tyr Leu Asp Glu
            355                 360                 365

Val His Ala Leu Gly Ala Glu Leu Ser Met Ser Thr Leu Met Val Asp
            370                 375                 380

Ala Ser Pro Glu Leu Leu Ala Leu Ala Glu Arg Ser Pro Asp His Ser
385                 390                 395                 400

Glu His Arg Ala Asp Glu Pro Tyr Arg Arg Ala Leu Ile Gly Ile Tyr
            405                 410                 415

Ala Arg Leu Ala Ala Thr Ser Lys Ala Leu Thr Gly His Ala Val Pro
            420                 425                 430

Arg Arg Pro Val Ala Pro Ala Glu Pro Tyr Asp Ser Ala Glu Ala Phe
            435                 440                 445

Ala Ala Asp Val Gln Val Val Asp Ser Leu Arg Ala Asn His Gly
450                 455                 460

Gln Ala Leu Ala Asn Gly Arg Ile Glu Ala Leu Ala Arg Ala Ile Gly
465                 470                 475                 480

Val Phe Gly Phe His Leu Ala Ser Val Asp Met Arg Gln Val Ser Asp
            485                 490                 495

Val His Glu Ala Val Ile Ala Glu Leu Phe Ala Ala Ala Gly Ile Ala
            500                 505                 510

Pro Asp Tyr Ala Ala Leu Pro Glu Ala Arg Lys Leu Glu Leu Leu
            515                 520                 525

Ala Glu Leu Arg Gln Pro Arg Leu Leu Thr Leu Pro Trp His Glu Tyr
            530                 535                 540

Ser Glu Gln Thr Arg Lys Glu Leu Ala Ile Phe Ala Ala Ala Arg Glu
545                 550                 555                 560

Leu Arg Ala Arg Tyr Gly Lys Arg Ile Ala Arg Asn Tyr Ile Ile Ser
            565                 570                 575

His Thr Glu Thr Leu Ser Asp Leu Val Glu Val Met Leu Leu Gln Lys
            580                 585                 590

Glu Ser Gly Met Leu Gln Gly Thr Leu Gly Ser Lys Thr Asp Pro Ala
            595                 600                 605

Arg Met Glu Leu Met Val Ile Pro Leu Phe Glu Thr Ile Glu Asp Leu
            610                 615                 620

Arg Asn Ala Ala Gly Ile Met Gln Ser Leu Leu Asp Leu Pro Gly Phe
625                 630                 635                 640

Asp Ser Val Ile Ala His His Gly Val Glu Gln Glu Val Met Leu Gly
            645                 650                 655

Tyr Ser Asp Ser Asn Lys Asp Gly Gly Phe Leu Thr Ser Thr Trp Glu
```

Leu Tyr Lys Ala Glu Leu Glu Leu Val Gln Leu Phe Glu Gln Arg Gln
            675                 680                 685

Val Lys Leu Arg Leu Phe His Gly Arg Gly Gly Thr Val Gly Arg Gly
        690                 695                 700

Gly Gly Pro Thr Tyr Gln Ala Ile Leu Ser Gln Pro Gly Thr Val
705                 710                 715                 720

Asn Gly Gln Ile Arg Leu Thr Glu Gln Gly Glu Ile Ile Asn Ser Lys
                    725                 730                 735

Phe Ala Asn Ala Glu Ile Gly Arg Arg Asn Leu Glu Thr Val Val Ala
            740                 745                 750

Ala Thr Leu Glu Ala Ser Leu Leu Pro Gln Gln Asn Ala Pro Lys Asp
        755                 760                 765

Leu Asp Met Phe Glu Ala Val Met Gln Gln Leu Ser Asp Arg Ala Phe
770                 775                 780

Thr Ala Tyr Arg Asp Leu Val Tyr Glu Thr Pro Gly Phe Lys Asp Tyr
785                 790                 795                 800

Phe Phe Ala Thr Thr Pro Ile Thr Glu Ile Ala Asp Leu Asn Leu Gly
            805                 810                 815

Ser Arg Pro Ala Ser Arg Lys Leu Met Asp Lys Lys Asn Arg Arg Ile
        820                 825                 830

Glu Asp Leu Arg Ala Ile Pro Trp Gly Phe Ser Trp Gly Gln Cys Arg
835                 840                 845

Leu Leu Leu Pro Gly Trp Tyr Gly Phe Gly Ser Ala Val Lys Ser Leu
850                 855                 860

Leu Asp Thr Ala Pro Asp Asp Lys Ala Arg Lys Leu Ala Val Thr Thr
865                 870                 875                 880

Leu Arg Arg Met Val Lys Thr Trp Pro Phe Phe Ser Thr Leu Leu Ser
            885                 890                 895

Asn Met Asp Met Val Leu Ala Lys Thr Asp Leu Ala Val Ala Ser Arg
        900                 905                 910

Tyr Ala Gln Leu Cys Asp Asp Ala Ala Leu Arg Arg Thr Val Phe Asn
915                 920                 925

Arg Ile Ser Lys Glu Trp His Leu Thr Cys Glu Met Leu Thr Leu Val
930                 935                 940

Thr Gly His Gln Glu Arg Leu Ala Asp Asn Pro Leu Leu Ala Arg Ser
945                 950                 955                 960

Ile Lys Asn Arg Phe Ala Tyr Leu Asp Pro Leu Asn His Leu Gln Val
            965                 970                 975

Glu Leu Leu Lys Arg Tyr Arg Ser Gly Lys Asp Gly Asp Asp Ile Arg
        980                 985                 990

Val Arg Arg Gly Ile His Leu Thr Ile Asn Gly Val Ala Ala Gly Leu
995                 1000                1005

Arg Asn Thr Gly
    1010

<210> SEQ ID NO 5
<211> LENGTH: 3504
<212> TYPE: DNA
<213> ORGANISM: C. necator

<400> SEQUENCE: 5
atggactacg cccctatccg ctccctgctg attgccaacc gttccgagat cgcgatccgc    60
gtgatgcgcg cggccgccga gatgaacgtg cgcacggtgg caatctattc gaaggaagac   120

```
cggctcgcgc tccatcgctt caaggccgat gagagctacc tggtcggcga gggcaagaag    180
ccactggcgg cttacctcga catcgacgat atcctgcgca ttgccaggca ggcgaaggtc    240
gacgccattc atccgggcta tggcttcctt tcagagaacc cggacttcgc gcaggccgtg    300
atcgacgcgg tatccgctg gatcggcccg tcgcccgagg tcatgcgcaa gcttggcaac    360
aaggtggcgg cgcgcaacgc ggcgatcgac gcgggcgtgc cggtgatgcc ggcaaccgat    420
ccgctgccgc atgaccctgga cacgtgcaag cgcctcgccg ccggcatcgg ctatccgctg    480
atgctcaagg caagctgggg cggcggcgga cgcggcatgc gggtcctgga acgcgagcag    540
gaccttgagg gggcgctcgc cgcggcgcgg cgcgaggcgc tggctgcgtt cggcaacgac    600
gaggtgtatg tcgagaagct ggtgcgcaac gcgcgccatg tcgaagtgca ggtgctcggc    660
gacacgcacg gcaacctcgt gcatctctat gagcgcgact gtaccgtgca gcggcgcaac    720
cagaaggtgg tggagcgggc gcccgcgcca tacctcgacg atgccggccg ggccgcgctg    780
tgcgaatcgg ccctgcggct gatgcgcgcg gtcggctaca cgcatgccgg tacggtcgag    840
ttcctgatgg atgccgactc cggccagttc tacttcatcg aggtcaatcc gcgcatccag    900
gtcgagcaca cggtcacgga gatggtcacc gggatcgata tcgtcaaggc gcagatccgc    960
gtgaccgaag gcggccatct cggcatgacc gagaacacgc gcaatgagaa cggcgagatc   1020
gtcgtgcgcg ccgcgggcgt gccggtgcag gaagcgattt cgctcaacgg tcacgcgctg   1080
caatgccgga tcaccaccga ggacccggag aacgggttcc tgccggacta cggccgcctc   1140
actgcctacc gcagcgcggc cggcttcggc gtgcgcctgg acgccggcac cgcctacggc   1200
ggcgcggtga tcacgccgta ctacgattcg ctgctggtca aggttaccac ctgggcgccg   1260
accgcgcccg aatcgatccg gcgcatggac cgcgcgctgc gcgagttccg catccgcggc   1320
gtcgcgtcca acctgcagtt cctcgagaac gtcatcaacc atccctcgtt ccggtccggc   1380
gacgtcacca cgcgctttat cgacctgacg ccggaactgc tggcgttcac caagcgcctg   1440
gaccgcgcca ccaagctgct gcgctacctg ggcgaggtca gcgtcaacgg caccccggag   1500
atgagcggcc gcacgctgcc atcgctgccg ctgcccgcac cggtgctgcc gccttcgac    1560 accggcggcg cgctgcccta cggtacgcgc gaccggctgc gcgagctggg cgcggagaag   1620
ttctcgcgct ggatgctgga gcagaagcag gtgctgctga ccgataccac catgcgcgac   1680
gcgcaccagt cgctgttcgc cacgcgcatg cgcaccgccg acatgctgcc gatcgcgccg   1740
ttctatgcgc gcgaactgtc gcagctgttc tcgctggagt gctggggcgg cgccaccttc   1800
gacgtggcgc tgcgcttcct caaggaagac ccgtggcagc gccttgagca actgcgcgag   1860
cgcgttccca acgtgctgtt ccagatgctg ctgcgcggct ccaacgcggt tggctacacc   1920
aattatgcgc acaacgtggt gcgcttcttc gtgcgccagg cggccagcgc cggcgtggat   1980
gtgttccgcg tgttcgattc actgaactgg gtgcgcaaca tgcgcgtggc gatcgatgct   2040
gtcggcgaga gcgcgcgcgt gtgcgaaggc gcgatctgct ataccggcga cctgttcgac   2100
aagtcgcgcg ccaaatacga cctgaagtac tacgtaggca tcgcgcgcga gctgaagcag   2160
gccggcgtgc acgtgctggg catcaaggac atggccggca tctgccgtcc gcaggccgcg   2220
gcggcactgg tcagggcgct caaggaagag accgggctgc cggtgcattt ccatacccac   2280
gataccagcg gcatctcggc cgcttcggcg ctggccgcga tcgaggccgg ctgcgatgcg   2340
gtcgacggcg cgctcgacgc catgagcggg ctgacctcgc aacccaacct gtcgagcatc   2400
gccgcggccc tggccggcag cgagcgcgat cccggcctca gcctggagcg cctgcacgag   2460
```

```
gcgtcgatgt actgggaagg ggtgcgccgc tactacgcgc cgttcgaatc cgaaatccgc   2520
gccggcaccg ccgacgtgta ccgccacgag atgcccggcg ccagtacac caacctgcgc    2580 gagcaggcgc gctcgctcgg catcgagcat cgctggaccg aggtgtcgcg ggcctatgcc   2640
gaggtcaacc agatgtttgg cgacatcgtc aaggtgacgc cgacgtccaa ggtggtcggc   2700
gacctggcct tgatgatggt ggccaacgac ctgagcgccg ccgatgtgtg cgatcccgcc   2760
agggagactg ccttccctga atcggtggtg tcgctgttca agggcgagct gggctttccg   2820
ccggacggct tccccgcgga actgtcgcgc aaggtgctgc gcggcgagcc gcccgtgccg   2880
taccggcccg cgaccagat cccgccggtc gacctgacg cggcgcgcgc cgcggccgaa     2940
gcggcgtgcg agcagccgct cgacgaccgc cagctggctt cgtacctgat gtacccgaag   3000
caggccggcg agtaccacgc gcatgtgcgc aactacagcg acacctcggt ggtacccacg   3060
ccggcatacc tgtacggcct gcagccgcag gaagaagtgg cgatcgacat cgctgccggc   3120
aagaccctgc tggtctcgct gcaaggcacg caccccgatg ccgaagaggg tgtcatcaag   3180
gtccagttcg agctgaacgg gcagtcgcgc accacgctgg tcgagcagcg cagcaccacg   3240
caagcggcgg cagcgcgcca tggccgtccg gttgccgaac ccgacaatcc gctgcatgtc   3300
gccgcgccca tgccgggctc gatcgtgacg gtggcggtga gccggggca gcgcgtggcc    3360 gcgggcacga cgctgctggc gctggaggcg atgaagatgg aaacccatat cgcggcggag   3420
cgggactgcg agatcgccgc agtccatgtt cagcaggggg atcgcgtggc ggcgaaggat   3480
ctgctgatcg aactgaaggg ctga                                         3504
```

<210> SEQ ID NO 6
<211> LENGTH: 1167
<212> TYPE: PRT
<213> ORGANISM: C. necator

<400> SEQUENCE: 6

```
Met Asp Tyr Ala Pro Ile Arg Ser Leu Leu Ile Ala Asn Arg Ser Glu
1               5                   10                  15

Ile Ala Ile Arg Val Met Arg Ala Ala Ala Glu Met Asn Val Arg Thr
            20                  25                  30

Val Ala Ile Tyr Ser Lys Glu Asp Arg Leu Ala Leu His Arg Phe Lys
        35                  40                  45

Ala Asp Glu Ser Tyr Leu Val Gly Glu Gly Lys Lys Pro Leu Ala Ala
    50                  55                  60

Tyr Leu Asp Ile Asp Asp Ile Leu Arg Ile Ala Arg Gln Ala Lys Val
65                  70                  75                  80

Asp Ala Ile His Pro Gly Tyr Gly Phe Leu Ser Glu Asn Pro Asp Phe
                85                  90                  95

Ala Gln Ala Val Ile Asp Ala Gly Ile Arg Trp Ile Gly Pro Ser Pro
            100                 105                 110

Glu Val Met Arg Lys Leu Gly Asn Lys Val Ala Arg Asn Ala Ala
        115                 120                 125

Ile Asp Ala Gly Val Pro Val Met Pro Ala Thr Asp Pro Leu Pro His
    130                 135                 140

Asp Leu Asp Thr Cys Lys Arg Leu Ala Ala Gly Ile Gly Tyr Pro Leu
145                 150                 155                 160

Met Leu Lys Ala Ser Trp Gly Gly Gly Gly Arg Gly Met Arg Val Leu
                165                 170                 175

Glu Arg Glu Gln Asp Leu Glu Gly Ala Leu Ala Ala Ala Arg Arg Glu
            180                 185                 190
```

```
Ala Leu Ala Ala Phe Gly Asn Asp Glu Val Tyr Val Glu Lys Leu Val
        195                 200                 205

Arg Asn Ala Arg His Val Glu Val Gln Val Leu Gly Asp Thr His Gly
        210                 215                 220

Asn Leu Val His Leu Tyr Glu Arg Asp Cys Thr Val Gln Arg Arg Asn
225                 230                 235                 240

Gln Lys Val Val Glu Arg Ala Pro Ala Pro Tyr Leu Asp Asp Ala Gly
                245                 250                 255

Arg Ala Ala Leu Cys Glu Ser Ala Leu Arg Leu Met Arg Ala Val Gly
                260                 265                 270

Tyr Thr His Ala Gly Thr Val Glu Phe Leu Met Asp Ala Asp Ser Gly
                275                 280                 285

Gln Phe Tyr Phe Ile Glu Val Asn Pro Arg Ile Gln Val Glu His Thr
            290                 295                 300

Val Thr Glu Met Val Thr Gly Ile Asp Ile Val Lys Ala Gln Ile Arg
305                 310                 315                 320

Val Thr Glu Gly Gly His Leu Gly Met Thr Glu Asn Thr Arg Asn Glu
                325                 330                 335

Asn Gly Glu Ile Val Val Arg Ala Ala Gly Val Pro Val Gln Glu Ala
                340                 345                 350

Ile Ser Leu Asn Gly His Ala Leu Gln Cys Arg Ile Thr Thr Glu Asp
            355                 360                 365

Pro Glu Asn Gly Phe Leu Pro Asp Tyr Gly Arg Leu Thr Ala Tyr Arg
        370                 375                 380

Ser Ala Ala Gly Phe Gly Val Arg Leu Asp Ala Gly Thr Ala Tyr Gly
385                 390                 395                 400

Gly Ala Val Ile Thr Pro Tyr Tyr Asp Ser Leu Leu Val Lys Val Thr
                405                 410                 415

Thr Trp Ala Pro Thr Ala Pro Glu Ser Ile Arg Arg Met Asp Arg Ala
                420                 425                 430

Leu Arg Glu Phe Arg Ile Arg Gly Val Ala Ser Asn Leu Gln Phe Leu
        435                 440                 445

Glu Asn Val Ile Asn His Pro Ser Phe Arg Ser Gly Asp Val Thr Thr
        450                 455                 460

Arg Phe Ile Asp Leu Thr Pro Glu Leu Leu Ala Phe Thr Lys Arg Leu
465                 470                 475                 480

Asp Arg Ala Thr Lys Leu Leu Arg Tyr Leu Gly Glu Val Ser Val Asn
                485                 490                 495

Gly His Pro Glu Met Ser Gly Arg Thr Leu Pro Ser Leu Pro Leu Pro
                500                 505                 510

Ala Pro Val Leu Pro Ala Phe Asp Thr Gly Gly Ala Leu Pro Tyr Gly
            515                 520                 525

Thr Arg Asp Arg Leu Arg Glu Leu Gly Ala Glu Lys Phe Ser Arg Trp
        530                 535                 540

Met Leu Glu Gln Lys Gln Val Leu Leu Thr Asp Thr Thr Met Arg Asp
545                 550                 555                 560

Ala His Gln Ser Leu Phe Ala Thr Arg Met Arg Thr Ala Asp Met Leu
                565                 570                 575

Pro Ile Ala Pro Phe Tyr Ala Arg Glu Leu Ser Gln Leu Phe Ser Leu
            580                 585                 590

Glu Cys Trp Gly Gly Ala Thr Phe Asp Val Ala Leu Arg Phe Leu Lys
        595                 600                 605
```

```
Glu Asp Pro Trp Gln Arg Leu Glu Gln Leu Arg Glu Arg Val Pro Asn
610                 615                 620
Val Leu Phe Gln Met Leu Leu Arg Gly Ser Asn Ala Val Gly Tyr Thr
625                 630                 635                 640
Asn Tyr Ala Asp Asn Val Val Arg Phe Phe Val Arg Gln Ala Ala Ser
            645                 650                 655
Ala Gly Val Asp Val Phe Arg Val Phe Asp Ser Leu Asn Trp Val Arg
            660                 665                 670
Asn Met Arg Val Ala Ile Asp Ala Val Gly Glu Ser Gly Ala Leu Cys
            675                 680                 685
Glu Gly Ala Ile Cys Tyr Thr Gly Asp Leu Phe Asp Lys Ser Arg Ala
690                 695                 700
Lys Tyr Asp Leu Lys Tyr Tyr Val Gly Ile Ala Arg Glu Leu Lys Gln
705                 710                 715                 720
Ala Gly Val His Val Leu Gly Ile Lys Asp Met Ala Gly Ile Cys Arg
            725                 730                 735
Pro Gln Ala Ala Ala Leu Val Arg Ala Leu Lys Glu Glu Thr Gly
            740                 745                 750
Leu Pro Val His Phe His Thr His Asp Thr Ser Gly Ile Ser Ala Ala
            755                 760                 765
Ser Ala Leu Ala Ala Ile Glu Ala Gly Cys Asp Ala Val Asp Gly Ala
770                 775                 780
Leu Asp Ala Met Ser Gly Leu Thr Ser Gln Pro Asn Leu Ser Ser Ile
785                 790                 795                 800
Ala Ala Ala Leu Ala Gly Ser Glu Arg Asp Pro Gly Leu Ser Leu Glu
            805                 810                 815
Arg Leu His Glu Ala Ser Met Tyr Trp Glu Gly Val Arg Arg Tyr Tyr
            820                 825                 830
Ala Pro Phe Glu Ser Glu Ile Arg Ala Gly Thr Ala Asp Val Tyr Arg
            835                 840                 845
His Glu Met Pro Gly Gly Gln Tyr Thr Asn Leu Arg Glu Gln Ala Arg
850                 855                 860
Ser Leu Gly Ile Glu His Arg Trp Thr Glu Val Ser Arg Ala Tyr Ala
865                 870                 875                 880
Glu Val Asn Gln Met Phe Gly Asp Ile Val Lys Val Thr Pro Thr Ser
            885                 890                 895
Lys Val Val Gly Asp Leu Ala Leu Met Met Val Ala Asn Asp Leu Ser
            900                 905                 910
Ala Ala Asp Val Cys Asp Pro Ala Arg Glu Thr Ala Phe Pro Glu Ser
            915                 920                 925
Val Val Ser Leu Phe Lys Gly Glu Leu Gly Phe Pro Pro Asp Gly Phe
930                 935                 940
Pro Ala Glu Leu Ser Arg Lys Val Leu Arg Gly Glu Pro Val Pro
945                 950                 955                 960
Tyr Arg Pro Gly Asp Gln Ile Pro Pro Val Asp Leu Asp Ala Ala Arg
            965                 970                 975
Ala Ala Ala Glu Ala Ala Cys Glu Gln Pro Leu Asp Asp Arg Gln Leu
            980                 985                 990
Ala Ser Tyr Leu Met Tyr Pro Lys Gln Ala Gly Glu Tyr His Ala His
            995                 1000                1005
Val Arg Asn Tyr Ser Asp Thr Ser Val Val Pro Thr Pro Ala Tyr
    1010                1015                1020
Leu Tyr Gly Leu Gln Pro Gln Glu Glu Val Ala Ile Asp Ile Ala
```

Ala Gly Lys Thr Leu Leu Val Ser Leu Gln Gly Thr His Pro Asp
1040                1045                1050

Ala Glu Glu Gly Val Ile Lys Val Gln Phe Glu Leu Asn Gly Gln
1055                1060                1065

Ser Arg Thr Thr Leu Val Glu Gln Arg Ser Thr Thr Gln Ala Ala
1070                1075                1080

Ala Ala Arg His Gly Arg Pro Val Ala Glu Pro Asp Asn Pro Leu
1085                1090                1095

His Val Ala Ala Pro Met Pro Gly Ser Ile Val Thr Val Ala Val
1100                1105                1110

Gln Pro Gly Gln Arg Val Ala Ala Gly Thr Thr Leu Leu Ala Leu
1115                1120                1125

Glu Ala Met Lys Met Glu Thr His Ile Ala Ala Glu Arg Asp Cys
1130                1135                1140

Glu Ile Ala Ala Val His Val Gln Gln Gly Asp Arg Val Ala Ala
1145                1150                1155

Lys Asp Leu Leu Ile Glu Leu Lys Gly
1160                1165

<210> SEQ ID NO 7
<211> LENGTH: 1617
<212> TYPE: DNA
<213> ORGANISM: Actinobacillus succinogenes

<400> SEQUENCE: 7
atgactgact taaacaaact cgttaaagaa cttaatgact tagggcttac cgatgttaag      60
gaaattgtgt ataacccgag ttatgaacaa cttttcgagg aagaaaccaa accgggtttg     120
gagggtttcg ataaagggac gttaaccacg cttggcgcgg ttgccgtcga tacggggatt     180
tttaccggtc gttcaccgaa agataaatat atcgtttgcg atgaaactac gaaagacacc     240
gtttggtgga acagcgaagc ggcgaaaaac gataacaaac cgatgacgca gaaacttgg      300 aaaagtttga gagaattagt ggcgaaacaa cttccggta  aacgtttatt cgtggtagaa     360
ggttactgcg gcgccagtga aaacaccgt  atcggtgtgc gtatggttac tgaagtggca     420
tggcaggcgc attttgtgaa aaacatgttt atccgaccga ccgatgaaga gttgaaaaat     480
ttcaaagcgg attttaccgt gttaaacggt gctaatgta  ctaatccgaa ctggaaagaa     540
caaggtttga cagtgaaaaa ctttgtcgct ttcaatatta ccgaaggtat tcagcttatc     600
ggcggtactt ggtacggcgg tgaaatgaaa aaaggtatgt tctcaatgat gaactacttc     660
ctgccgttaa aggtgtggc  ttccatgcac tgttccgcca acgtaggtaa agacggtgac     720
gtggctattt tcttcggttt atccggtacg ggtaaaacaa cgcttttcga cgatcctaaa     780
cgccaattaa tcggtgatga cgaacacggt tgggatgaat ccggcgtatt taactttgaa     840
ggcggttgtt acgcgaaaac cattaactta tctcaagaaa acgaaccgga tatttacggc     900
gcaatccgtc gtgacgcatt attagaaaac gtcgtggttc gtgcagacgg ttccgttgac     960
tttgacgacg gttcaaaaac agaaaatacc cgtgtttcat atccgattta ccacatcgac    1020
aacatcgttc gtccggtatc gaaagccggt catgcaacca agtgattttt cttaaccgcg    1080
gacgcattcg gcgtattgcc gccggttcca aaactgactc cggaacaaac cgaatactac    1140
ttcttatccg gctttactgc aaaattagcg ggtacggaac gcggcgtaac cgaaccgact    1200
ccgacattct cggcctgttt cggtgcggca ttcttaagcc tgcatccgat tcaatatgcg    1260

```
gacgtgttgg tcgaacgcat gaaagcctcc ggtgcggaag cttatttggt gaacaccggt    1320
tggaacggca cgggtaaacg tatttcaatc aaagataccc gcggtattat cgatgcgatt    1380
ttggacggtt caatcgaaaa agcggaaatg ggcgaattgc caatctttaa tttagcgatt    1440
cctaaagcat taccgggtgt tgatcctgct attttggatc cgcgcgatac ttacgcagac    1500
aaagcgcaat ggcaagttaa agcggaagat ttggcaaacc gtttcgtgaa aaactttgtg    1560
aaatatacgg cgaatccgga agcggctaaa ttagttggcg ccggtccaaa agcataa       1617
```

<210> SEQ ID NO 8
<211> LENGTH: 538
<212> TYPE: PRT
<213> ORGANISM: Actinobacillus succinogenes

<400> SEQUENCE: 8

```
Met Thr Asp Leu Asn Lys Leu Val Lys Glu Leu Asn Asp Leu Gly Leu
1               5                   10                  15

Thr Asp Val Lys Glu Ile Val Tyr Asn Pro Ser Tyr Glu Gln Leu Phe
            20                  25                  30

Glu Glu Glu Thr Lys Pro Gly Leu Glu Gly Phe Asp Lys Gly Thr Leu
        35                  40                  45

Thr Thr Leu Gly Ala Val Ala Val Asp Thr Gly Ile Phe Thr Gly Arg
    50                  55                  60

Ser Pro Lys Asp Lys Tyr Ile Val Cys Asp Glu Thr Thr Lys Asp Thr
65                  70                  75                  80

Val Trp Trp Asn Ser Glu Ala Ala Lys Asn Asp Asn Lys Pro Met Thr
                85                  90                  95

Gln Glu Thr Trp Lys Ser Leu Arg Glu Leu Val Ala Lys Gln Leu Ser
            100                 105                 110

Gly Lys Arg Leu Phe Val Val Glu Gly Tyr Cys Gly Ala Ser Glu Lys
        115                 120                 125

His Arg Ile Gly Val Arg Met Val Thr Glu Val Ala Trp Gln Ala His
    130                 135                 140

Phe Val Lys Asn Met Phe Ile Arg Pro Thr Asp Glu Glu Leu Lys Asn
145                 150                 155                 160

Phe Lys Ala Asp Phe Thr Val Leu Asn Gly Ala Lys Cys Thr Asn Pro
                165                 170                 175

Asn Trp Lys Glu Gln Gly Leu Asn Ser Glu Asn Phe Val Ala Phe Asn
            180                 185                 190

Ile Thr Glu Gly Ile Gln Leu Ile Gly Gly Thr Trp Tyr Gly Gly Glu
        195                 200                 205

Met Lys Lys Gly Met Phe Ser Met Met Asn Tyr Phe Leu Pro Leu Lys
    210                 215                 220

Gly Val Ala Ser Met His Cys Ser Ala Asn Val Gly Lys Asp Gly Asp
225                 230                 235                 240

Val Ala Ile Phe Phe Gly Leu Ser Gly Thr Gly Lys Thr Thr Leu Ser
                245                 250                 255

Thr Asp Pro Lys Arg Gln Leu Ile Gly Asp Asp Glu His Gly Trp Asp
            260                 265                 270

Glu Ser Gly Val Phe Asn Phe Glu Gly Gly Cys Tyr Ala Lys Thr Ile
        275                 280                 285

Asn Leu Ser Gln Glu Asn Glu Pro Asp Ile Tyr Gly Ala Ile Arg Arg
    290                 295                 300

Asp Ala Leu Leu Glu Asn Val Val Val Arg Ala Asp Gly Ser Val Asp
305                 310                 315                 320
```

```
Phe Asp Asp Gly Ser Lys Thr Glu Asn Thr Arg Val Ser Tyr Pro Ile
            325                 330                 335

Tyr His Ile Asp Asn Ile Val Arg Pro Val Ser Lys Ala Gly His Ala
            340                 345                 350

Thr Lys Val Ile Phe Leu Thr Ala Asp Ala Phe Gly Val Leu Pro Pro
            355                 360                 365

Val Ser Lys Leu Thr Pro Glu Gln Thr Glu Tyr Tyr Phe Leu Ser Gly
        370                 375                 380

Phe Thr Ala Lys Leu Ala Gly Thr Glu Arg Gly Val Thr Glu Pro Thr
385                 390                 395                 400

Pro Thr Phe Ser Ala Cys Phe Gly Ala Ala Phe Leu Ser Leu His Pro
                405                 410                 415

Ile Gln Tyr Ala Asp Val Leu Val Glu Arg Met Lys Ala Ser Gly Ala
                420                 425                 430

Glu Ala Tyr Leu Val Asn Thr Gly Trp Asn Gly Thr Gly Lys Arg Ile
            435                 440                 445

Ser Ile Lys Asp Thr Arg Gly Ile Ile Asp Ala Ile Leu Asp Gly Ser
        450                 455                 460

Ile Glu Lys Ala Glu Met Gly Glu Leu Pro Ile Phe Asn Leu Ala Ile
465                 470                 475                 480

Pro Lys Ala Leu Pro Gly Val Asp Pro Ala Ile Leu Asp Pro Arg Asp
                485                 490                 495

Thr Tyr Ala Asp Lys Ala Gln Trp Gln Val Lys Ala Glu Asp Leu Ala
                500                 505                 510

Asn Arg Phe Val Lys Asn Phe Val Lys Tyr Thr Ala Asn Pro Glu Ala
            515                 520                 525

Ala Lys Leu Val Gly Ala Gly Pro Lys Ala
        530                 535

<210> SEQ ID NO 9
<211> LENGTH: 1857
<212> TYPE: DNA
<213> ORGANISM: R. eutropha

<400> SEQUENCE: 9
atgaaccacc cctcgatgca aggcacgacg gcgttgaacg tcccggcctg ggtcaggaac      60
cagaagctgg tggcctgggt tgcggagatc gccgcgctga ccaagccgga gcgcattcac     120
tggtgcgacg gttcgcagga agaatatgat cgcctctgcg aacagatggt cgccgcgggc     180
acgctcaagc gcctgaatcc cgccaagcgc aagaactctt acctcgccct gtccgacccg     240
tccgacgtcg cacgtgtcga agaccgcacc ttcatctgct cgcagaagaa ggaagacgcc     300
ggcccgacca caactgggt ggctccggcc gaaatgcgca cgacgctcaa cggcctgttc     360
gacggctgca tgcgcggccg cacgctgtac gtggtgccgt tctcgatggg cccgctgggc     420
tcgccgatcg cccacattgg cgtggagctg tccgattccc cgtacgtggc cgtcaacatg     480
cgcatcatga cgcgcatggg caaggccgtg tacgacgtgc tgggcaccga tggcgacttc     540
gtcccgtgcg tgcacaccgt aggcaagccg ctcgccgccg gcgagaagga tgtgccgtgg     600
ccgtgcaacc cgaccaagta catcgtccac ttcccggagt cgcgcgagat ctggtcgttc     660
ggctcggggt acggcggcaa cgcgctgctc ggcaagaagt gcttcgcact gcgtatcgca     720
tcgaccatgg ccgcgacga aggctggctg ccgagcaca tgctgatcct gggcgtgact     780
tcgcccgagg gcaagaaatt ccatgttgcg gccgcgttcc cgtcggcctg cggcaagacc     840
```

```
aacttcgcca tgctgatccc gcccaaggga ttcgaaggct ggaaggtcac gacaatcggc    900
gacgacatcg cgtggatcaa gccgggcaag gacggccgcc tgtacgcgat caacccggaa    960
gccggctact tcggcgtggc cccgggcacg agcgagaaga ccaacttcaa cgccatggcg   1020
acgctgaagg aaaacgtcat cttcaccaat gtggcgctga ccgacgacgg cgacgtgtgg   1080
tgggagggca tgaccaagga agcgccggcg catctgaccg actggcaggg caaggactgg   1140
accccggaga tcgccaaggc caccggcgcc aaggccgcgc acccgaacgc ccgcttcacc   1200
gccccggcat cgcagtgccc gtcgatcgac gagaattggg acaacccggc aggcgtaccc   1260
attgatgcgt tcatcttcgg cggccgccgc tcgaccaccg tgccgctggt gactgaggcg   1320
cgcaattgga ccgaaggcgt gtacatggct gcgaccatgg gctccgaaac caccgctgcg   1380
gccgctggcc agcagggcgt ggtgcgccgc gacccgttcg ccatgctgcc gttctgcggc   1440
tacaacatga gcgactattt tggccactgg ctcgcactgg gccaaaagct cgaagccgct   1500
ggcgcgaagc tgccgaaaat ctactgtgtg aactggttcc gcaaggacgc cgacggcaac   1560
ttcgtgtggc cgggctttgg cgagaacatg cgcgtgctgt cgtggatgat cgaccgcgtg   1620
gaaggcaaag cgagggcgc cgagcacgtg ttcgggacga cccgcgcta cgaagacctg   1680
aactggagcg gcgtggaatt ctccgtggcg cagttcacgc aggtcacgtc gatcgatgcc   1740
gatgcctgga agcaggaact ggcgctgcac gacgaactgt tcacgcaact gaagcacaac   1800
ctgccacagg cgctggccga agcgcgcgcg cgctgggca agcggctgga gggctaa     1857
```

<210> SEQ ID NO 10
<211> LENGTH: 618
<212> TYPE: PRT
<213> ORGANISM: R. eutropha

<400> SEQUENCE: 10

```
Met Asn His Pro Ser Met Gln Gly Thr Thr Ala Leu Asn Val Pro Ala
1               5                   10                  15

Trp Val Arg Asn Gln Lys Leu Val Ala Trp Val Ala Glu Ile Ala Ala
            20                  25                  30

Leu Thr Lys Pro Glu Arg Ile His Trp Cys Asp Gly Ser Gln Glu Glu
        35                  40                  45

Tyr Asp Arg Leu Cys Glu Gln Met Val Ala Ala Gly Thr Leu Lys Arg
    50                  55                  60

Leu Asn Pro Ala Lys Arg Lys Asn Ser Tyr Leu Ala Leu Ser Asp Pro
65                  70                  75                  80

Ser Asp Val Ala Arg Val Glu Asp Arg Thr Phe Ile Cys Ser Gln Lys
                85                  90                  95

Lys Glu Asp Ala Gly Pro Thr Asn Asn Trp Val Ala Pro Ala Glu Met
            100                 105                 110

Arg Thr Thr Leu Asn Gly Leu Phe Asp Gly Cys Met Arg Gly Arg Thr
        115                 120                 125

Leu Tyr Val Val Pro Phe Ser Met Gly Pro Leu Gly Ser Pro Ile Ala
    130                 135                 140

His Ile Gly Val Glu Leu Ser Asp Ser Pro Tyr Val Ala Val Asn Met
145                 150                 155                 160

Arg Ile Met Thr Arg Met Gly Lys Ala Val Tyr Asp Val Leu Gly Thr
                165                 170                 175

Asp Gly Asp Phe Val Pro Cys Val His Thr Val Gly Lys Pro Leu Ala
            180                 185                 190

Ala Gly Glu Lys Asp Val Pro Trp Pro Cys Asn Pro Thr Lys Tyr Ile
```

```
              195                 200                 205
Val His Phe Pro Glu Ser Arg Glu Ile Trp Ser Phe Gly Ser Gly Tyr
210                 215                 220

Gly Gly Asn Ala Leu Leu Gly Lys Lys Cys Phe Ala Leu Arg Ile Ala
225                 230                 235                 240

Ser Thr Met Gly Arg Asp Glu Gly Trp Leu Ala Glu His Met Leu Ile
                245                 250                 255

Leu Gly Val Thr Ser Pro Glu Gly Lys Lys Phe His Val Ala Ala Ala
                260                 265                 270

Phe Pro Ser Ala Cys Gly Lys Thr Asn Phe Ala Met Leu Ile Pro Pro
            275                 280                 285

Lys Gly Phe Glu Gly Trp Lys Val Thr Thr Ile Gly Asp Asp Ile Ala
290                 295                 300

Trp Ile Lys Pro Gly Lys Asp Gly Arg Leu Tyr Ala Ile Asn Pro Glu
305                 310                 315                 320

Ala Gly Tyr Phe Gly Val Ala Pro Gly Thr Ser Glu Lys Thr Asn Phe
                325                 330                 335

Asn Ala Met Ala Thr Leu Lys Glu Asn Val Ile Phe Thr Asn Val Ala
            340                 345                 350

Leu Thr Asp Asp Gly Asp Val Trp Glu Gly Met Thr Lys Glu Ala
            355                 360                 365

Pro Ala His Leu Thr Asp Trp Gln Gly Lys Asp Trp Thr Pro Glu Ile
370                 375                 380

Ala Lys Ala Thr Gly Ala Lys Ala Ala His Pro Asn Ala Arg Phe Thr
385                 390                 395                 400

Ala Pro Ala Ser Gln Cys Pro Ser Ile Asp Glu Asn Trp Asp Asn Pro
                405                 410                 415

Ala Gly Val Pro Ile Asp Ala Phe Ile Phe Gly Gly Arg Arg Ser Thr
            420                 425                 430

Thr Val Pro Leu Val Thr Glu Ala Arg Asn Trp Thr Glu Gly Val Tyr
            435                 440                 445

Met Ala Ala Thr Met Gly Ser Glu Thr Thr Ala Ala Ala Gly Gln
            450                 455                 460

Gln Gly Val Val Arg Arg Asp Pro Phe Ala Met Leu Pro Phe Cys Gly
465                 470                 475                 480

Tyr Asn Met Ser Asp Tyr Phe Gly His Trp Leu Ala Leu Gly Gln Lys
                485                 490                 495

Leu Glu Ala Ala Gly Ala Lys Leu Pro Lys Ile Tyr Cys Val Asn Trp
            500                 505                 510

Phe Arg Lys Asp Ala Asp Gly Asn Phe Val Trp Pro Gly Phe Gly Glu
            515                 520                 525

Asn Met Arg Val Leu Ser Trp Met Ile Asp Arg Val Glu Gly Lys Gly
            530                 535                 540

Glu Gly Ala Glu His Val Phe Gly Thr Ser Pro Arg Tyr Glu Asp Leu
545                 550                 555                 560

Asn Trp Ser Gly Val Glu Phe Ser Val Ala Gln Phe Thr Gln Val Thr
                565                 570                 575

Ser Ile Asp Ala Asp Ala Trp Lys Gln Glu Leu Ala Leu His Asp Glu
            580                 585                 590

Leu Phe Thr Gln Leu Lys His Asn Leu Pro Gln Ala Leu Ala Glu Ala
        595                 600                 605

Arg Ala Ala Leu Gly Lys Arg Leu Glu Gly
        610                 615
```

<210> SEQ ID NO 11
<211> LENGTH: 1869
<212> TYPE: DNA
<213> ORGANISM: R. solanacearum

<400> SEQUENCE: 11

| | | | | | |
|---|---|---|---|---|---|
| atgaatcaac | ccgtgatgca | gggtgttccc | gcattgaacg | tgcccgccta | tgtgaaacac | 60 |
| gcgcggctgg | tggcgtgggt | cagcgagatc | gctgcgctca | ccaagccgga | gcgcgtggtc | 120 |
| tggtgcgatg | gctcgcagga | ggaatacgac | cgcctgtgcg | ccgagatggt | cgccgccggc | 180 |
| acgctcaagc | agctcaatcc | cgccaagcgc | aagaactcgt | acctggcgct | gtccgacccc | 240 |
| tcggacgtgg | cgcgtgtgga | ggatcggacc | ttcatctgct | cgcagaagca | ggaagacgcg | 300 |
| ggcccgacca | caactggac | cgccccggcc | gagatgcgcc | agacgctgaa | cggcctgttc | 360 |
| gacggttgca | tgcgcggtcg | cacgctgtac | gtggtgccgt | tctcgatggg | cccgctgggc | 420 |
| tcgccgatcg | cgcacatcgg | cgtggagctg | tccgacagcc | gtatgtggc | cgtcaacatg | 480 |
| cgcatcatga | cccgcatggg | ccgtgccgtg | tacgacgtgc | tgggcgccga | cggcgagttc | 540 |
| gtgccgtgcg | tgcataccgt | cggtaagccg | ctggccgcgg | gtgaacagga | tgtgccgtgg | 600 |
| ccgtgcaacc | cgaccaagta | catcgtgcac | ttcccggaaa | cgcgcgagat | ctggtcgttc | 660 |
| ggctcgggct | acgcggcaa | cgcgctgctg | ggcaagaagt | gcttcgcgct | gcggatcgct | 720 |
| tccaccatgg | gccgcgacca | gggctggctg | gccgagcaca | tgctgatcct | gggcgtgacc | 780 |
| tcgcccgagg | gcaagaccta | ccacgtggcc | gcggccttcc | gtcggcctg | cggcaagacc | 840 |
| aacttcgcga | tgctgattcc | gccggccggc | ttcgacggct | ggaaggtcac | caccatcggc | 900 |
| gacgacatcg | cctggatcaa | gccgcgccag | gacgccaacg | tcagacgcg | cctgtacgcc | 960 |
| atcaacccgg | aagccggttt | cttcggtgtg | gcgccgggca | cgggcgagaa | gaccaacttc | 1020 |
| aacgcgatgg | ccacgctcaa | ggaaaacgtc | atcttcacca | acgtcgcgct | taccgatgac | 1080 |
| ggcgacgtgt | ggtgggaagg | catgaccgac | acgccgcccg | cgcacctgac | cgactggcaa | 1140 |
| ggccaggact | ggaccccggc | gatcgccaag | gaaaccggcc | gcaaggccgc | gcacccgaac | 1200 |
| tcgcgcttca | cggcgccggc | tgcgcagtgc | ccgtcgatcg | atccggagtg | ggacaacccg | 1260 |
| gccggcgtgg | ccatcgatgc | gttcatcttc | ggcggccgcc | gctcgaccac | cgtgccgctg | 1320 |
| gtgaccgaag | cgcgcgactg | gaccgaaggc | gtgtacatgg | ccgccacgat | gggctcggaa | 1380 |
| accaccgccg | ccgccgtcgg | ccagcagggc | gtggtgcgcc | gcgatccgtt | cgccatgctg | 1440 |
| ccgttctgcg | gctacaacat | ggccgactat | ttcgcgcact | ggctcaagct | gggcgaccag | 1500 |
| ctggccaaga | gcggcgccga | gctgccgaag | atcttctgcg | tcaactggtt | ccgcaaggat | 1560 |
| gagcagggcc | gcttcgtgtg | gccgggcttc | ggcgagaaca | tgcgcgtgct | gaagtggatg | 1620 |
| atcgaccgga | tcgaaggcca | ggctcgcggc | gacgagcatg | tctttggcgt | gtcgccgcgc | 1680 |
| tacgaggagc | tgcgctggga | tgggctggac | ttctccgccg | agcagttcgc | caaggtgatc | 1740 |
| tcgctggatg | cgcaggcctg | gcagcaggaa | ctgacgctgc | acgccgagct | gttcgcccag | 1800 |
| ctggcgcatc | acctgccgca | ggcgctgccg | gaagccaagg | cacgtctgga | ggcccgcctg | 1860 |
| cagggctga | | | | | 1869 |

<210> SEQ ID NO 12
<211> LENGTH: 622
<212> TYPE: PRT
<213> ORGANISM: R. solanacearum

```
<400> SEQUENCE: 12

Met Asn Gln Pro Val Met Gln Gly Val Pro Ala Leu Asn Val Pro Ala
1               5                   10                  15

Tyr Val Lys His Ala Arg Leu Val Ala Trp Val Ser Glu Ile Ala Ala
            20                  25                  30

Leu Thr Lys Pro Glu Arg Val Val Trp Cys Asp Gly Ser Gln Glu Glu
        35                  40                  45

Tyr Asp Arg Leu Cys Ala Glu Met Val Ala Gly Thr Leu Lys Gln
    50                  55                  60

Leu Asn Pro Ala Lys Arg Lys Asn Ser Tyr Leu Ala Leu Ser Asp Pro
65                  70                  75                  80

Ser Asp Val Ala Arg Val Glu Asp Arg Thr Phe Ile Cys Ser Gln Lys
                85                  90                  95

Gln Glu Asp Ala Gly Pro Thr Asn Asn Trp Thr Ala Pro Ala Glu Met
            100                 105                 110

Arg Gln Thr Leu Asn Gly Leu Phe Asp Gly Cys Met Arg Gly Arg Thr
        115                 120                 125

Leu Tyr Val Val Pro Phe Ser Met Gly Pro Leu Gly Ser Pro Ile Ala
    130                 135                 140

His Ile Gly Val Glu Leu Ser Asp Ser Pro Tyr Val Ala Val Asn Met
145                 150                 155                 160

Arg Ile Met Thr Arg Met Gly Arg Ala Val Tyr Asp Val Leu Gly Ala
                165                 170                 175

Asp Gly Glu Phe Val Pro Cys Val His Thr Val Gly Lys Pro Leu Ala
            180                 185                 190

Ala Gly Glu Gln Asp Val Pro Trp Pro Cys Asn Pro Thr Lys Tyr Ile
        195                 200                 205

Val His Phe Pro Glu Thr Arg Glu Ile Trp Ser Phe Gly Ser Gly Tyr
    210                 215                 220

Gly Gly Asn Ala Leu Leu Gly Lys Lys Cys Phe Ala Leu Arg Ile Ala
225                 230                 235                 240

Ser Thr Met Gly Arg Asp Gln Gly Trp Leu Ala Glu His Met Leu Ile
                245                 250                 255

Leu Gly Val Thr Ser Pro Glu Gly Lys Thr Tyr His Val Ala Ala Ala
            260                 265                 270

Phe Pro Ser Ala Cys Gly Lys Thr Asn Phe Ala Met Leu Ile Pro Pro
        275                 280                 285

Ala Gly Phe Asp Gly Trp Lys Val Thr Thr Ile Gly Asp Asp Ile Ala
    290                 295                 300

Trp Ile Lys Pro Arg Gln Asp Ala Asn Gly Gln Thr Arg Leu Tyr Ala
305                 310                 315                 320

Ile Asn Pro Glu Ala Gly Phe Phe Gly Val Ala Pro Gly Thr Gly Glu
                325                 330                 335

Lys Thr Asn Phe Asn Ala Met Ala Thr Leu Lys Glu Asn Val Ile Phe
            340                 345                 350

Thr Asn Val Ala Leu Thr Asp Asp Gly Asp Val Trp Trp Glu Gly Met
        355                 360                 365

Thr Asp Thr Pro Pro Ala His Leu Thr Asp Trp Gln Gly Gln Asp Trp
    370                 375                 380

Thr Pro Ala Ile Ala Lys Glu Thr Gly Arg Lys Ala Ala His Pro Asn
385                 390                 395                 400

Ser Arg Phe Thr Ala Pro Ala Ala Gln Cys Pro Ser Ile Asp Pro Glu
                405                 410                 415
```

```
Trp Asp Asn Pro Ala Gly Val Ala Ile Asp Ala Phe Ile Phe Gly Gly
                420                 425                 430

Arg Arg Ser Thr Thr Val Pro Leu Val Thr Glu Ala Arg Asp Trp Thr
            435                 440                 445

Glu Gly Val Tyr Met Ala Ala Thr Met Gly Ser Glu Thr Thr Ala Ala
        450                 455                 460

Ala Val Gly Gln Gln Gly Val Val Arg Arg Asp Pro Phe Ala Met Leu
465                 470                 475                 480

Pro Phe Cys Gly Tyr Asn Met Ala Asp Tyr Phe Ala His Trp Leu Lys
                485                 490                 495

Leu Gly Asp Gln Leu Ala Lys Ser Gly Ala Glu Leu Pro Lys Ile Phe
            500                 505                 510

Cys Val Asn Trp Phe Arg Lys Asp Glu Gln Gly Arg Phe Val Trp Pro
        515                 520                 525

Gly Phe Gly Glu Asn Met Arg Val Leu Lys Trp Met Ile Asp Arg Ile
530                 535                 540

Glu Gly Gln Ala Arg Gly Asp Glu His Val Phe Gly Val Ser Pro Arg
545                 550                 555                 560

Tyr Glu Glu Leu Arg Trp Asp Gly Leu Asp Phe Ser Ala Glu Gln Phe
                565                 570                 575

Ala Lys Val Ile Ser Leu Asp Ala Gln Ala Trp Gln Gln Glu Leu Thr
            580                 585                 590

Leu His Ala Glu Leu Phe Ala Gln Leu Ala His His Leu Pro Gln Ala
        595                 600                 605

Leu Pro Glu Ala Lys Ala Arg Leu Glu Ala Arg Leu Gln Gly
610                 615                 620

<210> SEQ ID NO 13
<211> LENGTH: 1866
<212> TYPE: DNA
<213> ORGANISM: Burkholderia pseudomallei

<400> SEQUENCE: 13
atgacccgaa gcaacgtggt cgcggcgacg cgcaccgttc cgatcgacgt tcccgaatac      60
gtgaagcacc gcggcctgat cgactgggtc gcgcgtatcg cggagttgac cgagccggat     120
cgcgttgtct ggtgcgacgg ttcgcagcag gagtacgacc gcctctgcga cgcgatggtc     180
gaacagcgca cgatggtgcg cctcaatccg gcgaagcggc cgaactcgtt tctcgcgctg     240
tccgatccgt ccgacgtcgc gcgtgtcgaa accgcacgt tcatctgcag cgagcatcgc     300
gacgacgcgg gcccgaccaa tcactgggtc gcgcccgccg aaatgcgcgc gacgctcaac     360
ggcctgtttc gcggcgcgat gcgcggccgc acgctgtacg tcgtgccgtt ctcgatgggc     420
ccgctcggct cgccgatcgc gcacatcggc gtcgagctct cggatagccc ctacgtcgtc     480
gtcaacatgc ggatcatgac gcgcatgggg gcgcgcggtgc tcgacgcgct cggcgagcgc     540
ggcgagtacg tgccgtgcgt gcacagcgtc gggcgcccgc tcgcggcggg cgagcaggat     600
gtgccgtggc cgtgcaatcc gaccaagtac atcgtgcatt ttcccgagtc gcgcgagatc     660
tggagcttcg gctcgggcta cggcggcaac gcgctcctcg gcaagaagtg cttcgcgctg     720
cggatcgcgt cgacgatggg gcgcgacgaa ggctggctcg ccgagcacat gctgatcctc     780
ggcgtgacct cgcccgaggg ccgcaagtat cacatcgccg cggcgtttcc ttccgcgtgc     840
ggcaagacca acttcgcgat gctgatcccg ccgaagggct tcgagggctg gcgcgtgacg     900
acgatcggcg acgacatcgc gtggctcaag ccgggccgcg acgggcggct gtatgcgatc     960
```

```
aacccggagg cgggctattt cggcgtcgcg ccgggcacgg gcgagaagac caatccgaac    1020
gcgctcgcga cgctcaggga gaacgtgatc ttcacgaacg tcgcgctcac ggaggacggc    1080
gacgtctggt gggaaggcct caccgacacg ccgcccgcgc ggctcaccga ttggcagggc    1140
aacgcatgga cgcccgagat cggccgcgag acgggccgca aggccgcgca tccgaactcg    1200
cgcttcacgg cgcccgcgtc gcagtgcccg tcgatcgacg acgactggga gaacccgggc    1260
ggcgtgccga tcgacgcatt catcttcggc ggccgccgct cgacgacggt gccgctcgtc    1320
accgaggcgc gcgactggat cgaaggcgtg tacatggcgg cgacgatggg ctcggagacg    1380
acggccgcgg cggcggggca gcagggcatc gtgcggcgcg atccgttcgc gatgctgccg    1440
ttctgcggct acaacatgag cgactatttc tcgcactggc tcgcgctcgg cgagaagctc    1500
gcggcggcgg gcgcgacgtt gccgaagatc tactgcgtga actggttccg caaggacgcg    1560
gacggccgct cgcgtggccc cggcttcggc gagaacatgc gcgtgctgaa gtggatgctc    1620
gaccggatcg acgccgcgg cgagggcgtc gagcacgcgt tcggcgtgac gccgcgctac    1680
gaggatctgc attgggcggg gctcgcgttc tcgcccgcgc agtatgcgca ggtcacgtcg    1740
atgaatccgg acgaatggcg cgccgagctc gcgctgcacg cggagctgtt cgacaagctg    1800
agcgcgcggc tgccggatgc gctcgccgaa acgaaggcga ggatcgagaa aaggctcggc    1860
ggctga                                                              1866
```

<210> SEQ ID NO 14
<211> LENGTH: 621
<212> TYPE: PRT
<213> ORGANISM: Burkholderia pseudomallei

<400> SEQUENCE: 14

```
Met Thr Arg Ser Asn Val Val Ala Ala Thr Arg Thr Val Pro Ile Asp
1               5                   10                  15

Val Pro Glu Tyr Val Lys His Arg Gly Leu Ile Asp Trp Val Ala Arg
            20                  25                  30

Ile Ala Glu Leu Thr Glu Pro Asp Arg Val Val Trp Cys Asp Gly Ser
        35                  40                  45

Gln Gln Glu Tyr Asp Arg Leu Cys Asp Ala Met Val Glu Gln Arg Thr
    50                  55                  60

Met Val Arg Leu Asn Pro Ala Lys Arg Pro Asn Ser Phe Leu Ala Leu
65                  70                  75                  80

Ser Asp Pro Ser Asp Val Ala Arg Val Glu Asp Arg Thr Phe Ile Cys
                85                  90                  95

Ser Glu His Arg Asp Asp Ala Gly Pro Thr Asn His Trp Val Ala Pro
            100                 105                 110

Ala Glu Met Arg Ala Thr Leu Asn Gly Leu Phe Arg Gly Ala Met Arg
        115                 120                 125

Gly Arg Thr Leu Tyr Val Val Pro Phe Ser Met Gly Pro Leu Gly Ser
    130                 135                 140

Pro Ile Ala His Ile Gly Val Glu Leu Ser Asp Ser Pro Tyr Val Val
145                 150                 155                 160

Val Asn Met Arg Ile Met Thr Arg Met Gly Arg Ala Val Leu Asp Ala
                165                 170                 175

Leu Gly Glu Arg Gly Glu Tyr Val Pro Cys Val His Ser Val Gly Arg
            180                 185                 190

Pro Leu Ala Ala Gly Glu Gln Asp Val Pro Trp Pro Cys Asn Pro Thr
        195                 200                 205
```

```
Lys Tyr Ile Val His Phe Pro Glu Ser Arg Glu Ile Trp Ser Phe Gly
    210                 215                 220
Ser Gly Tyr Gly Gly Asn Ala Leu Leu Gly Lys Lys Cys Phe Ala Leu
225                 230                 235                 240
Arg Ile Ala Ser Thr Met Gly Arg Asp Glu Gly Trp Leu Ala Glu His
                245                 250                 255
Met Leu Ile Leu Gly Val Thr Ser Pro Glu Gly Arg Lys Tyr His Ile
            260                 265                 270
Ala Ala Ala Phe Pro Ser Ala Cys Gly Lys Thr Asn Phe Ala Met Leu
        275                 280                 285
Ile Pro Pro Lys Gly Phe Glu Gly Trp Arg Val Thr Thr Ile Gly Asp
290                 295                 300
Asp Ile Ala Trp Leu Lys Pro Gly Arg Asp Gly Arg Leu Tyr Ala Ile
305                 310                 315                 320
Asn Pro Glu Ala Gly Tyr Phe Gly Val Ala Pro Gly Thr Gly Glu Lys
                325                 330                 335
Thr Asn Pro Asn Ala Leu Ala Thr Leu Arg Glu Asn Val Ile Phe Thr
            340                 345                 350
Asn Val Ala Leu Thr Glu Asp Gly Asp Val Trp Trp Glu Gly Leu Thr
        355                 360                 365
Asp Thr Pro Pro Ala Arg Leu Thr Asp Trp Gln Gly Asn Ala Trp Thr
370                 375                 380
Pro Glu Ile Gly Arg Glu Thr Gly Arg Lys Ala Ala His Pro Asn Ser
385                 390                 395                 400
Arg Phe Thr Ala Pro Ala Ser Gln Cys Pro Ser Ile Asp Asp Asp Trp
                405                 410                 415
Glu Asn Pro Gly Gly Val Pro Ile Asp Ala Phe Ile Phe Gly Gly Arg
            420                 425                 430
Arg Ser Thr Thr Val Pro Leu Val Thr Glu Ala Arg Asp Trp Ile Glu
        435                 440                 445
Gly Val Tyr Met Ala Ala Thr Met Gly Ser Glu Thr Thr Ala Ala Ala
450                 455                 460
Ala Gly Gln Gln Gly Ile Val Arg Arg Asp Pro Phe Ala Met Leu Pro
465                 470                 475                 480
Phe Cys Gly Tyr Asn Met Ser Asp Tyr Phe Ser His Trp Leu Ala Leu
                485                 490                 495
Gly Glu Lys Leu Ala Ala Ala Gly Ala Thr Leu Pro Lys Ile Tyr Cys
            500                 505                 510
Val Asn Trp Phe Arg Lys Asp Ala Asp Gly Arg Phe Ala Trp Pro Gly
        515                 520                 525
Phe Gly Glu Asn Met Arg Val Leu Lys Trp Met Leu Asp Arg Ile Asp
530                 535                 540
Gly Arg Gly Glu Gly Val Glu His Ala Phe Gly Val Thr Pro Arg Tyr
545                 550                 555                 560
Glu Asp Leu His Trp Ala Gly Leu Ala Phe Ser Pro Ala Gln Tyr Ala
                565                 570                 575
Gln Val Thr Ser Met Asn Pro Asp Glu Trp Arg Ala Glu Leu Ala Leu
            580                 585                 590
His Ala Glu Leu Phe Asp Lys Leu Ser Ala Arg Leu Pro Asp Ala Leu
        595                 600                 605
Ala Glu Thr Lys Ala Arg Ile Glu Lys Arg Leu Gly Gly
610                 615                 620
```

<210> SEQ ID NO 15
<211> LENGTH: 1857
<212> TYPE: DNA
<213> ORGANISM: C. taiwanensis

<400> SEQUENCE: 15

| | | | | | |
|---|---|---|---|---|---|
| atgaaccacc | ccacgatgca | aggtacggcc | gccgtcaatg | cgccggcctg | ggtcaagcac | 60 |
| cccaagctga | ttgcctgggt | cgcggaaatc | gccgcgctga | ccaagccaga | caacatctac | 120 |
| tggtgcgacg | gctcgcagga | agaatatgac | cgcctgtgcg | agcagatggt | cgcggccggc | 180 |
| accatgaagc | ggctgaaccc | ggccaagcgc | aagaactcct | tcctggccct | gtcggacccg | 240 |
| tcagacgtgg | cgcgcgtcga | agaccgtacc | ttcatctgct | ccgagaagca | ggaagacgcc | 300 |
| ggcccgacca | caactggac | cccgccggcc | gagatgcgcc | agacgctggc | cggcctgttc | 360 |
| gacggctgca | tgcgcggccg | caccctgtat | gtggtgccgt | tctcgatggg | accgctgggt | 420 |
| cgccgatcg | cccatatcgg | cgtggaactg | tccgattcgc | cgtatgtggc | ggtcaatatg | 480 |
| cgcatcatga | cccgcatggg | caaggccgtg | tacgaggtgc | tgggtagcga | cggcgccttc | 540 |
| gtgccgtgcg | tgcacaccgt | gggcaagccg | ctggcggctg | gcgagaaaga | cgtggcgtgg | 600 |
| ccgtgcaatc | ccaccaagta | catccgtgcat | tccccggaaa | cgcgcgagat | ctggtcgttc | 660 |
| ggctcgggct | acggcggcaa | tgcgctgctg | ggcaagaagt | gcttcgcgct | cgtattgcc | 720 |
| tcgaccatgg | gccgcgacga | aggctggctc | gccgagcaca | tgctgatcct | cggcgtgacc | 780 |
| tcgcccgagg | gcaagaaata | ccatgtcgcc | gccgccttcc | gtcggcctg | cggcaagacc | 840 |
| aacttcgcca | tgctgatccc | gcccaagggc | ttcgagggct | ggaaggtcac | caccatcggc | 900 |
| gacgacatcg | cctggatcaa | gccgggcaag | gacggccgcc | tgtacgcgat | caacccggaa | 960 |
| gccggctact | cggcgtggc | gccgggcacc | agcgagaaga | ccaactacaa | cgcgatggcg | 1020 |
| acgctgaagg | aaaacgtcat | cttcaccaac | gtggcgctga | ccgacgacgg | cgacgtctgg | 1080 |
| tgggaaggca | tgaccaagga | agcgcccgcg | cacctgatcg | actggcaggg | caaggactgg | 1140 |
| accccggaga | tcgccaaggc | caccggcgcc | aaggccgcgc | accgaacgc | gcgcttcacc | 1200 |
| gcgcccgcgt | cgcaatgccc | gtcgatcgac | gacaactggg | acaacccggc | cggcgtaccc | 1260 |
| atcgatgcgt | tcatcttcgg | cggccgccgc | tcgaccacgg | tgccgctggt | gaccgaggca | 1320 |
| cgcgactgga | ccgaaggcgt | ctacatggcc | gccaccatgg | gctcggaaac | caccgccgcg | 1380 |
| gccgccggcc | agcaaggcgt | ggtgcgccgc | gacccgttcg | ccatgctgcc | gttctgcggc | 1440 |
| tacaacatga | gcgactactt | cggccactgg | ctcgaactgg | gcaagaagct | cgaagccgcg | 1500 |
| ggcgcgaagc | tgccgaagat | ctactgcgtc | aactggttcc | gcaaggatgc | cgacggcaac | 1560 |
| ttcgtgtggc | cgggctttgg | cgagaacatg | cgcgtgctgt | cgtggatgat | cgaccgcgtc | 1620 |
| gaaggccggg | ggcagggcgc | cgagcatgtg | ttcggcacct | cgccgcgcta | ccaggacctg | 1680 |
| aactggaacg | cgtcgagtt | ctcgccggcg | cagttcgagc | aggtgacctc | gatcgaccgc | 1740 |
| gacgcctggc | agaaggagct | ggcgctgcat | gacgagctgt | tcacgcaact | gaagcaccat | 1800 |
| ctgccgcagg | cactggcgca | gacgcgcgcg | gcgctcggca | gcgactcga | cggctaa | 1857 |

<210> SEQ ID NO 16
<211> LENGTH: 618
<212> TYPE: PRT
<213> ORGANISM: C. taiwanensis

<400> SEQUENCE: 16

Met Asn His Pro Thr Met Gln Gly Thr Ala Ala Val Asn Ala Pro Ala

-continued

```
1               5                   10                  15

Trp Val Lys His Pro Lys Leu Ile Ala Trp Val Ala Glu Ile Ala Ala
                20                  25                  30

Leu Thr Lys Pro Asp Asn Ile Tyr Trp Cys Asp Gly Ser Gln Glu Glu
                35                  40                  45

Tyr Asp Arg Leu Cys Glu Gln Met Val Ala Ala Gly Thr Met Lys Arg
            50                  55                  60

Leu Asn Pro Ala Lys Arg Lys Asn Ser Phe Leu Ala Leu Ser Asp Pro
65                  70                  75                  80

Ser Asp Val Ala Arg Val Glu Asp Arg Thr Phe Ile Cys Ser Glu Lys
                85                  90                  95

Gln Glu Asp Ala Gly Pro Thr Asn Asn Trp Thr Pro Ala Glu Met
            100                 105                 110

Arg Gln Thr Leu Ala Gly Leu Phe Asp Gly Cys Met Arg Gly Arg Thr
                115                 120                 125

Leu Tyr Val Val Pro Phe Ser Met Gly Pro Leu Gly Ser Pro Ile Ala
            130                 135                 140

His Ile Gly Val Glu Leu Ser Asp Ser Pro Tyr Val Ala Val Asn Met
145                 150                 155                 160

Arg Ile Met Thr Arg Met Gly Lys Ala Val Tyr Glu Val Leu Gly Ser
                165                 170                 175

Asp Gly Ala Phe Val Pro Cys Val His Thr Val Gly Lys Pro Leu Ala
            180                 185                 190

Ala Gly Glu Lys Asp Val Ala Trp Pro Cys Asn Pro Thr Lys Tyr Ile
            195                 200                 205

Val His Phe Pro Glu Thr Arg Glu Ile Trp Ser Phe Gly Ser Gly Tyr
210                 215                 220

Gly Gly Asn Ala Leu Leu Gly Lys Lys Cys Phe Ala Leu Arg Ile Ala
225                 230                 235                 240

Ser Thr Met Gly Arg Asp Glu Gly Trp Leu Ala Glu His Met Leu Ile
                245                 250                 255

Leu Gly Val Thr Ser Pro Glu Gly Lys Lys Tyr His Val Ala Ala Ala
            260                 265                 270

Phe Pro Ser Ala Cys Gly Lys Thr Asn Phe Ala Met Leu Ile Pro Pro
            275                 280                 285

Lys Gly Phe Glu Gly Trp Lys Val Thr Thr Ile Gly Asp Asp Ile Ala
290                 295                 300

Trp Ile Lys Pro Gly Lys Asp Gly Arg Leu Tyr Ala Ile Asn Pro Glu
305                 310                 315                 320

Ala Gly Tyr Phe Gly Val Ala Pro Gly Thr Ser Glu Lys Thr Asn Tyr
                325                 330                 335

Asn Ala Met Ala Thr Leu Lys Glu Asn Val Ile Phe Thr Asn Val Ala
                340                 345                 350

Leu Thr Asp Asp Gly Asp Val Trp Trp Glu Gly Met Thr Lys Glu Ala
                355                 360                 365

Pro Ala His Leu Ile Asp Trp Gln Gly Lys Asp Trp Thr Pro Glu Ile
            370                 375                 380

Ala Lys Ala Thr Gly Ala Lys Ala His Pro Asn Ala Arg Phe Thr
385                 390                 395                 400

Ala Pro Ala Ser Gln Cys Pro Ser Ile Asp Asp Trp Asp Asn Pro
                405                 410                 415

Ala Gly Val Pro Ile Asp Ala Phe Ile Phe Gly Gly Arg Arg Ser Thr
            420                 425                 430
```

```
Thr Val Pro Leu Val Thr Glu Ala Arg Asp Trp Thr Glu Gly Val Tyr
        435                 440                 445

Met Ala Ala Thr Met Gly Ser Glu Thr Thr Ala Ala Ala Ala Gly Gln
    450                 455                 460

Gln Gly Val Val Arg Arg Asp Pro Phe Ala Met Leu Pro Phe Cys Gly
465                 470                 475                 480

Tyr Asn Met Ser Asp Tyr Phe Gly His Trp Leu Glu Leu Gly Lys Lys
                485                 490                 495

Leu Glu Ala Ala Gly Ala Lys Leu Pro Lys Ile Tyr Cys Val Asn Trp
            500                 505                 510

Phe Arg Lys Asp Ala Asp Gly Asn Phe Val Trp Pro Gly Phe Gly Glu
        515                 520                 525

Asn Met Arg Val Leu Ser Trp Met Ile Asp Arg Val Glu Gly Arg Gly
    530                 535                 540

Gln Gly Ala Glu His Val Phe Gly Thr Ser Pro Arg Tyr Gln Asp Leu
545                 550                 555                 560

Asn Trp Asn Gly Val Glu Phe Ser Pro Ala Gln Phe Glu Gln Val Thr
                565                 570                 575

Ser Ile Asp Arg Asp Ala Trp Gln Lys Glu Leu Ala Leu His Asp Glu
            580                 585                 590

Leu Phe Thr Gln Leu Lys His His Leu Pro Gln Ala Leu Ala Gln Thr
        595                 600                 605

Arg Ala Ala Leu Gly Lys Arg Leu Asp Gly
    610                 615

<210> SEQ ID NO 17
<211> LENGTH: 1857
<212> TYPE: DNA
<213> ORGANISM: R. metallidurans

<400> SEQUENCE: 17
atgaaccacc ccacaatgca aggcactccg gcactgaacg tgccggcttg ggtcaagaac      60
cagaaactgg tcgcctgggt tgccgacatc gccgcattga ccaagcccga ccaggtctac     120
tggtgcgatg gctcgcagga agaatatgac cgcctgtgcg agcagatggt cgccgccggc     180
acgatgcgcc gcctgaaccc ggccaagcgc aagaactcgt tcctggccct gtcggatccc     240
tccgatgtgg cacgtgtcga agaccgcact ttcatctgct cgcagaagca ggaagacgcc     300
ggcccgacca caactggac cgcaccggcc gaaatgcgcc agacgctgaa cggcctgttc     360
gacggctgca tgcgtggccg caccctgtac gtggtgccgt tctcgatggg cccgctgggt     420 cgccgatcg cccacatcgg cgtcgagctg tccgattcgc cgtacgtcgc cgtgaacatg     480
cgcatcatga cccgcatggg ccgcgccgtg tacgacgtgc tgggtgccga cggcgagttc     540
gtgccgtgcg tgcataccgt gggcaagcct ctggccgccg gcgagaagga cgtggcatgg     600
ccgtgcaatc cgaccaagta catcgtgcac ttccccgaga cgcgcgaaat ctggtcgttc     660
ggttcgggct acggcggcaa tgcgctgctg ggcaagaagt gcttcgcact gcggatcgcc     720
tcgacgatgg ccgcgacga aggctggctg ccgagcaca tgctgatcct cggcgtgacc     780
tcgccggaag caagaagta ccacgtggct gccgcgttcc cgtcggcctg cggcaagacc     840
aacttcgcca tgctgatccc gcccaagggc ttcgagggct ggaaggtcac gacgatcgt     900 gacgacatcg cctggatcaa gcaggcaag acggccgcc tgtacgccat caacccggaa     960
gccggctact tcggcgtggc cccgggcacg agcgagaaga ccaacttcaa cgcgatggcg    1020
```

```
acgctcaagg aaaacgtcat cttcaccaac gtggcactga ccgacgacgg cgacgtgtgg    1080
tgggaaggca tgacgaagga agccccggcg cacctgatcg actggcaggg caaggactgg    1140
acgcccgaga tcgccaagtc gaccggcgcc aaggctgccc acccgaacgc ccgcttcacc    1200
gcgccggcct cgcaatgccc gtcgatcgac gacaactggg acaacccggc tggcgtggcc    1260
atcgatgcat tcatcttcgg cggccgccgc agctccaccg tgccactggt gaccgaagcc    1320
cgcaactgga ccgaaggcgt ctacatggcc gccacgatgg gttcggaaac caccgccgcc    1380
gctgccggcc agcaaggcgt ggtccgccgc gatccgttcg cgatgctgcc gttctgcggc    1440
tacaacatga cgactactt cggccactgg ctggcgttgg gcaagaagct cgaagccgcc    1500
ggtgccaagc tgccgcgcat ctactgcgtg aactggttcc gcaaggacgc cgacggcaac    1560
ttcgtgtggc cgggctttgg cgagaacatg cgcgtgctgt cgtggatgat cgaccgcgtg    1620
gaaggccgtg gcgaaggcgc cgagcacgtg ttcggcacgt cgccgcgcta cacggacctg    1680
aactggaacg gcctggcctt caccgccgag caattcaccc aggtcacgtc gatcgaccgt    1740
gacgcatggc aaaaggaact ggcgctgcac gacgaactgt tcacgcagct caagcacaac    1800
ctgccgcaag cgctggcgga aaccaaggac gcactggcca agcgcctgtc ggcctga      1857
```

<210> SEQ ID NO 18
<211> LENGTH: 618
<212> TYPE: PRT
<213> ORGANISM: R. metallidurans

<400> SEQUENCE: 18

```
Met Asn His Pro Thr Met Gln Gly Thr Pro Ala Leu Asn Val Pro Ala
1               5                   10                  15

Trp Val Lys Asn Gln Lys Leu Val Ala Trp Val Ala Asp Ile Ala Ala
            20                  25                  30

Leu Thr Lys Pro Asp Gln Val Tyr Trp Cys Asp Gly Ser Gln Glu Glu
        35                  40                  45

Tyr Asp Arg Leu Cys Glu Gln Met Val Ala Ala Gly Thr Met Arg Arg
    50                  55                  60

Leu Asn Pro Ala Lys Arg Lys Asn Ser Phe Leu Ala Leu Ser Asp Pro
65                  70                  75                  80

Ser Asp Val Ala Arg Val Glu Asp Arg Thr Phe Ile Cys Ser Gln Lys
                85                  90                  95

Gln Glu Asp Ala Gly Pro Thr Asn Asn Trp Thr Ala Pro Ala Glu Met
            100                 105                 110

Arg Gln Thr Leu Asn Gly Leu Phe Asp Gly Cys Met Arg Gly Arg Thr
        115                 120                 125

Leu Tyr Val Val Pro Phe Ser Met Gly Pro Leu Gly Ser Pro Ile Ala
    130                 135                 140

His Ile Gly Val Glu Leu Ser Asp Ser Pro Tyr Val Ala Val Asn Met
145                 150                 155                 160

Arg Ile Met Thr Arg Met Gly Arg Ala Val Tyr Asp Val Leu Gly Ala
                165                 170                 175

Asp Gly Glu Phe Val Pro Cys Val His Thr Val Gly Lys Pro Leu Ala
            180                 185                 190

Ala Gly Glu Lys Asp Val Ala Trp Pro Cys Asn Pro Thr Lys Tyr Ile
        195                 200                 205

Val His Phe Pro Glu Thr Arg Glu Ile Trp Ser Phe Gly Ser Gly Tyr
    210                 215                 220

Gly Gly Asn Ala Leu Leu Gly Lys Lys Cys Phe Ala Leu Arg Ile Ala
```

|   | 225 |   |   | 230 |   |   | 235 |   |   | 240 |   |
|---|---|---|---|---|---|---|---|---|---|---|---|

Ser Thr Met Gly Arg Asp Glu Gly Trp Leu Ala Glu His Met Leu Ile
                245                 250                 255

Leu Gly Val Thr Ser Pro Glu Gly Lys Lys Tyr His Val Ala Ala Ala
                260                 265                 270

Phe Pro Ser Ala Cys Gly Lys Thr Asn Phe Ala Met Leu Ile Pro Pro
                275                 280                 285

Lys Gly Phe Glu Gly Trp Lys Val Thr Thr Ile Gly Asp Asp Ile Ala
                290                 295                 300

Trp Ile Lys Pro Gly Lys Asp Gly Arg Leu Tyr Ala Ile Asn Pro Glu
305                 310                 315                 320

Ala Gly Tyr Phe Gly Val Ala Pro Gly Thr Ser Glu Lys Thr Asn Phe
                325                 330                 335

Asn Ala Met Ala Thr Leu Lys Glu Asn Val Ile Phe Thr Asn Val Ala
                340                 345                 350

Leu Thr Asp Asp Gly Asp Val Trp Trp Glu Gly Met Thr Lys Glu Ala
                355                 360                 365

Pro Ala His Leu Ile Asp Trp Gln Gly Lys Asp Trp Thr Pro Glu Ile
370                 375                 380

Ala Lys Ser Thr Gly Ala Lys Ala His Pro Asn Ala Arg Phe Thr
385                 390                 395                 400

Ala Pro Ala Ser Gln Cys Pro Ser Ile Asp Asp Asn Trp Asp Asn Pro
                405                 410                 415

Ala Gly Val Ala Ile Asp Ala Phe Ile Phe Gly Gly Arg Arg Ser Ser
                420                 425                 430

Thr Val Pro Leu Val Thr Glu Ala Arg Asn Trp Thr Glu Gly Val Tyr
                435                 440                 445

Met Ala Ala Thr Met Gly Ser Glu Thr Thr Ala Ala Ala Gly Gln
                450                 455                 460

Gln Gly Val Val Arg Arg Asp Pro Phe Ala Met Leu Pro Phe Cys Gly
465                 470                 475                 480

Tyr Asn Met Ser Asp Tyr Phe Gly His Trp Leu Ala Leu Gly Lys Lys
                485                 490                 495

Leu Glu Ala Ala Gly Ala Lys Leu Pro Arg Ile Tyr Cys Val Asn Trp
                500                 505                 510

Phe Arg Lys Asp Ala Asp Gly Asn Phe Val Trp Pro Gly Phe Gly Glu
                515                 520                 525

Asn Met Arg Val Leu Ser Trp Met Ile Asp Arg Val Glu Gly Arg Gly
                530                 535                 540

Glu Gly Ala Glu His Val Phe Gly Thr Ser Pro Arg Tyr Thr Asp Leu
545                 550                 555                 560

Asn Trp Asn Gly Leu Ala Phe Thr Ala Glu Gln Phe Thr Gln Val Thr
                565                 570                 575

Ser Ile Asp Arg Asp Ala Trp Gln Lys Glu Leu Ala Leu His Asp Glu
                580                 585                 590

Leu Phe Thr Gln Leu Lys His Asn Leu Pro Gln Ala Leu Ala Glu Thr
                595                 600                 605

Lys Asp Ala Leu Ala Lys Arg Leu Ser Ala
610                 615

<210> SEQ ID NO 19
<211> LENGTH: 3339
<212> TYPE: DNA
<213> ORGANISM: R. eutropha

<400> SEQUENCE: 19

```
atgctggggc gggtgcccca tgcctcaccg ctatccgaca tgaatccgcc gaagctcctg        60
atcgccaacc gcggcgaaat cgccatccgc atcgcccgcg cggcagcggc cctggacatg       120
ccgagcgtgg ccatccacag cgaggacgac cgcgacgcgc tgcacgtgcg caaggccgat       180
gatgccgtgg cgctgcccgg cagcggtccg cgcgcttatc tcgatatcga acaggtggtt       240
gccgccgcg ggcgcgccgg ctgccagcta gttcatcccg gctatgggtt cctgtccgag       300
aacgcggact cgcgcaggc ctgtctggac gcgggtctga tcttcgtcgg tccggcgccc       360
gatgtgctgc ggctcttcgg cgacaaggcg cgggcgcgcg cactggcccg cgaacatggc       420
gtgccagtgg tgccgggaac gaccgggccc accacgctgg ccgaagcaca tgccttcttt       480
gccgacttgc cgaacggtac cggcatgatg atcaaggcgc tggccggcgg cggcggacgc       540
ggcatgcgtg cagtccatga tgtggcgcag atcgacgaag catggacacg ttgcgcgtcg       600
gaagcgacgg cggcattcgg caacggcgcg gtctatgtcg aacagatcgt cacggcgccg       660
cgccacatcg aaattcaggt ggtcgcggac accaatgggc aagtcgtcac gctcggcgaa       720
cgcgagtgca gcctgcaacg ccgccaccag aagctcgtgg aagtcgcgcc cagccccgcg       780
ctcgacgatg cgacgcgcgc gcgcctcgcc gaggctgccg ccacgctggc acgcgcggcc       840
gcgtaccggg gcatcggcac gtttgaattc cttgtgcagg aacgcgacgg ccagccgccc       900
gcgttctggt tcatggaagc caacccgcgc ctgcaggtcg aacataccgt gaccgagatg       960
gtcaccggcg tggatctcgt gcaaacccaa ctcgccattg cgatgggcgc agatctcgcg      1020
caactgagta tggcacgcgc gccggtaccg cgcggcgttg ccgtgcagct gcgcatcaat      1080
gccgaacatc tcgacggaca gggcaacctg cgcccggccg cgggcacgct caccgcgttc      1140
gaggcgccga gcggccccgg cgtgcgggtc gatagcgcgg gctacgcggg catggcagcc      1200
aacccgcgct tcgactcgct gctcgcaaag ctgatcgtgc acgaacccag cggcaactac      1260
gcacgtgcgc tgggtctggc gtaccgcgcg ctgtgcaagt ccgcatcga gggcatcaac      1320
accaaccggc gcctgctgca ggacttgctg caacaggacg ccgtgcagcg caacgcggtc      1380
cacacgcaat accttgacca tgcattgcct gcgctcgccg cagccgatag cgatcatcct      1440
gcgctgcatg ccaccgcaac cgcgatcccg gagcagcacc ccgacgacga ggatggcctg      1500
cccaccgatg cgttcgccgt gcaggcgccg atggacggcg cgctggccgc actccatgtg      1560
aagccgggcg acaccgtgcg ccgtggccag ccgctagccg tcatcgaagc gatgaagatg      1620
gagcacccgg tcgaggcacc agccgccggc accgtgctgg ccgtgcggac ggaggccggc      1680
gccaccgtac gtgccggcgc cacgctggtg ctgatcgaag ccggcgacga caccggccat      1740
gccgagcagg cctgcgccgc cgctgatctc gagcatatcc gcgccgacct gcgcgaagcg      1800
ctcgagcgcc acgcactcgg ccacgatgcc gcgcgcgacg ctgccgtggc aaaacgccac      1860
gcacagggcg gccgtaccgc gcgcgagaac atcgcgcaac tatgcgacgc cgactccttc      1920
atcgaatacg gcgcgctggc catcgcggcc cagcgccagc gccgcacgga agacgacctg      1980
atccgctcga cgccggccga tggcatcgtc accggcatcg gcaccgtgaa tgcggagcag      2040
cttcccgatg ctgacgcgcg ttgcatggtc ctcgcctacg actacacggt gctggccggc      2100
acgcagggct actacggcca caagaagctg gaccgcatgc tcgccctggc gcggcagtgg      2160
cgactgccgg tggtgctgtt cgccgaaggt ggcggcggcc gccccggcga caccgacatg      2220
ccggtagtgg ctggactcga ctgcacctcg ttcatccagt tcgcgcggct ttccggccaa      2280
```

```
gtgccgctgg tcggaatcgt gcacgggcgc tgcttcgccg gcaatgcggc gctgctcggc    2340
tgcgccgacg tgatcatcgc cacgcgtagc gcgaccatcg gcatgggcgg cccggccatg    2400
atcgagggcg gcggcctcgg cgtgtacgca cccgaggaag tcggcccggt cggcgtgcag    2460
gcgcccaatg gcgtcatcga tgtcgtcgtc gacgacgagc aggccgctgt cgacaccgcg    2520
cgccgctacc tggcctactt ccagggcgat gcccccggct ggcggggcga agacccacgc    2580
catctgcgcc atgcgattcc cgagaaccgc ctgcgcagct acgacatgcg tgccgtcatc    2640
cacgcgctgg cggacacaga ttccgtgctc gaactgcgcg ctgcgttcgg caccggcatc    2700
atcaccgcgc tgatccgcat cgaaggccgt gcgttcggct gcatcgccaa caacccgcgc    2760
cacctcggcg gcgcgatcga cagcgccgcc ggggacaagg ccgcacgctt catgcagctg    2820
tgcgatgcgc acggcctgcc gatcctgtcg ctgtgcgaca caccgggctt catggtcggc    2880
ccgcaggccg agaaaagcgc cacggtgcgc cacgtctcgc gcctgttcgt ggtggccggc    2940
gcgctgcgcg tgccgttctt cacagttgtg ctgcgcaagg gctacgggct cggcgcgcaa    3000
gcgatggccg cggcagcttt gccgcgccg ttcttcacgg cagcgtggcc aagcggcgaa    3060
tttggcgcca tggggctgga gggttcgatc cggctcggct ccgcaagga actggaagcc    3120
gtggccgacc ccgacgagcg cgaggcgctg ttcgcgcgca tggtcgatgc cgcgtaccaa    3180
cgcggccgcg cactgaacat ggcgagccac ctcgagatcg acgccgtgat cgaccctgcc    3240
gacacgcgcc gctggctgtt gcgcggcctc gcctcggtgc cgccccgcag cctcgggcgg    3300
cgcactggcg aggaccgccg cttcatcgac acctggtaa                          3339
```

<210> SEQ ID NO 20
<211> LENGTH: 1112
<212> TYPE: PRT
<213> ORGANISM: R. eutropha

<400> SEQUENCE: 20

```
Met Leu Gly Arg Val Pro His Ala Ser Pro Leu Ser Asp Met Asn Pro
1               5                   10                  15

Pro Lys Leu Leu Ile Ala Asn Arg Gly Glu Ile Ala Ile Arg Ile Ala
            20                  25                  30

Arg Ala Ala Ala Leu Asp Met Pro Ser Val Ala Ile His Ser Glu
        35                  40                  45

Asp Asp Arg Asp Ala Leu His Val Arg Lys Ala Asp Ala Val Ala
    50                  55                  60

Leu Pro Gly Ser Gly Pro Arg Ala Tyr Leu Asp Ile Glu Gln Val Val
65                  70                  75                  80

Ala Ala Ala Arg Arg Ala Gly Cys Gln Leu Val His Pro Gly Tyr Gly
                85                  90                  95

Phe Leu Ser Glu Asn Ala Asp Phe Ala Gln Ala Cys Leu Asp Ala Gly
            100                 105                 110

Leu Ile Phe Val Gly Pro Ala Pro Asp Val Leu Arg Leu Phe Gly Asp
        115                 120                 125

Lys Ala Arg Ala Arg Ala Leu Ala Arg Glu His Gly Val Pro Val Val
    130                 135                 140

Pro Gly Thr Thr Gly Pro Thr Thr Leu Ala Glu Ala His Ala Phe Phe
145                 150                 155                 160

Ala Asp Leu Pro Asn Gly Thr Gly Met Met Ile Lys Ala Leu Ala Gly
                165                 170                 175

Gly Gly Gly Arg Gly Met Arg Ala Val His Asp Val Ala Gln Ile Asp
            180                 185                 190
```

-continued

Glu Ala Trp Thr Arg Cys Ala Ser Glu Ala Thr Ala Ala Phe Gly Asn
    195                 200                 205

Gly Ala Val Tyr Val Glu Gln Ile Val Thr Ala Pro Arg His Ile Glu
    210                 215                 220

Ile Gln Val Val Ala Asp Thr Asn Gly Gln Val Val Thr Leu Gly Glu
225                 230                 235                 240

Arg Glu Cys Ser Leu Gln Arg Arg His Gln Lys Leu Val Glu Val Ala
                245                 250                 255

Pro Ser Pro Ala Leu Asp Asp Ala Thr Arg Ala Arg Leu Ala Glu Ala
            260                 265                 270

Ala Ala Thr Leu Ala Arg Ala Ala Tyr Arg Gly Ile Gly Thr Phe
        275                 280                 285

Glu Phe Leu Val Gln Glu Arg Asp Gly Gln Pro Pro Ala Phe Trp Phe
    290                 295                 300

Met Glu Ala Asn Pro Arg Leu Gln Val Glu His Thr Val Thr Glu Met
305                 310                 315                 320

Val Thr Gly Val Asp Leu Val Gln Thr Gln Leu Ala Ile Ala Met Gly
                325                 330                 335

Ala Asp Leu Ala Gln Leu Ser Met Ala Arg Ala Pro Val Pro Arg Gly
            340                 345                 350

Val Ala Val Gln Leu Arg Ile Asn Ala Glu His Leu Asp Gly Gln Gly
        355                 360                 365

Asn Leu Arg Pro Ala Ala Gly Thr Leu Thr Ala Phe Glu Ala Pro Ser
    370                 375                 380

Gly Pro Gly Val Arg Val Asp Ser Ala Gly Tyr Ala Gly Met Ala Ala
385                 390                 395                 400

Asn Pro Arg Phe Asp Ser Leu Leu Ala Lys Leu Ile Val His Glu Pro
                405                 410                 415

Ser Gly Asn Tyr Ala Arg Ala Leu Gly Leu Ala Tyr Arg Ala Leu Cys
            420                 425                 430

Lys Phe Arg Ile Glu Gly Ile Asn Thr Asn Arg Arg Leu Leu Gln Asp
        435                 440                 445

Leu Leu Gln Gln Asp Ala Val Gln Arg Asn Ala Val His Thr Gln Tyr
    450                 455                 460

Leu Asp His Ala Leu Pro Ala Leu Ala Ala Asp Ser Asp His Pro
465                 470                 475                 480

Ala Leu His Ala Thr Ala Thr Ala Ile Pro Glu Gln His Pro Asp Asp
                485                 490                 495

Glu Asp Gly Leu Pro Thr Asp Ala Phe Ala Val Gln Ala Pro Met Asp
            500                 505                 510

Gly Ala Leu Ala Ala Leu His Val Lys Pro Gly Asp Thr Val Arg Arg
        515                 520                 525

Gly Gln Pro Leu Ala Val Ile Glu Ala Met Lys Met Glu His Pro Val
    530                 535                 540

Glu Ala Pro Ala Ala Gly Thr Val Leu Ala Val Arg Thr Glu Ala Gly
545                 550                 555                 560

Ala Thr Val Arg Ala Gly Ala Thr Leu Val Leu Ile Glu Ala Gly Asp
                565                 570                 575

Asp Thr Gly His Ala Glu Gln Ala Cys Ala Ala Ala Asp Leu Glu His
            580                 585                 590

Ile Arg Ala Asp Leu Arg Glu Ala Leu Glu Arg His Ala Leu Gly His
        595                 600                 605

Asp Ala Ala Arg Asp Ala Ala Val Ala Lys Arg His Ala Gln Gly Gly
610                 615                 620

Arg Thr Ala Arg Glu Asn Ile Ala Gln Leu Cys Asp Ala Asp Ser Phe
625                 630                 635                 640

Ile Glu Tyr Gly Ala Leu Ala Ile Ala Ala Gln Arg Gln Arg Thr
            645                 650                 655

Glu Asp Asp Leu Ile Arg Ser Thr Pro Ala Asp Gly Ile Val Thr Gly
            660                 665                 670

Ile Gly Thr Val Asn Ala Glu Gln Leu Pro Asp Ala Asp Ala Arg Cys
        675                 680                 685

Met Val Leu Ala Tyr Asp Tyr Thr Val Leu Ala Gly Thr Gln Gly Tyr
690                 695                 700

Tyr Gly His Lys Lys Leu Asp Arg Met Leu Ala Leu Ala Arg Gln Trp
705                 710                 715                 720

Arg Leu Pro Val Val Leu Phe Ala Glu Gly Gly Gly Arg Pro Gly
            725                 730                 735

Asp Thr Asp Met Pro Val Val Ala Gly Leu Asp Cys Thr Ser Phe Ile
            740                 745                 750

Gln Phe Ala Arg Leu Ser Gly Gln Val Pro Leu Val Gly Ile Val His
    755                 760                 765

Gly Arg Cys Phe Ala Gly Asn Ala Ala Leu Leu Gly Cys Ala Asp Val
770                 775                 780

Ile Ile Ala Thr Arg Ser Ala Thr Ile Gly Met Gly Gly Pro Ala Met
785                 790                 795                 800

Ile Glu Gly Gly Gly Leu Gly Val Tyr Ala Pro Glu Glu Val Gly Pro
            805                 810                 815

Val Gly Val Gln Ala Pro Asn Gly Val Ile Asp Val Val Asp Asp
            820                 825                 830

Glu Gln Ala Ala Val Asp Thr Ala Arg Arg Tyr Leu Ala Tyr Phe Gln
        835                 840                 845

Gly Asp Ala Pro Gly Trp Arg Gly Glu Asp Pro Arg His Leu Arg His
850                 855                 860

Ala Ile Pro Glu Asn Arg Leu Arg Ser Tyr Asp Met Arg Ala Val Ile
865                 870                 875                 880

His Ala Leu Ala Asp Thr Asp Ser Val Leu Glu Leu Arg Ala Ala Phe
            885                 890                 895

Gly Thr Gly Ile Ile Thr Ala Leu Ile Arg Ile Glu Gly Arg Ala Phe
            900                 905                 910

Gly Cys Ile Ala Asn Asn Pro Arg His Leu Gly Gly Ala Ile Asp Ser
        915                 920                 925

Ala Ala Gly Asp Lys Ala Ala Arg Phe Met Gln Leu Cys Asp Ala His
930                 935                 940

Gly Leu Pro Ile Leu Ser Leu Cys Asp Thr Pro Gly Phe Met Val Gly
945                 950                 955                 960

Pro Gln Ala Glu Lys Ser Ala Thr Val Arg His Val Ser Arg Leu Phe
            965                 970                 975

Val Val Ala Gly Ala Leu Arg Val Pro Phe Phe Thr Val Val Leu Arg
            980                 985                 990

Lys Gly Tyr Gly Leu Gly Ala Gln Ala Met Ala Gly Gly Ser Phe Ala
        995                 1000                1005

Ala Pro Phe Phe Thr Ala Ala Trp Pro Ser Gly Glu Phe Gly Ala
        1010                1015                1020

Met Gly Leu Glu Gly Ser Ile Arg Leu Gly Phe Arg Lys Glu Leu

| | | | | | | | | | | | |
|---|---|---|---|---|---|---|---|---|---|---|---|
| | | 1025 | | | | 1030 | | | | 1035 | |

Glu Ala Val Ala Asp Pro Asp Glu Arg Glu Ala Leu Phe Ala Arg
    1040                                 1045                            1050

Met Val Asp Ala Ala Tyr Gln Arg Gly Arg Ala Leu Asn Met Ala
    1055                                 1060                            1065

Ser His Leu Glu Ile Asp Ala Val Ile Asp Pro Ala Asp Thr Arg
    1070                                 1075                            1080

Arg Trp Leu Leu Arg Gly Leu Ala Ser Val Pro Pro Arg Ser Leu
    1085                                 1090                            1095

Gly Arg Arg Thr Gly Glu Asp Arg Arg Phe Ile Asp Thr Trp
    1100                                 1105                            1110

<210> SEQ ID NO 21
<211> LENGTH: 3318
<212> TYPE: DNA
<213> ORGANISM: R. eutropha

<400> SEQUENCE: 21

```
ttgaacaagc tgttgatcgc caatcggggc gagattgcct tgcgcgtgct gcgcgcggca      60
cgcgacctgg atatcgccac ggtggccgtg tattcgcagg acgacgccag ctcgcggcat     120
cgtatgctgg ctgacgaggc gattgccctc gacggctcag ggccggccgc ctatatcgac     180
attgcgggaa tcatcaccgc cgcgaaggca tccggttgcg atgcgatcca cccgggctat     240
ggcttcctga gcgagcgcgc tgattttgcg caggcgtgcg ccgacgccgg catccggttc     300
atcgggccga cggtcgaaca gcttgcgttg tttggcgaca agggaagggc gcttgagctg     360
gcgatggaaa gcgatgtgcg cgtcatgccc gccacgcgcg gcggtgcttc gctcgaagac     420
atcacgagct tcttcgacaa gcagggcgat gccggcgtgg tgatcaaggc cgttggcggc     480
ggcggtggcc gcggcatgcg cgtggtcagg cggcgcgaag acctggccga agcgtatgcg     540
cgctgccggt cggaggcagc ttccgcgttc ggcgtcgatg cgctgtacgc cgaacggcta     600
gtgagccgcg cgcgccatat cgaagtgcag atcgccggcg acggcaccca tgtcgtcgcg     660
ctgggcgagc gtgactgcac cttgcagcgc cgcttccaga aactcgtgga gatcgcgccg     720
agccccgtgc tgcggcccca gctgcgcgac gagatcatca agtccgccct gaggcttgcg     780
cgctgtgtga attaccgcag ccttggcacg ttcgaattcc tggtcgagga aacggaatcg     840
ggcgagcaga aggacttcgt ctttatcgaa gccaaccccg cctgcaggt cgaacacacc     900
atcaccgagc aggtcaccgg tgtcgacctt gtcgcgctgc agatcggcct cgcggcaggg     960
cgcacgcttg ccgatctcgg gctggacccg cgtcgccgc cgcaacccaa gggctttgcg    1020
atccaggtgc gcatcaacgc ggaaagtacc gatgcacagg ggcttgcgcg tcccgcgtat    1080
ggccggctca aacgcttcga tccgccgtcc ggtcccgacg tccgcgtcga ttcccacggc    1140
tacaccggct atgagccgtc gcccaacttc gacacgctgc tcgccaagct gatcgtcagc    1200
agcgccgcac caaagttcga ggccgccgtg cggcgcctgc agcgcagcct ggcggagttc    1260
cgcatcgtcg gcgtgccgac caacatcaac ctgctgcgcg cgctggtgca gcgcgacgac    1320
ttcctcacgc aggatgtcca tacccgccac ttcgaggcga tcctgccggc gctggcggct    1380
tcggcagagg cggtcgcgga agccggccgc gcgcaggagg cgctgctcgg cgatgcctct    1440
cgctcgcccg ctgcacacgc gtccagatcg catgaagccg aggaagaagt cgaggacggc    1500
ctcgtggcaa tccgtgcccc gctgaccggc cgcgtcgtgg agatcgccgt tggtcttgac    1560
gagatcgtca agcccggaca gaccgttgcc gtgctcgatg ccatgaagat ggaacacgcg    1620
```

-continued

```
atcaccgccg aatgcggtgg ccgcgtggtc gacctgcggc tggagaaggg tgcgctggca    1680
gcggaaggcc agatcctgat cgtggtggag caggttgagg cggagggcgt ggcggtggat    1740
gcggcgcaga aggccgaccc gaacgccatc cgcgcggatc tgcagcgcgt gctggaccgg    1800
cacgcgtttc tcgatgacgc cgcgcgtccc gacgccgtcg cgcggcgccg ctcgcgtggc    1860
cagcgcactg cgcgcgagaa tctggccgac ctgtgcgatg ccgataccct cgtggaatat    1920
ggcgggctgg cccttgcggc gcagtcgtct cgccgtacga aggacgatct catcgtcaac    1980
acgcccgcgg acgggctgat caccggcatc ggcaacatca cggcgcact ggtcggcaag    2040 gaccgtgcgc gcagcgcggt catggcctac gacgcgacgg tgctcgccgg gacgcaaggc    2100
aagcgcaacc atatcaagac cgaccgtatc gtcgaagtgg cgttgcgcga tgaactgccg    2160
ctggtgctgt cgccgaagg cggtggcggc cggcccggag atgtcgattt cccgtctgtg    2220
tcaggcctct accagccgtc ctttgccgcg ttcgcggaac tgagcggcga ggtgccggtg    2280
gtcggcatcg tgtcgggccg ctgctttgcg ggcaatgcgg ctttcctcgg ctgctgcgac    2340
gtgatcatcg ccgacaagtc ggccaacatc ggcatgcagg gccccgcgat gatcgaaggg    2400
ggcggtctcg gcatctaccg ccccgaagag gtcggtcccg cgcccgtgca gttcgccaat    2460
ggcgtgatcg acgtgctggt agagaacgag gcggaagccg tgcaggtcgc gaagcactac    2520
ctgtccatgt tccagggacg cgtcgagcac tggagtgcgc cggacccgct ggcgctgcgc    2580
catgtcgttc ctgaaaaccg tctgcgcgtg tacgacacgc gcaaggccat agaaggcatt    2640
gccgatgccg gcagcgtgct gatgctgcgc ggcgggtttg gcgcgggcat ccacaccgcg    2700
ctggcgcgcg tggaagggca gcggttggc atcatggcca acaaccccta ccacctcggc    2760
ggcgccatcg acgccgatgc ggccgacaag gcatcgcgct tcatgcagct gtgcgatgcg    2820
catgggctgc cgatcgtctc gctgatcgac acgccgggat tcatggtcgg gccggagtgc    2880
gaagcgcaag cgcaggtgcg gcacgtatcg cgcatgttcc tcacagccgc gaagctgcgc    2940
gtcgcgctgc tggccgtgac gctgcgcaag gctatgggc ttggcgccat ggcgatggcg    3000
ggcggtggct ccgctccgc gagcttcact gtctcgtggc ccaccggcga gttcggaccg    3060
atgggtctgg aagtgccgt gagactgggc ttcaagaagg aactcgaagc agtgccggat    3120
ggccccgagc gcaaggcgct gttcgaccag ctcgtcgggc agtcctatga gcgcgggcat    3180
gcgatcaata cagcagcggc cgtggagatc gatgccgtga tcgacccggc ccagacccgg    3240
aaatggatcg cgcagggcat cgcctccgcc gaactgcgaa gccgccgcgc gcgccgcggc    3300
ttcgtcgatg catggtga                                                  3318
```

<210> SEQ ID NO 22
<211> LENGTH: 1105
<212> TYPE: PRT
<213> ORGANISM: R. eutropha

<400> SEQUENCE: 22

```
Met Asn Lys Leu Leu Ile Ala Asn Arg Gly Glu Ile Ala Leu Arg Val
1               5                   10                  15

Leu Arg Ala Ala Arg Asp Leu Asp Ile Ala Thr Val Ala Val Tyr Ser
            20                  25                  30

Gln Asp Asp Ala Ser Ser Arg His Arg Met Leu Ala Asp Glu Ala Ile
        35                  40                  45

Ala Leu Asp Gly Ser Gly Pro Ala Ala Tyr Ile Asp Ile Ala Gly Ile
    50                  55                  60

Ile Thr Ala Ala Lys Ala Ser Gly Cys Asp Ala Ile His Pro Gly Tyr
```

```
            65                  70                  75                  80
Gly Phe Leu Ser Glu Arg Ala Asp Phe Ala Gln Ala Cys Ala Asp Ala
                85                  90                  95

Gly Ile Arg Phe Ile Gly Pro Thr Val Glu Gln Leu Ala Leu Phe Gly
                100                 105                 110

Asp Lys Gly Arg Ala Leu Glu Leu Ala Met Glu Ser Asp Val Arg Val
                115                 120                 125

Met Pro Ala Thr Arg Gly Gly Ala Ser Leu Glu Asp Ile Thr Ser Phe
                130                 135                 140

Phe Asp Lys Gln Gly Asp Ala Gly Val Val Ile Lys Ala Val Gly Gly
145                 150                 155                 160

Gly Gly Gly Arg Gly Met Arg Val Val Arg Arg Glu Asp Leu Ala
                165                 170                 175

Glu Ala Tyr Ala Arg Cys Arg Ser Glu Ala Ala Ser Ala Phe Gly Val
                180                 185                 190

Asp Ala Leu Tyr Ala Glu Arg Leu Val Ser Arg Ala Arg His Ile Glu
                195                 200                 205

Val Gln Ile Ala Gly Asp Gly Thr His Val Val Ala Leu Gly Glu Arg
                210                 215                 220

Asp Cys Thr Leu Gln Arg Arg Phe Gln Lys Leu Val Glu Ile Ala Pro
225                 230                 235                 240

Ser Pro Val Leu Arg Pro Gln Leu Arg Asp Glu Ile Ile Lys Ser Ala
                245                 250                 255

Leu Arg Leu Ala Arg Cys Val Asn Tyr Arg Ser Leu Gly Thr Phe Glu
                260                 265                 270

Phe Leu Val Glu Glu Thr Glu Ser Gly Glu Gln Lys Asp Phe Val Phe
                275                 280                 285

Ile Glu Ala Asn Pro Arg Leu Gln Val Glu His Thr Ile Thr Glu Gln
                290                 295                 300

Val Thr Gly Val Asp Leu Val Ala Leu Gln Ile Gly Leu Ala Ala Gly
305                 310                 315                 320

Arg Thr Leu Ala Asp Leu Gly Leu Asp Pro Ala Ser Pro Gln Pro
                325                 330                 335

Lys Gly Phe Ala Ile Gln Val Arg Ile Asn Ala Glu Ser Thr Asp Ala
                340                 345                 350

Gln Gly Leu Ala Arg Pro Ala Tyr Gly Arg Leu Glu Arg Phe Asp Pro
                355                 360                 365

Pro Ser Gly Pro Asp Val Arg Val Asp Ser His Gly Tyr Thr Gly Tyr
                370                 375                 380

Glu Pro Ser Pro Asn Phe Asp Thr Leu Leu Ala Lys Leu Ile Val Ser
385                 390                 395                 400

Ser Ala Ala Pro Lys Phe Glu Ala Ala Val Arg Arg Leu Gln Arg Ser
                405                 410                 415

Leu Ala Glu Phe Arg Ile Val Gly Val Pro Thr Asn Ile Asn Leu Leu
                420                 425                 430

Arg Ala Leu Val Gln Arg Asp Asp Phe Leu Thr Gln Asp Val His Thr
                435                 440                 445

Arg His Phe Glu Ala Ile Leu Pro Ala Leu Ala Ala Ser Ala Glu Ala
                450                 455                 460

Val Ala Glu Ala Gly Arg Ala Gln Glu Ala Leu Leu Gly Asp Ala Ser
465                 470                 475                 480

Arg Ser Pro Ala Ala His Ala Ser Arg Ser His Glu Ala Glu Glu Glu
                485                 490                 495
```

```
Val Glu Asp Gly Leu Val Ala Ile Arg Ala Pro Leu Thr Gly Arg Val
            500                 505                 510

Val Glu Ile Ala Val Gly Leu Asp Glu Ile Val Lys Pro Gly Gln Thr
        515                 520                 525

Val Ala Val Leu Asp Ala Met Lys Met Glu His Ala Ile Thr Ala Glu
    530                 535                 540

Cys Gly Gly Arg Val Val Asp Leu Arg Leu Glu Lys Gly Ala Leu Ala
545                 550                 555                 560

Ala Glu Gly Gln Ile Leu Ile Val Val Glu Gln Val Glu Ala Glu Gly
                565                 570                 575

Val Ala Val Asp Ala Ala Gln Lys Ala Asp Pro Asn Ala Ile Arg Ala
            580                 585                 590

Asp Leu Gln Arg Val Leu Asp Arg His Ala Phe Leu Asp Asp Ala Ala
        595                 600                 605

Arg Pro Asp Ala Val Ala Arg Arg Ser Arg Gly Gln Arg Thr Ala
    610                 615                 620

Arg Glu Asn Leu Ala Asp Leu Cys Asp Ala Asp Thr Phe Val Glu Tyr
625                 630                 635                 640

Gly Gly Leu Ala Leu Ala Ala Gln Ser Ser Arg Arg Thr Lys Asp Asp
                645                 650                 655

Leu Ile Val Asn Thr Pro Ala Asp Gly Leu Ile Thr Gly Ile Gly Asn
            660                 665                 670

Ile Asn Gly Ala Leu Val Gly Lys Asp Arg Ala Arg Ser Ala Val Met
        675                 680                 685

Ala Tyr Asp Ala Thr Val Leu Ala Gly Thr Gln Gly Lys Arg Asn His
    690                 695                 700

Ile Lys Thr Asp Arg Ile Val Glu Val Ala Leu Arg Asp Glu Leu Pro
705                 710                 715                 720

Leu Val Leu Phe Ala Glu Gly Gly Gly Arg Pro Gly Asp Val Asp
                725                 730                 735

Phe Pro Ser Val Ser Gly Leu Tyr Gln Pro Ser Phe Ala Ala Phe Ala
            740                 745                 750

Glu Leu Ser Gly Glu Val Pro Val Gly Ile Val Ser Gly Arg Cys
        755                 760                 765

Phe Ala Gly Asn Ala Ala Phe Leu Gly Cys Cys Asp Val Ile Ile Ala
    770                 775                 780

Asp Lys Ser Ala Asn Ile Gly Met Ala Gly Pro Ala Met Ile Glu Gly
785                 790                 795                 800

Gly Gly Leu Gly Ile Tyr Arg Pro Glu Glu Val Gly Pro Ala Pro Val
                805                 810                 815

Gln Phe Ala Asn Gly Val Ile Asp Val Leu Val Glu Asn Glu Ala Glu
            820                 825                 830

Ala Val Gln Val Ala Lys His Tyr Leu Ser Met Phe Gln Gly Arg Val
        835                 840                 845

Glu His Trp Ser Ala Pro Asp Pro Leu Ala Leu Arg His Val Val Pro
    850                 855                 860

Glu Asn Arg Leu Arg Val Tyr Asp Thr Arg Lys Ala Ile Glu Gly Ile
865                 870                 875                 880

Ala Asp Ala Gly Ser Val Leu Met Leu Arg Gly Gly Phe Gly Ala Gly
                885                 890                 895

Ile His Thr Ala Leu Ala Arg Val Glu Gly Gln Ala Val Gly Ile Met
            900                 905                 910
```

```
Ala Asn Asn Pro Tyr His Leu Gly Gly Ala Ile Asp Ala Asp Ala Ala
            915                 920                 925

Asp Lys Ala Ser Arg Phe Met Gln Leu Cys Asp Ala His Gly Leu Pro
        930                 935                 940

Ile Val Ser Leu Ile Asp Thr Pro Gly Phe Met Val Gly Pro Glu Cys
945                 950                 955                 960

Glu Ala Gln Ala Gln Val Arg His Val Ser Arg Met Phe Leu Thr Ala
            965                 970                 975

Ala Lys Leu Arg Val Ala Leu Leu Ala Val Thr Leu Arg Lys Gly Tyr
            980                 985                 990

Gly Leu Gly Ala Met Ala Met Ala Gly Gly Gly Phe Arg Ser Ala Ser
            995                 1000                1005

Phe Thr Val Ser Trp Pro Thr Gly Glu Phe Gly Pro Met Gly Leu
    1010                1015                1020

Glu Gly Ala Val Arg Leu Gly Phe Lys Lys Glu Leu Glu Ala Val
    1025                1030                1035

Pro Asp Gly Pro Glu Arg Lys Ala Leu Phe Asp Gln Leu Val Gly
    1040                1045                1050

Gln Ser Tyr Glu Arg Gly His Ala Ile Asn Thr Ala Ala Ala Val
    1055                1060                1065

Glu Ile Asp Ala Val Ile Asp Pro Ala Gln Thr Arg Lys Trp Ile
    1070                1075                1080

Ala Gln Gly Ile Ala Ser Ala Glu Leu Arg Ser Arg Arg Ala Arg
    1085                1090                1095

Arg Gly Phe Val Asp Ala Trp
    1100                1105

<210> SEQ ID NO 23
<211> LENGTH: 3510
<212> TYPE: DNA
<213> ORGANISM: R. eutropha

<400> SEQUENCE: 23
atgaactaca cccccaatcaa atccctgctg attgccaacc gatccgaaat cgcgattcgc     60
gtgatgcgcg ccgccgccga gatgaacatc cgcacggttg cgatctattc gaaggaagac    120
cggctcgcgc tccatcgctt caaggccgat gaaagctacc ttgtcggcga gggcaagaag    180
ccgctggcgg cctacctcga tatcgacgac atcttgcgca ttgcgcgcca ggcgaaggtc    240
gacgccattc acccgggcta cggcttcctc tcggagaacc ctgatttcgc gcaggccgtg    300
atggatgccg gtatccgctg gatcggcccg tcgcccgatg tcatgcgcaa gctcggcaac    360
aaggtcgcgg cgcgcaatgc cgcgatcgag gcgggcgtgc cggtgatgcc ggccaccgac    420
ccgttgccgc aagatctgga cgagtgcaag cgcctggcag ccggcatcgg ctatccgcta    480
atgctcaagg cgagctgggg tggcggcgga cgcggcatgc gtatgctgga gaatgaacag    540
gatctcgaaa cgttgctgcc ggcggcaagg cgggaggcgc tggctgcgtt cggcaacgat    600
gaggtctatg tcgagaaact ggtacgcaat gcgcgccacg tcgaagtgca ggcgctcggc    660
gatacgcatg caacctggt gcacctgtac gagcgcgatt gtaccgtgca gcggcgcaac    720
cagaaggtgg tggagcgcgc gcctgcgcca tacctcgacg ccgccggtcg cgcagcactg    780
tgcgacgcgg cgatgcggct gatgcgcgcg gtcggctaca gcatgcgggg cacgatcgaa    840
ttcctgatgg atgccgactc cggccagttc tacttcatcg aagtcaatcc gcgcatccag    900
gtcgagcaca cggtcaccga gatggtcacc ggcgtcgata tcgtcaaggc gcagatccgc    960
```

```
atcactgaag gcggccatat cggcatgacc gagaacacgc gcgacgctga gggcaagatc    1020
gtggtgcgcg ctgcgggtgt gccggaacag tcggggattt cgctgaacgg gcatgccttg    1080
caatgccgga tcaccacaga ggaccctgag aacggcttcc tgcccgacta tggccgcctg    1140
tccgcgtatc gcagcgccgc aggcttcggc gtgcggctcg atgccggcac cgcctacggc    1200
ggcgcggtga tcacgcccta ctacgattcg ctgctggtca aggtcacgac ctgggcgccc    1260
actgctcccg agtcgatccg gcgcatggac cgcgcgctgc gcgagttccg catccgcggc    1320
gtcgcgtcca acctgcagtt cctcgagaac gtcatcaacc acccatcgtt caaggccggt    1380
gacgtcacca cgcgctttat cgacaagacg cccgaactgc tggcgttcac caagcggcag    1440
gatcgcgcga ccaagctgct gcactatctc ggcgatgtct gcgtcaatgg ccatccagaa    1500
atggcgggcc gctcgctgcc gtccttgcca ctgcccgcac cggtgcttcc ctcggtagac    1560
gcaacgagcc cggtgccgac cggcacgcgc gatctgctgc gcgagcttgg tgcagagaag    1620
ttctcgcaat ggatgctcga gcagaagcgg gtgctgctga ccgacaccac catgcgcgat    1680
gcgcaccagt cgctgttcgc cacgcgcatg cgcaccgccg acatgctgcc gatcgcgccg    1740
ttctacgcgc gcgaactgcc gcagctgttc tcgatggagt gctggggtgg cgcgacgttc    1800
gatgtggcgc tgcgcttcct caaggaagac ccgtggcagc gtctcgagca actgcgcgag    1860
cgggtgccga acatcctgtt ccagatgctg ttgcgcggct cgaacgcggt cggctacacc    1920
aactacgcgg acaacgtggt gaagttcttc gtgcgccagg ccgccagcgc cggcgtggac    1980
gtgttccgcg tgttcgattc cctgaactgg gtgcgcaata tgcgcgtggc catcgatgcc    2040
gtgggcgaaa gcggcgcgct atgcgaaggc gcgatctgct acaccggcga cgtcttcgac    2100
ggctcccgtc ccaagtacga cctgaagtac tacgtcggca tcgcgcgcga gctgaagcag    2160
gccggcgtgc atgtgctggg catcaaggac atggccggca tctgccgtcc gcaagcggcg    2220
gccgcgctgg tcaaggcgct caaggaagag accggcctgc ccgtgcactt ccatacccac    2280
gacaccagcg gcatctcggc cgcgtccgcg ctggccgcca tcgaggcagg ctgcgatgca    2340
gtggatggtg cgctcgatgc catgagcgga ctgacgtcgc aaccgaacct gtctagcatc    2400
gcggcggcgc tggccggcag cgagcgcgac ccggggctca gcctggagcg gctgcacgag    2460
gcgtcgatgt actgggaagg cgtgcgtcgc tactacgcgc cgttcgagtc ggaaatccgc    2520
gcgggtaccg ccgatgtcta ccgccacgaa atgcccggcg ccagtacac caacctgcgc    2580 gagcaggcac gttcgctcgg tatcgagcat cgctggaccg aggtgtcgcg cgcgtacgca    2640
gacgtcaaca agatgttcgg cgatatcgtg aaggtgacgc cgacttcaaa ggtagtcggc    2700
gacatggcgc tgatgatggt cgccaacgac atgagcgcag ccgacgtctg cgatccggcc    2760
cgcgaagttg ccttccccga atcggtggtc tcgctgttca agggcgagct gggcttcccg    2820
cccgacggct tccccgcgga actgtcgcgc aaggtgctgc gcggcgagcc gcccgcacct    2880
taccgcccgg gcgaccagat tccgcggtt gacctcgagg cagcgcgcgc cgaagccagc    2940
gcggcgtgcg aacagcctgt cgacgaccgc cagctggcgt cgtacctgat gtatcccaag    3000
caggccgttg cttatcacgc gcacgtgcgc acctacagcg atacctcggt ggtgccgacg    3060
ccggccttcc tgtacggcct gcagccacag gaagaagtgg gcatcgacat cgagccgggc    3120
aagacgctgc tggtatcgct gcagggcacg catgccgacg cggaagaggg caacatcaag    3180
gtccagttcg aactgaacgg gcagtcgcgc acgcggtga tcgagcagcg cagcaccgtg    3240
caggccggta cgtcacgcca cagccgtccg gttgcggacc ctgagaatcc gctgcatatc    3300
gccgcgccga tgccaggctc gatcgtgacc gtagcggtcc agccgggcca acgcgtggcg    3360
```

```
gcgggcacga cgctgattgc gttggaagcc atgaagatgg aaacccacat cgcggctgag    3420
cgcgactgtg agatcgcggc cgtgcatgtg aagtctggtg accgggtgtc ggcgaaggat    3480
ctgctgatcg agctgaaggg aacggagtaa                                     3510
```

<210> SEQ ID NO 24
<211> LENGTH: 1169
<212> TYPE: PRT
<213> ORGANISM: R. eutropha

<400> SEQUENCE: 24

```
Met Asn Tyr Thr Pro Ile Lys Ser Leu Leu Ile Ala Asn Arg Ser Glu
1               5                   10                  15

Ile Ala Ile Arg Val Met Arg Ala Ala Ala Glu Met Asn Ile Arg Thr
            20                  25                  30

Val Ala Ile Tyr Ser Lys Glu Asp Arg Leu Ala Leu His Arg Phe Lys
        35                  40                  45

Ala Asp Glu Ser Tyr Leu Val Gly Glu Gly Lys Lys Pro Leu Ala Ala
    50                  55                  60

Tyr Leu Asp Ile Asp Asp Ile Leu Arg Ile Ala Arg Gln Ala Lys Val
65                  70                  75                  80

Asp Ala Ile His Pro Gly Tyr Gly Phe Leu Ser Glu Asn Pro Asp Phe
                85                  90                  95

Ala Gln Ala Val Met Asp Ala Gly Ile Arg Trp Ile Gly Pro Ser Pro
            100                 105                 110

Asp Val Met Arg Lys Leu Gly Asn Lys Val Ala Ala Arg Asn Ala Ala
        115                 120                 125

Ile Glu Ala Gly Val Pro Val Met Pro Ala Thr Asp Pro Leu Pro Gln
    130                 135                 140

Asp Leu Asp Glu Cys Lys Arg Leu Ala Ala Gly Ile Gly Tyr Pro Leu
145                 150                 155                 160

Met Leu Lys Ala Ser Trp Gly Gly Gly Arg Gly Met Arg Met Leu
                165                 170                 175

Glu Asn Glu Gln Asp Leu Glu Thr Leu Leu Pro Ala Ala Arg Arg Glu
            180                 185                 190

Ala Leu Ala Ala Phe Gly Asn Asp Glu Val Tyr Val Glu Lys Leu Val
        195                 200                 205

Arg Asn Ala Arg His Val Glu Val Gln Ala Leu Gly Asp Thr His Gly
    210                 215                 220

Asn Leu Val His Leu Tyr Glu Arg Asp Cys Thr Val Gln Arg Arg Asn
225                 230                 235                 240

Gln Lys Val Val Glu Arg Ala Pro Ala Pro Tyr Leu Asp Ala Ala Gly
                245                 250                 255

Arg Ala Ala Leu Cys Asp Ala Ala Met Arg Leu Met Arg Ala Val Gly
            260                 265                 270

Tyr Thr His Ala Gly Thr Ile Glu Phe Leu Met Asp Ala Asp Ser Gly
        275                 280                 285

Gln Phe Tyr Phe Ile Glu Val Asn Pro Arg Ile Gln Val Glu His Thr
    290                 295                 300

Val Thr Glu Met Val Thr Gly Val Asp Ile Val Lys Ala Gln Ile Arg
305                 310                 315                 320

Ile Thr Glu Gly Gly His Ile Gly Met Thr Glu Asn Thr Arg Asp Ala
                325                 330                 335

Glu Gly Lys Ile Val Val Arg Ala Ala Gly Val Pro Glu Gln Ser Gly
```

-continued

```
                340             345             350
Ile Ser Leu Asn Gly His Ala Leu Gln Cys Arg Ile Thr Thr Glu Asp
        355                 360                 365

Pro Glu Asn Gly Phe Leu Pro Asp Tyr Gly Arg Leu Ser Ala Tyr Arg
    370                 375                 380

Ser Ala Ala Gly Phe Gly Val Arg Leu Asp Ala Gly Thr Ala Tyr Gly
385                 390                 395                 400

Gly Ala Val Ile Thr Pro Tyr Tyr Asp Ser Leu Leu Lys Val Thr
                405                 410                 415

Thr Trp Ala Pro Thr Ala Pro Glu Ser Ile Arg Arg Met Asp Arg Ala
                420                 425                 430

Leu Arg Glu Phe Arg Ile Arg Gly Val Ala Ser Asn Leu Gln Phe Leu
        435                 440                 445

Glu Asn Val Ile Asn His Pro Ser Phe Lys Ala Gly Asp Val Thr Thr
    450                 455                 460

Arg Phe Ile Asp Lys Thr Pro Glu Leu Leu Ala Phe Thr Lys Arg Gln
465                 470                 475                 480

Asp Arg Ala Thr Lys Leu Leu His Tyr Leu Gly Asp Val Cys Val Asn
                485                 490                 495

Gly His Pro Glu Met Ala Gly Arg Ser Leu Pro Ser Leu Pro Leu Pro
            500                 505                 510

Ala Pro Val Leu Pro Ser Val Asp Ala Thr Ser Pro Val Pro Thr Gly
        515                 520                 525

Thr Arg Asp Leu Leu Arg Glu Leu Gly Ala Glu Lys Phe Ser Gln Trp
    530                 535                 540

Met Leu Glu Gln Lys Arg Val Leu Leu Thr Asp Thr Thr Met Arg Asp
545                 550                 555                 560

Ala His Gln Ser Leu Phe Ala Thr Arg Met Arg Thr Ala Asp Met Leu
                565                 570                 575

Pro Ile Ala Pro Phe Tyr Ala Arg Glu Leu Pro Gln Leu Phe Ser Met
            580                 585                 590

Glu Cys Trp Gly Gly Ala Thr Phe Asp Val Ala Leu Arg Phe Leu Lys
        595                 600                 605

Glu Asp Pro Trp Gln Arg Leu Glu Gln Leu Arg Glu Arg Val Pro Asn
    610                 615                 620

Ile Leu Phe Gln Met Leu Leu Arg Gly Ser Asn Ala Val Gly Tyr Thr
625                 630                 635                 640

Asn Tyr Ala Asp Asn Val Val Lys Phe Phe Val Arg Gln Ala Ala Ser
                645                 650                 655

Ala Gly Val Asp Val Phe Arg Val Phe Asp Ser Leu Asn Trp Val Arg
            660                 665                 670

Asn Met Arg Val Ala Ile Asp Ala Val Gly Glu Ser Gly Ala Leu Cys
        675                 680                 685

Glu Gly Ala Ile Cys Tyr Thr Gly Asp Val Phe Asp Gly Ser Arg Pro
    690                 695                 700

Lys Tyr Asp Leu Lys Tyr Tyr Val Gly Ile Ala Arg Glu Leu Lys Gln
705                 710                 715                 720

Ala Gly Val His Val Leu Gly Ile Lys Asp Met Ala Gly Ile Cys Arg
                725                 730                 735

Pro Gln Ala Ala Ala Ala Leu Val Lys Ala Leu Lys Glu Glu Thr Gly
            740                 745                 750

Leu Pro Val His Phe His Thr His Asp Thr Ser Gly Ile Ser Ala Ala
        755                 760                 765
```

-continued

Ser Ala Leu Ala Ala Ile Glu Ala Gly Cys Asp Ala Val Asp Gly Ala
770             775                 780

Leu Asp Ala Met Ser Gly Leu Thr Ser Gln Pro Asn Leu Ser Ser Ile
785                 790                 795                 800

Ala Ala Ala Leu Ala Gly Ser Glu Arg Asp Pro Gly Leu Ser Leu Glu
            805                 810                 815

Arg Leu His Glu Ala Ser Met Tyr Trp Glu Gly Val Arg Arg Tyr Tyr
            820                 825                 830

Ala Pro Phe Glu Ser Glu Ile Arg Ala Gly Thr Ala Asp Val Tyr Arg
        835                 840                 845

His Glu Met Pro Gly Gly Gln Tyr Thr Asn Leu Arg Glu Gln Ala Arg
        850                 855                 860

Ser Leu Gly Ile Glu His Arg Trp Thr Glu Val Ser Arg Ala Tyr Ala
865                 870                 875                 880

Asp Val Asn Lys Met Phe Gly Asp Ile Val Lys Val Thr Pro Thr Ser
                885                 890                 895

Lys Val Val Gly Asp Met Ala Leu Met Met Val Ala Asn Asp Met Ser
                900                 905                 910

Ala Ala Asp Val Cys Asp Pro Ala Arg Glu Val Ala Phe Pro Glu Ser
            915                 920                 925

Val Val Ser Leu Phe Lys Gly Glu Leu Gly Phe Pro Pro Asp Gly Phe
930                 935                 940

Pro Ala Glu Leu Ser Arg Lys Val Leu Arg Gly Glu Pro Pro Ala Pro
945                 950                 955                 960

Tyr Arg Pro Gly Asp Gln Ile Pro Ala Val Asp Leu Glu Ala Ala Arg
                965                 970                 975

Ala Glu Ala Ser Ala Ala Cys Glu Gln Pro Val Asp Asp Arg Gln Leu
            980                 985                 990

Ala Ser Tyr Leu Met Tyr Pro Lys Gln Ala Val Ala Tyr His Ala His
        995                 1000                1005

Val Arg Thr Tyr Ser Asp Thr Ser Val Val Pro Thr Pro Ala Phe
    1010                1015                1020

Leu Tyr Gly Leu Gln Pro Gln Glu Glu Val Gly Ile Asp Ile Glu
    1025                1030                1035

Pro Gly Lys Thr Leu Leu Val Ser Leu Gln Gly Thr His Ala Asp
    1040                1045                1050

Ala Glu Glu Gly Asn Ile Lys Val Gln Phe Glu Leu Asn Gly Gln
    1055                1060                1065

Ser Arg Thr Ala Val Ile Glu Gln Arg Ser Thr Val Gln Ala Gly
    1070                1075                1080

Thr Ser Arg His Ser Arg Pro Val Ala Asp Pro Glu Asn Pro Leu
    1085                1090                1095

His Ile Ala Ala Pro Met Pro Gly Ser Ile Val Thr Val Ala Val
    1100                1105                1110

Gln Pro Gly Gln Arg Val Ala Ala Gly Thr Thr Leu Ile Ala Leu
    1115                1120                1125

Glu Ala Met Lys Met Glu Thr His Ile Ala Ala Glu Arg Asp Cys
    1130                1135                1140

Glu Ile Ala Ala Val His Val Lys Ser Gly Asp Arg Val Ser Ala
    1145                1150                1155

Lys Asp Leu Leu Ile Glu Leu Lys Gly Thr Glu
    1160                1165

<210> SEQ ID NO 25
<211> LENGTH: 3504
<212> TYPE: DNA
<213> ORGANISM: C. taiwanensis

<400> SEQUENCE: 25

| | | | | | |
|---|---|---|---|---|---|
| atggactatc | gcccgatcca | atcgctgctg | attgccaacc | gttccgagat | cgccatccgc | 60 |
| gtgatgcgcg | cggccgccga | gatgaacgtg | cgcacggtgg | cgatctattc | gaaggaagac | 120 |
| cgcctcgcgc | tgcatcgttt | caaggccgac | gagagctacc | tggtcggcgc | gggcaagaag | 180 |
| ccgctggcgg | cttatctcga | catcgacgac | atcctgcgca | ttgcgcgcca | ggcgcgggtt | 240 |
| gacgcgatcc | atccgggcta | tgcttcctg | tcggagaacc | cggagttcgc | gcaggccgtg | 300 |
| atcgatgccg | gcatccgctg | gtcggcccg | ttgccggagg | tgatgcgcaa | gctcggcaac | 360 |
| aaggtggcgg | cgcgcaacgc | ggcgatcgcg | gcgggcgtgc | cggtgatgcc | ggctaccgat | 420 |
| ccattgccgc | atgacctgga | ggcgtgcaag | cgcctggccg | ccgccatcgg | ctatccgctg | 480 |
| atgctcaagg | cgagctgggg | cggcggcggg | cgcggcatgc | gcgtgctgga | gggcgagcag | 540 |
| gacctggagg | tgcgctggc | cgcggcgcgg | cgcgaggcgc | tggcggcatt | cggcaatgac | 600 |
| gaggtctacg | tcgagaagct | ggtacgcaac | gcgcgccatg | tcgaagtgca | ggtgctgggc | 660 |
| gacacgcacg | gcaacctggt | gcacctgtac | gagcgcgact | gcacggtgca | gcggcgcaac | 720 |
| cagaaggtgg | tcgagcgcgc | gccggcgccc | tacctgacg | ctgccggccg | cggcgcgctg | 780 |
| tgcgattcgg | cgctgcggct | gatgcgcgcg | gtcggctaca | cccatgccgg | cacggtcgag | 840 |
| ttcctgatgg | atgccgactc | gggccagttc | tatttcatcg | aggtcaatcc | gcgcatccag | 900 |
| gtcgagcata | ccgtcaccga | gatggtcacc | ggcatcgata | tcgtcaaggc | gcagatccgc | 960 |
| atcaccgagg | gcgccatat | cggcatgacc | gagaacacgc | gcgatgccga | cggcaagatc | 1020 |
| gtggtgcgcg | ccgcgggcgt | gccggtgcag | caggacatcg | ccctgaacgg | ccatgcgctg | 1080 |
| cagtgccgga | tcaccaccga | ggacccggag | aacggtttct | tgcccgacta | tggccgcctg | 1140 |
| actgcgtatc | gcagcgccgc | gggctttggt | gtgcggctgg | acgcgggtac | cgcctacggc | 1200 |
| ggcgcggtga | tcacgccgta | ttacgattcg | ctgctggtca | aggtcaccac | ctgggcgccg | 1260 |
| accgcgccgg | aatcgatgcg | cgcatggac | cgggcgctgc | gcgagttccg | catccgcggc | 1320 |
| gtcgcgtcca | acctgcagtt | cctcgagaac | gtcatcaacc | atcccgcgtt | ccgttcgggc | 1380 |
| gacgtgacca | cgcgctttat | cgacaagacc | ccggagctgc | tggctttcgc | caaacgccag | 1440 |
| gatcgtgcca | ccaagctgct | gcgctacctg | ggcgaagtct | gcgtcaacgg | gcatcccgag | 1500 |
| atgagcggcc | gcgcgctgcc | gtcgctgccg | ctgcccgcgc | cggtgctgcc | ggcgatcgac | 1560 |
| accaatgccg | cgctgcctta | cggcacgcgc | gaccgcctgc | gcgagcttgg | cgccgagaag | 1620 |
| ttctcgcgct | ggatgctgga | gcagaagcag | gtgctgctga | ccgacaccac | catgcgcgac | 1680 |
| gcgcaccagt | cgctgttcgc | cacgcgcatg | cgcaccgccg | acatgctgcc | gatcgcgccg | 1740 |
| ttctatgcgc | gcgagctgtc | gcagctgttt | tcgctggagt | gctggggcgg | cgccaccttc | 1800 |
| gacgtggcgc | tgcgcttcct | gaaggaagac | ccgtggcagc | gcctggagca | gttgcgcgag | 1860 |
| cgcgtgccca | acgtgctgtt | ccagatgctg | ctgcgcggct | ccaacgcggt | cggctacacc | 1920 |
| aactatgcgg | acaacgtggt | gcgcttcttc | gtgcgccagg | cggccagcgc | cggcgtggat | 1980 |
| gtgttccgcg | tgttcgattc | gctcaactgg | gtgcgcaata | tgcgcgtggc | gatcgatgcg | 2040 |
| gtcggcgaga | gcggcgcgct | gtgcgagggt | gcgatctgct | ataccggcga | cctgttcgac | 2100 |
| ccgaagcgct | ccaagtacga | cctgaagtac | tacgtcggca | tcgcgcgcga | gctgcagcag | 2160 |

```
gccggcgtgc atgtgctggg catcaaggac atggcgggca tctgccgccc gcaggcggcg    2220
gccgcactgg tcagggcgct caaggaagag accgggctgc cggtgcattt ccacacgcac    2280
gacaccagcg gcatctcggc ggcgtcggcg ctggccgcga tcgaggccgg ctgcgatgcg    2340
gtcgacggcg cgctcgatgc aatgagcggg ctgacgtcgc agcccaacct gtcgagcatc    2400
gccgcggcgc tggccggcag cgagcgcgac cccggcctgg acctggaacg gctgcacgag    2460
gcgtcgatgt actgggaagg gtacgccgc tactacgcgc cgttcgaatc cgagatccgc     2520
gccggcaccg ccgacgtgta ccgccatgag atgcccggcg ccagtacac caacctgcgc     2580
gagcaggcgc gctcgcttgg tatcgagcat cgctggaccg aggtgtcgcg cgcgtacgcc    2640
gaggtcaacc agatgttcgg cgacatcgtc aaggtgacgc cgacctccaa ggtggtcggg    2700
gacctggcgc tgatgatggt ggccaacgac ctgagcgccg ccgacgtgtg cgatccggcc    2760
agggagatgg ccttcccgga atcggtggtg tcgctgttca agggcgagct cggcttcccg    2820
cccgacggct tcccggcggc gctgtcgcgc aaggtgctgc gcggcgaccc gcccgcgccg    2880
taccgccccg gcgaccagat cgcgccggtc gacctcgacg cggcccgcgc cgcgggcgcg    2940
gcggcgtgcg agcagccgct cgacgaccgc cagctggcct cgtacctgat gtatcccaag    3000
caggccgccg agtaccatgc gcatgtgcgc cagtacagcg acacctcggt ggtgccgacg    3060
ccggcctacc tgtatggcct gcagccgcag gaagaggtgg ccatcgacat cgagcccggc    3120
aagacgctgc tggtctcgct gcagggcacc caccccgatg ccggcgaagg caagatcaag    3180
gtgcagttcg agctgaacgg caatcgcgc accacgctgg tcgaaccgcg cagcaccgcg     3240
caggcggcgg ccgcgcgcca gggcagggcg gtggccgaac cggacaaccc gctgcatgtc    3300
gccgcgccga tgccgggctc gatcgtgacg gtggcggtgc agccgggcca gcgcgtcgcc    3360
gcgggcacca cgctgctggc gctggaggcg atgaagatgg agacccatat cgccgcggac    3420
cgggactgcg agattgccgc ggtgcatgtg aaggcgggcg atcgggtggc ggcgaaggac    3480
ctgctggtgg aactgaagga ctga                                          3504
```

<210> SEQ ID NO 26
<211> LENGTH: 1167
<212> TYPE: PRT
<213> ORGANISM: C. taiwanensis

<400> SEQUENCE: 26

```
Met Asp Tyr Arg Pro Ile Gln Ser Leu Leu Ile Ala Asn Arg Ser Glu
1               5                   10                  15

Ile Ala Ile Arg Val Met Arg Ala Ala Ala Glu Met Asn Val Arg Thr
            20                  25                  30

Val Ala Ile Tyr Ser Lys Glu Asp Arg Leu Ala Leu His Arg Phe Lys
        35                  40                  45

Ala Asp Glu Ser Tyr Leu Val Gly Ala Gly Lys Lys Pro Leu Ala Ala
    50                  55                  60

Tyr Leu Asp Ile Asp Asp Ile Leu Arg Ile Ala Arg Gln Ala Arg Val
65                  70                  75                  80

Asp Ala Ile His Pro Gly Tyr Gly Phe Leu Ser Glu Asn Pro Glu Phe
                85                  90                  95

Ala Gln Ala Val Ile Asp Ala Gly Ile Arg Trp Val Gly Pro Leu Pro
            100                 105                 110

Glu Val Met Arg Lys Leu Gly Asn Lys Val Ala Ala Arg Asn Ala Ala
        115                 120                 125
```

Ile Ala Ala Gly Val Pro Val Met Pro Ala Thr Asp Pro Leu Pro His
130                 135                 140

Asp Leu Glu Ala Cys Lys Arg Leu Ala Ala Ile Gly Tyr Pro Leu
145                 150                 155                 160

Met Leu Lys Ala Ser Trp Gly Gly Gly Arg Gly Met Arg Val Leu
            165                 170                 175

Glu Gly Glu Gln Asp Leu Gly Ala Leu Ala Ala Arg Arg Glu
            180                 185                 190

Ala Leu Ala Ala Phe Gly Asn Asp Glu Val Tyr Val Glu Lys Leu Val
            195                 200                 205

Arg Asn Ala Arg His Val Glu Val Gln Val Leu Gly Asp Thr His Gly
210                 215                 220

Asn Leu Val His Leu Tyr Glu Arg Asp Cys Thr Val Gln Arg Arg Asn
225                 230                 235                 240

Gln Lys Val Val Glu Arg Ala Pro Ala Pro Tyr Leu Asp Ala Ala Gly
                245                 250                 255

Arg Gly Ala Leu Cys Asp Ser Ala Leu Arg Leu Met Arg Ala Val Gly
            260                 265                 270

Tyr Thr His Ala Gly Thr Val Glu Phe Leu Met Asp Ala Asp Ser Gly
    275                 280                 285

Gln Phe Tyr Phe Ile Glu Val Asn Pro Arg Ile Gln Val Glu His Thr
290                 295                 300

Val Thr Glu Met Val Thr Gly Ile Asp Ile Val Lys Ala Gln Ile Arg
305                 310                 315                 320

Ile Thr Glu Gly Gly His Ile Gly Met Thr Glu Asn Thr Arg Asp Ala
            325                 330                 335

Asp Gly Lys Ile Val Arg Ala Ala Gly Val Pro Val Gln Gln Asp
            340                 345                 350

Ile Ala Leu Asn Gly His Ala Leu Gln Cys Arg Ile Thr Thr Glu Asp
            355                 360                 365

Pro Glu Asn Gly Phe Leu Pro Asp Tyr Gly Arg Leu Thr Ala Tyr Arg
370                 375                 380

Ser Ala Ala Gly Phe Gly Val Arg Leu Asp Ala Gly Thr Ala Tyr Gly
385                 390                 395                 400

Gly Ala Val Ile Thr Pro Tyr Tyr Asp Ser Leu Leu Val Lys Val Thr
                405                 410                 415

Thr Trp Ala Pro Thr Ala Pro Glu Ser Met Arg Arg Met Asp Arg Ala
            420                 425                 430

Leu Arg Glu Phe Arg Ile Arg Gly Val Ala Ser Asn Leu Gln Phe Leu
            435                 440                 445

Glu Asn Val Ile Asn His Pro Ala Phe Arg Ser Gly Asp Val Thr Thr
450                 455                 460

Arg Phe Ile Asp Lys Thr Pro Glu Leu Leu Ala Phe Ala Lys Arg Gln
465                 470                 475                 480

Asp Arg Ala Thr Lys Leu Leu Arg Tyr Leu Gly Glu Val Cys Val Asn
            485                 490                 495

Gly His Pro Glu Met Ser Gly Arg Ala Leu Pro Ser Leu Pro Leu Pro
            500                 505                 510

Ala Pro Val Leu Pro Ala Ile Asp Thr Asn Ala Ala Leu Pro Tyr Gly
            515                 520                 525

Thr Arg Asp Arg Leu Arg Glu Leu Gly Ala Glu Lys Phe Ser Arg Trp
530                 535                 540

Met Leu Glu Gln Lys Gln Val Leu Leu Thr Asp Thr Thr Met Arg Asp

```
                    -continued
545             550             555             560
Ala His Gln Ser Leu Phe Ala Thr Arg Met Arg Thr Ala Asp Met Leu
            565             570             575

Pro Ile Ala Pro Phe Tyr Ala Arg Glu Leu Ser Gln Leu Phe Ser Leu
            580             585             590

Glu Cys Trp Gly Gly Ala Thr Phe Asp Val Ala Leu Arg Phe Leu Lys
            595             600             605

Glu Asp Pro Trp Gln Arg Leu Glu Gln Leu Arg Glu Arg Val Pro Asn
            610             615             620

Val Leu Phe Gln Met Leu Leu Arg Gly Ser Asn Ala Val Gly Tyr Thr
625             630             635             640

Asn Tyr Ala Asp Asn Val Val Arg Phe Phe Val Arg Gln Ala Ala Ser
            645             650             655

Ala Gly Val Asp Val Phe Arg Val Phe Asp Ser Leu Asn Trp Val Arg
            660             665             670

Asn Met Arg Val Ala Ile Asp Ala Val Gly Glu Ser Gly Ala Leu Cys
            675             680             685

Glu Gly Ala Ile Cys Tyr Thr Gly Asp Leu Phe Asp Pro Lys Arg Ser
            690             695             700

Lys Tyr Asp Leu Lys Tyr Tyr Val Gly Ile Ala Arg Glu Leu Gln Gln
705             710             715             720

Ala Gly Val His Val Leu Gly Ile Lys Asp Met Ala Gly Ile Cys Arg
            725             730             735

Pro Gln Ala Ala Ala Leu Val Arg Ala Leu Lys Glu Glu Thr Gly
            740             745             750

Leu Pro Val His Phe His Thr His Asp Thr Ser Gly Ile Ser Ala Ala
            755             760             765

Ser Ala Leu Ala Ala Ile Glu Ala Gly Cys Asp Ala Val Asp Gly Ala
            770             775             780

Leu Asp Ala Met Ser Gly Leu Thr Ser Gln Pro Asn Leu Ser Ser Ile
785             790             795             800

Ala Ala Ala Leu Ala Gly Ser Glu Arg Asp Pro Gly Leu Asp Leu Glu
            805             810             815

Arg Leu His Glu Ala Ser Met Tyr Trp Glu Gly Val Arg Arg Tyr Tyr
            820             825             830

Ala Pro Phe Glu Ser Glu Ile Arg Ala Gly Thr Ala Asp Val Tyr Arg
            835             840             845

His Glu Met Pro Gly Gly Gln Tyr Thr Asn Leu Arg Glu Gln Ala Arg
            850             855             860

Ser Leu Gly Ile Glu His Arg Trp Thr Glu Val Ser Arg Ala Tyr Ala
865             870             875             880

Glu Val Asn Gln Met Phe Gly Asp Ile Val Lys Val Thr Pro Thr Ser
            885             890             895

Lys Val Val Gly Asp Leu Ala Leu Met Met Val Ala Asn Asp Leu Ser
            900             905             910

Ala Ala Asp Val Cys Asp Pro Ala Arg Glu Met Ala Phe Pro Glu Ser
            915             920             925

Val Val Ser Leu Phe Lys Gly Glu Leu Gly Phe Pro Pro Asp Gly Phe
            930             935             940

Pro Ala Ala Leu Ser Arg Lys Val Leu Arg Gly Asp Pro Ala Pro
945             950             955             960

Tyr Arg Pro Gly Asp Gln Ile Ala Pro Val Asp Leu Asp Ala Ala Arg
            965             970             975
```

Ala Ala Gly Ala Ala Ala Cys Glu Gln Pro Leu Asp Asp Arg Gln Leu
            980                 985                 990

Ala Ser Tyr Leu Met Tyr Pro Lys Gln Ala Ala Glu Tyr His Ala His
            995                1000                1005

Val Arg Gln Tyr Ser Asp Thr Ser Val Val Pro Thr Pro Ala Tyr
        1010                1015                1020

Leu Tyr Gly Leu Gln Pro Gln Glu Glu Val Ala Ile Asp Ile Glu
        1025                1030                1035

Pro Gly Lys Thr Leu Leu Val Ser Leu Gln Gly Thr His Pro Asp
        1040                1045                1050

Ala Gly Glu Gly Lys Ile Lys Val Gln Phe Glu Leu Asn Gly Gln
        1055                1060                1065

Ser Arg Thr Thr Leu Val Glu Pro Arg Ser Thr Ala Gln Ala Ala
        1070                1075                1080

Ala Ala Arg Gln Gly Arg Ala Val Ala Glu Pro Asp Asn Pro Leu
        1085                1090                1095

His Val Ala Ala Pro Met Pro Gly Ser Ile Val Thr Val Ala Val
        1100                1105                1110

Gln Pro Gly Gln Arg Val Ala Ala Gly Thr Thr Leu Leu Ala Leu
        1115                1120                1125

Glu Ala Met Lys Met Glu Thr His Ile Ala Ala Asp Arg Asp Cys
        1130                1135                1140

Glu Ile Ala Ala Val His Val Lys Ala Gly Asp Arg Val Ala Ala
        1145                1150                1155

Lys Asp Leu Leu Val Glu Leu Lys Asp
        1160                1165

<210> SEQ ID NO 27
<211> LENGTH: 3504
<212> TYPE: DNA
<213> ORGANISM: R. metallidurans

<400> SEQUENCE: 27
atggacttcg ccccgatcaa gtcgttgttg attgccaacc gttccgagat cgcgattcgc    60
gtgatgcggg ccgccgccga gatgagcatc cgcacagtcg ctatctactc gaaggaggac   120
cggctcgcgc ttcatcgctt caaggccgat gagagctatc tggttggcga cggcaagaag   180
ccgctggcgg cttacctcga tatcgaagac gttctgcgga tcgcccggca ggcaaaggtc   240
gacgcgattc acccgggggta tggttttctg tccgagaacc cggacttcgc ccaggcggtc   300
atcgacgctg gcattcgctg gatcgggcca tcgcctgaag tcatgcggat gctcggcaac   360
aaggtggcgg cgcgtaatgc ggccattgcg gcgggtgtgc ccgtcatgcc ggcgaccgat   420
ccgctgccgc tcgatctggc cgagtgcaag cgcctggcgg ccggcattgg ctatccgttg   480
atgctcaagg cgagctgggg tggtggtggc cgtggcatgc gggtactgga gagcgaacag   540
gacctggagc cttcgctggc ggcggccccgt cgcgaggcgc tggccgcgtt tggcaacgac   600
gaggtgtacc tggagaagct ggtgcgcaac gcgcgccacg tcgaggtgca gatcctgggc   660
gacacgcacg gcaatctcgt gcatctgcac gagcgtgact gcacggtgca gcggcgcaac   720
cagaaggtta tcgaacgcgc gcctgcgcca tacatggatg cggccggtcg cgcgtcactg   780
tgcgacgcgg cgctgcgcct gatgggcgcg tcggctatt cgcacgccgg cacggtggaa   840
ttcctgatgg atgcggacac gaacaagttc tacttcatcg aggtcaatcc acgtatccag   900
gtggaacaca cggtcaccga aatgatcacg gggatcgaca tcgtcaaggc acagatccgc   960

```
gtcacggaag gcggccggat cggcatgacc gaagacacgc tcgacgagaa cggcgatatc   1020
accacgcgcg cggcgggcgt gccgccgcag gcccagattc cgctcaatgg ccacgcgctg   1080
caatgccgga tcacgtccga ggaccctgag aatggcttcc tgccggacta tggccgtctc   1140
accgcgtatc gcagcgcggc cggcttcggg gtgcgcctgg atgccggcac cgcctatggc   1200
ggcgcggtga tcacgccgta ctacgattcg ctgctggtca aggtcaccac ctgggcgccg   1260
acggccgcca gtcgatccg ccgcatggat cgcgccctgc gcgagttccg cattcgcggg   1320
gtgtcctcca acctgcagtt cctggagaac gtcatcaacc atcccgcgtt tgggagcggt   1380
gacgtcacca cgcgctttat cgacctgacg ccggaactgc tggccttcac caaacgcgt   1440 gataccgcca ccaagctgtt gagctatctg ggcgacgtca gcatcaacgg tcatcaggaa   1500
atgacgggcc gcgcggtgcc gcagttgccg cttccgaggc cagtcctgcc ggtggttgac   1560
accaccagac cgcttcccct cggcacgcgc gatcgactgc gtgaactggg cgcggagaaa   1620
ttcgcaagct ggatgctgga tcagaagcag gtgctgctga ccgacaccac catgcgcgat   1680
gcgcaccagt cgttgtttgc cacacggatg cgtacggcag acatgctgcc gatcgcgccg   1740
ttctacgcca gcgagctgtc gcaactgttt tcgatggagt gctggggcgg cgccacgttc   1800
gacgtggcct tgcgcttcct gaaggaagac ccgtggcagc gcctggcgca actgcgcgag   1860
cgcgtgccga acatcctgtt ccagatgctg ctgcgcggct cgaatgccgt cggttacacg   1920
aactacgcgg acaacgtggt gcgtttcttc gtcaagcagg ccgccagtac cggcgtggac   1980
gtattccgcg tgttcgattc gttgaactgg gtgcgcaaca tgcgcgtggc gatcgacgcc   2040
gtaggcgaaa ccggcgcgct gtgcgaaggt gcgatttgct atacgggcga tctgttcgat   2100
ggctcccgcc ccaagtacga cctgaagtac tacgtgggca tcgcccgcga actgcaacgc   2160
gctggcgtgc acgtgctcgg catcaaggac atggcgggta tctgccgccc ccaggccgct   2220
gcggcgctgg tcaaggcgct gaaggaagag accgggctgc ccgtgcattt ccacacacac   2280
gataccagcg gcatttcagc ggcatcggca ctggctgcca tcgaggcggg ctgcgatgcc   2340
gtcgacggcg cgctggacgc gatgagcggg ctcacgtcgc aaccgaacct gtcgagtatt   2400
gtcgccgcgc tggccggcag cgagcgcgat cccggactca gtctggaccg cctgcacgaa   2460
gcgtcgatgt attgggaggg cgtgcgccgc tactacgcgc cgttcgagtc cgaaattcgc   2520
gctggtactg ccgacgtcta tcgccacgag atgccgggtg ccagtacac gaacctgcgc   2580 gagcaggctc gctcgcttgg catcgagcat cgatggaccg aagtgtcgcg cgcctacgcc   2640
gacgtcaacc ggatgttcgg tgacatcgtg aaggtgacgc ctacgtcgaa ggtggttggc   2700
gatctggcgc tgatgatggt ggccaacgat atgacggcag cggatgtgtg cgatccgaac   2760
aaggaggtgg cattccccga atccgtggtg tcgctgttca agggcgaact gggcttcccg   2820
ccggatggct tcccggccga gctttcgcgc aaggtgctcc gaggtgagcc gcccgcgccg   2880
taccgtccgg gcgacctgat cccggccgtc gatctcgatg tcgtccgcgc acagggtgag   2940
gccgcctgcg agcagccgct cgatgacatg caactggcgt cgtacctgat gtatccgaag   3000
cagacggtcg agtaccacgc gcatgtgcgc gcctatagcg atacatcggt gctgccgacc   3060
ccggcctatc tgtacgggct gcagccccag gaagaagtgg ccgtcgacat tgcggcgggc   3120
aagacactcc tcgtctcgct gcaaggcact caccccgatg ccgaagaggg cgtgatcaag   3180
gtccagttcg agctgaacgg ccagtcgcgc acggccctga tcgagcagcg cagtacggtc   3240
agcgtggcca cggcccgaca gggccgccag gttgcggatc ccgagaaccc gttgcacatc   3300
```

```
gccgcgccga tgccgggctc gatcgtgacc gtggcggtgc agcccgggca gcgtgtggca   3360
gccggcacga cgctgctcgc gctggaggcg atgaagatgg agacccacat cgcggccgat   3420
cgcgacggcg agatcgctgc cgtgcacgtc aagcctggcg accgcgtggc agcgaaggat   3480
ctgctgatcg agttgaaggg ttga                                         3504
```

<210> SEQ ID NO 28
<211> LENGTH: 1167
<212> TYPE: PRT
<213> ORGANISM: R. metallidurans

<400> SEQUENCE: 28

```
Met Asp Phe Ala Pro Ile Lys Ser Leu Leu Ile Ala Asn Arg Ser Glu
1               5                   10                  15

Ile Ala Ile Arg Val Met Arg Ala Ala Ala Glu Met Ser Ile Arg Thr
            20                  25                  30

Val Ala Ile Tyr Ser Lys Glu Asp Arg Leu Ala Leu His Arg Phe Lys
        35                  40                  45

Ala Asp Glu Ser Tyr Leu Val Gly Asp Gly Lys Lys Pro Leu Ala Ala
    50                  55                  60

Tyr Leu Asp Ile Glu Asp Val Leu Arg Ile Ala Arg Gln Ala Lys Val
65                  70                  75                  80

Asp Ala Ile His Pro Gly Tyr Gly Phe Leu Ser Glu Asn Pro Asp Phe
                85                  90                  95

Ala Gln Ala Val Ile Asp Ala Gly Ile Arg Trp Ile Gly Pro Ser Pro
            100                 105                 110

Glu Val Met Arg Met Leu Gly Asn Lys Val Ala Ala Arg Asn Ala Ala
        115                 120                 125

Ile Ala Ala Gly Val Pro Val Met Pro Ala Thr Asp Pro Leu Pro Leu
    130                 135                 140

Asp Leu Ala Glu Cys Lys Arg Leu Ala Ala Gly Ile Gly Tyr Pro Leu
145                 150                 155                 160

Met Leu Lys Ala Ser Trp Gly Gly Gly Gly Arg Gly Met Arg Val Leu
                165                 170                 175

Glu Ser Glu Gln Asp Leu Glu Pro Ser Leu Ala Ala Arg Arg Glu
            180                 185                 190

Ala Leu Ala Ala Phe Gly Asn Asp Glu Val Tyr Leu Glu Lys Leu Val
        195                 200                 205

Arg Asn Ala Arg His Val Glu Val Gln Ile Leu Gly Asp Thr His Gly
    210                 215                 220

Asn Leu Val His Leu His Glu Arg Asp Cys Thr Val Gln Arg Arg Asn
225                 230                 235                 240

Gln Lys Val Ile Glu Arg Ala Pro Ala Pro Tyr Met Asp Ala Ala Gly
                245                 250                 255

Arg Ala Ser Leu Cys Asp Ala Ala Leu Arg Leu Met Gly Ala Val Gly
            260                 265                 270

Tyr Ser His Ala Gly Thr Val Glu Phe Leu Met Asp Ala Asp Thr Asn
        275                 280                 285

Lys Phe Tyr Phe Ile Glu Val Asn Pro Arg Ile Gln Val Glu His Thr
    290                 295                 300

Val Thr Glu Met Ile Thr Gly Ile Asp Ile Val Lys Ala Gln Ile Arg
305                 310                 315                 320

Val Thr Glu Gly Gly Arg Ile Gly Met Thr Glu Asp Thr Leu Asp Glu
                325                 330                 335
```

```
Asn Gly Asp Ile Thr Thr Arg Ala Ala Gly Val Pro Pro Gln Ala Gln
                340                 345                 350

Ile Pro Leu Asn Gly His Ala Leu Gln Cys Arg Ile Thr Ser Glu Asp
            355                 360                 365

Pro Glu Asn Gly Phe Leu Pro Asp Tyr Gly Arg Leu Thr Ala Tyr Arg
        370                 375                 380

Ser Ala Ala Gly Phe Gly Val Arg Leu Asp Ala Gly Thr Ala Tyr Gly
385                 390                 395                 400

Gly Ala Val Ile Thr Pro Tyr Tyr Asp Ser Leu Leu Val Lys Val Thr
                405                 410                 415

Thr Trp Ala Pro Thr Ala Ala Glu Ser Ile Arg Arg Met Asp Arg Ala
            420                 425                 430

Leu Arg Glu Phe Arg Ile Arg Gly Val Ser Ser Asn Leu Gln Phe Leu
        435                 440                 445

Glu Asn Val Ile Asn His Pro Ala Phe Gly Ser Gly Asp Val Thr Thr
        450                 455                 460

Arg Phe Ile Asp Leu Thr Pro Glu Leu Leu Ala Phe Thr Lys Arg Arg
465                 470                 475                 480

Asp Thr Ala Thr Lys Leu Leu Ser Tyr Leu Gly Asp Val Ser Ile Asn
                485                 490                 495

Gly His Gln Glu Met Thr Gly Arg Ala Val Pro Gln Leu Pro Leu Pro
            500                 505                 510

Arg Pro Val Leu Pro Val Val Asp Thr Thr Arg Pro Leu Pro Leu Gly
        515                 520                 525

Thr Arg Asp Arg Leu Arg Glu Leu Gly Ala Glu Lys Phe Ala Ser Trp
        530                 535                 540

Met Leu Asp Gln Lys Gln Val Leu Leu Thr Asp Thr Thr Met Arg Asp
545                 550                 555                 560

Ala His Gln Ser Leu Phe Ala Thr Arg Met Arg Thr Ala Asp Met Leu
                565                 570                 575

Pro Ile Ala Pro Phe Tyr Ala Ser Glu Leu Ser Gln Leu Phe Ser Met
            580                 585                 590

Glu Cys Trp Gly Gly Ala Thr Phe Asp Val Ala Leu Arg Phe Leu Lys
        595                 600                 605

Glu Asp Pro Trp Gln Arg Leu Ala Gln Leu Arg Glu Arg Val Pro Asn
        610                 615                 620

Ile Leu Phe Gln Met Leu Leu Arg Gly Ser Asn Ala Val Gly Tyr Thr
625                 630                 635                 640

Asn Tyr Ala Asp Asn Val Val Arg Phe Phe Val Lys Gln Ala Ala Ser
                645                 650                 655

Thr Gly Val Asp Val Phe Arg Val Phe Asp Ser Leu Asn Trp Val Arg
            660                 665                 670

Asn Met Arg Val Ala Ile Asp Ala Val Gly Glu Thr Gly Ala Leu Cys
        675                 680                 685

Glu Gly Ala Ile Cys Tyr Thr Gly Asp Leu Phe Asp Gly Ser Arg Pro
        690                 695                 700

Lys Tyr Asp Leu Lys Tyr Tyr Val Gly Ile Ala Arg Glu Leu Gln Arg
705                 710                 715                 720

Ala Gly Val His Val Leu Gly Ile Lys Asp Met Ala Gly Ile Cys Arg
                725                 730                 735

Pro Gln Ala Ala Ala Ala Leu Val Lys Ala Leu Lys Glu Glu Thr Gly
            740                 745                 750

Leu Pro Val His Phe His Thr His Asp Thr Ser Gly Ile Ser Ala Ala
```

```
                755                 760                 765
Ser Ala Leu Ala Ala Ile Glu Ala Gly Cys Asp Ala Val Asp Gly Ala
770                 775                 780

Leu Asp Ala Met Ser Gly Leu Thr Ser Gln Pro Asn Leu Ser Ser Ile
785                 790                 795                 800

Val Ala Ala Leu Ala Gly Ser Glu Arg Asp Pro Gly Leu Ser Leu Asp
                805                 810                 815

Arg Leu His Glu Ala Ser Met Tyr Trp Glu Gly Val Arg Arg Tyr Tyr
                820                 825                 830

Ala Pro Phe Glu Ser Glu Ile Arg Ala Gly Thr Ala Asp Val Tyr Arg
                835                 840                 845

His Glu Met Pro Gly Gly Gln Tyr Thr Asn Leu Arg Glu Gln Ala Arg
850                 855                 860

Ser Leu Gly Ile Glu His Arg Trp Thr Glu Val Ser Arg Ala Tyr Ala
865                 870                 875                 880

Asp Val Asn Arg Met Phe Gly Asp Ile Val Lys Val Thr Pro Thr Ser
                885                 890                 895

Lys Val Val Gly Asp Leu Ala Leu Met Met Val Ala Asn Asp Met Thr
                900                 905                 910

Ala Ala Asp Val Cys Asp Pro Asn Lys Glu Val Ala Phe Pro Glu Ser
                915                 920                 925

Val Val Ser Leu Phe Lys Gly Glu Leu Gly Phe Pro Pro Asp Gly Phe
                930                 935                 940

Pro Ala Glu Leu Ser Arg Lys Val Leu Arg Gly Glu Pro Pro Ala Pro
945                 950                 955                 960

Tyr Arg Pro Gly Asp Leu Ile Pro Ala Val Asp Leu Asp Val Val Arg
                965                 970                 975

Ala Gln Gly Glu Ala Ala Cys Glu Gln Pro Leu Asp Asp Met Gln Leu
                980                 985                 990

Ala Ser Tyr Leu Met Tyr Pro Lys Gln Thr Val Glu Tyr His Ala His
                995                1000                1005

Val Arg Ala Tyr Ser Asp Thr Ser Val Leu Pro Thr Pro Ala Tyr
                1010                1015                1020

Leu Tyr Gly Leu Gln Pro Gln Glu Glu Val Ala Val Asp Ile Ala
                1025                1030                1035

Ala Gly Lys Thr Leu Leu Val Ser Leu Gln Gly Thr His Pro Asp
                1040                1045                1050

Ala Glu Glu Gly Val Ile Lys Val Gln Phe Glu Leu Asn Gly Gln
                1055                1060                1065

Ser Arg Thr Ala Leu Ile Glu Gln Arg Ser Thr Val Ser Val Ala
                1070                1075                1080

Thr Ala Arg Gln Gly Arg Gln Val Ala Asp Pro Glu Asn Pro Leu
                1085                1090                1095

His Ile Ala Ala Pro Met Pro Gly Ser Ile Val Thr Val Ala Val
                1100                1105                1110

Gln Pro Gly Gln Arg Val Ala Ala Gly Thr Thr Leu Leu Ala Leu
                1115                1120                1125

Glu Ala Met Lys Met Glu Thr His Ile Ala Ala Asp Arg Asp Gly
                1130                1135                1140

Glu Ile Ala Ala Val His Val Lys Pro Gly Asp Arg Val Ala Ala
                1145                1150                1155

Lys Asp Leu Leu Ile Glu Leu Lys Gly
                1160                1165
```

<210> SEQ ID NO 29
<211> LENGTH: 3021
<212> TYPE: DNA
<213> ORGANISM: R. eutropha

<400> SEQUENCE: 29

| | | | | | |
|---|---|---|---|---|---|
| atgacgcagc | atgctgcgcg | ccccggccga | cgctcggcca | atcgagaagc | cccctcccag | 60 |
| gcctcaggcc | agagtgacgc | gaacggcgca | tcaacccgca | agaccgcttc | caagacccct | 120 |
| ggcatcaaac | cgatttcgaa | ggccaatctg | atggtcgtgc | cgcaaatgg | cgccctgaac | 180 |
| gccagcccgg | cacgccgctc | ggcgaccgac | aaggacgtgc | cgctgcgcga | ggacatccgc | 240 |
| ttcctgggcc | gctgctgggg | cgaatgcctg | cgcgagcagg | aaggtgatgc | caccttcgag | 300 |
| gtggtcgaga | ccatccgcca | gaccgccgtg | cgattccgac | gcgagaacga | ccgcgccgct | 360 |
| ggcaccgagc | tcgaccgcct | gctcaagcgc | ctctcgcgtg | accagaccaa | ccaggtcgtg | 420 |
| cgcgcgttca | gctatttctc | gcatctggcc | aatatcgccg | aggaccagca | ccacaaccgc | 480 |
| cgccgccgca | tccacgcgct | ggccggttcg | ccgccccaag | acggcagcct | gcagcacgcg | 540 |
| ctcgagaaga | tcgacgccgc | tggtgtcacg | ggcaagcagc | tgcgcaagtt | cctggacgag | 600 |
| gcactgatcg | tgccggtgct | gacggcgcac | ccgaccgaag | tccagcgcaa | gagcatcctg | 660 |
| gacgccgagc | gcgagatcgc | gcgcctgctg | gcggagcgcg | acctgccgat | gaccgcgcgc | 720 |
| gagcgcgacc | gcaacaccgc | tcagcttcgc | gccaaagtca | ccacgctgtg | gcagacccgc | 780 |
| atgctgcgtg | actcgcggct | gacggtggcc | gacgaaatcg | acaacgcact | gtcgtactac | 840 |
| cgcaccacct | tcctgcacgg | catcccgcaa | ctgatgagcg | aactggaaga | ggacatcgcc | 900 |
| gcgatcttcc | cggcctcacg | caagaccaag | ggcgccgctg | ccgaagccgc | gccgctggcg | 960 |
| ccgtttatgc | aaatgggttc | gtggatcggc | ggcgaccgcg | acggcaatcc | gaacgtgacg | 1020 |
| gccgaaacgc | tcgaccacgc | cgccacccag | cagtcgcgga | tgatcctggg | ctggtacctc | 1080 |
| gacgaggtgc | atgcgctggg | cgccgagctg | tcgatgtcga | cgctgatggt | cgacgcgagc | 1140 |
| cccgaactgc | tcgcactggc | cgaggcatcg | cccgaccact | ccgcccaccg | cgccgacgag | 1200 |
| ccgtaccgcc | gcgcgctgat | cggcatctat | gcgcgccttg | ccgcgaccag | caagatgctg | 1260 |
| accggtcagg | gcgcgccgcg | ccatccggtg | gcggacgccg | aaccgtacag | cagcgccgaa | 1320 |
| gctttcgcgg | ccgacgtaca | gatcgtgatc | gactcgctgc | gcgcccacca | cggccgcgcg | 1380 |
| ctgaccagca | cgcgcatcga | cgcactggtg | cgtgccattg | ccgtgttcgg | cttccatctg | 1440 |
| gcatcggtcg | atatgcgcca | ggtgtccgac | gtgcacgaag | ccgtcgtcgc | cgagctgttt | 1500 |
| gccgccgccg | gcgtcgagaa | ggactacgcc | gcgctgccgg | aatcccgcaa | gctcgaacta | 1560 |
| ctgctcgccg | aactacgcca | gccgcgcctg | ctgacgctgc | cgtatcacga | gtattcggag | 1620 |
| cagacccgca | acgagctggc | catcctggca | accgcgcgcg | aactgcgcgc | gcgctacggc | 1680 |
| cagcgcgtcg | cgcgcaacta | catcatctcg | cacacgaaa | cgctgtccga | cctggtggaa | 1740 |
| gtcatgctgt | tgcagaagga | agccggcatg | ctcaagggca | cgctgggcag | caagaccgat | 1800 |
| ccggcacgca | tggagctgat | ggtcattccg | ctgttcgaaa | ccatcgaaga | cttgcagaac | 1860 |
| gcagcaggga | tcatgcagtc | gctgctggac | ctgccgggct | cgattcggt | gatcgagcac | 1920 |
| cacggtgtcg | agcaggaagt | gatgctcggc | tattccgatt | ccaacaagga | cggcggcttc | 1980 |
| ctgacttcca | actgggagct | gtacaaggcc | gaactcgcac | tggtccagct | gttcgagcaa | 2040 |
| cgcaaggtca | agctgcgcct | gttccacggc | cgcggcggca | ccgtcggccg | cggcggcggc | 2100 |

```
ccgacctacc aggccatcct gtcgcagccg ccgggcacgg tgaacgggca gatccgcctg    2160
accgagcagg gcgagatcat caacagcaag ttcgccaatg ccgagatcgg gcggcgcaac    2220
ctggaaacgg tgatcgccgc gacgctcgaa gcctcgctgc tgccgcagca gaacgcgccg    2280
aaggaactga gcacgttcga aggcatcatg cagcagcttt ccgaccgtgc gttcggcgcc    2340
taccgcaacc tggtatatga accccgggc ttcaaggact atttcttcgc caccacgccg    2400
atcaccgaga tcgccgacct gaacctcggt tcgcgtccgg cctcgcgcaa gctgatggac    2460
aagaagaacc gccgcatcga agacctgcgc gcgattccgt ggggcttctc gtggggccag    2520
tgccgactgc tgctgccggg ctggtacggc ttcggcagcg cggtcaagtc gctgctcgac    2580
accgcgccgg acgaaaaggc acgtaaagcc gccgtggcga cgctgcgcaa gatggtcaag    2640
acctggccgt tcttctccac gctgctgtcc aacatggaca tggtgctggc caagacggac    2700
ctggccgtgg cctcgcgcta tgcccagctc tgtgacgacg ccgcgctgcg caagaacgtg    2760
ttcgcgcgca tcagcaagga atggcacctg acctgcgaga tgctggcgct ggtcaccggg    2820
catcaggaac ggctggccga caacccgctg ctcgcgcgtt cgatcaagaa ccgctttgcg    2880
taccttgatc cgctcaacca cttgcaggtg gaactgctca agcgctaccg ctcgggcaag    2940
gatggggacg atatccgggt acggcgcggt atccatctga ccatcaacgg ggtggctgcg    3000
gggttgcgca atacgggttg a                                              3021
```

<210> SEQ ID NO 30
<211> LENGTH: 1006
<212> TYPE: PRT
<213> ORGANISM: R. eutropha

<400> SEQUENCE: 30

```
Met Thr Gln His Ala Ala Arg Pro Gly Arg Arg Ser Ala Asn Arg Glu
1               5                   10                  15

Ala Pro Ser Gln Ala Ser Gly Gln Ser Asp Ala Asn Gly Ala Ser Thr
            20                  25                  30

Arg Lys Thr Ala Ser Lys Thr Pro Gly Ile Lys Pro Ile Ser Lys Ala
        35                  40                  45

Asn Leu Met Val Val Pro Ala Asn Gly Ala Leu Asn Ala Ser Pro Ala
    50                  55                  60

Arg Arg Ser Ala Thr Asp Lys Asp Val Pro Leu Arg Glu Asp Ile Arg
65                  70                  75                  80

Phe Leu Gly Arg Leu Leu Gly Glu Cys Leu Arg Glu Gln Glu Gly Asp
                85                  90                  95

Ala Thr Phe Glu Val Val Glu Thr Ile Arg Gln Thr Ala Val Arg Phe
            100                 105                 110

Arg Arg Glu Asn Asp Arg Ala Ala Gly Thr Glu Leu Asp Arg Leu Leu
        115                 120                 125

Lys Arg Leu Ser Arg Asp Gln Thr Asn Gln Val Val Arg Ala Phe Ser
    130                 135                 140

Tyr Phe Ser His Leu Ala Asn Ile Ala Glu Asp Gln His His Asn Arg
145                 150                 155                 160

Arg Arg Arg Ile His Ala Leu Ala Gly Ser Pro Pro Gln Asp Gly Ser
                165                 170                 175

Leu Gln His Ala Leu Glu Lys Ile Asp Ala Ala Gly Val Thr Gly Lys
            180                 185                 190

Gln Leu Arg Lys Phe Leu Asp Glu Ala Leu Ile Val Pro Val Leu Thr
        195                 200                 205
```

```
Ala His Pro Thr Glu Val Gln Arg Lys Ser Ile Leu Asp Ala Glu Arg
    210                 215                 220

Glu Ile Ala Arg Leu Leu Ala Glu Arg Asp Leu Pro Met Thr Ala Arg
225                 230                 235                 240

Glu Arg Asp Arg Asn Thr Ala Gln Leu Arg Ala Lys Val Thr Thr Leu
                245                 250                 255

Trp Gln Thr Arg Met Leu Arg Asp Ser Arg Leu Thr Val Ala Asp Glu
                260                 265                 270

Ile Asp Asn Ala Leu Ser Tyr Tyr Arg Thr Thr Phe Leu His Gly Ile
                275                 280                 285

Pro Gln Leu Met Ser Glu Leu Glu Glu Asp Ile Ala Ala Ile Phe Pro
    290                 295                 300

Ala Ser Arg Lys Thr Lys Gly Ala Ala Ala Glu Ala Ala Pro Leu Ala
305                 310                 315                 320

Pro Phe Met Gln Met Gly Ser Trp Ile Gly Gly Asp Arg Asp Gly Asn
                325                 330                 335

Pro Asn Val Thr Ala Glu Thr Leu Asp His Ala Ala Thr Gln Gln Ser
                340                 345                 350

Arg Met Ile Leu Gly Trp Tyr Leu Asp Glu Val His Ala Leu Gly Ala
                355                 360                 365

Glu Leu Ser Met Ser Thr Leu Met Val Asp Ala Ser Pro Glu Leu Leu
    370                 375                 380

Ala Leu Ala Glu Ala Ser Pro Asp His Ser Ala His Arg Ala Asp Glu
385                 390                 395                 400

Pro Tyr Arg Arg Ala Leu Ile Gly Ile Tyr Ala Arg Leu Ala Ala Thr
                405                 410                 415

Ser Lys Met Leu Thr Gly Gln Gly Ala Pro Arg His Pro Val Ala Asp
                420                 425                 430

Ala Glu Pro Tyr Ser Ser Ala Glu Ala Phe Ala Ala Asp Val Gln Ile
    435                 440                 445

Val Ile Asp Ser Leu Arg Ala His His Gly Arg Ala Leu Thr Ser Thr
    450                 455                 460

Arg Ile Asp Ala Leu Val Arg Ala Ile Ala Val Phe Gly Phe His Leu
465                 470                 475                 480

Ala Ser Val Asp Met Arg Gln Val Ser Asp Val His Glu Ala Val Val
                485                 490                 495

Ala Glu Leu Phe Ala Ala Gly Val Glu Lys Asp Tyr Ala Ala Leu
                500                 505                 510

Pro Glu Ser Arg Lys Leu Glu Leu Leu Ala Glu Leu Arg Gln Pro
    515                 520                 525

Arg Leu Leu Thr Leu Pro Tyr His Glu Tyr Ser Glu Gln Thr Arg Asn
530                 535                 540

Glu Leu Ala Ile Leu Ala Thr Ala Arg Glu Leu Arg Ala Arg Tyr Gly
545                 550                 555                 560

Gln Arg Val Ala Arg Asn Tyr Ile Ile Ser His Thr Glu Thr Leu Ser
                565                 570                 575

Asp Leu Val Glu Val Met Leu Leu Gln Lys Glu Ala Gly Met Leu Lys
                580                 585                 590

Gly Thr Leu Gly Ser Lys Thr Asp Pro Ala Arg Met Glu Leu Met Val
                595                 600                 605

Ile Pro Leu Phe Glu Thr Ile Glu Asp Leu Gln Asn Ala Ala Gly Ile
    610                 615                 620

Met Gln Ser Leu Leu Asp Leu Pro Gly Phe Asp Ser Val Ile Glu His
```

|  | 625 |  |  |  | 630 |  |  |  | 635 |  |  |  | 640 |  |
|---|---|---|---|---|---|---|---|---|---|---|---|---|---|---|
| His | Gly | Val | Glu | Gln | Glu | Val | Met | Leu | Gly | Tyr | Ser | Asp | Ser | Asn | Lys |
|  |  |  |  | 645 |  |  |  |  | 650 |  |  |  | 655 |  |  |
| Asp | Gly | Gly | Phe | Leu | Thr | Ser | Asn | Trp | Glu | Leu | Tyr | Lys | Ala | Glu | Leu |
|  |  |  | 660 |  |  |  |  | 665 |  |  |  |  | 670 |  |  |
| Ala | Leu | Val | Gln | Leu | Phe | Glu | Gln | Arg | Lys | Val | Lys | Leu | Arg | Leu | Phe |
|  |  | 675 |  |  |  |  | 680 |  |  |  |  | 685 |  |  |  |
| His | Gly | Arg | Gly | Thr | Val | Gly | Arg | Gly | Gly | Pro | Thr | Tyr | Gln |
|  | 690 |  |  |  |  | 695 |  |  |  |  | 700 |  |  |
| Ala | Ile | Leu | Ser | Gln | Pro | Pro | Gly | Thr | Val | Asn | Gly | Gln | Ile | Arg | Leu |
| 705 |  |  |  |  | 710 |  |  |  |  | 715 |  |  |  |  | 720 |
| Thr | Glu | Gln | Gly | Glu | Ile | Ile | Asn | Ser | Lys | Phe | Ala | Asn | Ala | Glu | Ile |
|  |  |  |  | 725 |  |  |  |  | 730 |  |  |  |  | 735 |  |
| Gly | Arg | Arg | Asn | Leu | Glu | Thr | Val | Ile | Ala | Ala | Thr | Leu | Glu | Ala | Ser |
|  |  |  | 740 |  |  |  |  | 745 |  |  |  |  | 750 |  |  |
| Leu | Leu | Pro | Gln | Gln | Asn | Ala | Pro | Lys | Glu | Leu | Ser | Thr | Phe | Glu | Gly |
|  |  | 755 |  |  |  |  | 760 |  |  |  |  | 765 |  |  |  |
| Ile | Met | Gln | Gln | Leu | Ser | Asp | Arg | Ala | Phe | Gly | Ala | Tyr | Arg | Asn | Leu |
|  | 770 |  |  |  |  | 775 |  |  |  |  | 780 |  |  |  |  |
| Val | Tyr | Glu | Thr | Pro | Gly | Phe | Lys | Asp | Tyr | Phe | Phe | Ala | Thr | Thr | Pro |
| 785 |  |  |  |  | 790 |  |  |  |  | 795 |  |  |  |  | 800 |
| Ile | Thr | Glu | Ile | Ala | Asp | Leu | Asn | Leu | Gly | Ser | Arg | Pro | Ala | Ser | Arg |
|  |  |  |  | 805 |  |  |  |  | 810 |  |  |  |  | 815 |  |
| Lys | Leu | Met | Asp | Lys | Lys | Asn | Arg | Arg | Ile | Glu | Asp | Leu | Arg | Ala | Ile |
|  |  |  | 820 |  |  |  |  | 825 |  |  |  |  | 830 |  |  |
| Pro | Trp | Gly | Phe | Ser | Trp | Gly | Gln | Cys | Arg | Leu | Leu | Leu | Pro | Gly | Trp |
|  |  | 835 |  |  |  |  | 840 |  |  |  |  | 845 |  |  |  |
| Tyr | Gly | Phe | Gly | Ser | Ala | Val | Lys | Ser | Leu | Leu | Asp | Thr | Ala | Pro | Asp |
|  | 850 |  |  |  |  | 855 |  |  |  |  | 860 |  |  |  |  |
| Glu | Lys | Ala | Arg | Lys | Ala | Ala | Val | Ala | Thr | Leu | Arg | Lys | Met | Val | Lys |
| 865 |  |  |  |  | 870 |  |  |  |  | 875 |  |  |  |  | 880 |
| Thr | Trp | Pro | Phe | Phe | Ser | Thr | Leu | Leu | Ser | Asn | Met | Asp | Met | Val | Leu |
|  |  |  |  | 885 |  |  |  |  | 890 |  |  |  |  | 895 |  |
| Ala | Lys | Thr | Asp | Leu | Ala | Val | Ala | Ser | Arg | Tyr | Ala | Gln | Leu | Cys | Asp |
|  |  |  | 900 |  |  |  |  | 905 |  |  |  |  | 910 |  |  |
| Asp | Ala | Ala | Leu | Arg | Lys | Asn | Val | Phe | Ala | Arg | Ile | Ser | Lys | Glu | Trp |
|  |  | 915 |  |  |  |  | 920 |  |  |  |  | 925 |  |  |  |
| His | Leu | Thr | Cys | Glu | Met | Leu | Ala | Leu | Val | Thr | Gly | His | Gln | Glu | Arg |
|  | 930 |  |  |  |  | 935 |  |  |  |  | 940 |  |  |  |  |
| Leu | Ala | Asp | Asn | Pro | Leu | Leu | Ala | Arg | Ser | Ile | Lys | Asn | Arg | Phe | Ala |
| 945 |  |  |  |  | 950 |  |  |  |  | 955 |  |  |  |  | 960 |
| Tyr | Leu | Asp | Pro | Leu | Asn | His | Leu | Gln | Val | Glu | Leu | Leu | Lys | Arg | Tyr |
|  |  |  |  | 965 |  |  |  |  | 970 |  |  |  |  | 975 |  |
| Arg | Ser | Gly | Lys | Asp | Gly | Asp | Asp | Ile | Arg | Val | Arg | Gly | Ile | His |
|  |  |  | 980 |  |  |  |  | 985 |  |  |  |  | 990 |  |
| Leu | Thr | Ile | Asn | Gly | Val | Ala | Ala | Gly | Leu | Arg | Asn | Thr | Gly |
|  |  | 995 |  |  |  |  | 1000 |  |  |  |  | 1005 |  |

<210> SEQ ID NO 31
<211> LENGTH: 2958
<212> TYPE: DNA
<213> ORGANISM: R. solanacearum

<400> SEQUENCE: 31

-continued

| | |
|---|---:|
| atgacgcagt ccgccgcgcg ccgcgcatcc tcgcgcgcga ccccccgcgcg caagacgcca | 60 |
| cccgcccccg ccagccagac cccggcgccc tcgcccggcg gcacggccgg caccgccctg | 120 |
| ggcccgacct cgcgccggtc ctccggcagc gcggcggcca aggaccagcc gctcaaggag | 180 |
| gacatccgct tcctcgggcg cctgctgggc gacgtgctgc gcgagcagga aggcgccgcc | 240 |
| gccttcgaga ccgtcgagac catccgccag accgcggtgc gcttccgccg cgacggcgac | 300 |
| cgccaggccg agcaggagct cgaccggctg ctcaagacgc tgtcgcgcga ccagaccacc | 360 |
| tcggtggtgc gcgccttcag ctacttctcg cacttggcca acatcgccga agaccagcac | 420 |
| cataaccgcc gccgccgcgt gcacgcgctg gccggctcgt cgccgcagcc gggcagcctg | 480 |
| ctgcgcgcgc tgctgtcggc ggccgacgag ggcctctcgg gcgatgcgct gcggcgcttc | 540 |
| ttcgacgccg cgctgatcgt gccggtgctg acggcccacc cgaccgaagt gcagcgcaag | 600 |
| agcattctcg acgcgcagcg cgagatcgcc cgcctgctgg ccgagcgcga tgcgccgttg | 660 |
| accgtgcgcg agcgcgagcg caacgtcacc ctgctgcgcg cccacgtcac caagctgtgg | 720 |
| cagacgcgca tgctgcgcac cacgcgcctg atggtggccg acgagatcga gaacgcgctg | 780 |
| tcgtactacc agaccaccttt cctgcgcgag attcccgcgc tgtaccgcga gctggaagag | 840 |
| gacgtcgcca cggtgttccc gcgccggggc gcgcgcggcc agccggcccc gctgcccgcc | 900 |
| ttcttccaga tgggctcgtg gatcggcggc gatcgcgacg gcaacccgtt cgtcaccgcg | 960 |
| cagacgctgc gccatgccgc gcaacggcag gccagcgtga tcctcacgtg gtacctcgac | 1020 |
| gagatccacg cgctgggcgc ggagttgtcg atgtccacct tgctcgtcga cgtgagcgcc | 1080 |
| gacctgctgg ccctggccga acgctcgccc gatcactccg agcaccgcgc ggatgagcct | 1140 |
| taccggcgcg cgctgatcgg cgtgtatgcg cgcctggcgg ccacctgccg cgagctgacc | 1200 |
| ggcgaggatg ccggccgcca cgcggtcggc ccggcccccg cctacacgcg cgcggaggaa | 1260 |
| ctgcgcgccg atctccagat cgtcatcgat tccctcgcgg cgcaccacgg cgaggcgctg | 1320 |
| gccgatgcgc ggctggcctc gctggcgcgg gcgatcgacg tgttcggctt ccacctcgcg | 1380 |
| tcgatcgatc tgcgccaggt gtcggacgtg cacgaggcca ccgtggccga gctgctccgg | 1440 |
| gtggccggc tggaaggcgc ctatgcgcg ctgtcggaag ccgacaagcg cacgctgctg | 1500 |
| ctgcgcgagc tgcagcagcc gcgcctgctg acgctgccct tccacaccta cagcgagacg | 1560 |
| accgcgtcgg agctcgacat cttccgtgcc gcgcgcgagg tgcgcgcgcg ctacggcagc | 1620 |
| cgcatcgtgc gcaactacat catctcgcac accgagacgc tgtcggacct gctggaagtg | 1680 |
| atgctgctgc agaaggaggc gggcatgttc cgccacggca ccaacggcag cggcggcgcg | 1740 |
| ggcctggatg tgatggtgat cccgctgttc gagaccatcg aagacttgcg caacgccccg | 1800 |
| cagatcatgg gcgagctgct cgccctgccc ggcttcgatg ccgtgctggc cgcgcagggc | 1860 |
| aacgagcagg aagtgatgct cggctattcg gattccaaca aggacggcgg cttcctgacc | 1920 |
| tccaactggg agctgtacaa gaccgagctg gcgctggtgg agctgttcga gcgcaaaggc | 1980 |
| gtgcgcctgc gcctgttcca cggccgcggc ggcacggtgg gccgcggcgg cggcccgacc | 2040 |
| taccaggcca tcctgtcgca gccgccgggc acggtgaacg ggcagatccg cctgaccgag | 2100 |
| cagggcgaga tcatctccag caagttcgcc aaccccgaga tcgggcggcg caacctcgag | 2160 |
| accatcgtgg ccgccacgct cgaagccacg ctgctgccca cgcgcaaccg gcccaagggg | 2220 |
| ctggaggaat cgaggccgc gatgcaggcg ctgtcggacc acgcgttctc ggcctaccgc | 2280 |
| cacctcgtct acgagacccc gggcttcaag gactacttct tcgccaccac gcccatcacc | 2340 |
| gagatcgccg acctgaacct cggctcgcgg ccggcctcgc gcaagctgat ggacaggaag | 2400 |

```
cagcgccgca tcgaagacct gcgcgcgatt ccgtggggct tctcgtgggg ccagtgccgg   2460
ctgctgctgc cgggctggtt cggcttcggc agcgcggtgc agcgctggct ggacgaggcc   2520
ggcagcgcca aggcgaaggc ggcgcgcctg gcgacgctca agcgcatgca caagcaatgg   2580
ccgttctttg ccaacctgct ctccaacatg gacatggtgc tgtccaaggc cgacctgaac   2640
gtggcttcgc gctatgccca gctgtgcgaa gaccgcaagc tgcgcaacgc ggtgttctcg   2700
cgcatctcgg ccgagttcac gctcaccgag caggtgctgg gggccatcac cggccagtcg   2760
gagcggctgg cggacaaccc gctgctggcg cgctcgatca agaaccgctt cccctacctc   2820
gatccgctca accacctgca ggtggagctg ctcaagcggt tccgttcggg caaggccggc   2880
agcaacgatg cgcgcgtgcg gcgcggcatc cacctgtcga tcaacgggat cgcggcgggg   2940
ctgcgcaata gcggctga                                                 2958
```

<210> SEQ ID NO 32
<211> LENGTH: 985
<212> TYPE: PRT
<213> ORGANISM: R. solanacearum

<400> SEQUENCE: 32

```
Met Thr Gln Ser Ala Ala Arg Arg Ala Ser Ser Arg Ala Thr Pro Ala
1               5                   10                  15

Arg Lys Thr Pro Pro Ala Pro Ala Ser Gln Thr Pro Ala Pro Ser Pro
            20                  25                  30

Gly Gly Thr Ala Gly Thr Ala Leu Gly Pro Thr Ser Arg Arg Ser Ser
        35                  40                  45

Gly Ser Ala Ala Ala Lys Asp Gln Pro Leu Lys Glu Asp Ile Arg Phe
    50                  55                  60

Leu Gly Arg Leu Leu Gly Asp Val Leu Arg Glu Gln Glu Gly Ala Ala
65                  70                  75                  80

Ala Phe Glu Thr Val Glu Thr Ile Arg Gln Thr Ala Val Arg Phe Arg
                85                  90                  95

Arg Asp Gly Asp Arg Gln Ala Glu Gln Glu Leu Asp Arg Leu Leu Lys
            100                 105                 110

Thr Leu Ser Arg Asp Gln Thr Thr Ser Val Val Arg Ala Phe Ser Tyr
        115                 120                 125

Phe Ser His Leu Ala Asn Ile Ala Glu Asp Gln His His Asn Arg Arg
    130                 135                 140

Arg Arg Val His Ala Leu Ala Gly Ser Ser Pro Gln Pro Gly Ser Leu
145                 150                 155                 160

Leu Arg Ala Leu Leu Ser Ala Ala Asp Glu Gly Leu Ser Gly Asp Ala
                165                 170                 175

Leu Arg Arg Phe Phe Asp Ala Ala Leu Ile Val Pro Val Leu Thr Ala
            180                 185                 190

His Pro Thr Glu Val Gln Arg Lys Ser Ile Leu Asp Ala Gln Arg Glu
        195                 200                 205

Ile Ala Arg Leu Leu Ala Glu Arg Asp Ala Pro Leu Thr Val Arg Glu
    210                 215                 220

Arg Glu Arg Asn Val Thr Leu Leu Arg Ala His Val Thr Lys Leu Trp
225                 230                 235                 240

Gln Thr Arg Met Leu Arg Thr Thr Arg Leu Met Val Ala Asp Glu Ile
                245                 250                 255

Glu Asn Ala Leu Ser Tyr Tyr Gln Thr Thr Phe Leu Arg Glu Ile Pro
            260                 265                 270
```

```
Ala Leu Tyr Arg Glu Leu Glu Asp Val Ala Thr Val Phe Pro Arg
            275                 280                 285

Arg Gly Ala Arg Gly Glu Pro Ala Pro Leu Pro Ala Phe Phe Gln Met
290                 295                 300

Gly Ser Trp Ile Gly Gly Asp Arg Asp Gly Asn Pro Phe Val Thr Ala
305                 310                 315                 320

Gln Thr Leu Arg His Ala Ala Gln Arg Gln Ala Ser Val Ile Leu Thr
                325                 330                 335

Trp Tyr Leu Asp Glu Ile His Ala Leu Gly Ala Glu Leu Ser Met Ser
                340                 345                 350

Thr Leu Leu Val Asp Val Ser Ala Asp Leu Leu Ala Leu Ala Glu Arg
            355                 360                 365

Ser Pro Asp His Ser Glu His Arg Ala Asp Glu Pro Tyr Arg Arg Ala
370                 375                 380

Leu Ile Gly Val Tyr Ala Arg Leu Ala Ala Thr Cys Arg Glu Leu Thr
385                 390                 395                 400

Gly Glu Asp Ala Gly Arg His Ala Val Gly Pro Ala Pro Ala Tyr Thr
                405                 410                 415

Arg Ala Glu Glu Leu Arg Ala Asp Leu Gln Ile Val Ile Asp Ser Leu
            420                 425                 430

Ala Ala His His Gly Glu Ala Leu Ala Asp Ala Arg Leu Ala Ser Leu
            435                 440                 445

Ala Arg Ala Ile Asp Val Phe Gly Phe His Leu Ala Ser Ile Asp Leu
450                 455                 460

Arg Gln Val Ser Asp Val His Glu Ala Thr Val Ala Glu Leu Leu Arg
465                 470                 475                 480

Val Ala Gly Val Glu Gly Ala Tyr Ala Ala Leu Ser Glu Ala Asp Lys
                485                 490                 495

Arg Thr Leu Leu Leu Arg Glu Leu Gln Gln Pro Arg Leu Leu Thr Leu
            500                 505                 510

Pro Phe His Thr Tyr Ser Glu Thr Thr Ala Ser Glu Leu Asp Ile Phe
            515                 520                 525

Arg Ala Ala Arg Glu Val Arg Ala Arg Tyr Gly Ser Arg Ile Val Arg
530                 535                 540

Asn Tyr Ile Ile Ser His Thr Glu Thr Leu Ser Asp Leu Leu Glu Val
545                 550                 555                 560

Met Leu Leu Gln Lys Glu Ala Gly Met Phe Arg His Gly Thr Asn Gly
                565                 570                 575

Ser Gly Gly Ala Gly Leu Asp Val Met Val Ile Pro Leu Phe Glu Thr
            580                 585                 590

Ile Glu Asp Leu Arg Asn Ala Pro Gln Ile Met Gly Glu Leu Leu Ala
            595                 600                 605

Leu Pro Gly Phe Asp Ala Val Leu Ala Ala Gln Gly Asn Glu Gln Glu
610                 615                 620

Val Met Leu Gly Tyr Ser Asp Ser Asn Lys Asp Gly Gly Phe Leu Thr
625                 630                 635                 640

Ser Asn Trp Glu Leu Tyr Lys Thr Glu Leu Ala Leu Val Glu Leu Phe
                645                 650                 655

Glu Arg Lys Gly Val Arg Leu Arg Leu Phe His Gly Arg Gly Gly Thr
            660                 665                 670

Val Gly Arg Gly Gly Gly Pro Thr Tyr Gln Ala Ile Leu Ser Gln Pro
            675                 680                 685
```

-continued

Pro Gly Thr Val Asn Gly Gln Ile Arg Leu Thr Glu Gln Gly Glu Ile
690 695 700

Ile Ser Ser Lys Phe Ala Asn Pro Glu Ile Gly Arg Arg Asn Leu Glu
705 710 715 720

Thr Ile Val Ala Ala Thr Leu Glu Ala Thr Leu Leu Pro Thr Arg Asn
725 730 735

Arg Pro Lys Gly Leu Glu Glu Phe Glu Ala Ala Met Gln Ala Leu Ser
740 745 750

Asp His Ala Phe Ser Ala Tyr Arg His Leu Val Tyr Glu Thr Pro Gly
755 760 765

Phe Lys Asp Tyr Phe Phe Ala Thr Thr Pro Ile Thr Glu Ile Ala Asp
770 775 780

Leu Asn Leu Gly Ser Arg Pro Ala Ser Arg Lys Leu Met Asp Arg Lys
785 790 795 800

Gln Arg Arg Ile Glu Asp Leu Arg Ala Ile Pro Trp Gly Phe Ser Trp
805 810 815

Gly Gln Cys Arg Leu Leu Leu Pro Gly Trp Phe Gly Phe Gly Ser Ala
820 825 830

Val Gln Arg Trp Leu Asp Glu Ala Gly Ser Ala Lys Ala Lys Ala Ala
835 840 845

Arg Leu Ala Thr Leu Lys Arg Met His Lys Gln Trp Pro Phe Phe Ala
850 855 860

Asn Leu Leu Ser Asn Met Asp Met Val Leu Ser Lys Ala Asp Leu Asn
865 870 875 880

Val Ala Ser Arg Tyr Ala Gln Leu Cys Glu Asp Arg Lys Leu Arg Asn
885 890 895

Ala Val Phe Ser Arg Ile Ser Ala Glu Phe Thr Leu Thr Glu Gln Val
900 905 910

Leu Gly Ala Ile Thr Gly Gln Ser Glu Arg Leu Ala Asp Asn Pro Leu
915 920 925

Leu Ala Arg Ser Ile Lys Asn Arg Phe Pro Tyr Leu Asp Pro Leu Asn
930 935 940

His Leu Gln Val Glu Leu Leu Lys Arg Phe Arg Ser Gly Lys Ala Gly
945 950 955 960

Ser Asn Asp Ala Arg Val Arg Arg Gly Ile His Leu Ser Ile Asn Gly
965 970 975

Ile Ala Ala Gly Leu Arg Asn Ser Gly
980 985

<210> SEQ ID NO 33
<211> LENGTH: 3258
<212> TYPE: DNA
<213> ORGANISM: Burkholderia pseudomallei

<400> SEQUENCE: 33
ttgcccgccc gcccgccggg cgggctgcgc gaacggcccg tccggtccgc gtcaagatcc 60
cgaacggccg ttcggttcga gaaggcatcc ggcatccgcc agcgggtccg gttcgccgcc 120
gcatcgcctg ccgcgtcatt cgccgcgtcg tccggtttca tcgtccgacg cgcgtcgcca 180
gccgtgcggc atgcgccgcc gcgccgcctg atcgcgcccg ctgttgctgg accgcagttc 240
ccgttcactc gtgctttccc aaggaaatcg atcgtgaagt cttccggatc ggcgcgcgcg 300
acgcgccgca atgctgtctc gtcctcttcc gcccccggcgc acgccgagcc ccccgcccgc 360
cgcgccgcga aacccgcacg caagctcgac ggcgccgccg cgcgcccgct cgcgccgacg 420

| | | | | |
|---|---|---|---|---|
| aacgccgcat | ccgcgaaacc | gcaaggccgc | acgcgcgaag | acaaggaccg cccgctcttc 480 |
| gaggacattc | gctatctcgg | ccgcctgctc | ggcgacgtcg | ttcgcgaaca ggaaggcgac 540 |
| gccgtgttcg | acgtcgtcga | gacgattcgc | cagaccgcgg | tcaagttccg ccgcgaggac 600 |
| gacaaggccg | ccgcgcagac | gctcgagaaa | atgctgcgca | agctcacgcc cgagcagacg 660 |
| gtgagcgtcg | tgcgcgcgtt | cagctatttc | tcgcacctcg | cgaacatcgc cgaggaccgc 720 |
| catcacaacc | gccgccgccg | catccacgcg | ctcgcgggct | ccgcggcgca ggcgggcacc 780 |
| gtcgcgtacg | cgctcgacaa | gctcaagcag | gcgggcgacg | cgtcgtcgaa gacgatcaag 840 |
| cagttcttcg | aaggcgcgct | gatcgtgccc | gtgctcaccg | cgcacccgac cgaggtgcag 900 |
| cgcaagagca | ttctcgacgc | gcagcacgac | atcgcgcggc | tgctcgccga gcgcgaccag 960 |
| ccgctgaccg | cgcgcgagct | cgcgcacaac | gaggcgctgc | tgcgcgcgcg cgtgacgacg 1020 |
| ctctggcaga | cccggatgct | gcgcgacgcg | cgcctgaccg | tcgccgacga gatcgagaac 1080 |
| gcgctgtcgt | actaccgcgc | gacgttcctc | gacgagctgc | ccgcgctcta cgcggacatc 1140 |
| gaggaggcgc | tcgccgagca | cggcctgcgc | gcgcgcgtgc | cggcgttctt ccagatgggc 1200 |
| agctggatcg | gcggcgaccg | cgacggcaac | ccgaacgtca | ccgccgcgac gctcgacgag 1260 |
| gcgatcagcc | gccaggcggc | ggtgatcttc | gagcattacc | tcgaacaggt gcacaagctc 1320 |
| ggcgcggagc | tgtccgtgtc | gaacctgctc | gtcggcgcga | gcgacgcgct caaggcgctc 1380 |
| gccgccgcgt | cgccggacca | gtcgccgcac | gcgtcgacg | agccgtaccg ccgcgcgctg 1440 |
| atcggcgtct | acacgcggct | cgcggccagc | gcgcgcgtgc | ggctcggcga gggcacggtg 1500 |
| cccgtgcgca | gcgcgggccg | cggcgccgcg | cccgtgcgcg | cgacgccgta cgcggacgcg 1560 |
| gaggagttcg | ccgccgatct | gcgcgtgctg | accgattcgc | tcgcgctgca tcacggcgaa 1620 |
| tcgctcgcga | cgccgcgcct | cgccgcgctc | atgcgcgcgg | ccgaggtgtt cggcttccat 1680 |
| ctcgcgagca | tcgatttgcg | gcagagctcg | gacatccatg | aagcggtggt cgccgaactg 1740 |
| ctcgcgcgcg | gcgcgtcga | ggccgactac | gcggcgctgc | ccgaagcgga caagctgcgc 1800 |
| gtgctgctcg | cggcgctcgc | ggacccgcgg | ccgctgcgct | cgccgtatct cgactactcg 1860 |
| gacctcgcga | aaagcgagct | cggcgtgctc | gagcgcgcgc | acgcgatccg cgcgcagttc 1920 |
| ggcgcgcgcg | cggtgcgcaa | ctacatcatt | tcgcataccg | agacagtgag cgatctcgtc 1980 |
| gaggtgctgc | tgctgcagaa | ggaaacgggc | ctcttcgagg | gcacgctcgg cacgccgcac 2040 |
| gcgaacgcgc | gcaacggcct | gatggtgatt | ccgctcttcg | agacgatcgc cgacctgcgc 2100 |
| aacgcgtccg | acatcatgcg | cgcgttcttc | gcgctgccgg | gcgtgggcga gctgctcgcg 2160 |
| caccagggcc | acgagcagga | agtgatgctc | ggctattcgg | acagcaacaa ggacggcggc 2220 |
| ttcctcacgt | cgaactggga | gctctatcgc | gcggaactgg | cgctcgtcga tctgttcgac 2280 |
| gagcgcggga | tcaagctgcg | cctgttccat | ggccgcggcg | gcacggtggg acgcggcggc 2340 |
| ggcccgacct | atcaggcgat | cctgtcgcag | ccgcccggca | cggtaaacgg ccagatccgg 2400 |
| ctcaccgagc | agggcgaggt | gatcgcgagc | aagttcgcga | acccggagat cggccggcgc 2460 |
| aatctggaga | cggtcgtcgc | cgcgacgctc | gaggcgacgc | tcgcgccgca cagcaacgcg 2520 |
| ccgaagcagt | tgcccgcgtt | cgaggcgacg | atgcagacgc | tgtcggacgc ggcgatggcg 2580 |
| tcgtaccgcg | cgctcgtcta | cgagacgccc | ggcttcaccg | actacttctt ctcgtcgacg 2640 |
| ccgatcaccg | agatcgccga | gctgaacatc | ggcagccggc | ccgcgtcgcg caagctgcag 2700 |
| gatccgaaga | accgcaagat | cgaggacctg | cgcgcgattc | cgtggggctt ctcatggggc 2760 |
| cagtgccggc | tgctgctcac | cggctggtac | ggcttcggca | gcgcggtcgc cgcgtatctc 2820 |

```
gacggcgcgc cggacgcggc cgagcgcggc aagcgcgtcg cgctgctgaa gaaaatgaac    2880
aagacctggc cgttcttcgc gaacctgctg tcgaacatgg acatggtgct cgcgaagacc    2940
gatctcgcgg ttgcgtcgcg ctacgcgcag ctcgtcgccg acaagaagct gcgcaagcac    3000
gtgttcgagc ggatcgtcgc cgaatggcat cgcacggcgg atgcgctcgc cgagatcacc    3060
ggcgcgcacg cgcggctcgc cgcgaatccg cttctcgcgc gctcgatcaa gaaccgcttc    3120
ccgtacctcg atccgctgaa ccacctgcaa gtcgagctga tcaagcggca ccgcgcgggc    3180
gacacgaacg cgcggctgcg cgcgcgggatc catctgacga tcaacgggat cgcggccggc    3240
ctgcgcaata cgggctga                                                    3258
```

<210> SEQ ID NO 34
<211> LENGTH: 1085
<212> TYPE: PRT
<213> ORGANISM: Burkholderia pseudomallei

<400> SEQUENCE: 34

```
Met Pro Ala Arg Pro Pro Gly Gly Leu Arg Glu Arg Pro Val Arg Ser
1               5                   10                  15

Ala Ser Arg Ser Arg Thr Ala Val Arg Phe Glu Lys Ala Ser Gly Ile
            20                  25                  30

Arg Gln Arg Val Arg Phe Ala Ala Ala Ser Pro Ala Ala Ser Phe Ala
        35                  40                  45

Ala Ser Ser Gly Phe Ile Val Arg Arg Ala Ser Pro Ala Val Arg His
    50                  55                  60

Ala Pro Pro Arg Arg Leu Ile Ala Pro Ala Val Ala Gly Pro Gln Phe
65                  70                  75                  80

Pro Phe Thr Arg Ala Phe Pro Arg Lys Ser Ile Val Lys Ser Ser Gly
                85                  90                  95

Ser Ala Arg Ala Thr Arg Arg Asn Ala Val Ser Ser Ser Ala Pro
            100                 105                 110

Ala His Ala Glu Pro Pro Ala Arg Arg Ala Ala Lys Pro Ala Arg Lys
        115                 120                 125

Leu Asp Gly Ala Ala Ala Arg Pro Leu Ala Pro Thr Asn Ala Ala Ser
    130                 135                 140

Ala Lys Pro Gln Gly Arg Thr Arg Glu Asp Lys Asp Arg Pro Leu Phe
145                 150                 155                 160

Glu Asp Ile Arg Tyr Leu Gly Arg Leu Leu Gly Asp Val Val Arg Glu
                165                 170                 175

Gln Glu Gly Asp Ala Val Phe Asp Val Val Glu Thr Ile Arg Gln Thr
            180                 185                 190

Ala Val Lys Phe Arg Arg Glu Asp Asp Lys Ala Ala Ala Gln Thr Leu
        195                 200                 205

Glu Lys Met Leu Arg Lys Leu Thr Pro Glu Gln Thr Val Ser Val Val
    210                 215                 220

Arg Ala Phe Ser Tyr Phe Ser His Leu Ala Asn Ile Ala Glu Asp Arg
225                 230                 235                 240

His His Asn Arg Arg Arg Ile His Ala Leu Ala Gly Ser Ala Ala
                245                 250                 255

Gln Ala Gly Thr Val Ala Tyr Ala Leu Asp Lys Leu Lys Gln Ala Gly
            260                 265                 270

Asp Ala Ser Ser Lys Thr Ile Lys Gln Phe Phe Glu Gly Ala Leu Ile
        275                 280                 285
```

```
Val Pro Val Leu Thr Ala His Pro Thr Glu Val Gln Arg Lys Ser Ile
    290                 295                 300

Leu Asp Ala Gln His Asp Ile Ala Arg Leu Leu Ala Glu Arg Asp Gln
305                 310                 315                 320

Pro Leu Thr Ala Arg Glu Leu Ala His Asn Glu Ala Leu Leu Arg Ala
                325                 330                 335

Arg Val Thr Thr Leu Trp Gln Thr Arg Met Leu Arg Asp Ala Arg Leu
                340                 345                 350

Thr Val Ala Asp Glu Ile Glu Asn Ala Leu Ser Tyr Tyr Arg Ala Thr
            355                 360                 365

Phe Leu Asp Glu Leu Pro Ala Leu Tyr Ala Asp Ile Glu Glu Ala Leu
370                 375                 380

Ala Glu His Gly Leu Arg Ala Arg Val Pro Ala Phe Phe Gln Met Gly
385                 390                 395                 400

Ser Trp Ile Gly Gly Asp Arg Asp Gly Asn Pro Asn Val Thr Ala Ala
                405                 410                 415

Thr Leu Asp Glu Ala Ile Ser Arg Gln Ala Ala Val Ile Phe Glu His
                420                 425                 430

Tyr Leu Glu Gln Val His Lys Leu Gly Ala Glu Leu Ser Val Ser Asn
            435                 440                 445

Leu Leu Val Gly Ala Ser Asp Ala Leu Lys Ala Leu Ala Ala Ala Ser
450                 455                 460

Pro Asp Gln Ser Pro His Arg Val Asp Glu Pro Tyr Arg Arg Ala Leu
465                 470                 475                 480

Ile Gly Val Tyr Thr Arg Leu Ala Ala Ser Ala Arg Val Arg Leu Gly
                485                 490                 495

Glu Gly Thr Val Pro Val Arg Ser Ala Gly Arg Gly Ala Ala Pro Val
            500                 505                 510

Arg Ala Thr Pro Tyr Ala Asp Ala Glu Glu Phe Ala Ala Asp Leu Arg
            515                 520                 525

Val Leu Thr Asp Ser Leu Ala Leu His His Gly Glu Ser Leu Ala Thr
530                 535                 540

Pro Arg Leu Ala Pro Leu Met Arg Ala Ala Glu Val Phe Gly Phe His
545                 550                 555                 560

Leu Ala Ser Ile Asp Leu Arg Gln Ser Ser Asp Ile His Glu Ala Val
                565                 570                 575

Val Ala Glu Leu Leu Ala Arg Gly Gly Val Glu Ala Asp Tyr Ala Ala
            580                 585                 590

Leu Pro Glu Ala Asp Lys Leu Arg Val Leu Leu Ala Ala Leu Ala Asp
            595                 600                 605

Pro Arg Pro Leu Arg Ser Pro Tyr Leu Asp Tyr Ser Asp Leu Ala Lys
610                 615                 620

Ser Glu Leu Gly Val Leu Glu Arg Ala His Ala Ile Arg Ala Gln Phe
625                 630                 635                 640

Gly Ala Arg Ala Val Arg Asn Tyr Ile Ile Ser His Thr Glu Thr Val
                645                 650                 655

Ser Asp Leu Val Glu Val Leu Leu Gln Lys Glu Thr Gly Leu Phe
                660                 665                 670

Glu Gly Thr Leu Gly Thr Pro His Ala Asn Ala Arg Asn Gly Leu Met
            675                 680                 685

Val Ile Pro Leu Phe Glu Thr Ile Ala Asp Leu Arg Asn Ala Ser Asp
690                 695                 700

Ile Met Arg Ala Phe Phe Ala Leu Pro Gly Val Gly Glu Leu Leu Ala
```

```
        705                 710                 715                 720
His Gln Gly His Glu Gln Glu Val Met Leu Gly Tyr Ser Asp Ser Asn
                725                 730                 735

Lys Asp Gly Gly Phe Leu Thr Ser Asn Trp Glu Leu Tyr Arg Ala Glu
                740                 745                 750

Leu Ala Leu Val Asp Leu Phe Asp Glu Arg Gly Ile Lys Leu Arg Leu
                755                 760                 765

Phe His Gly Arg Gly Gly Thr Val Gly Arg Gly Gly Gly Pro Thr Tyr
                770                 775                 780

Gln Ala Ile Leu Ser Gln Pro Pro Gly Thr Val Asn Gly Gln Ile Arg
785                 790                 795                 800

Leu Thr Glu Gln Gly Glu Val Ile Ala Ser Lys Phe Ala Asn Pro Glu
                805                 810                 815

Ile Gly Arg Arg Asn Leu Glu Thr Val Val Ala Ala Thr Leu Glu Ala
                820                 825                 830

Thr Leu Ala Pro His Ser Asn Ala Pro Lys Gln Leu Pro Ala Phe Glu
                835                 840                 845

Ala Thr Met Gln Thr Leu Ser Asp Ala Ala Met Ala Ser Tyr Arg Ala
                850                 855                 860

Leu Val Tyr Glu Thr Pro Gly Phe Thr Asp Tyr Phe Phe Ser Ser Thr
865                 870                 875                 880

Pro Ile Thr Glu Ile Ala Glu Leu Asn Ile Gly Ser Arg Pro Ala Ser
                885                 890                 895

Arg Lys Leu Gln Asp Pro Lys Asn Arg Lys Ile Glu Asp Leu Arg Ala
                900                 905                 910

Ile Pro Trp Gly Phe Ser Trp Gly Gln Cys Arg Leu Leu Leu Thr Gly
                915                 920                 925

Trp Tyr Gly Phe Gly Ser Ala Val Ala Ala Tyr Leu Asp Gly Ala Pro
                930                 935                 940

Asp Ala Ala Glu Arg Gly Lys Arg Val Ala Leu Leu Lys Lys Met Asn
945                 950                 955                 960

Lys Thr Trp Pro Phe Phe Ala Asn Leu Leu Ser Asn Met Asp Met Val
                965                 970                 975

Leu Ala Lys Thr Asp Leu Ala Val Ala Ser Arg Tyr Ala Gln Leu Val
                980                 985                 990

Ala Asp Lys Lys Leu Arg Lys His Val Phe Glu Arg Ile Val Ala Glu
                995                 1000                1005

Trp His Arg Thr Ala Asp Ala Leu Ala Glu Ile Thr Gly Ala His
                1010                1015                1020

Ala Arg Leu Ala Ala Asn Pro Leu Leu Ala Arg Ser Ile Lys Asn
                1025                1030                1035

Arg Phe Pro Tyr Leu Asp Pro Leu Asn His Leu Gln Val Glu Leu
                1040                1045                1050

Ile Lys Arg His Arg Ala Gly Asp Thr Asn Ala Arg Leu Arg Arg
                1055                1060                1065

Gly Ile His Leu Thr Ile Asn Gly Ile Ala Ala Gly Leu Arg Asn
                1070                1075                1080

Thr Gly
    1085

<210> SEQ ID NO 35
<211> LENGTH: 3030
<212> TYPE: DNA
<213> ORGANISM: C. taiwanensis
```

<400> SEQUENCE: 35

```
atgacgcagc atgctgcgcg gcccaacggt cggaagaccg gcggcgccgc caaggattcg      60
tccgccgcga aggtgacgc aagcggcgca accagcgcca aaccgccccg ctccgccccc     120
cgcgcagcca agcgttccac caagcccacg ctttccatcg tgtcgagcaa cggaaccacc     180
atcgccccca ctcccgcccg ccgcaccacc gacaaggacg tgccgctgcg cgaggacatc     240
cgcttcctgg gccgcctgct gggcgactgc ctgcgcgagc aggaaggcga cgccgccttc     300
gaggtggtcg agaccatccg ccagaccgcg gtgcgcttcc gccgcgaaaa cgaccgcgcc     360 gccgcgccg agctggaccg cctgctcaag cgcctgtcgc gcgaccagac caaccaggtg     420
gtgcgcgcgt tcagctattt ctcgcacctg gccaatattg ccgaggacca gcaccacaac     480
cgccgccgcc gcgtgcatgc gctggccggc tcgccgccgc aggccggcag cctgcagcac     540
gcgctggaaa agatcgatgc cgccggcgtt accggcaagc agctgcgcaa gttcctggac     600
gaggcgctga tcgtgccggt gctgaccgcg cacccgaccg aagtccagcg caagagcatc     660
ctcgacgccg aacgcgagat cgcccgcctg ctggccgagc gcgacctgcc gatgaccgcg     720
cgcgagcgca tcacaacac cgcgcagctg cgcgccaagg tcaccacgct gtggcagacc     780
cgcatgctgc gcgacgcgcg cctgacggtg ccgacgaga tcgagaacgc gctgtcgtac     840
taccgcacca ccttcctgcg cggcatcccg cagctgatga gcgagctgga agaagcatc     900 gccgcggtgt tccccgccac gcggcggcgc aagggcgccc ccggcgacgc caagacggcg     960
ccgctgtcgc cgttcctgca gatgggttcc tggatcggcg gcgaccgcga cggcaatccc    1020
aacgtgaccg ccgaaacgct ggagcacgcc gccggccagc aggcgcagct catcctggac    1080
tggtacctgg aagaagtgca tgcgctcggc gccgagctgt cgatgtcgat gctgatggtc    1140
gacgccagcc cggaactgct ggcgctggcc gagcgctcgc ccgaccattc cgagcaccgc    1200
gccgacgaac cgtaccggcg cgcgctgatc ggcatctacg cccgcctggc ggccacctgc    1260
aaggcgctga gcggccatgc cgcgaccgcc cgcccggtgg cgccggccga gccctatgac    1320
agcgccgagg ccttcggcgc cgacatccag gtcgtcatcg attccctgcg cgcgcaccac    1380
ggccaggcgc tggccagcca ccgcatcgac gcgctcgcgc gcgccatcgc cgtgtttggc    1440
ttccacctgg cctcggtcga catgcgccag gtgtcggacg tgcacgaggc ggtcatcgcc    1500
gaactgttcg ccgccgccgg catcgccccc gactacgccg cgctgcccga gcaacgcaag    1560
ctggaactgc tgctggccga actgcgccag ccgcgcctgc tgacgctgcc gtggcacgag    1620
tactcggagc agaccgcaa ggaactggcg atctttgccg ccgcgcgcga gctgcgggcg    1680
cgctatggca agcgcgtggc gcgcaactac atcatctcgc acaccgagac gctgtcggac    1740
ctggtcgagg tgatgctgct gcagaaggaa tcgggcatgc tgcggggcac gctgggcagc    1800
aagaccgacc cggcgcgcat ggaactgatg gtgatcccgc tgttcgagac catcgaagac    1860
ttgcgcaacg ccgccggcat catgcagtcg ctgctggacc tgccgggctt cgatgccgtg    1920
ctcgcgcacc atggggtcga gcaggaagtg atgctcggct actcggattc gaacaaggac    1980
ggcggcttcc tgacgtccaa ctgggagctg tacaaggccg agctggcgct ggtgcagctg    2040
ttcgagcagc gcaacgtcaa gctgcgcctg ttccacggcc gcggcggcac cgtcggccgc    2100
ggcggcggcc cgacctacga cgccatcctg tcgcagccgc cgggcaccgt gaacggccag    2160
atccgcctga ccgagcaggg cgagatcatc aacagcaagt cgccaacgc cgagatcggc    2220 cggcgcaacc tggaaacggt ggtcgccgcc acgctagagg cctcgctgct gccgcagcag    2280
```

```
aacgcgccga aggacctgga caccttcgag gccgtcatgc agcagttgtc ggaccgcgcc    2340
ttcaccgctt atcgcgacct ggtctacgag acccccggct tcaaggacta cttcttcgcc    2400
accacgccga tcaccgagat cgccgacctg aacctcggtt cgcgtccggc ctcgcgcaag    2460
ctgatggaca agaagaaccg ccgcatcgaa gacctgcgcg cgatcccatg gggtttctcg    2520
tggggtcaat gccgcctgct gctgccgggc tggtacggct tcggcagcgc ggtccgctcg    2580
ctgctcgaca gcgcgccgga tgacaaggcg cgcaagcagg ccgtcaccac gctgcggcgc    2640
atggtcaaga cctggccgtt cttctcgacg ctgctgtcca acatggacat ggtgctggcc    2700
aagaccgacc tggcggtagc ctcgcgctac gcccagctgt gcgacgacgc ggcgctgcgc    2760
cgcaacgtgt tcaaccgcat cagcaaggaa tggcacctga cctgcgacat gctggcgctg    2820
atcaccggcc accaggagcg gctggcggac aacccgctgc tggcgcgctc gatcaagaac    2880
cgctttgcgt atctcgatcc gctgaaccac ttgcaggtgg agctgctcaa cgctaccgg    2940 gcgggcaagg acggcgatga tatccgcgta cggcgcggga tccacctgac catcaatggg    3000
gtggcggcag gattgcgcaa tacgggctga                                      3030
```

<210> SEQ ID NO 36
<211> LENGTH: 1009
<212> TYPE: PRT
<213> ORGANISM: C. taiwanensis

<400> SEQUENCE: 36

```
Met Thr Gln His Ala Ala Arg Pro Asn Gly Arg Lys Thr Gly Gly Ala
1               5                   10                  15

Ala Lys Asp Ser Ser Ala Ala Lys Gly Asp Ala Ser Gly Ala Thr Ser
            20                  25                  30

Ala Lys Pro Pro Arg Ser Ala Pro Arg Ala Ala Lys Arg Ser Thr Lys
        35                  40                  45

Pro Thr Leu Ser Ile Val Ser Ser Asn Gly Thr Thr Ile Ala Pro Thr
    50                  55                  60

Pro Ala Arg Arg Thr Thr Asp Lys Asp Val Pro Leu Arg Glu Asp Ile
65                  70                  75                  80

Arg Phe Leu Gly Arg Leu Leu Gly Asp Cys Leu Arg Glu Gln Glu Gly
                85                  90                  95

Asp Ala Ala Phe Glu Val Val Glu Thr Ile Arg Gln Thr Ala Val Arg
            100                 105                 110

Phe Arg Arg Glu Asn Asp Arg Ala Ala Gly Ala Glu Leu Asp Arg Leu
        115                 120                 125

Leu Lys Arg Leu Ser Arg Asp Gln Thr Asn Gln Val Val Arg Ala Phe
    130                 135                 140

Ser Tyr Phe Ser His Leu Ala Asn Ile Ala Glu Asp Gln His Asn
145                 150                 155                 160

Arg Arg Arg Arg Val His Ala Leu Ala Gly Ser Pro Pro Gln Ala Gly
                165                 170                 175

Ser Leu Gln His Ala Leu Glu Lys Ile Asp Ala Ala Gly Val Thr Gly
            180                 185                 190

Lys Gln Leu Arg Lys Phe Leu Asp Glu Ala Leu Ile Val Pro Val Leu
        195                 200                 205

Thr Ala His Pro Thr Glu Val Gln Arg Lys Ser Ile Leu Asp Ala Glu
    210                 215                 220

Arg Glu Ile Ala Arg Leu Leu Ala Glu Arg Asp Leu Pro Met Thr Ala
225                 230                 235                 240
```

```
Arg Glu Arg Asp His Asn Thr Ala Gln Leu Arg Ala Lys Val Thr Thr
                245                 250                 255
Leu Trp Gln Thr Arg Met Leu Arg Asp Ala Arg Leu Thr Val Ala Asp
            260                 265                 270
Glu Ile Glu Asn Ala Leu Ser Tyr Tyr Arg Thr Thr Phe Leu Arg Gly
        275                 280                 285
Ile Pro Gln Leu Met Ser Glu Leu Glu Glu Asp Ile Ala Ala Val Phe
    290                 295                 300
Pro Ala Thr Arg Arg Arg Lys Gly Ala Pro Gly Asp Ala Lys Thr Ala
305                 310                 315                 320
Pro Leu Ser Pro Phe Leu Gln Met Gly Ser Trp Ile Gly Gly Asp Arg
                325                 330                 335
Asp Gly Asn Pro Asn Val Thr Ala Glu Thr Leu Glu His Ala Ala Gly
            340                 345                 350
Gln Gln Ala Gln Leu Ile Leu Asp Trp Tyr Leu Glu Glu Val His Ala
        355                 360                 365
Leu Gly Ala Glu Leu Ser Met Ser Met Leu Met Val Asp Ala Ser Pro
    370                 375                 380
Glu Leu Leu Ala Leu Ala Glu Arg Ser Pro Asp His Ser Glu His Arg
385                 390                 395                 400
Ala Asp Glu Pro Tyr Arg Arg Ala Leu Ile Gly Ile Tyr Ala Arg Leu
                405                 410                 415
Ala Ala Thr Cys Lys Ala Leu Ser Gly His Ala Ala Thr Arg Arg Pro
            420                 425                 430
Val Ala Pro Ala Glu Pro Tyr Asp Ser Ala Glu Ala Phe Gly Ala Asp
        435                 440                 445
Ile Gln Val Val Ile Asp Ser Leu Arg Ala His His Gly Gln Ala Leu
    450                 455                 460
Ala Ser His Arg Ile Asp Ala Leu Ala Arg Ala Ile Ala Val Phe Gly
465                 470                 475                 480
Phe His Leu Ala Ser Val Asp Met Arg Gln Val Ser Asp Val His Glu
                485                 490                 495
Ala Val Ile Ala Glu Leu Phe Ala Ala Ala Gly Ile Ala Pro Asp Tyr
            500                 505                 510
Ala Ala Leu Pro Glu Gln Arg Lys Leu Glu Leu Leu Ala Glu Leu
        515                 520                 525
Arg Gln Pro Arg Leu Leu Thr Leu Pro Trp His Glu Tyr Ser Glu Gln
    530                 535                 540
Thr Arg Lys Glu Leu Ala Ile Phe Ala Ala Ala Arg Glu Leu Arg Ala
545                 550                 555                 560
Arg Tyr Gly Lys Arg Val Ala Arg Asn Tyr Ile Ile Ser His Thr Glu
                565                 570                 575
Thr Leu Ser Asp Leu Val Glu Val Met Leu Leu Gln Lys Glu Ser Gly
            580                 585                 590
Met Leu Arg Gly Thr Leu Gly Ser Lys Thr Asp Pro Ala Arg Met Glu
        595                 600                 605
Leu Met Val Ile Pro Leu Phe Glu Thr Ile Glu Asp Leu Arg Asn Ala
    610                 615                 620
Ala Gly Ile Met Gln Ser Leu Leu Asp Leu Pro Gly Phe Asp Ala Val
625                 630                 635                 640
Leu Ala His His Gly Val Glu Gln Glu Val Met Leu Gly Tyr Ser Asp
                645                 650                 655
Ser Asn Lys Asp Gly Gly Phe Leu Thr Ser Asn Trp Glu Leu Tyr Lys
```

```
                    660             665              670
Ala Glu Leu Ala Leu Val Gln Leu Phe Glu Gln Arg Asn Val Lys Leu
            675                 680                 685

Arg Leu Phe His Gly Arg Gly Thr Val Gly Arg Gly Gly Pro
        690                 695                 700

Thr Tyr Asp Ala Ile Leu Ser Gln Pro Pro Gly Thr Val Asn Gly Gln
705                 710                 715                 720

Ile Arg Leu Thr Glu Gln Gly Glu Ile Ile Asn Ser Lys Phe Ala Asn
                725                 730                 735

Ala Glu Ile Gly Arg Arg Asn Leu Glu Thr Val Val Ala Ala Thr Leu
            740                 745                 750

Glu Ala Ser Leu Leu Pro Gln Gln Asn Ala Pro Lys Asp Leu Asp Thr
        755                 760                 765

Phe Glu Ala Val Met Gln Gln Leu Ser Asp Arg Ala Phe Thr Ala Tyr
    770                 775                 780

Arg Asp Leu Val Tyr Glu Thr Pro Gly Phe Lys Asp Tyr Phe Phe Ala
785                 790                 795                 800

Thr Thr Pro Ile Thr Glu Ile Ala Asp Leu Asn Leu Gly Ser Arg Pro
                805                 810                 815

Ala Ser Arg Lys Leu Met Asp Lys Lys Asn Arg Arg Ile Glu Asp Leu
            820                 825                 830

Arg Ala Ile Pro Trp Gly Phe Ser Trp Gly Gln Cys Arg Leu Leu Leu
        835                 840                 845

Pro Gly Trp Tyr Gly Phe Gly Ser Ala Val Arg Ser Leu Leu Asp Ser
    850                 855                 860

Ala Pro Asp Asp Lys Ala Arg Lys Gln Ala Val Thr Thr Leu Arg Arg
865                 870                 875                 880

Met Val Lys Thr Trp Pro Phe Phe Ser Thr Leu Leu Ser Asn Met Asp
                885                 890                 895

Met Val Leu Ala Lys Thr Asp Leu Ala Val Ala Ser Arg Tyr Ala Gln
            900                 905                 910

Leu Cys Asp Asp Ala Ala Leu Arg Arg Asn Val Phe Asn Arg Ile Ser
        915                 920                 925

Lys Glu Trp His Leu Thr Cys Asp Met Leu Ala Leu Ile Thr Gly His
    930                 935                 940

Gln Glu Arg Leu Ala Asp Asn Pro Leu Leu Ala Arg Ser Ile Lys Asn
945                 950                 955                 960

Arg Phe Ala Tyr Leu Asp Pro Leu Asn His Leu Gln Val Glu Leu Leu
                965                 970                 975

Lys Arg Tyr Arg Ala Gly Lys Asp Gly Asp Ile Arg Val Arg Arg
            980                 985                 990

Gly Ile His Leu Thr Ile Asn Gly Val Ala Ala Gly Leu Arg Asn Thr
        995                 1000                1005

Gly

<210> SEQ ID NO 37
<211> LENGTH: 3030
<212> TYPE: DNA
<213> ORGANISM: R. metallidurans

<400> SEQUENCE: 37
atgacgcagc ctgctgcgcg ccccaccggc cgttcacgct ctaccggccg caagtctgtt       60
acgccagcct caggccagct tgaccccgaa ggcgcatccc ccaagacccc gaaagccacg      120
```

| | |
|---|---|
| aaaccccgca ccaaagcggc agccaggcca aagctcgctg tcgtggccgc caagggcgcc | 180 |
| gccccaaccg ccgcggccac cactatcccc gcccgccgca ccgccgacaa ggacctgccg | 240 |
| ctgcgcgagg acatccgctt cctcggccgc ctgctgggcg actgcgtgcg cgagcaggaa | 300 |
| ggcgatgccg cgttcgacct ggtcgagacg attcgccaga ccgcagtgcg cttccggcgc | 360 |
| gagaacgacc gcgccgccgg caccgaactc gaccgcctgc tgaaacgcct gtcgcgcgac | 420 |
| cagaccaatt cggtggtgcg cgccttcagc tacttctcgc atctggccaa tatcgccgaa | 480 |
| gaccagcacc acaaccgccg ccgccgggtg cacgcactgg ccggatcgcc gccgcagccg | 540 |
| ggcagtctgt cgcgcgcgct gcaggccatt gacgccgccg gcgtgactgg caagcaactt | 600 |
| cgcgaattcc ttgacgacgc gctgatcatg ccggtgctga ccgcgcaccc gaccgaagtc | 660 |
| cagcgcaaga gcatcctgga cgcggagcgc gagatcgcgc gcctgctggc cgagcgcgac | 720 |
| ctgccaatga ccacccgcga gcgcgaccac aacacggccc agctccgcgc acgcgtgacc | 780 |
| acgctgtggc agaccgcat gttgcggaac acgcgcttga tggtggtcga tgaaatcgag | 840 |
| aacgcgctct cgtactaccg caccacgttc ctccaggaa ttccgcgcct gatggccgag | 900 |
| ctggaggaag acatcgccga agtcttcccg cgccgttcca agaccggcgc cacgcccgcg | 960 |
| ccgctggcgc cgttcctgca gatgggctcg tggatcggcg cgaccgcga cggcaacccc | 1020 |
| aacgtcacgg ccgaaaccct cgagcacgcg gcgcgccagc aagccaccct gctgttcgac | 1080 |
| tggtacctcg atgaactgca cgcgctgggc gccgagctgc cgctgtcgtc gctgatggtc | 1140 |
| gatgccagcc ccgaactgct ggcgctggcc gaagcctcac cggaccactc cgaacaccgt | 1200 |
| gcggacgaac cctaccgccg cgcgctgatc ggtatgtacg cgcgcctggc cgccacctcg | 1260 |
| cagttgctga ctggccatgt cgcgcaacgc catccggtgg ccgacgtcgc cccctatgag | 1320 |
| aacgccgaag cattcgcggc cgacgtgcag atcgtggtcg attcgctacg cacccatcat | 1380 |
| ggtgaggcgt tggcgcgcgg ccgcgtcgac gcgctggtgc gcgcgatcgc ggtcttcggc | 1440 |
| ttccacctgg cctcgatcga catgcgtcag gtatctgacg tgcacgaggc cgtgatcgcc | 1500 |
| gaactgttcg cgacggccgg catcgagtcc gactacgctg cgctgccgga agcacgcaag | 1560 |
| ctggagctgc tgctggctga actgcgccag ccgcgcctgc tgacgctgcc gtggcacgac | 1620 |
| tactcggaac agacacgcag cgaactggcg atcttcgcga tggcccgcga cctgcgcgcc | 1680 |
| cgctatggcg cccgcatcgc gcgcaactac atcatctcgc acaccgagac gctgtccgac | 1740 |
| cttatcgagg tgatgctgct gcagaaggaa gccggcatgt tgcgcggcac gctgggcagc | 1800 |
| aagaccgatc cggcgcgcat ggagctgatg gtcatcccgc tgttcgaaac catcgaggat | 1860 |
| ttgcgcaatg cggccggcat catggagtcg ctgctggatc tgccgggctt cgattcggtg | 1920 |
| atcgcccacc atggcgtcga gcaggaagtg atgctcggct attcggattc gaacaaggat | 1980 |
| ggcggttttc ctgacgtcgaa ctgggagctc tacaaggccg aactggcgct ggtgaagctg | 2040 |
| ttcgaggaac gccgtgtgaa gctcgcgcct ttccatggcc ggggcggcac ggtgggtcgc | 2100 |
| ggcggtggcc cgacctatca ggccatcctg tcgcagccac ccggcaccgt gaacggccag | 2160 |
| atccgcctga cggaacaggg cgaaatcatc aacagcaagt tcgcgaatgc cgagatcggc | 2220 |
| cggcgcaacc tggaaacggt gatcgctgcc acgctggaag catcgctgct gcccacccag | 2280 |
| aacgcgccga aggacctggc gacgttcgaa ggcgtcatgc aacagctgtc cgaccatgcg | 2340 |
| ttctccgcgt accgtgacct ggtctacgag accccgggct tcaaggacta cttcttcgcc | 2400 |
| acgaccccga tcaccgagat cgcggacctg aacctcggat cgcggccggc atcgcgcaag | 2460 |
| ctgatggaca agaagcaccg ccgcatcgaa gacctgcggg cgattccatg gggcttctcg | 2520 |

-continued

```
tggggccagt gccgtctgct gctgccgggc tggttcggtt tcggcagtgc cgtgcaggcc    2580
ctgctggacg ccgcgccgga cgagaagtcg cgcaaggcca cggtggccac gctgaagcgg    2640
atggtgaagt cgtggccgtt cttcagcacg ctgctatcga acatggatat ggtgctggcc    2700
aagaccgacc tggccgtggc gtcacgctac gcggggctgt gcgaggacac cgcgctgcgc    2760
aaggccgtgt tctcacgcat cagtgccgaa tggcacctga ccagtgacat gctcggactg    2820
atcaccggcc ggcaggaacg actggctgac aacccgctgc tggcgcgctc gatcaagaac    2880
cgctttgcct acctggatcc gctgaaccac ctgcaggtgg aactgctcaa gcggtaccgg    2940
gccggcaagg atggcgacga cgtgcgcgtg cgacgcggga tccacctgac gatcaacggg    3000
gtggcggccg ggttgcgtaa tagcggttga                                    3030
```

<210> SEQ ID NO 38
<211> LENGTH: 1009
<212> TYPE: PRT
<213> ORGANISM: R. metallidurans

<400> SEQUENCE: 38

Met Thr Gln Pro Ala Ala Arg Pro Thr Gly Arg Ser Arg Ser Thr Gly
1               5                   10                  15

Arg Lys Ser Val Thr Pro Ala Ser Gly Gln Leu Asp Pro Glu Gly Ala
            20                  25                  30

Ser Pro Lys Thr Pro Lys Ala Thr Lys Pro Arg Thr Lys Ala Ala Ala
        35                  40                  45

Arg Pro Lys Leu Ala Val Val Ala Ala Lys Gly Ala Ala Pro Thr Ala
    50                  55                  60

Ala Ala Thr Thr Ile Pro Ala Arg Arg Thr Ala Asp Lys Asp Leu Pro
65                  70                  75                  80

Leu Arg Glu Asp Ile Arg Phe Leu Gly Arg Leu Leu Gly Asp Cys Val
                85                  90                  95

Arg Glu Gln Glu Gly Asp Ala Ala Phe Asp Leu Val Glu Thr Ile Arg
            100                 105                 110

Gln Thr Ala Val Arg Phe Arg Arg Glu Asn Asp Arg Ala Ala Gly Thr
        115                 120                 125

Glu Leu Asp Arg Leu Leu Lys Arg Leu Ser Arg Asp Gln Thr Asn Ser
    130                 135                 140

Val Val Arg Ala Phe Ser Tyr Phe Ser His Leu Ala Asn Ile Ala Glu
145                 150                 155                 160

Asp Gln His His Asn Arg Arg Arg Val His Ala Leu Ala Gly Ser
                165                 170                 175

Pro Pro Gln Pro Gly Ser Leu Ser Arg Ala Leu Gln Ala Ile Asp Ala
            180                 185                 190

Ala Gly Val Thr Gly Lys Gln Leu Arg Glu Phe Leu Asp Asp Ala Leu
        195                 200                 205

Ile Met Pro Val Leu Thr Ala His Pro Thr Glu Val Gln Arg Lys Ser
    210                 215                 220

Ile Leu Asp Ala Glu Arg Glu Ile Ala Arg Leu Ala Glu Arg Asp
225                 230                 235                 240

Leu Pro Met Thr Thr Arg Glu Arg Asp His Asn Thr Ala Gln Leu Arg
                245                 250                 255

Ala Arg Val Thr Thr Leu Trp Gln Thr Arg Met Leu Arg Asn Thr Arg
            260                 265                 270

Leu Met Val Val Asp Glu Ile Glu Asn Ala Leu Ser Tyr Tyr Arg Thr

-continued

```
            275                 280                 285
Thr Phe Leu Gln Gly Ile Pro Arg Leu Met Ala Glu Leu Glu Glu Asp
290                 295                 300

Ile Ala Glu Val Phe Pro Arg Arg Ser Lys Thr Gly Ala Thr Pro Ala
305                 310                 315                 320

Pro Leu Ala Pro Phe Leu Gln Met Gly Ser Trp Ile Gly Gly Asp Arg
                325                 330                 335

Asp Gly Asn Pro Asn Val Thr Ala Glu Thr Leu Glu His Ala Ala Arg
            340                 345                 350

Gln Gln Ala Thr Leu Leu Phe Asp Trp Tyr Leu Asp Glu Leu His Ala
            355                 360                 365

Leu Gly Ala Glu Leu Pro Leu Ser Ser Leu Met Val Asp Ala Ser Pro
370                 375                 380

Glu Leu Leu Ala Leu Ala Glu Ala Ser Pro Asp His Ser Glu His Arg
385                 390                 395                 400

Ala Asp Glu Pro Tyr Arg Arg Ala Leu Ile Gly Met Tyr Ala Arg Leu
                405                 410                 415

Ala Ala Thr Ser Gln Leu Leu Thr Gly His Val Ala Gln Arg His Pro
            420                 425                 430

Val Ala Asp Val Ala Pro Tyr Glu Asn Ala Glu Ala Phe Ala Ala Asp
            435                 440                 445

Val Gln Ile Val Asp Ser Leu Arg Thr His His Gly Glu Ala Leu
450                 455                 460

Ala Arg Gly Arg Val Asp Ala Leu Val Arg Ala Ile Ala Val Phe Gly
465                 470                 475                 480

Phe His Leu Ala Ser Ile Asp Met Arg Gln Val Ser Asp Val His Glu
                485                 490                 495

Ala Val Ile Ala Glu Leu Phe Ala Thr Ala Gly Ile Glu Ser Asp Tyr
            500                 505                 510

Ala Ala Leu Pro Glu Ala Arg Lys Leu Glu Leu Leu Ala Glu Leu
            515                 520                 525

Arg Gln Pro Arg Leu Leu Thr Leu Pro Trp His Asp Tyr Ser Glu Gln
530                 535                 540

Thr Arg Ser Glu Leu Ala Ile Phe Ala Met Ala Arg Asp Leu Arg Ala
545                 550                 555                 560

Arg Tyr Gly Ala Arg Ile Ala Arg Asn Tyr Ile Ile Ser His Thr Glu
                565                 570                 575

Thr Leu Ser Asp Leu Ile Glu Val Met Leu Leu Gln Lys Glu Ala Gly
            580                 585                 590

Met Leu Arg Gly Thr Leu Gly Ser Lys Thr Asp Pro Ala Arg Met Glu
            595                 600                 605

Leu Met Val Ile Pro Leu Phe Glu Thr Ile Glu Asp Leu Arg Asn Ala
610                 615                 620

Ala Gly Ile Met Glu Ser Leu Leu Asp Leu Pro Gly Phe Asp Ser Val
625                 630                 635                 640

Ile Ala His His Gly Val Glu Gln Glu Val Met Leu Gly Tyr Ser Asp
                645                 650                 655

Ser Asn Lys Asp Gly Gly Phe Leu Thr Ser Asn Trp Glu Leu Tyr Lys
            660                 665                 670

Ala Glu Leu Ala Leu Val Lys Leu Phe Glu Glu Arg Val Lys Leu
            675                 680                 685

Arg Leu Phe His Gly Arg Gly Gly Thr Val Gly Arg Gly Gly Gly Pro
690                 695                 700
```

-continued

Thr Tyr Gln Ala Ile Leu Ser Gln Pro Pro Gly Thr Val Asn Gly Gln
705                 710                 715                 720

Ile Arg Leu Thr Glu Gln Gly Glu Ile Ile Asn Ser Lys Phe Ala Asn
            725                 730                 735

Ala Glu Ile Gly Arg Arg Asn Leu Glu Thr Val Ile Ala Ala Thr Leu
        740                 745                 750

Glu Ala Ser Leu Leu Pro Thr Gln Asn Ala Pro Lys Asp Leu Ala Thr
    755                 760                 765

Phe Glu Gly Val Met Gln Leu Ser Asp His Ala Phe Ser Ala Tyr
770                 775                 780

Arg Asp Leu Val Tyr Glu Thr Pro Gly Phe Lys Asp Tyr Phe Phe Ala
785                 790                 795                 800

Thr Thr Pro Ile Thr Glu Ile Ala Asp Leu Asn Leu Gly Ser Arg Pro
                805                 810                 815

Ala Ser Arg Lys Leu Met Asp Lys Lys His Arg Arg Ile Glu Asp Leu
            820                 825                 830

Arg Ala Ile Pro Trp Gly Phe Ser Trp Gly Gln Cys Arg Leu Leu Leu
835                 840                 845

Pro Gly Trp Phe Gly Phe Gly Ser Ala Val Gln Ala Leu Leu Asp Ala
    850                 855                 860

Ala Pro Asp Glu Lys Ser Arg Lys Ala Thr Val Ala Thr Leu Lys Arg
865                 870                 875                 880

Met Val Lys Ser Trp Pro Phe Phe Ser Thr Leu Leu Ser Asn Met Asp
                885                 890                 895

Met Val Leu Ala Lys Thr Asp Leu Ala Val Ala Ser Arg Tyr Ala Gly
            900                 905                 910

Leu Cys Glu Asp Thr Ala Leu Arg Lys Ala Val Phe Ser Arg Ile Ser
        915                 920                 925

Ala Glu Trp His Leu Thr Ser Asp Met Leu Gly Leu Ile Thr Gly Arg
    930                 935                 940

Gln Glu Arg Leu Ala Asp Asn Pro Leu Leu Ala Arg Ser Ile Lys Asn
945                 950                 955                 960

Arg Phe Ala Tyr Leu Asp Pro Leu Asn His Leu Gln Val Glu Leu Leu
                965                 970                 975

Lys Arg Tyr Arg Ala Gly Lys Asp Gly Asp Asp Val Arg Val Arg Arg
            980                 985                 990

Gly Ile His Leu Thr Ile Asn Gly Val Ala Ala Gly Leu Arg Asn Ser
        995                 1000                1005

Gly

<210> SEQ ID NO 39
<211> LENGTH: 1452
<212> TYPE: DNA
<213> ORGANISM: Methanobacter thermoautotrophicus

<400> SEQUENCE: 39
atgaaggttc caagatgcat gagtacacag catccagaca acgttaaccc gccgttcttt      60
gcagaagaac ctgaactggg tggtgaagac gagataaggg aggcatacta cgtcttctca     120
cacctgggat gtgacgaaca gatgtgggac tgcgagggca aggaagtgga caactacgtt     180
gtaaagaaac tcctcacaaa gtaccaggcc ttcttcaggg accatgtcct gggtgaggat     240
ctgaggctca ccctcagggt gcccaacccc acagttgaga gggccgaggc aaagatactc     300
cttgagaccc ttgagagcat acccagatcc tatgacaccg caagcctctt ctacgggatg     360

```
gacgcagccc cggtcttcga ggtcatccta cccatgacct catcaagcag ctgcctcaac    420
cggatccaca gctactacct ggactttgtg aagggtaagg agaggctgca gctcgcagat    480
ggtgtgaccg tcaaggagtg gataggtgaa ttccggcccg acgagatcaa cgttatcccc    540
ctcttcgagg accatgaggg gatgctgaac gccgccaaga tcacaggcga gtaccttgat    600
ggtaaggata tccaggagca gagggtcttc cttgcaaggt cagaccccgc catgaactac    660
ggtatgatat cagccacact cctcaacagg atagccctct cagacttccg ggaccttgag    720
gaagagtcag gagttaaact ctaccccata ataggtatgg gctcagctcc cttcaggggt    780
aacctccgcc ccgataatgt ggaggacgtt acctgggagt accgtggcgc ctacaccttc    840
actgtccagt catccttcaa gtacgaccat gaaccatcag atgtcatcag gggcataaag    900
aaactcaggt ctgttaaacc gggcagggca gctgaaatcg agcgtgaaag tgtcctggag    960
ataatttcag cctactgcag ggagtacagg aggcaggtca tggacctcgt ggacatcata   1020 aacaggttg cgaggtacgt gcccggcagg aggaagagga agctccacat cggactcttc    1080
ggatactcca ggagcatggg aaacgtttca ctcccaaggg caataacctt cacagcggcc   1140
ctctactcgc tggggttcc cccggagctg ctcgggttca acgcgctatc atcaggtgac    1200
cttgaattca ttgaggaggt ctacccgggt cttggaaggg acctccatga cgctgcaagg   1260
tacgccaacc ctgaatcacc attcctcagc cctgaggtta aatcatcctt tgaggagtac   1320
cttgaacctg agtatgatga gggacacatg aagaccacag aggagatcat aagggccctc   1380
agaatcaaca ggacagccaa cctccaggag ctcatccttg aggctgcaag ccagaggaag   1440
ttcctcggct ga                                                       1452

<210> SEQ ID NO 40
<211> LENGTH: 483
<212> TYPE: PRT
<213> ORGANISM: Methanobacter thermoautotrophicus

<400> SEQUENCE: 40

Met Lys Val Pro Arg Cys Met Ser Thr Gln His Pro Asp Asn Val Asn
1               5                   10                  15

Pro Pro Phe Phe Ala Glu Glu Pro Glu Leu Gly Gly Glu Asp Glu Ile
            20                  25                  30

Arg Glu Ala Tyr Tyr Val Phe Ser His Leu Gly Cys Asp Glu Gln Met
        35                  40                  45

Trp Asp Cys Glu Gly Lys Glu Val Asp Asn Tyr Val Val Lys Lys Leu
    50                  55                  60

Leu Thr Lys Tyr Gln Ala Phe Phe Arg Asp His Val Leu Gly Glu Asp
65                  70                  75                  80

Leu Arg Leu Thr Leu Arg Val Pro Asn Pro Thr Val Glu Arg Ala Glu
                85                  90                  95

Ala Lys Ile Leu Leu Glu Thr Leu Glu Ser Ile Pro Arg Ser Tyr Asp
            100                 105                 110

Thr Ala Ser Leu Phe Tyr Gly Met Asp Ala Ala Pro Val Phe Glu Val
        115                 120                 125

Ile Leu Pro Met Thr Ser Ser Ser Cys Leu Asn Arg Ile His Ser
    130                 135                 140

Tyr Tyr Leu Asp Phe Val Lys Gly Lys Glu Arg Leu Gln Leu Ala Asp
145                 150                 155                 160

Gly Val Thr Val Lys Glu Trp Ile Gly Glu Phe Arg Pro Asp Glu Ile
                165                 170                 175
```

Asn Val Ile Pro Leu Phe Glu Asp His Glu Gly Met Leu Asn Ala Ala
            180                 185                 190

Lys Ile Thr Gly Glu Tyr Leu Asp Gly Lys Asp Ile Gln Glu Gln Arg
            195                 200                 205

Val Phe Leu Ala Arg Ser Asp Pro Ala Met Asn Tyr Gly Met Ile Ser
            210                 215                 220

Ala Thr Leu Leu Asn Arg Ile Ala Leu Ser Asp Phe Arg Asp Leu Glu
225                 230                 235                 240

Glu Glu Ser Gly Val Lys Leu Tyr Pro Ile Ile Gly Met Gly Ser Ala
            245                 250                 255

Pro Phe Arg Gly Asn Leu Arg Pro Asp Asn Val Glu Asp Val Thr Trp
            260                 265                 270

Glu Tyr Arg Gly Ala Tyr Thr Phe Thr Val Gln Ser Ser Phe Lys Tyr
            275                 280                 285

Asp His Glu Pro Ser Asp Val Ile Arg Gly Ile Lys Lys Leu Arg Ser
            290                 295                 300

Val Lys Pro Gly Arg Ala Ala Glu Ile Glu Arg Glu Ser Val Leu Glu
305                 310                 315                 320

Ile Ile Ser Ala Tyr Cys Arg Glu Tyr Arg Arg Gln Val Met Asp Leu
            325                 330                 335

Val Asp Ile Ile Asn Arg Val Ala Arg Tyr Val Pro Gly Arg Arg Lys
            340                 345                 350

Arg Lys Leu His Ile Gly Leu Phe Gly Tyr Ser Arg Ser Met Gly Asn
            355                 360                 365

Val Ser Leu Pro Arg Ala Ile Thr Phe Thr Ala Ala Leu Tyr Ser Leu
            370                 375                 380

Gly Val Pro Pro Glu Leu Leu Gly Phe Asn Ala Leu Ser Ser Gly Asp
385                 390                 395                 400

Leu Glu Phe Ile Glu Glu Val Tyr Pro Gly Leu Gly Arg Asp Leu His
            405                 410                 415

Asp Ala Ala Arg Tyr Ala Asn Pro Glu Ser Pro Phe Leu Ser Pro Glu
            420                 425                 430

Val Lys Ser Ser Phe Glu Glu Tyr Leu Glu Pro Glu Tyr Asp Glu Gly
            435                 440                 445

His Met Lys Thr Thr Glu Glu Ile Ile Arg Ala Leu Arg Ile Asn Arg
450                 455                 460

Thr Ala Asn Leu Gln Glu Leu Ile Leu Glu Ala Ala Ser Gln Arg Lys
465                 470                 475                 480

Phe Leu Gly

<210> SEQ ID NO 41
<211> LENGTH: 981
<212> TYPE: DNA
<213> ORGANISM: C. necator

<400> SEQUENCE: 41
gtgcatcctt ccgaggtctt gttccagggc gaagccatcc cggtccagtt gccggtgtgt      60
gaccactacg cgggcagcga aaagctgatg cgcaaatcgc ttgccctgca acaagagctt     120
ggcccggtct tcgacatcac cttcgactgc gaggacggcg ccgccgtcgg ccgtgagagc     180
gagcatgccg agctgtgcgc gcagctggtc aacagcccgc tcaatgccca caatcgcgtc     240
ggcgtgcgca tccatgaccc ggcccacccg aactggcgcg aggacgtcga cgtgctggtg     300
cgcgccgccg gcgcgcgcct ggcctatgtg gtggtgccca aggtcagcga cgtggtcgag     360

-continued

```
gttgcgcgcg tgaccgatca tgtcaaccag gtggcgcgca atgccggcat cgcccggcat    420
atcccgatcc atgtgctggt cgagacccac gccgcgctgg aacaggcctt cgatattgcc    480
gcgctggtgc aggtggaatg cctgagcttc ggcctgatgg actttgtctc ggcccatcat    540
ggcgccatcc cgggcgaagc catgcgctcc ccacagcaat cgaacaccc gctgatccgc    600 cgcgccatgc tggagatctc cgccgcctgc caccgccacg gcaaggtgcc gtcgcacaac    660
gtcagcaccg acgtgcaggc gccgcagcgc gccggcgacg atgcgctgcg cgcgcgcagc    720
gagttcggct acctgcgcaa atggagcatc catccgggcc agatcgcgcc gatcgtggcg    780
gcgttccgcc ccgtgccga agaaatcggc gcggccagcc agatcctgct ggccgcgcac    840
gagaacagct gggccccgat ccgccacgag ggccagctgc acgaccgcgc cagctaccgc    900
tactactggt cgctgctgca gcgcgcgcag gccaccggca cgccgctgcc ggccaatgtg    960
gaggcattgt ttttcgcctg a                                              981
```

<210> SEQ ID NO 42
<211> LENGTH: 326
<212> TYPE: PRT
<213> ORGANISM: C. necator

<400> SEQUENCE: 42

```
Met His Pro Ser Glu Val Leu Phe Gln Gly Glu Ala Ile Pro Val Gln
1               5                   10                  15

Leu Pro Val Cys Asp His Tyr Ala Gly Ser Glu Lys Leu Met Arg Lys
                20                  25                  30

Ser Leu Ala Leu Gln Gln Glu Leu Gly Pro Val Phe Asp Ile Thr Phe
            35                  40                  45

Asp Cys Glu Asp Gly Ala Ala Val Gly Arg Glu Ser Glu His Ala Glu
        50                  55                  60

Leu Cys Ala Gln Leu Val Asn Ser Pro Leu Asn Ala His Asn Arg Val
65                  70                  75                  80

Gly Val Arg Ile His Asp Pro Ala His Pro Asn Trp Arg Glu Asp Val
                85                  90                  95

Asp Val Leu Val Arg Ala Ala Gly Ala Arg Leu Ala Tyr Val Val Val
            100                 105                 110

Pro Lys Val Ser Asp Val Val Glu Val Ala Arg Val Thr Asp His Val
        115                 120                 125

Asn Gln Val Ala Arg Asn Ala Gly Ile Ala Arg His Ile Pro Ile His
    130                 135                 140

Val Leu Val Glu Thr His Ala Ala Leu Glu Gln Ala Phe Asp Ile Ala
145                 150                 155                 160

Ala Leu Val Gln Val Glu Cys Leu Ser Phe Gly Leu Met Asp Phe Val
                165                 170                 175

Ser Ala His His Gly Ala Ile Pro Gly Glu Ala Met Arg Ser Pro Gln
            180                 185                 190

Gln Phe Glu His Pro Leu Ile Arg Arg Ala Met Leu Glu Ile Ser Ala
        195                 200                 205

Ala Cys His Arg His Gly Lys Val Pro Ser His Asn Val Ser Thr Asp
    210                 215                 220

Val Gln Ala Pro Gln Arg Ala Gly Asp Asp Ala Leu Arg Ala Arg Ser
225                 230                 235                 240

Glu Phe Gly Tyr Leu Arg Lys Trp Ser Ile His Pro Gly Gln Ile Ala
                245                 250                 255
```

```
Pro Ile Val Ala Ala Phe Arg Pro Gly Ala Glu Ile Gly Ala Ala
            260                 265                 270

Ser Gln Ile Leu Leu Ala Ala His Glu Asn Ser Trp Ala Pro Ile Arg
        275                 280                 285

His Glu Gly Gln Leu His Asp Arg Ala Ser Tyr Arg Tyr Tyr Trp Ser
        290                 295                 300

Leu Leu Gln Arg Ala Gln Ala Thr Gly Thr Pro Leu Pro Ala Asn Val
305                 310                 315                 320

Glu Ala Leu Phe Phe Ala
                325

<210> SEQ ID NO 43
<211> LENGTH: 996
<212> TYPE: DNA
<213> ORGANISM: C. necator

<400> SEQUENCE: 43
atgatcaccc caacgcatcc gaacgacgcc ctctttgcag gcgaaaaggc ctttcccgtg      60
ctggccgcgt gcgagcactt tgccggcagc gggaagctga tcggcaaggc catggacctg     120
caggtcgagt acggcgcggc ctttgacgtg acctgcgact gcgaagacgg cgctgccgcc     180
gggcaggagc gcgagcacgc gcaaatggtg gcgcgcatga tcgcgtcgga acgcaaccgc     240
ttcggccgtg ccgcgcacg catccatgac cgtcgcacc ccgcctggcg ccaggacgtg      300
gacatcatcg tgagagaagc cggcagccgg ctggcctaca tcaccgtgcc aaggccacc      360 ggcagcggac aggtcgcgga ggtcatccgg tatatcgacg aggtccggac aaaaaccgga     420
ttggacaagc ccgtgccggt acacgtgctc atcgagaccc acggcgcgct gcgcgacgtc     480
ttcgagatcg ccgaattgcc ccacatcgag gtactggact tcggcctgat ggatttcgtc     540
agcggccacc acggcgctat tcccgcagcg gccatgcgta gtccgggcca gttcgaacat     600
gcgctgctgg ggcgtgcgaa ggccgacatg gtggcagcag cgctggccaa cggtatcgta     660
ccggcgcaca acgtctgcct gaatctgaag gacgctgagg tgatagcgag cgatgcccgg     720
cgcgcgcgcg acgagtttgg ctttctcgcg atgtggagca tctatccggc gcagatccag     780
ccaatcgtga acgccatgcg tcccgacctt gccgaagtcg aagacgcggc cggcatcctg     840
tcggcggcgc aggacgcgga ttggggggccg atccagtaca agggcgaact gcatgaccgc     900
gccacctacc gctatttctg ggaaatcctg cggaaggcga aggtcaccgg catgacgctt     960
ccggccgagg cggtccgcag attttttcgtc cgttag                                996

<210> SEQ ID NO 44
<211> LENGTH: 331
<212> TYPE: PRT
<213> ORGANISM: C. necator

<400> SEQUENCE: 44

Met Ile Thr Pro Thr His Pro Asn Asp Ala Leu Phe Ala Gly Glu Lys
1               5                   10                  15

Ala Phe Pro Val Leu Ala Ala Cys Glu His Phe Ala Gly Ser Gly Lys
            20                  25                  30

Leu Ile Gly Lys Ala Met Asp Leu Gln Val Glu Tyr Gly Ala Ala Phe
        35                  40                  45

Asp Val Thr Cys Asp Cys Glu Asp Gly Ala Ala Gly Gln Glu Arg
        50                  55                  60

Glu His Ala Gln Met Val Ala Arg Met Ile Ala Ser Glu Arg Asn Arg
65                  70                  75                  80
```

```
Phe Gly Arg Ala Gly Ala Arg Ile His Asp Pro Ser His Pro Ala Trp
                85                  90                  95
Arg Gln Asp Val Asp Ile Ile Val Arg Glu Ala Gly Ser Arg Leu Ala
            100                 105                 110
Tyr Ile Thr Val Pro Lys Ala Thr Gly Ser Gly Gln Val Ala Glu Val
        115                 120                 125
Ile Arg Tyr Ile Asp Glu Val Arg Thr Lys Thr Gly Leu Asp Lys Pro
    130                 135                 140
Val Pro Val His Val Leu Ile Glu Thr His Gly Ala Leu Arg Asp Val
145                 150                 155                 160
Phe Glu Ile Ala Glu Leu Pro His Ile Glu Val Leu Asp Phe Gly Leu
                165                 170                 175
Met Asp Phe Val Ser Gly His His Gly Ala Ile Pro Ala Ala Ala Met
            180                 185                 190
Arg Ser Pro Gly Gln Phe Glu His Ala Leu Leu Gly Arg Ala Lys Ala
        195                 200                 205
Asp Met Val Ala Ala Ala Leu Ala Asn Gly Ile Val Pro Ala His Asn
    210                 215                 220
Val Cys Leu Asn Leu Lys Asp Ala Glu Val Ile Ala Ser Asp Ala Arg
225                 230                 235                 240
Arg Ala Arg Asp Glu Phe Gly Phe Leu Arg Met Trp Ser Ile Tyr Pro
                245                 250                 255
Ala Gln Ile Gln Pro Ile Val Asn Ala Met Arg Pro Asp Leu Ala Glu
            260                 265                 270
Val Glu Asp Ala Ala Gly Ile Leu Ser Ala Ala Gln Asp Ala Asp Trp
        275                 280                 285
Gly Pro Ile Gln Tyr Lys Gly Glu Leu His Asp Arg Ala Thr Tyr Arg
    290                 295                 300
Tyr Phe Trp Glu Ile Leu Arg Lys Ala Lys Val Thr Gly Met Thr Leu
305                 310                 315                 320
Pro Ala Glu Ala Val Arg Arg Phe Phe Val Arg
                325                 330

<210> SEQ ID NO 45
<211> LENGTH: 825
<212> TYPE: DNA
<213> ORGANISM: C. necator

<400> SEQUENCE: 45
atgtccactg cagtcaccta cctgttcgtg ccgggcgacc ggccggaacg cttcgacaag      60
gccgctgccg ccggccccga tgtgatgatc ctggacctcg aggacgcggt ccatccggac     120
gccaagcccg ccgcgcgcgc agccatcgcc gcgtggctgg ccggactgcc gcggccaat     180 gcctttgtcc gcatcaacga cagcgcctcg ccgtcctttg ccgccgacct ggcctggctg     240
cgcgcgctgc ccccgggtac cgcgctggca ggcctgctgg tgcccaaggc agaagatgcc     300
gccgcgctgg ccaccatcgc gcaggccctg cactcgatca acccgcaggg cgaactggtc     360
gcgatcatcg aaaccgcgct gggcctgcat cagatcgacg ccgtggccac cgccaccggc     420
gtggcacgtc ttgccttcgg ctcgctcgac tatgcggtcg acctgggctg cagccatacg     480
cgcgacgcgc tcgcctttgc acgcgcgcgc atcgtgctgg cctcacgcgt ggccgggctg     540
ccgccgccgg tcgacggcgt gaccaccgca ctgaaagacg aagccgtgct ggccagcgac     600
gttgcctatg cgcgcgaact cggctttgcc ggcaagctct gcatccaccc ggcccagctg     660
```

```
ggcgcggcgc gcgcaggctt cctgcccagc cccgagcagc tcgactgggc cgccgtgtg     720 ctggaagcta ccgccagcgg cagccatgcg gtgcaggtcg atggcaagat ggtggaccgg    780
cccgtgatcg agcaggcccg ccggctgctg gcactggcgc aataa                    825
```

```
<210> SEQ ID NO 46
<211> LENGTH: 274
<212> TYPE: PRT
<213> ORGANISM: C. necator

<400> SEQUENCE: 46
```

| | | | | | | | | | | | | | | |
|---|---|---|---|---|---|---|---|---|---|---|---|---|---|---|
| Met | Ser | Thr | Ala | Val | Thr | Tyr | Leu | Phe | Val | Pro | Gly | Asp | Arg | Pro | Glu |
| 1 | | | | 5 | | | | | 10 | | | | | 15 | |
| Arg | Phe | Asp | Lys | Ala | Ala | Ala | Ala | Gly | Pro | Asp | Val | Met | Ile | Leu | Asp |
| | | | 20 | | | | | 25 | | | | | 30 | | |
| Leu | Glu | Asp | Ala | Val | His | Pro | Asp | Ala | Lys | Pro | Ala | Ala | Arg | Ala | Ala |
| | | 35 | | | | | 40 | | | | | 45 | | | |
| Ile | Ala | Ala | Trp | Leu | Ala | Gly | Leu | Pro | Ala | Ala | Asn | Ala | Phe | Val | Arg |
| | 50 | | | | | 55 | | | | | 60 | | | | |
| Ile | Asn | Asp | Ser | Ala | Ser | Pro | Ser | Phe | Ala | Ala | Asp | Leu | Ala | Trp | Leu |
| 65 | | | | | 70 | | | | | 75 | | | | | 80 |
| Arg | Ala | Leu | Pro | Pro | Gly | Thr | Ala | Leu | Ala | Gly | Leu | Leu | Val | Pro | Lys |
| | | | | 85 | | | | | 90 | | | | | 95 | |
| Ala | Glu | Asp | Ala | Ala | Ala | Leu | Ala | Thr | Ile | Ala | Gln | Ala | Leu | His | Ser |
| | | | 100 | | | | | 105 | | | | | 110 | | |
| Ile | Asn | Pro | Gln | Gly | Glu | Leu | Val | Ala | Ile | Ile | Glu | Thr | Ala | Leu | Gly |
| | | | 115 | | | | | 120 | | | | | 125 | | |
| Leu | His | Gln | Ile | Asp | Ala | Val | Ala | Thr | Ala | Thr | Gly | Val | Ala | Arg | Leu |
| | | 130 | | | | | 135 | | | | | 140 | | | |
| Ala | Phe | Gly | Ser | Leu | Asp | Tyr | Ala | Val | Asp | Leu | Gly | Cys | Ser | His | Thr |
| 145 | | | | | 150 | | | | | 155 | | | | | 160 |
| Arg | Asp | Ala | Leu | Ala | Phe | Ala | Arg | Ala | Arg | Ile | Val | Leu | Ala | Ser | Arg |
| | | | | 165 | | | | | 170 | | | | | 175 | |
| Val | Ala | Gly | Leu | Pro | Pro | Pro | Val | Asp | Gly | Val | Thr | Thr | Ala | Leu | Lys |
| | | | 180 | | | | | 185 | | | | | 190 | | |
| Asp | Glu | Ala | Val | Leu | Ala | Ser | Asp | Val | Ala | Tyr | Ala | Arg | Glu | Leu | Gly |
| | | | 195 | | | | | 200 | | | | | 205 | | |
| Phe | Ala | Gly | Lys | Leu | Cys | Ile | His | Pro | Ala | Gln | Leu | Gly | Ala | Ala | Arg |
| | | 210 | | | | | 215 | | | | | 220 | | | |
| Ala | Gly | Phe | Leu | Pro | Ser | Pro | Glu | Gln | Leu | Asp | Trp | Ala | Arg | Arg | Val |
| 225 | | | | | 230 | | | | | 235 | | | | | 240 |
| Leu | Glu | Ala | Thr | Ala | Ser | Gly | Ser | His | Ala | Val | Gln | Val | Asp | Gly | Lys |
| | | | | 245 | | | | | 250 | | | | | 255 | |
| Met | Val | Asp | Arg | Pro | Val | Ile | Glu | Gln | Ala | Arg | Arg | Leu | Leu | Ala | Leu |
| | | | 260 | | | | | 265 | | | | | 270 | | |
| Ala | Gln | | | | | | | | | | | | | | |

```
<210> SEQ ID NO 47
<211> LENGTH: 822
<212> TYPE: DNA
<213> ORGANISM: C. necator

<400> SEQUENCE: 47
```

```
atgccgatcg ccaatcctcg cagctacctg tttgtcccgg cctcgcgccc ggagcgcatc     60
gccaaggcga tcggctccgg cgccgatgcc gtcattgtcg atttcgagga tgcggtcgcg    120
```

```
cccgccgaca agggggcaggc ccgcgacggg cttggcgccc cgtgggcggc gctgggccag    180
caggcagcgg cagccggcgt cgccatgctg gtgcgcatca acggcgccga taccgcgtac    240
tacgaagacg atctcgcctg gtgccgcgca cagggtgtct cggaaatcgt gctgccgaag    300
gccgattcgg ccggcgtcga tgcgcttgct gcggcattgc ccgtgtgcg ctgtttcccg     360 ctggtcgaga acgccgccgg cttcgccggc ttacgcgagc tggcccgtgc cggcggcgtg    420
gtccggctgc tgttcggcag catcgacctg atgttcgatc tcgacgtgca ggacgacggt    480
gaggcgttgc actactttcg cagccggctg gtgcttcatt cccgcgcggc gggtttgccc    540
gcgcccgtgg atggcgtttg caccgcaatc ggcaatgacg ccgcacttgc cgcggaaacg    600
cgccgcgccc gggccttcgg ctttggcgcc aagctgctga tccacccggg ccaggtctgc    660
ggcgtgcacg acggcctggc gccgtcggcc gatgaacggc actgggccgg cgcgtcatg    720 gccgcggctg ccgctgccga tggcgccgcg gtggcggtgg acggcaagat ggtggaccgc    780
ccggtgctgg agcgcgcgcg ccggatcttg tccggtgggt ag                       822
```

<210> SEQ ID NO 48
<211> LENGTH: 273
<212> TYPE: PRT
<213> ORGANISM: C. necator

<400> SEQUENCE: 48

```
Met Pro Ile Ala Asn Pro Arg Ser Tyr Leu Phe Val Pro Ala Ser Arg
1               5                   10                  15

Pro Glu Arg Ile Ala Lys Ala Ile Gly Ser Gly Ala Asp Ala Val Ile
            20                  25                  30

Val Asp Phe Glu Asp Ala Val Ala Pro Ala Asp Lys Gly Gln Ala Arg
        35                  40                  45

Asp Gly Leu Gly Ala Pro Trp Ala Ala Leu Gly Gln Gln Ala Ala Ala
    50                  55                  60

Ala Gly Val Ala Met Leu Val Arg Ile Asn Gly Ala Asp Thr Ala Tyr
65                  70                  75                  80

Tyr Glu Asp Asp Leu Ala Trp Cys Arg Ala Gln Gly Val Ser Glu Ile
                85                  90                  95

Val Leu Pro Lys Ala Asp Ser Ala Gly Val Asp Ala Leu Ala Ala Ala
            100                 105                 110

Leu Pro Gly Val Arg Cys Phe Pro Leu Val Glu Asn Ala Ala Gly Phe
        115                 120                 125

Ala Gly Leu Arg Glu Leu Ala Arg Ala Gly Gly Val Val Arg Leu Leu
    130                 135                 140

Phe Gly Ser Ile Asp Leu Met Phe Asp Leu Asp Val Gln Asp Asp Gly
145                 150                 155                 160

Glu Ala Leu His Tyr Phe Arg Ser Arg Leu Val Leu His Ser Arg Ala
                165                 170                 175

Ala Gly Leu Pro Ala Pro Val Asp Gly Val Cys Thr Ala Ile Gly Asn
            180                 185                 190

Asp Ala Ala Leu Ala Ala Glu Thr Arg Arg Ala Arg Ala Phe Gly Phe
        195                 200                 205

Gly Ala Lys Leu Leu Ile His Pro Gly Gln Val Cys Gly Val His Asp
    210                 215                 220

Gly Leu Ala Pro Ser Ala Asp Glu Arg His Trp Ala Gly Arg Val Met
225                 230                 235                 240

Ala Ala Ala Ala Ala Ala Asp Gly Ala Val Ala Val Asp Gly Lys
                245                 250                 255
```

```
Met Val Asp Arg Pro Val Leu Glu Arg Ala Arg Arg Ile Leu Ser Gly
            260                 265                 270

Gly

<210> SEQ ID NO 49
<211> LENGTH: 894
<212> TYPE: DNA
<213> ORGANISM: C. necator

<400> SEQUENCE: 49
atgataatgc gccctacccc ctcccgccgc ccggttacgc tgcgccgaag ctggctgttc      60
acctcaggca tggacgagcg cgcgcaggcg gccgcgcttg ccagcggcgc cgacgtactg     120
gttcccgacc ttgaggagtt cactgcgccg ccgaccgtc tcgtggcgcg cccacgcgtg     180
gccgcgctga tgtcgcgctg ccgcgcgctg ggtattgtcg cggcggtacg catcaaccga     240
ctaactggtg acggctggga cgacctgcgc ggcgtcatgc ctggatcgcc ggacgcggtt     300
tttctaccct acgtagagag tgccgacgag atcgccacac tggatcgcgc catatcggca     360
ctcgaagccg agttgggact gccgaaaggg accaccgaga tcgtcccgac cattgaatcg     420
gcgcttggct tcattcatat ccagcacatc ctggcagcaa gcgagcgcgt tcgtgcgtgc     480
ctgcttgcgg ccgaggatct cacggccgat ctcggcgccg agcgcggccc cgacagccta     540
gaactcaacc atctgcgcag ccgcttccac gttgagtgcc gggccgccgg ccgcgtggcc     600
atcgactgtc cgtacaacta ccgagatatg caggcgcagg ctgaggatct tgcctgggcc     660
cgccgcatcg gcctcaaagc caagtgcgca gtgtatccgg agcaggtcgc gcagatccat     720
gcagcattca cgccatccat cgcgcaggtt gaactcgcaa agaactggt ggcgcgtttc     780 gaagcagctc gccgcggcga acccattggt gacgcgctcg tggagagtcc cgactaccac     840
acggcgcggc gcctgttgac ccgtgacgcc gaatttaaaa cctggaccgc ctag           894

<210> SEQ ID NO 50
<211> LENGTH: 297
<212> TYPE: PRT
<213> ORGANISM: C. necator

<400> SEQUENCE: 50

Met Ile Met Arg Pro Thr Pro Ser Arg Arg Pro Val Thr Leu Arg Arg
1               5                   10                  15

Ser Trp Leu Phe Thr Ser Gly Met Asp Glu Arg Ala Gln Ala Ala Ala
            20                  25                  30

Leu Ala Ser Gly Ala Asp Val Leu Val Pro Asp Leu Glu Glu Phe Thr
        35                  40                  45

Ala Pro Ala Asp Arg Leu Val Ala Arg Pro Arg Val Ala Ala Leu Met
    50                  55                  60

Ser Arg Cys Arg Ala Leu Gly Ile Val Ala Ala Val Arg Ile Asn Arg
65                  70                  75                  80

Leu Thr Gly Asp Gly Trp Asp Asp Leu Arg Gly Val Met Pro Gly Ser
                85                  90                  95

Pro Asp Ala Val Phe Leu Pro Tyr Val Glu Ser Ala Asp Glu Ile Ala
            100                 105                 110

Thr Leu Asp Arg Ala Ile Ser Ala Leu Glu Ala Glu Leu Gly Leu Pro
        115                 120                 125

Lys Gly Thr Thr Glu Ile Val Pro Thr Ile Glu Ser Ala Leu Gly Phe
    130                 135                 140
```

```
Ile His Ile Gln His Ile Leu Ala Ala Ser Glu Arg Val Arg Ala Cys
145                 150                 155                 160

Leu Leu Ala Ala Glu Asp Leu Thr Ala Asp Leu Gly Ala Glu Arg Gly
            165                 170                 175

Pro Asp Ser Leu Glu Leu Asn His Leu Arg Ser Arg Phe His Val Glu
        180                 185                 190

Cys Arg Ala Ala Gly Arg Val Ala Ile Asp Cys Pro Tyr Asn Tyr Arg
    195                 200                 205

Asp Met Gln Ala Gln Ala Glu Asp Leu Ala Trp Ala Arg Arg Ile Gly
210                 215                 220

Leu Lys Ala Lys Cys Ala Val Tyr Pro Glu Gln Val Ala Gln Ile His
225                 230                 235                 240

Ala Ala Phe Thr Pro Ser Ile Ala Gln Val Glu Leu Ala Lys Glu Leu
                245                 250                 255

Val Ala Arg Phe Glu Ala Arg Arg Gly Glu Pro Ile Gly Asp Ala
            260                 265                 270

Leu Val Glu Ser Pro Asp Tyr His Thr Ala Arg Arg Leu Leu Thr Arg
        275                 280                 285

Asp Ala Glu Phe Lys Thr Trp Thr Ala
    290                 295

<210> SEQ ID NO 51
<211> LENGTH: 744
<212> TYPE: DNA
<213> ORGANISM: C. necator

<400> SEQUENCE: 51
gtgcaggctt atgacgagaa cttcggcttc aaaccggcg ccggcggcat ttctcttgcc      60
gttgcggcag ccctgcgcga gataatggct cgccgcggca tcacgggaag cttcgcggca     120
ggtggaatca ccggctatct ggtagatatg ctcgagcaag gcctgtttcg cagcctgttc     180
gatgttcaat gcttcgactt gcgggccgtc gactccttcc gcgataaccc gcagcaccag     240
gcaatgtcag cctccttgta tgccaaccca tggaacaaag gtgccattgt caaccagctc     300
agcgccatga ttctcggcgc agccgaagtc gacctcgatt tcaacgtcaa tgtcaccaca     360
gcaagcaacg ggcgcatcat cggcggatcg ggcgggcata gcgacaccgc ggccggcgcc     420
gaactcgcca tcgtaacgac ccgactgcgg gcgggtaccg tacccaagat tgtcgagcgg     480
gttcgcaccg tgacgacacc aggagagact gtagacgtcg tcgtcaccga agctggcatc     540
gcggttaatc tcgtcgcgc ggatgttaag gagcgcttga tttccgcagg gattaaagtt     600
gttgccatcg aagctctcta tgatgaagcc aagcgaggac tcgacgtaaa ggcagcatcc     660
gcaagcacct ctggcgagat agtaggaatc gtggagtacc gagatgggac ggctctcgac     720
gtcatcgaga gagttgagtc ctaa                                             744

<210> SEQ ID NO 52
<211> LENGTH: 247
<212> TYPE: PRT
<213> ORGANISM: C. necator

<400> SEQUENCE: 52

Met Gln Ala Tyr Asp Glu Asn Phe Gly Phe Gln Thr Gly Ala Gly Gly
1               5                   10                  15

Ile Ser Leu Ala Val Ala Ala Ala Leu Arg Glu Ile Met Ala Arg Arg
            20                  25                  30

Gly Ile Thr Gly Ser Phe Ala Ala Gly Gly Ile Thr Gly Tyr Leu Val
```

```
                35                  40                  45
Asp Met Leu Glu Gln Gly Leu Phe Arg Ser Leu Phe Asp Val Gln Cys
     50                  55                  60

Phe Asp Leu Arg Ala Val Asp Ser Phe Arg Asp Asn Pro Gln His Gln
 65                  70                  75                  80

Ala Met Ser Ala Ser Leu Tyr Ala Asn Pro Trp Asn Lys Gly Ala Ile
                 85                  90                  95

Val Asn Gln Leu Ser Ala Met Ile Leu Gly Ala Ala Glu Val Asp Leu
            100                 105                 110

Asp Phe Asn Val Asn Val Thr Thr Ala Ser Asn Gly Arg Ile Ile Gly
            115                 120                 125

Gly Ser Gly His Ser Asp Thr Ala Gly Ala Glu Leu Ala Ile
        130                 135                 140

Val Thr Thr Arg Leu Arg Ala Gly Thr Val Pro Lys Ile Val Glu Arg
145                 150                 155                 160

Val Arg Thr Val Thr Thr Pro Gly Glu Thr Val Asp Val Val Thr
                165                 170                 175

Glu Ala Gly Ile Ala Val Asn Pro Arg Arg Ala Asp Val Lys Glu Arg
            180                 185                 190

Leu Ile Ser Ala Gly Ile Lys Val Val Ala Ile Glu Ala Leu Tyr Asp
            195                 200                 205

Glu Ala Lys Arg Gly Leu Asp Val Lys Ala Ala Ser Ala Ser Thr Ser
210                 215                 220

Gly Glu Ile Val Gly Ile Val Glu Tyr Arg Asp Gly Thr Ala Leu Asp
225                 230                 235                 240

Val Ile Glu Arg Val Glu Ser
                245
```

<210> SEQ ID NO 53
<211> LENGTH: 1251
<212> TYPE: DNA
<213> ORGANISM: C. necator

<400> SEQUENCE: 53

```
atgtaccaac atatcaaggt tccggccggc gaaaagatca cggtcaacca ggacttttcg    60
ctgaatgtcc cggacaatcc gatcattcct tacatcgaag cgacggtac gggcctcgat   120 atcaccccgg tgatgatcaa ggtggtcgac gcggctgtgg ccaaggccta tggcggcaag   180
cgcaagatcg cctggatgga gatctacgcc ggcgagaagt ccaccaaggt ctacggcccg   240
gacgtgtggc tgccggacga aaccctggag gtgctcaagg attacgtggt ctcgatcaag   300
ggtccgctga ccacgccggt gggcggcggc atccgctcgc tgaacgtggc actgcgccag   360
cagctggacc tgtacgtctg cctgcgcccg gtgcgctact tcaagggcgt gccctcgccg   420
gtgcgtgagc cggaaaagac cgacatggtg atcttccgcg agaactcgga agacatctac   480
gccggcatcg aatgggcggc ggaaagcgag caggcgaaga agctcatcaa gttcctgcag   540
gacgagatgg gcgtgaagaa gatccgcttc ccggcgacct cgggcatcgg catcaaaccg   600
gtctcgcgcg agggcaccga cgtctggtg cgcaaggcga tccagtacgc catcgacaac   660
gacaagccgt cggtgacgct ggtgcacaag gcaacatca tgaagttcac cgaaggtggc   720
ttccgtgact ggggctacga gctggcgcaa aaggaattcg gcgccgagct ggtcgacggc   780
ggcccgtggt gcaagttcaa gaacccgaag accggcaagg acatcgtgat caaggacgcc   840
attgccgacg ccttcctgca gcagatcctg ctgcgtccgg ccgaatactc ggtgatcgcc   900
```

```
acgctgaacc tgaacggcga ctatgtctcc gacgcgctgg ccgcacaggt cggcggcatc      960
ggcatcgccc cgggcgccaa tatgtctgac tcggttgcca tgttcgaggc cacccacggc     1020
accgcgccga agtacgccgg caaggactac gtcaacccgg gctcggaaat cctgtcggcc     1080
gaaatgatgc tgcgtcacat gggctggacc gaagccgcgg acctgatcat ctcgtcgatg     1140
gagcagtcga tcctgtccaa gaaggtgacg tatgacttcg cccgcctgct ggaaggcgcg     1200
acgcaggtgt cgtgctcggg ctttggccag gtgatgatcg acaatatgta a              1251
```

<210> SEQ ID NO 54
<211> LENGTH: 416
<212> TYPE: PRT
<213> ORGANISM: C. necator

<400> SEQUENCE: 54

```
Met Tyr Gln His Ile Lys Val Pro Ala Gly Glu Lys Ile Thr Val Asn
1               5                   10                  15

Gln Asp Phe Ser Leu Asn Val Pro Asp Asn Pro Ile Ile Pro Tyr Ile
            20                  25                  30

Glu Gly Asp Gly Thr Gly Leu Asp Ile Thr Pro Val Met Ile Lys Val
        35                  40                  45

Val Asp Ala Ala Val Ala Lys Ala Tyr Gly Gly Lys Arg Lys Ile Ala
    50                  55                  60

Trp Met Glu Ile Tyr Ala Gly Glu Lys Ser Thr Lys Val Tyr Gly Pro
65                  70                  75                  80

Asp Val Trp Leu Pro Asp Glu Thr Leu Glu Val Leu Lys Asp Tyr Val
                85                  90                  95

Val Ser Ile Lys Gly Pro Leu Thr Thr Pro Val Gly Gly Gly Ile Arg
            100                 105                 110

Ser Leu Asn Val Ala Leu Arg Gln Gln Leu Asp Leu Tyr Val Cys Leu
        115                 120                 125

Arg Pro Val Arg Tyr Phe Lys Gly Val Pro Ser Pro Val Arg Glu Pro
    130                 135                 140

Glu Lys Thr Asp Met Val Ile Phe Arg Glu Asn Ser Glu Asp Ile Tyr
145                 150                 155                 160

Ala Gly Ile Glu Trp Ala Ala Glu Ser Glu Gln Ala Lys Lys Leu Ile
                165                 170                 175

Lys Phe Leu Gln Asp Glu Met Gly Val Lys Lys Ile Arg Phe Pro Ala
            180                 185                 190

Thr Ser Gly Ile Gly Ile Lys Pro Val Ser Arg Glu Gly Thr Glu Arg
        195                 200                 205

Leu Val Arg Lys Ala Ile Gln Tyr Ala Ile Asp Asn Asp Lys Pro Ser
    210                 215                 220

Val Thr Leu Val His Lys Gly Asn Ile Met Lys Phe Thr Glu Gly Gly
225                 230                 235                 240

Phe Arg Asp Trp Gly Tyr Glu Leu Ala Gln Lys Glu Phe Gly Ala Glu
                245                 250                 255

Leu Val Asp Gly Gly Pro Trp Cys Lys Phe Lys Asn Pro Lys Thr Gly
            260                 265                 270

Lys Asp Ile Val Ile Lys Asp Ala Ile Ala Asp Ala Phe Leu Gln Gln
        275                 280                 285

Ile Leu Leu Arg Pro Ala Glu Tyr Ser Val Ile Ala Thr Leu Asn Leu
    290                 295                 300

Asn Gly Asp Tyr Val Ser Asp Ala Leu Ala Ala Gln Val Gly Gly Ile
305                 310                 315                 320
```

```
Gly Ile Ala Pro Gly Ala Asn Met Ser Asp Ser Val Ala Met Phe Glu
                325                 330                 335

Ala Thr His Gly Thr Ala Pro Lys Tyr Ala Gly Lys Asp Tyr Val Asn
            340                 345                 350

Pro Gly Ser Glu Ile Leu Ser Ala Glu Met Met Leu Arg His Met Gly
        355                 360                 365

Trp Thr Glu Ala Ala Asp Leu Ile Ile Ser Ser Met Glu Gln Ser Ile
    370                 375                 380

Leu Ser Lys Lys Val Thr Tyr Asp Phe Ala Arg Leu Leu Glu Gly Ala
385                 390                 395                 400

Thr Gln Val Ser Cys Ser Gly Phe Gly Gln Val Met Ile Asp Asn Met
                405                 410                 415

<210> SEQ ID NO 55
<211> LENGTH: 2238
<212> TYPE: DNA
<213> ORGANISM: C. necator

<400> SEQUENCE: 55
atgagtaccc agcaacccac catcatctac acgctgaccg acgaagctcc gctgctggcg      60
accagtgcgt tcctcccgat catccagacc ttcaccaagc ccgccggcat caacgtcacc     120
accagcgaca tctcggtggc gggccgtatc ctgggcgagt tccccgaatt cctgaccgaa     180
gcgcagcgcg tgccggacaa cctggccgag ctgggcaagc tgacccagct gccggacacc     240
aacatcatca gctgccgaa catcagcgcc tcggtgcacc agctggtcag cgccatccgc      300
gaactgcagg gcaagggcta caaggtgccg gactatccgg aagatccgaa gaacgacgaa     360
gaaaaggcaa tccagaagcg ctattccaag tgcctgggct cggccgtgaa cccggtcctg     420
cgcgaaggca actccgaccg ccgcgcaccg gcagcggtca gaacttcgc gcgcaagcac      480 ccgcacagca tgggcgagtg gagcatggcc tcgcgcacgc acgtggcgca catgaagcat     540
ggcgacttct accacggcga aaagtccatg accctggacc gcgcgcgtga cgtcaagatg     600
gagctggtca ccaagagcgg caagaccatc gtgctcaagc ccaaggtctc gctgctggat     660
ggcgagatca tcgacagcat gttcatgagc aagaaggcgc tgtgcgactt ctatgaagag     720
cagttcgaag acgcgcgcaa gaccggcgtg atgctgtcgc tgcacgtcaa ggcgaccatg     780
atgaaggtgt cgcaccccga tcgtgttcggc cacgccgtca agatcttcta caaggaagcc     840
ttcgccaagc acggcgcgct gttcgacgaa ctgggcgtga acgtcaacaa cggcctggtc     900
aacctgtacg agaagatcga ggcgctgccc agctccaagc gcgaagagat catccgcgac     960
ctgcacgcct gccacgagca tcgcccggaa ctggcgatgg tggattcggc caagggcatt    1020
tccaacctgc acgcgcccaa cgacgtgatc gtggatgcct cgatgccggc catgatccgc    1080
atcggcggca agatgtgggg tgccgacggc cgtccgaagg acaccaaggc cgtgatcccg    1140
gaaagcacct tgcccgcat ctaccaggag atcatcaact ctgcaagac caacggcaac      1200 ttcgacccga ccaccatggg caccgtgccc aacgtgggcc tgatggcgca gaaggccgaa    1260
gaatacggct cgcacgacaa gaccttcgag atcgccgaag acggcgtcgc caacatcgtc    1320
gacctggcca ctggtgaagt gctgctgacg caggacgtcg agcagggcga catctggcgc    1380
atgtgccagg tcaaggacgc gccgatccgc gactgggtca agctggccgt gacgcgcgcg    1440
cgcaactcgg gcatgccggc ggtgttctgg ctggacccgt accgtccgca cgaagccgag    1500
ctgatcaaga aggtcgagac ctacctgaag gactacgata ccaacggcct ggacatccag    1560
```

-continued

```
atcatgtcgc aggtgcgcgc catgcgctac acgctggagc gcgtgatccg cggcctggac   1620
accatctcgg tgaccggcaa catcctgcgc gactacctga ccgacctgtt cccgatcatg   1680
gaactgggca ccagcgccaa gatgctgtcg atcgttccgc tgatggccgg tggcggcatg   1740
tatgagaccg cgccggcgg ttcggctccg aagcatgtca agcaactggt ggaagaaaac    1800
cacctgcgct gggattcgct gggcgagttc ctggcgctgg cggtgtcgct ggaagacgtt   1860
ggcatcaaga ccggcaatgc caaggccaag atcctggcca ggacgctgga tgctgccacc   1920
ggcaagctgc tggacaacaa caagagcccg tcgcccaaga ccggccagct ggacaaccgc   1980
ggcagccagt tctacctggc gatgtactgg gcgcaggaac tggccggcca gtcggaggac   2040
gccgaactgg ccgcgaagtt cgcgccgctg gccaggacgc tgaccgacaa cgagcagaag   2100
atcgttggcg aactcggcgc cgtgcagggc cagccggtgg atatcggcgg ctattacatg   2160
ccggaagccg acaagctcag cgccgcgatg cgcccgagcc agacgctgaa cgccgcgctg   2220
tcgaccgtga cggcctga                                                 2238
```

<210> SEQ ID NO 56
<211> LENGTH: 745
<212> TYPE: PRT
<213> ORGANISM: C. necator

<400> SEQUENCE: 56

```
Met Ser Thr Gln Gln Pro Thr Ile Ile Tyr Thr Leu Thr Asp Glu Ala
1               5                   10                  15

Pro Leu Leu Ala Thr Ser Ala Phe Leu Pro Ile Ile Gln Thr Phe Thr
            20                  25                  30

Lys Pro Ala Gly Ile Asn Val Thr Thr Ser Asp Ile Ser Val Ala Gly
        35                  40                  45

Arg Ile Leu Gly Glu Phe Pro Glu Phe Leu Thr Glu Ala Gln Arg Val
    50                  55                  60

Pro Asp Asn Leu Ala Glu Leu Gly Lys Leu Thr Gln Leu Pro Asp Thr
65                  70                  75                  80

Asn Ile Ile Lys Leu Pro Asn Ile Ser Ala Ser Val His Gln Leu Val
                85                  90                  95

Ser Ala Ile Arg Glu Leu Gln Gly Lys Gly Tyr Lys Val Pro Asp Tyr
            100                 105                 110

Pro Glu Asp Pro Lys Asn Asp Glu Glu Lys Ala Ile Gln Lys Arg Tyr
        115                 120                 125

Ser Lys Cys Leu Gly Ser Ala Val Asn Pro Val Leu Arg Glu Gly Asn
    130                 135                 140

Ser Asp Arg Arg Ala Pro Ala Ala Val Lys Asn Phe Ala Arg Lys His
145                 150                 155                 160

Pro His Ser Met Gly Glu Trp Ser Met Ala Ser Arg Thr His Val Ala
                165                 170                 175

His Met Lys His Gly Asp Phe Tyr His Gly Glu Lys Ser Met Thr Leu
            180                 185                 190

Asp Arg Ala Arg Asp Val Lys Met Glu Leu Val Thr Lys Ser Gly Lys
        195                 200                 205

Thr Ile Val Leu Lys Pro Lys Val Ser Leu Leu Asp Gly Glu Ile Ile
    210                 215                 220

Asp Ser Met Phe Met Ser Lys Lys Ala Leu Cys Asp Phe Tyr Glu Glu
225                 230                 235                 240

Gln Phe Glu Asp Ala Arg Lys Thr Gly Val Met Leu Ser Leu His Val
                245                 250                 255
```

```
Lys Ala Thr Met Met Lys Val Ser His Pro Ile Val Phe Gly His Ala
            260                 265                 270

Val Lys Ile Phe Tyr Lys Glu Ala Phe Ala Lys His Gly Ala Leu Phe
            275                 280                 285

Asp Glu Leu Gly Val Asn Val Asn Asn Gly Leu Val Asn Leu Tyr Glu
            290                 295                 300

Lys Ile Glu Ala Leu Pro Ser Ser Lys Arg Glu Glu Ile Ile Arg Asp
305                 310                 315                 320

Leu His Ala Cys His Glu His Arg Pro Glu Leu Ala Met Val Asp Ser
                325                 330                 335

Ala Lys Gly Ile Ser Asn Leu His Ala Pro Asn Asp Val Ile Val Asp
                340                 345                 350

Ala Ser Met Pro Ala Met Ile Arg Ile Gly Gly Lys Met Trp Gly Ala
                355                 360                 365

Asp Gly Arg Pro Lys Asp Thr Lys Ala Val Ile Pro Glu Ser Thr Phe
            370                 375                 380

Ala Arg Ile Tyr Gln Glu Ile Ile Asn Phe Cys Lys Thr Asn Gly Asn
385                 390                 395                 400

Phe Asp Pro Thr Thr Met Gly Thr Val Pro Asn Val Gly Leu Met Ala
                405                 410                 415

Gln Lys Ala Glu Glu Tyr Gly Ser His Asp Lys Thr Phe Glu Ile Ala
                420                 425                 430

Glu Asp Gly Val Ala Asn Ile Val Asp Leu Ala Thr Gly Glu Val Leu
            435                 440                 445

Leu Thr Gln Asp Val Glu Gln Gly Asp Ile Trp Arg Met Cys Gln Val
            450                 455                 460

Lys Asp Ala Pro Ile Arg Asp Trp Val Lys Leu Ala Val Thr Arg Ala
465                 470                 475                 480

Arg Asn Ser Gly Met Pro Ala Val Phe Trp Leu Asp Pro Tyr Arg Pro
                485                 490                 495

His Glu Ala Glu Leu Ile Lys Lys Val Glu Thr Tyr Leu Lys Asp Tyr
                500                 505                 510

Asp Thr Asn Gly Leu Asp Ile Gln Ile Met Ser Gln Val Arg Ala Met
            515                 520                 525

Arg Tyr Thr Leu Glu Arg Val Ile Arg Gly Leu Asp Thr Ile Ser Val
            530                 535                 540

Thr Gly Asn Ile Leu Arg Asp Tyr Leu Thr Asp Leu Phe Pro Ile Met
545                 550                 555                 560

Glu Leu Gly Thr Ser Ala Lys Met Leu Ser Ile Val Pro Leu Met Ala
                565                 570                 575

Gly Gly Gly Met Tyr Glu Thr Gly Ala Gly Gly Ser Ala Pro Lys His
                580                 585                 590

Val Lys Gln Leu Val Glu Glu Asn His Leu Arg Trp Asp Ser Leu Gly
            595                 600                 605

Glu Phe Leu Ala Leu Ala Val Ser Leu Glu Asp Val Gly Ile Lys Thr
            610                 615                 620

Gly Asn Ala Lys Ala Lys Ile Leu Ala Arg Thr Leu Asp Ala Ala Thr
625                 630                 635                 640

Gly Lys Leu Leu Asp Asn Asn Lys Ser Pro Ser Pro Lys Thr Gly Gln
                645                 650                 655

Leu Asp Asn Arg Gly Ser Gln Phe Tyr Leu Ala Met Tyr Trp Ala Gln
                660                 665                 670
```

-continued

```
Glu Leu Ala Gly Gln Ser Glu Asp Ala Glu Leu Ala Ala Lys Phe Ala
            675                 680                 685

Pro Leu Ala Arg Thr Leu Thr Asp Asn Glu Gln Lys Ile Val Gly Glu
        690                 695                 700

Leu Gly Ala Val Gln Gly Gln Pro Val Asp Ile Gly Gly Tyr Tyr Met
705                 710                 715                 720

Pro Glu Ala Asp Lys Leu Ser Ala Ala Met Arg Pro Ser Gln Thr Leu
                725                 730                 735

Asn Ala Ala Leu Ser Thr Val Thr Ala
            740                 745
```

<210> SEQ ID NO 57
<211> LENGTH: 1041
<212> TYPE: DNA
<213> ORGANISM: C. necator

<400> SEQUENCE: 57

```
atggaaaacg gtgcacgcga acagatcccg gccacgctga tcccaggcga cgggatcggt    60
cccgaagtag tggacgccac cgtcagggtg ctggaagcgc tgggcgcccc gtttgcctgg   120
gatatccggc gcgcgggaat ggccggcgtc aatacagcg gcgatcccct gccgcaagac    180
acgctggaca gcatcggccg caccggcctg ccctgaagg ggccgctgac cacgccggtg    240
ggcggtggct ccgctcggt caatgtgcgc ctgcgcgagg cgttcaacct ctatgccaac    300
gtgcgccctg cccgcacgct ggtgccgggc cgcttcgaga atatcgacct ggtgctggtg    360
cgcgagaacg tcgcggcttt ctatgtggcc catgactact acatcccggt tggcgacgac    420
ccgcatgcgg tggcggtgtc caccggcacc aacacgcgcg acgcgtgccg gcgcattgcc    480
cgcttcgcct tcgagtacgc cgtcaggaac ggccgcaaga agatcacggt ggtgcacaag    540
gccaatatcc tgaaagcgct caccggcatc ttcctggaag cggcgcgcga agtcgccagg    600
gactacgcgg gccgcgtgga catggacgac atcattgtcg acgcctgcgc catgcagctg    660
gtgctcaacc cgtggcgctt cgacatgctg ctctgtacca acctgttcgg cgacatcctg    720
tcggaccaga tcgccggcct ggttggcggg cttggcatgg cgccgggcgc caacatcggc    780
gaccaggccg cgatcttcga ggcggtgcac ggctcggcgc agacatcgc tggcaaaggc    840
attgccaacc cgatctcgct gatgctggcc gccggcctga tgctcgacca cgtgggccgc    900
caggacctgg ccacgcgcct cgcacggcc atcgagctga cgctggtcca ggaccaggtg    960
aagaccggcg acctccacgg cacggccacc acgctgcagt cgcggacgc ggtagtgaaa   1020
cgcatcgctt ccgccagctg a                                             1041
```

<210> SEQ ID NO 58
<211> LENGTH: 346
<212> TYPE: PRT
<213> ORGANISM: C. necator

<400> SEQUENCE: 58

```
Met Glu Asn Gly Ala Arg Glu Gln Ile Pro Ala Thr Leu Ile Pro Gly
1               5                   10                  15

Asp Gly Ile Gly Pro Glu Val Val Asp Ala Thr Val Arg Val Leu Glu
            20                  25                  30

Ala Leu Gly Ala Pro Phe Ala Trp Asp Ile Arg Arg Ala Gly Met Ala
        35                  40                  45

Gly Val Glu Tyr Ser Gly Asp Pro Leu Pro Gln Asp Thr Leu Asp Ser
    50                  55                  60
```

-continued

```
Ile Gly Arg Thr Gly Leu Ala Leu Lys Gly Pro Leu Thr Thr Pro Val
 65              70                  75                  80

Gly Gly Gly Phe Arg Ser Val Asn Val Arg Leu Arg Glu Ala Phe Asn
             85                  90                  95

Leu Tyr Ala Asn Val Arg Pro Ala Arg Thr Leu Val Pro Gly Arg Phe
            100                 105                 110

Glu Asn Ile Asp Leu Val Leu Val Arg Glu Asn Val Gly Gly Phe Tyr
            115                 120                 125

Val Ala His Asp Tyr Tyr Ile Pro Val Gly Asp Asp Pro His Ala Val
            130                 135                 140

Ala Val Ser Thr Gly Thr Asn Thr Arg Asp Ala Cys Arg Arg Ile Ala
145                 150                 155                 160

Arg Phe Ala Phe Glu Tyr Ala Val Arg Asn Gly Arg Lys Lys Ile Thr
            165                 170                 175

Val Val His Lys Ala Asn Ile Leu Lys Ala Leu Thr Gly Ile Phe Leu
            180                 185                 190

Glu Ala Ala Arg Glu Val Ala Arg Asp Tyr Ala Gly Arg Val Asp Met
            195                 200                 205

Asp Asp Ile Ile Val Asp Ala Cys Ala Met Gln Leu Val Leu Asn Pro
            210                 215                 220

Trp Arg Phe Asp Met Leu Leu Cys Thr Asn Leu Phe Gly Asp Ile Leu
225                 230                 235                 240

Ser Asp Gln Ile Ala Gly Leu Val Gly Gly Leu Gly Met Ala Pro Gly
            245                 250                 255

Ala Asn Ile Gly Asp Gln Ala Ala Ile Phe Glu Ala Val His Gly Ser
            260                 265                 270

Ala Pro Asp Ile Ala Gly Lys Gly Ile Ala Asn Pro Ile Ser Leu Met
            275                 280                 285

Leu Ala Ala Gly Leu Met Leu Asp His Val Gly Arg Gln Asp Leu Ala
            290                 295                 300

Thr Arg Leu Arg Thr Ala Ile Glu Leu Thr Leu Val Gln Asp Gln Val
305                 310                 315                 320

Lys Thr Gly Asp Leu His Gly Thr Ala Thr Thr Leu Gln Phe Ala Asp
            325                 330                 335

Ala Val Val Lys Arg Ile Ala Ser Ala Ser
            340                 345
```